US012622951B2

(12) United States Patent
Cho et al.

(10) Patent No.: US 12,622,951 B2
(45) Date of Patent: *May 12, 2026

(54) URATE OXIDASE-ALBUMIN CONJUGATE, PREPARATION METHOD THEREOF, AND USE THEREOF

(71) Applicant: Proabtech Inc., Gwangju (KR)

(72) Inventors: Jeong Haeng Cho, Gimpo-si (KR); Sun Oh Shin, Gwangju (KR); Hyun Woo Kim, Seoul (KR); Hyeongseok Kim, Seoul (KR); Dong Ho Bak, Jeonju-si (KR); Inchan Kwon, Gwangju (KR); Byungseop Yang, Seoul (KR)

(73) Assignee: ProAbtech Co., LTD., Gwangju (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/773,516

(22) PCT Filed: Sep. 24, 2021

(86) PCT No.: PCT/KR2021/013037
§ 371 (c)(1),
(2) Date: Apr. 29, 2022

(87) PCT Pub. No.: WO2022/065913
PCT Pub. Date: Mar. 31, 2022

(65) Prior Publication Data
US 2023/0211002 A1 Jul. 6, 2023

(30) Foreign Application Priority Data

Sep. 25, 2020 (KR) ........................ 10-2020-0125215
Jan. 29, 2021 (KR) ........................ 10-2021-0013537

(51) Int. Cl.
| | |
|---|---|
| *A61K 38/44* | (2006.01) |
| *A61K 47/54* | (2017.01) |
| *A61K 47/60* | (2017.01) |
| *A61K 47/64* | (2017.01) |
| *A61P 19/06* | (2006.01) |
| *C12N 9/06* | (2006.01) |

(52) U.S. Cl.
CPC ............ *A61K 38/44* (2013.01); *A61K 47/545* (2017.08); *A61K 47/60* (2017.08); *A61K 47/643* (2017.08); *A61P 19/06* (2018.01); *C12N 9/0048* (2013.01); *C12Y 107/03003* (2013.01)

(58) Field of Classification Search
None
See application file for complete search history.

(56) References Cited

U.S. PATENT DOCUMENTS

| | | |
|---|---|---|
| 8,962,811 B2 | 2/2015 | Kieliszewski et al. |
| 12,161,699 B2 | 12/2024 | Cho et al. |
| 2013/0209466 A1 | 8/2013 | Walker et al. |
| 2014/0066378 A1 | 3/2014 | Dixit et al. |
| 2017/0175183 A1 | 6/2017 | Ju et al. |
| 2019/0077776 A1 | 3/2019 | Mehl et al. |
| 2020/0010450 A1 | 1/2020 | Yang et al. |
| 2023/0149517 A1 | 5/2023 | Cho et al. |
| 2023/0211002 A1 | 7/2023 | Cho et al. |

FOREIGN PATENT DOCUMENTS

| | | |
|---|---|---|
| CN | 102627615 A | 8/2012 |
| EP | 4218825 A1 | 8/2023 |
| EP | 4282876 A1 | 11/2023 |
| KR | 10 2011/0128827 A | 11/2011 |
| KR | 10 2015/0124999 A | 11/2015 |
| KR | 10-1637010 B1 | 7/2016 |
| KR | 10 2018/0002828 A | 1/2018 |
| KR | 10 2019/0045116 A | 5/2019 |
| WO | WO-2015/054658 A1 | 4/2015 |
| WO | WO-2021/246557 A1 | 12/2021 |
| WO | WO-2022/065913 A1 | 3/2022 |

OTHER PUBLICATIONS

Gil et al., "Bioengineered robust hybrid hydrogels enrich the stability and efficacy of biological drugs", Journal of Controlled Release 267: 119-132 (Year: 2017).*
Bak et al., "Recombinant peptide production platform coupled with site-specific albumin conjugation enables a convenient production of long-acting therapeutic peptide", Pharmaceutics 12(4): 364 (2020).
International Search Report and Written Opinion for International Application No. PCT/KR2021/013077 dated Jan. 24, 2023.
International Search Report and Written Opinion for International Application No. PCT/KR2022/001675 dated Dec. 27, 2022.
International Search Report and Written Opinion for International Application No. PCT/KR2022/009593 dated Oct. 14, 2022.
International Search Report and Written Opinion for International Application No. PCT/KR2022/014276 dated Dec. 27, 2022.
Kolodych et al. "CBTF: new amine-to-thiol coupling reagent for preparation of antibody conjugates with increased plasma stability." Bioconjugate chemistry 26.2 (2015): 197-200.
NCBI, Genbank accession No. 1AO6_A.
NCBI, Genbank accession No. E13225.
Yang et al., "Multivalent Albumin-Neonatal Fc Receptor Interactions Mediate a Prominent Extension of the Serum Half-Life of a Therapeutic Protein", Molecular Pharmaceutics 18.6 : 2397-2405 (2021).

(Continued)

*Primary Examiner* — Anand U Desai
(74) *Attorney, Agent, or Firm* — Foley Hoag LLP; David P. Halstead

(57) ABSTRACT

The present specification discloses a urate oxidase-albumin conjugate, a preparation method thereof, a urate oxidase variant contained in the urate oxidase-albumin conjugate, and a preparation method thereof. The urate oxidase-albumin conjugate is characterized in that three or more albumins are conjugated to the urate oxidase variant through a linker, thereby improving half-life and reducing immunogenicity. In addition, the urate oxidase-albumin conjugate can be used to prevent or treat various diseases, disorders and/or indications caused by uric acid.

12 Claims, 30 Drawing Sheets

Specification includes a Sequence Listing.

(56)                    References Cited

OTHER PUBLICATIONS

Yang et al., "Temporal control of efficient in vivo bioconjugation using a genetically encoded tetrazine-mediated inverse-electron-demand Diels-Alder reaction." Bioconjugate Chemistry 31.10 (2020): 2456-2464.

Lim et al., "Site-specific albumination of a therapeutic protein with multi-subunit to prolong activity in vivo," Journal of Controlled Release 207 (2015): 93-100.

Shi et al., "Structure-based design of a hyperthermostable AgUricase for hypemricemia and gout therapy", Acta Pharmacologica Sinica., 40(10): 1364-1372 (2019).

International Search Report and Written Opinion for PCT/KR2021/ 013037 with translated Search Report dated Jan. 24, 2022.

Cho, Jeong-Haeng et al. "Optimization of Cultivation Conditions for Production of Recombinant Urate Oxidase with Unnatural Amino Acids", KSBB Journal 35.1: 51-56 (2020).

Cho et al., "Albumin affibody-outfitted injectable gel enabling extended release of urate oxidase-albumin conjugates for hyperuricemia treatment," Journal of Controlled Release 324 (2020): 532-544.

Poznansky et al., "Biological macromolecules as carriers of drugs and enzymes," Drug Delivery Systems: Characteristics and Biomedical Applications (1980): 253-315.

Remy et al., "Immunogenicity and Antigenicity of Soluble Cross-Linked Enzyme/AlbuminPolymers" Advantages for Enzyme Therapy, The Lancet 312.8080 (1978): 68-70.

Supplementary European Search Report for EP Application No. 21872941.6 dated May 14, 2025.

Supplementary European Search Report for EP Application No. 21872964.8 dated Feb. 17, 2025.

Blizzard et al., "Ideal bioorthogonal reactions using a site-specifically encoded tetrazine amino acid", Journal of the American Chemical Society 137.32: 10044-10047(2015).

Blizzard, "In Vivo Reactions of Tetrazines Incorporated through Genetic Code Expansion", Oregon State University Biochemistry and Biophysics Doctor of Philosophy (Ph.D.) Dissertation, pp. 1-133 (2019).

Office Action for Korean Application No. 10 2023/7009860 dated Mar. 22, 2023.

Rajbhandary, "Site Specific Incorporation of Amino Acid Analogues into; Proteins In Vivo" Final Report, 137(32), pp. 1-55, (2010).

* cited by examiner

Albumin-Subunit conjugate

Uricase-Albumin conjugate (4 Albumins conjugated)

1st Albumin-Subunit conjugate      2nd Albumin-Subunit conjugate

3rd Albumin-Subunit conjugate      4th Albumin-Subunit conjugate

Uricase-Albumin conjugate (3 Albumins conjugated)

M: 1kb DNA ladder

1. Uncut
2. EcoRI/HindII double digestion

Figure 5:
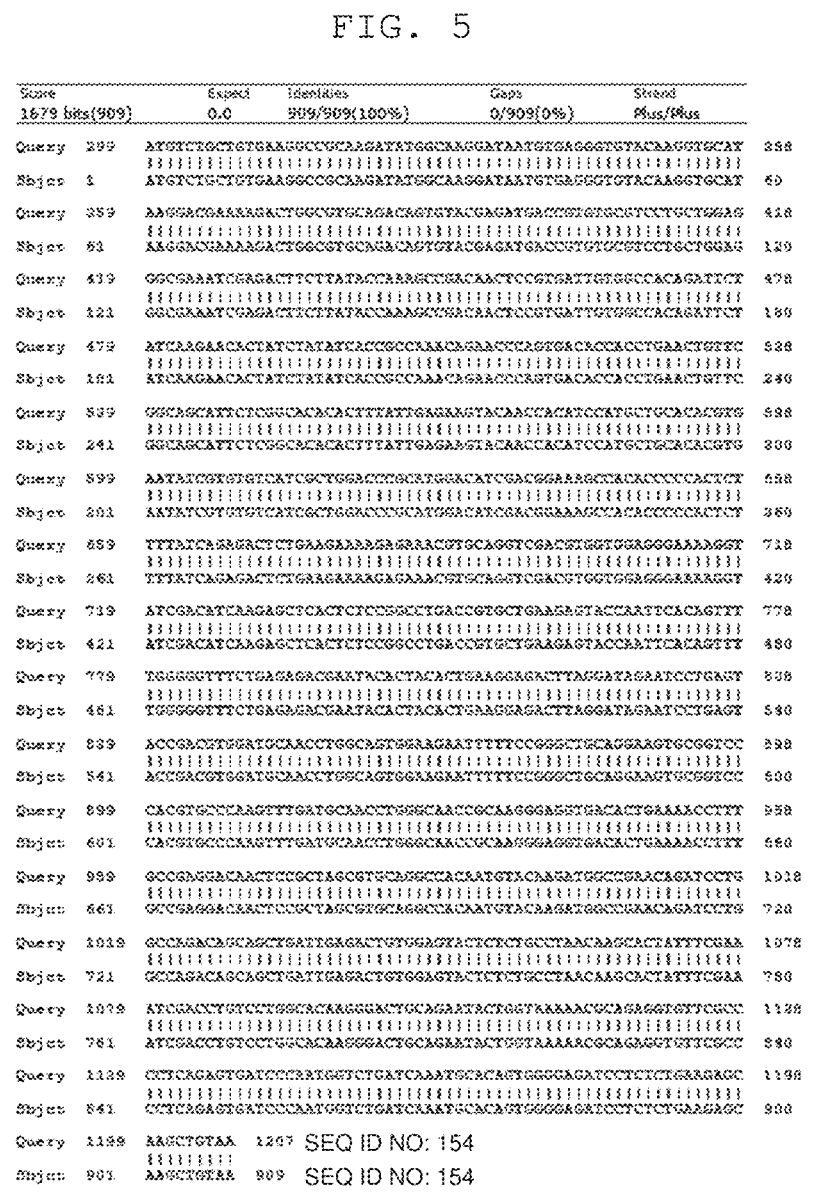

| Score | Expect | Identities | Gaps | Strand |
|---|---|---|---|---|
| 1679 bits(909) | 0.0 | 909/909(100%) | 0/909(0%) | Plus/Plus |

Query 299 ATGTCTGCTGTGAAGGCCTGCAAGATATGGCAAGGATAATGTGAGGGTGTACAAGGTGCAT 358
Sbjct 1   ATGTCTGCTGTGAAGGCCGCAAGATATGGCAAGGATAATGTGAGGGTGTACAAGGTGCAT 60

Query 359 AAGGACGAAAAGACTGGCGTGCAGACAGTGTACGAGATGACCGTGTGCGTCCTGCTGGAG 418
Sbjct 61  AAGGACGAAAAGACTGGCGTGCAGACAGTGTACGAGATGACCGTGTGCGTCCTGCTGGAG 120

Query 419 GGCGAAATCGAGACTTCTTATACCAAAGCTGACAACTCCGTGATTGTGGCCACAGATTCT 478
Sbjct 121 GGCGAAATCGAGACTTCTTATACCAAAGCTGACAACTCCGTGATTGTGGCCACAGATTCT 180

Query 479 ATCAAGAACACTATCTATATCACCGCCAAACAGAACTCAGTGACACCACCTGAACTGTTC 538
Sbjct 181 ATCAAGAACACTATCTATATCACCGCCAAACAGAACTCAGTGACACCACCTGAACTGTTC 240

Query 539 GGCAGCATTCTCGGCACACACTTTATTGAGAAGTACAACCACATCCATGCTGCACACGTG 598
Sbjct 241 GGCAGCATTCTCGGCACACACTTTATTGAGAAGTACAACCACATCCATGCTGCACACGTG 300

Query 599 AATATCGTGTGTCATCGCTGGACTTGCATGGACATCGACGGAAAGCTACACCCCCACTCT 658
Sbjct 301 AATATCGTGTGTCATCGCTGGACTTGCATGGACATCGACGGAAAGCTACACCCCCACTCT 360

Query 659 TTTATCAGAGACTCTGAAGAAAAGAGAAACGTGCAGGTCGACGTGGTGGAGGGAAAAGGT 718
Sbjct 361 TTTATCAGAGACTCTGAAGAAAAGAGAAACGTGCAGGTCGACGTGGTGGAGGGAAAAGGT 420

Query 719 ATCGACATCAAGAGCTCACTCTCCGGCCTGACCGTGCTGAAGAGTACCAAGTCACAGTTT 778
Sbjct 421 ATCGACATCAAGAGCTCACTCTCCGGCCTGACCGTGCTGAAGAGTACCAAGTCACAGTTT 480

Query 779 TGGGGGTTTCTGAGAGACGAATACACTACACTGAAGGAGACTTAGGATAGAATCCTGAGT 838
Sbjct 481 TGGGGGTTTCTGAGAGACGAATACACTACACTGAAGGAGACTTAGGATAGAATCCTGAGT 540

Query 839 ACCGACGTGGATGCAACCTGGCAGTGGAAGAATTTTTCCGGGCTGCAGGAAGTGCGGTCC 898
Sbjct 541 ACCGACGTGGATGCAACCTGGCAGTGGAAGAATTTTTCCGGGCTGCAGGAAGTGCGGTCC 600

Query 899 CACGTGCCCAAGTTTGATGCAACCTGGGCAACCGCAAGGGAGGTGACACTGAAAACCTTT 958
Sbjct 601 CACGTGCCCAAGTTTGATGCAACCTGGGCAACCGCAAGGGAGGTGACACTGAAAACCTTT 660

Query 959 GCCGAGGACAACTCCGCTAGCGTGCAGGCCACAATGTACAAGATGGCCGAACAGATCCTG 1018
Sbjct 661 GCCGAGGACAACTCCGCTAGCGTGCAGGCCACAATGTACAAGATGGCCGAACAGATCCTG 720

Query 1019 GCCAGACAGCAGCTGATTGAGACTGTGGAGTACTCTCTGCCTAACAAGCACTATTTCGAA 1078
Sbjct 721  GCCAGACAGCAGCTGATTGAGACTGTGGAGTACTCTCTGCCTAACAAGCACTATTTCGAA 780

Query 1079 ATCGACCTGTCCTGGCACAAGGGACTGCAGAATACTGGTAAAAACGCAGAGGTGTTCGCC 1138
Sbjct 781  ATCGACCTGTCCTGGCACAAGGGACTGCAGAATACTGGTAAAAACGCAGAGGTGTTCGCC 840

Query 1139 CCTCAGAGTGATCCCAATGGTCTGATCAAATGCACAGTGGGGGAGATCCTCTCTGAAGAGC 1198
Sbjct 841  CCTCAGAGTGATCCCAATGGTCTGATCAAATGCACAGTGGGGGAGATCCTCTCTGAAGAGC 900

Query 1199 AAGCTGTAA 1207  SEQ ID NO: 154
Sbjct 901  AAGCTGTAA 909  SEQ ID NO: 154

1 : 8h (induction X)

2 : 12h (induction X)

3 : 16h (induction 1h)

4 : 24h (induction 9h)

5 : 32h (induction 17h)

6 : 40h (induction 25h)

7 : 48h (induction 33h)

Uox-frTet(34kDa)

FIG. 16

PK profile

Fasturtec_IV
Uox-HSA_IV
Uox-HSA_IP
Uox-HSA_IM

FIG. 17

| Time (hrs) | Fasturtec_IV | | Uox-HSA_IV | | Uox-HSA_IP | | Uox-HSA_IM | |
|---|---|---|---|---|---|---|---|---|
| | AVG (mU/mL) | SD | AVG (mU/mL) | SD | AVG (mU/mL) | SD | AVG (mU/mL) | SD |
| 0.50 | 126.19 | 5.20 | 129.56 | 2.55 | 24.60 | 12.91 | 57.20 | 25.28 |
| 3.00 | 52.61 | 11.84 | 134.73 | 1.64 | 80.24 | 7.93 | 123.08 | 4.46 |
| 6.00 | 16.16 | 4.03 | 134.25 | 7.10 | 69.46 | 11.83 | 121.64 | 2.92 |
| 9.00 | 5.42 | 4.60 | 126.47 | 3.86 | 82.88 | 8.00 | 117.36 | 4.55 |
| 12.00 | 6.09 | 4.26 | 120.09 | 8.23 | 83.16 | 13.45 | 113.29 | 4.92 |
| 24.00 | 3.58 | 4.22 | 95.81 | 6.84 | 67.80 | 7.57 | 90.74 | 5.91 |
| 48.00 | 0.75 | _ | 44.22 | 7.85 | 27.17 | 15.72 | 47.47 | 6.60 |
| AUC | 476.40 | | 4,471.00 | | 2,879.00 | | 4,180.00 | |
| T1/2 (h) | 1.86 | | 26.22 | | 21.61 | | 28.21 | |
| Tmax (h) | 0.50 | | 0.50 | | 12.00 | | 3.00 | |
| Cmax (mU/mL) | 126.19 | | 134.73 | | 83.16 | | 123.08 | |

PD Profile

Negative control    Uox-HSA 1mg/kg    Uox-HSA 4mg/kg
Uox-HSA 10mg/kg    Fasturtec 1.33 mg/kg    Febuxostat 10mg/kg

FIG. 19

| Time (hrs) | Negative control | | Uox-HSA 1mg/kg | | Uox-HSA 4mg/kg | | Uox-HSA 10mg/kg | | Fasturtec 1.33 mg/kg | | Febuxostat 10mg/kg | |
|---|---|---|---|---|---|---|---|---|---|---|---|---|
| | AVG (mg/dL) | SD | AVG (mg/dL) | SD | AVG (mg/dL) | SD | AVG (mg/dL) | SD | AVG (mg/dL) | SD | AVG (mg/dL) | SD |
| 0.5 | 11.31 | 2.09 | 2.56 | 0.51 | 3.07 | 1.12 | 2.71 | 0.45 | 2.60 | 0.44 | 5.13 | 1.18 |
| 2 | 7.23 | 1.35 | 2.57 | 0.61 | 2.25 | 0.10 | 2.62 | 0.08 | 2.52 | 0.38 | 4.17 | 0.75 |
| 4 | 4.63 | 0.94 | 2.18 | 0.33 | 2.03 | 0.30 | 2.34 | 0.43 | 2.38 | 0.49 | 4.07 | 0.57 |
| 12 | 3.04 | 0.10 | 2.28 | 0.55 | 1.80 | 0.04 | 2.15 | 0.03 | 2.16 | 0.03 | 3.00 | 0.65 |
| 24 | 10.71 | 1.51 | 8.30 | 1.38 | 6.52 | 2.04 | 5.89 | 0.51 | 10.86 | 1.25 | 8.46 | 0.94 |
| 36 | 4.49 | 2.18 | 2.27 | 0.08 | 2.24 | 0.25 | 2.68 | 0.17 | 4.97 | 0.60 | 2.94 | 0.22 |
| 48 | 16.84 | 1.21 | 8.84 | 5.22 | 11.76 | 1.83 | 7.71 | 1.06 | 14.02 | 1.55 | 11.63 | 1.45 |

| Label | T1/2 (hrs) | AUC (mU/mL x h) | Range (hrs) |
|---|---|---|---|
| Uox-HSA (Tetra) | 60.3 | 18981.4 | 0.5 ~ 168 |
| Uox-HSA (tri/di) | 32.4 | 15165.5 | 0.5 ~ 168 |

| CD4 | Label | | | CD8 | Label | |
|---|---|---|---|---|---|---|
| | Uox-HSA | Fasturtec | | | Uox-HSA | Fasturtec |
| #1 | 3.85 | 3.77 | | #1 | 2.56 | 2.21 |
| #2 | 3.36 | 4.34 | | #2 | 2.64 | 3.51 |
| #3 | 3.05 | 4.48 | | #3 | 2.89 | 3.11 |
| Mean | 3.42 | 4.20 | | Mean | 2.70 | 2.94 |
| Stimulation Index | 1.0721 | 1.3156 | | Stimulation Index | 0.7575 | 0.8268 |
| Stimulation Index (SI) = test well/baseline, when SI ≥ 2, considered positive | | | | | | |

FIG. 23

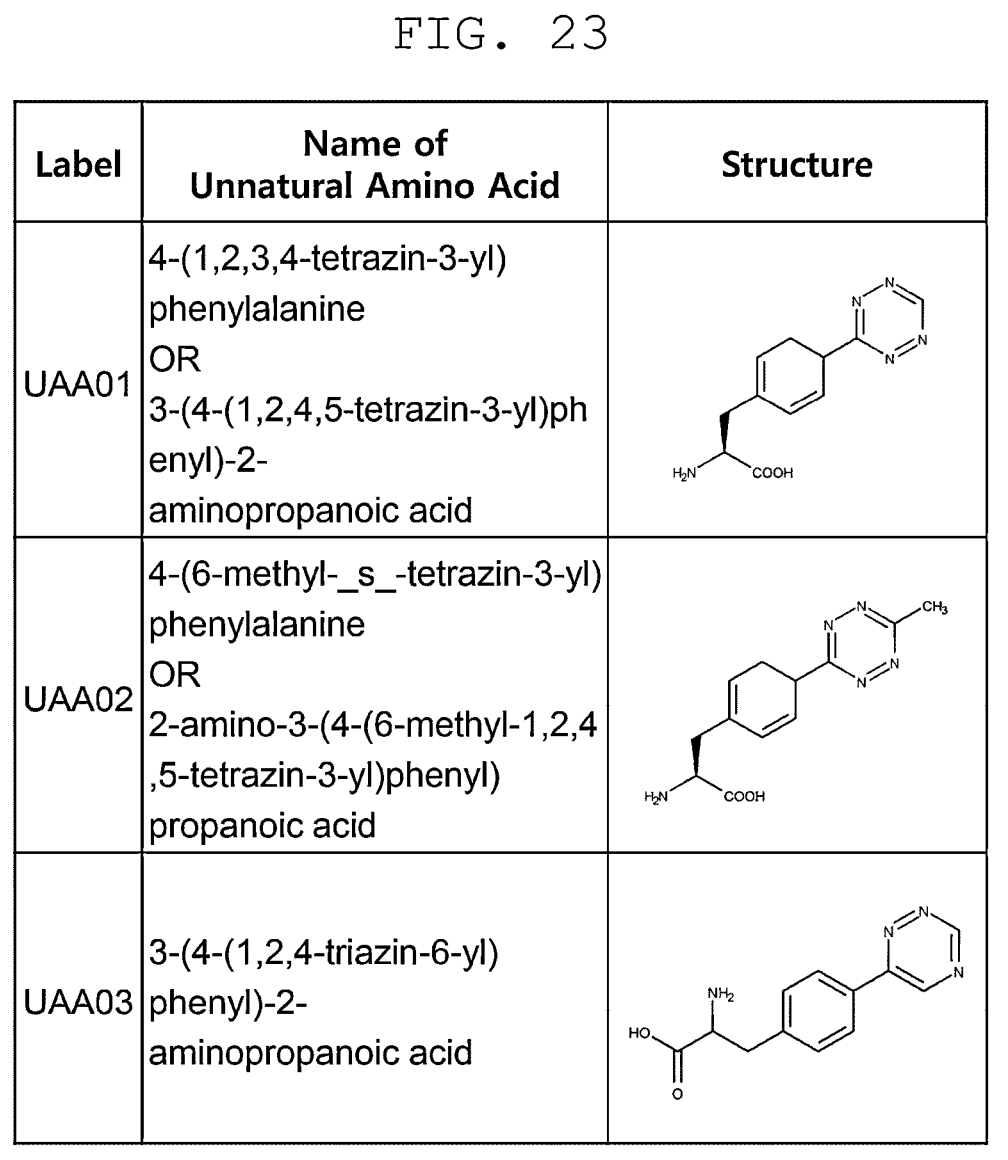

| Label | Name of Unnatural Amino Acid | Structure |
|---|---|---|
| UAA01 | 4-(1,2,3,4-tetrazin-3-yl) phenylalanine OR 3-(4-(1,2,4,5-tetrazin-3-yl)phenyl)-2-aminopropanoic acid | |
| UAA02 | 4-(6-methyl-_s_-tetrazin-3-yl) phenylalanine OR 2-amino-3-(4-(6-methyl-1,2,4,5-tetrazin-3-yl)phenyl) propanoic acid | |
| UAA03 | 3-(4-(1,2,4-triazin-6-yl) phenyl)-2-aminopropanoic acid | |

FIG. 24

| Label | Name of Unnatural Amino Acid | Structure |
|-------|------------------------------|-----------|
| UAA04 | 2-amino-3-(4-(2-(6-methyl-1,2,4,5-tetrazin-3-yl)ethyl)phenyl)propanoic acid | |
| UAA05 | 2-amino-3-(4-(6-phenyl-1,2,4,5-tetrazin-3-yl)phenyl)propanoic acid | |
| UAA06 | 3-(4-((1,2,4,5-tetrazin-3-yl)amino)phenyl)-2-aminopropanoic acid | |

FIG. 25

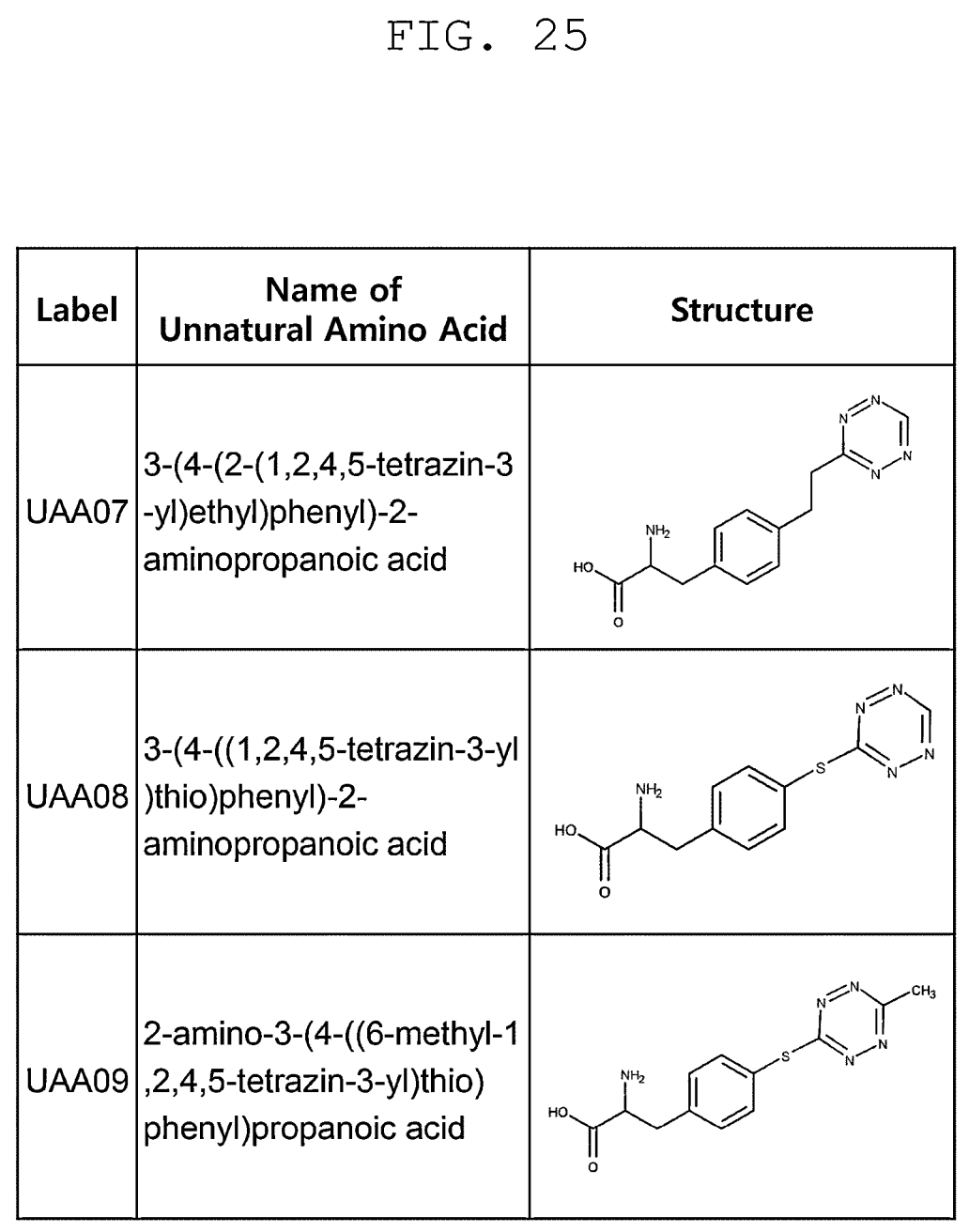

| Label | Name of Unnatural Amino Acid | Structure |
|---|---|---|
| UAA07 | 3-(4-(2-(1,2,4,5-tetrazin-3-yl)ethyl)phenyl)-2-aminopropanoic acid | |
| UAA08 | 3-(4-((1,2,4,5-tetrazin-3-yl)thio)phenyl)-2-aminopropanoic acid | |
| UAA09 | 2-amino-3-(4-((6-methyl-1,2,4,5-tetrazin-3-yl)thio)phenyl)propanoic acid | |

FIG. 26

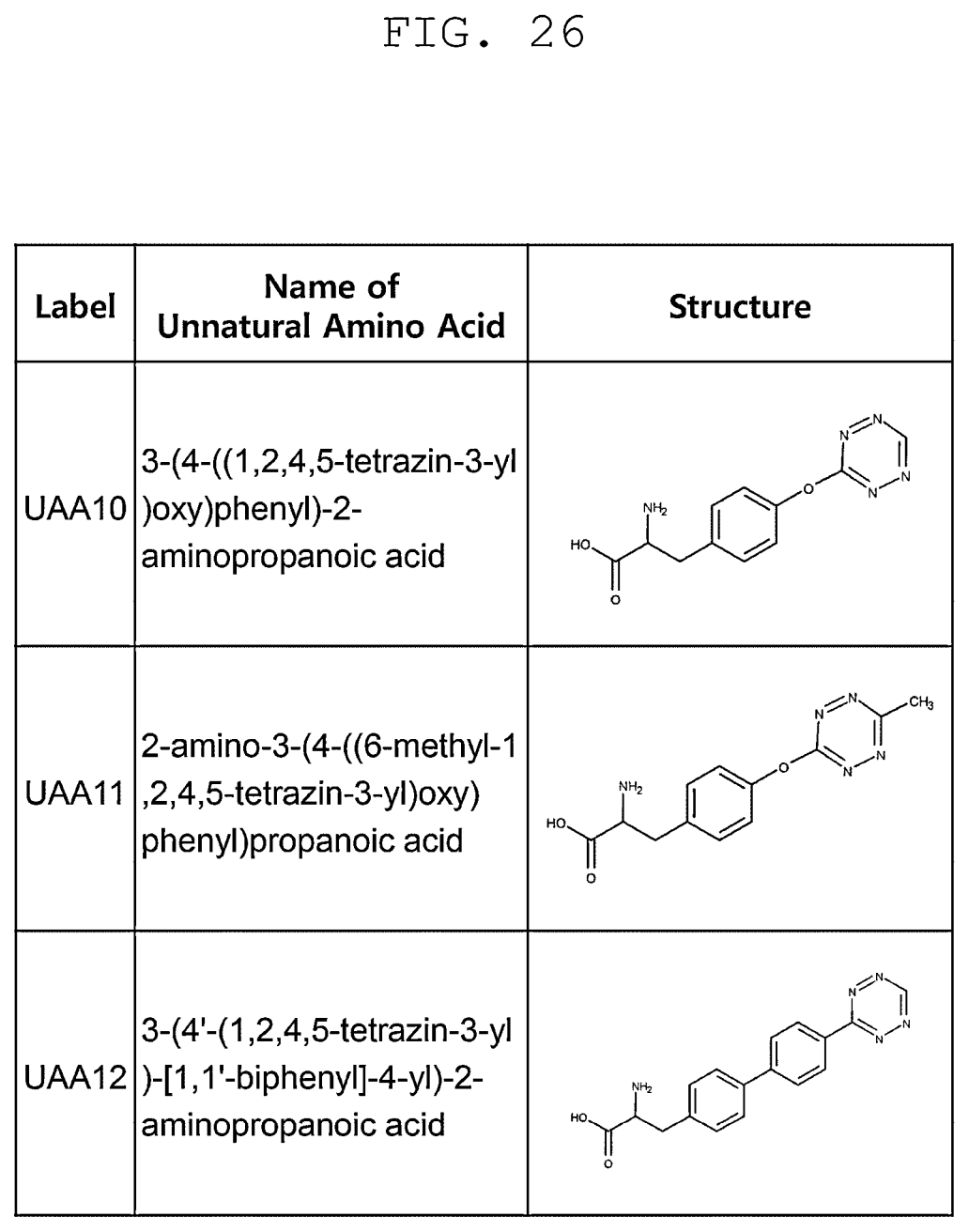

| Label | Name of Unnatural Amino Acid | Structure |
|---|---|---|
| UAA10 | 3-(4-((1,2,4,5-tetrazin-3-yl)oxy)phenyl)-2-aminopropanoic acid | |
| UAA11 | 2-amino-3-(4-((6-methyl-1,2,4,5-tetrazin-3-yl)oxy)phenyl)propanoic acid | |
| UAA12 | 3-(4'-(1,2,4,5-tetrazin-3-yl)-[1,1'-biphenyl]-4-yl)-2-aminopropanoic acid | |

FIG. 27

| Label | Name of Unnatural Amino Acid | Structure |
|-------|------------------------------|-----------|
| UAA13 | 2-amino-3-(4'-(6-methyl-1,2,4,5-tetrazin-3-yl)-[1,1'-biphenyl]-4-yl) propanoic acid | |
| UAA14 | 2-amino-3-(6-(6-(pyridin-2-yl)-1,2,4,5-tetrazin-3-yl)pyridin-3-yl)propanoic acid | |

FIG. 28

| Label | Corresponding unnatural amino acids | Uricase-Linker joint Structure |
|---|---|---|
| UL01 | UAA01, 06, 07, 08, 10, 12, | |
| UL02 | UAA02, 04, 09, 11, 13 | |
| UL03 | UAA05 | |
| UL04 | UAA14 | |
| UL05 | UAA03 | |

FIG. 29

| Label | Anchor Structure |
|-------|------------------|
| A01 | |
| A02 | |
| A03 | |
| A04 | |
| A05 | |

FIG. 30

| Label | Albumin-Linker joint Structure |
|---|---|
| AL01 | |
| AL02 | |

FIG. 31

| Label | Linker Structure |
|-------|------------------|
| L01 | |
| L02 | |
| L03 | |
| L04 | |
| L05 | |

(a)

(b)

(c)

|  | $t^e_{1/2}$ (h) | $t'_{1/2}$ (h) |
|---|---|---|
| AgUox-APN-HSA | 29.0 ± 2.4 | 17.1 ± 0.1 |
| AgUox-MAL-HSA | 25.7 ± 1.9 | 12.0 ± 0.3 |
| AgUox-WT | 1.8 ± 0.3 | |

SEQUENCE LISTING

<160> NUMBER OF SEQ ID NOS: 167

<210> SEQ ID NO 1
<211> LENGTH: 301
<212> TYPE: PRT
<213> ORGANISM: Aspergillus Flavus

<400> SEQUENCE: 1

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95
```

-continued

```
Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
            130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
            210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
            290                 295                 300
```

```
<210> SEQ ID NO 2
<211> LENGTH: 301
<212> TYPE: PRT
<213> ORGANISM: Artificial Sequence
<220> FEATURE:
<223> OTHER INFORMATION: Asp.Uox Variant Subunit (G137)
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 2
```

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
            50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125
```

```
Asn Val Gln Val Asp Val Val Glu Xaa Lys Gly Ile Asp Ile Lys Ser
    130             135             140

Ser Leu Ser Gly Leu Thr Val Leu Lys Ser Thr Asn Ser Gln Phe Trp
145             150             155             160

Gly Phe Leu Arg Asp Glu Tyr Thr Thr Leu Lys Glu Thr Trp Asp Arg
            165             170             175

Ile Leu Ser Thr Asp Val Asp Ala Thr Trp Gln Trp Lys Asn Phe Ser
            180             185             190

Gly Leu Gln Glu Val Arg Ser His Val Pro Lys Phe Asp Ala Thr Trp
            195             200             205

Ala Thr Ala Arg Glu Val Thr Leu Lys Thr Phe Ala Glu Asp Asn Ser
    210             215             220

Ala Ser Val Gln Ala Thr Met Tyr Lys Met Ala Glu Gln Ile Leu Ala
225             230             235             240

Arg Gln Gln Leu Ile Glu Thr Val Glu Tyr Ser Leu Pro Asn Lys His
            245             250             255

Tyr Phe Glu Ile Asp Leu Ser Trp His Lys Gly Leu Gln Asn Thr Gly
            260             265             270

Lys Asn Ala Glu Val Phe Ala Pro Gln Ser Asp Pro Asn Gly Leu Ile
            275             280             285

Lys Cys Thr Val Gly Arg Ser Ser Leu Lys Ser Lys Leu
    290             295             300

<210> SEQ ID NO 3
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 3

Ser Ala Val Lys Ala Ala Arg Tyr Gly Lys Asp Asn Val Arg Val Tyr
1               5               10              15

Lys Val His Lys Asp Xaa Lys Thr Gly Val Gln Thr Val Tyr Glu Met
            20              25              30

Thr Val Cys Val Leu Leu Glu Gly Glu Ile Glu Thr Ser Tyr Thr Lys
            35              40              45

Ala Asp Asn Ser Val Ile Val Ala Thr Asp Ser Ile Lys Asn Thr Ile
    50              55              60

Tyr Ile Thr Ala Lys Gln Asn Pro Val Thr Pro Pro Glu Leu Phe Gly
65              70              75              80

Ser Ile Leu Gly Thr His Phe Ile Glu Lys Tyr Asn His Ile His Ala
            85              90              95

Ala His Val Asn Ile Val Cys His Arg Trp Thr Arg Met Asp Ile Asp
            100             105             110

Gly Lys Pro His Pro His Ser Phe Ile Arg Asp Ser Glu Glu Lys Arg
            115             120             125

Asn Val Gln Val Asp Val Val Glu Gly Lys Gly Ile Asp Ile Lys Ser
    130             135             140

Ser Leu Ser Gly Leu Thr Val Leu Lys Ser Thr Asn Ser Gln Phe Trp
145             150             155             160
```

-continued

```
Gly Phe Leu Arg Asp Glu Tyr Thr Thr Leu Lys Glu Thr Trp Asp Arg
            165             170             175

Ile Leu Ser Thr Asp Val Asp Ala Thr Trp Gln Trp Lys Asn Phe Ser
            180             185             190

Gly Leu Gln Glu Val Arg Ser His Val Pro Lys Phe Asp Ala Thr Trp
            195             200             205

Ala Thr Ala Arg Glu Val Thr Leu Lys Thr Phe Ala Glu Asp Asn Ser
    210             215             220

Ala Ser Val Gln Ala Thr Met Tyr Lys Met Ala Glu Gln Ile Leu Ala
225             230             235             240

Arg Gln Gln Leu Ile Glu Thr Val Glu Tyr Ser Leu Pro Asn Lys His
            245             250             255

Tyr Phe Glu Ile Asp Leu Ser Trp His Lys Gly Leu Gln Asn Thr Gly
            260             265             270

Lys Asn Ala Glu Val Phe Ala Pro Gln Ser Asp Pro Asn Gly Leu Ile
            275             280             285

Lys Cys Thr Val Gly Arg Ser Ser Leu Lys Ser Lys Leu
    290             295             300
```

```
<210> SEQ ID NO 4
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 4
```

```
Ser Ala Val Lys Ala Ala Arg Tyr Gly Lys Asp Asn Val Arg Val Tyr
1               5               10              15

Lys Val His Lys Asp Glu Lys Thr Gly Val Gln Thr Val Tyr Glu Met
            20              25              30

Thr Val Cys Val Leu Leu Glu Gly Glu Ile Glu Thr Ser Tyr Thr Lys
            35              40              45

Ala Asp Asn Ser Val Ile Val Ala Thr Asp Ser Ile Lys Asn Thr Ile
    50              55              60

Tyr Ile Thr Ala Lys Gln Asn Pro Val Thr Pro Pro Glu Leu Phe Gly
65              70              75              80

Ser Ile Leu Gly Thr His Phe Ile Glu Lys Tyr Xaa His Ile His Ala
            85              90              95

Ala His Val Asn Ile Val Cys His Arg Trp Thr Arg Met Asp Ile Asp
            100             105             110

Gly Lys Pro His Pro His Ser Phe Ile Arg Asp Ser Glu Glu Lys Arg
            115             120             125

Asn Val Gln Val Asp Val Val Glu Gly Lys Gly Ile Asp Ile Lys Ser
    130             135             140

Ser Leu Ser Gly Leu Thr Val Leu Lys Ser Thr Asn Ser Gln Phe Trp
145             150             155             160

Gly Phe Leu Arg Asp Glu Tyr Thr Thr Leu Lys Glu Thr Trp Asp Arg
            165             170             175

Ile Leu Ser Thr Asp Val Asp Ala Thr Trp Gln Trp Lys Asn Phe Ser
            180             185             190
```

```
Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300
```

```
<210> SEQ ID NO 5
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 5
```

```
Ser Ala Val Lys Ala Ala Arg Tyr Gly Lys Asp Asn Val Arg Val Tyr
1               5                   10                  15

Lys Val His Lys Asp Glu Xaa Thr Gly Val Gln Thr Val Tyr Glu Met
        20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220
```

-continued

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
        290                 295                 300

<210> SEQ ID NO 6
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 6

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
                20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
                100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
        130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
        210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

-continued

```
Tyr Phe Glu Ile Asp Leu Ser Trp His Lys Gly Leu Gln Asn Thr Gly
        260                 265                 270

Lys Asn Ala Glu Val Phe Ala Pro Gln Ser Asp Pro Asn Gly Leu Ile
        275                 280                 285

Lys Cys Thr Val Gly Arg Xaa Ser Leu Lys Ser Lys Leu
        290                 295                 300

<210> SEQ ID NO 7
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 7

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
        20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Xaa Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
        130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
        210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
        275                 280                 285
```

-continued

```
Lys Cys Thr Val Gly Arg Ser Ser Leu Lys Ser Lys Leu
    290                 295                 300

<210> SEQ ID NO 8
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 8

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Xaa Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300

<210> SEQ ID NO 9
<211> LENGTH: 301
<212> TYPE: PRT
```

-continued

```
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 9

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Xaa Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300

<210> SEQ ID NO 10
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
```

<222> LOCATION: (1)..(301)
<223> OTHER INFORMATION: Xaa is unnatural amino acid containing
      tetrazine functional group, and/or triazine functional group.

<400> SEQUENCE: 10

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Xaa
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300

<210> SEQ ID NO 11
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 11

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Xaa Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300
```

<210> SEQ ID NO 12
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 12

```
Ser Ala Val Lys Ala Ala Arg Tyr Gly Lys Asp Asn Val Arg Val Tyr
1               5                   10                  15
```

-continued

```
Lys Val His Lys Asp Glu Lys Thr Gly Val Gln Thr Val Tyr Glu Met
         20                  25                  30

Thr Val Cys Val Leu Leu Glu Gly Glu Ile Glu Thr Ser Tyr Thr Lys
         35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
             85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
             165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
             245                 250                 255

Tyr Phe Glu Ile Asp Leu Ser Trp His Xaa Gly Leu Gln Asn Thr Gly
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300
```

```
<210> SEQ ID NO 13
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 13
```

```
Ser Ala Val Lys Ala Ala Arg Tyr Gly Lys Asp Asn Val Arg Val Tyr
1               5                   10                  15

Lys Val His Lys Asp Glu Lys Xaa Gly Val Gln Thr Val Tyr Glu Met
         20                  25                  30

Thr Val Cys Val Leu Leu Glu Gly Glu Ile Glu Thr Ser Tyr Thr Lys
         35                  40                  45
```

```
Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
               100                 105                 110

Gly Lys Pro His Pro His Ser Phe Ile Arg Asp Ser Glu Glu Lys Arg
           115                 120                 125

Asn Val Gln Val Asp Val Val Glu Gly Lys Gly Ile Asp Ile Lys Ser
       130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
               165                 170                 175

Ile Leu Ser Thr Asp Val Asp Ala Thr Trp Gln Trp Lys Asn Phe Ser
               180                 185                 190

Gly Leu Gln Glu Val Arg Ser His Val Pro Lys Phe Asp Ala Thr Trp
           195                 200                 205

Ala Thr Ala Arg Glu Val Thr Leu Lys Thr Phe Ala Glu Asp Asn Ser
       210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
               245                 250                 255

Tyr Phe Glu Ile Asp Leu Ser Trp His Lys Gly Leu Gln Asn Thr Gly
               260                 265                 270

Lys Asn Ala Glu Val Phe Ala Pro Gln Ser Asp Pro Asn Gly Leu Ile
           275                 280                 285

Lys Cys Thr Val Gly Arg Ser Ser Leu Lys Ser Lys Leu
    290                 295                 300
```

<210> SEQ ID NO 14
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
     tetrazine functional group, and/or triazine functional group.

<400> SEQUENCE: 14

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
               20                  25                  30

Thr Val Cys Val Leu Leu Glu Gly Glu Ile Glu Thr Ser Tyr Thr Xaa
           35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80
```

-continued

```
Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
               100                 105                 110

Gly Lys Pro His Pro His Ser Phe Ile Arg Asp Ser Glu Glu Lys Arg
           115                 120                 125

Asn Val Gln Val Asp Val Val Glu Gly Lys Gly Ile Asp Ile Lys Ser
       130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
               165                 170                 175

Ile Leu Ser Thr Asp Val Asp Ala Thr Trp Gln Trp Lys Asn Phe Ser
               180                 185                 190

Gly Leu Gln Glu Val Arg Ser His Val Pro Lys Phe Asp Ala Thr Trp
           195                 200                 205

Ala Thr Ala Arg Glu Val Thr Leu Lys Thr Phe Ala Glu Asp Asn Ser
       210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
               245                 250                 255

Tyr Phe Glu Ile Asp Leu Ser Trp His Lys Gly Leu Gln Asn Thr Gly
               260                 265                 270

Lys Asn Ala Glu Val Phe Ala Pro Gln Ser Asp Pro Asn Gly Leu Ile
           275                 280                 285

Lys Cys Thr Val Gly Arg Ser Ser Leu Lys Ser Lys Leu
       290                 295                 300
```

<210> SEQ ID NO 15
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 15

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
               20                  25                  30

Thr Val Cys Val Leu Leu Glu Gly Glu Ile Glu Thr Ser Tyr Thr Lys
           35                  40                  45

Ala Asp Asn Ser Val Ile Val Ala Thr Asp Ser Ile Lys Asn Thr Ile
       50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
               100                 105                 110
```

```
Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
        130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Xaa
                180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
        210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
        290                 295                 300

<210> SEQ ID NO 16
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (202)..(202)
<223> OTHER INFORMATION: Xaa is unnatural amino acid containing
      tetrazine functional group, and/or triazine functional group.

<400> SEQUENCE: 16

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
                20                  25                  30

Thr Val Cys Val Leu Leu Glu Gly Glu Ile Glu Thr Ser Tyr Thr Lys
                35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
                100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
        130                 135                 140
```

-continued

```
Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Xaa Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300
```

```
<210> SEQ ID NO 17
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (110)..(110)
<223> OTHER INFORMATION: Xaa is unnatural amino acid containing
      tetrazine functional group, and/or triazine functional group.

<400> SEQUENCE: 17
```

```
Ser Ala Val Lys Ala Ala Arg Tyr Gly Lys Asp Asn Val Arg Val Tyr
1                 5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Xaa Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175
```

```
Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
            290                 295                 300
```

<210> SEQ ID NO 18
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 18

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205
```

-continued

```
Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Xaa Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300
```

<210> SEQ ID NO 19
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (195)..(195)
<223> OTHER INFORMATION: Xaa is unnatural amino acid containing
      tetrazine functional group, and/or triazine functional group.

<400> SEQUENCE: 19

```
Ser Ala Val Lys Ala Ala Arg Tyr Gly Lys Asp Asn Val Arg Val Tyr
1                   5                  10                  15

Lys Val His Lys Asp Glu Lys Thr Gly Val Gln Thr Val Tyr Glu Met
                20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
                100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Xaa Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240
```

```
Arg Gln Gln Leu Ile Glu Thr Val Glu Tyr Ser Leu Pro Asn Lys His
              245             250             255

Tyr Phe Glu Ile Asp Leu Ser Trp His Lys Gly Leu Gln Asn Thr Gly
              260             265             270

Lys Asn Ala Glu Val Phe Ala Pro Gln Ser Asp Pro Asn Gly Leu Ile
          275             280             285

Lys Cys Thr Val Gly Arg Ser Ser Leu Lys Ser Lys Leu
      290             295             300

<210> SEQ ID NO 20
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (138)..(138)
<223> OTHER INFORMATION: Xaa is unnatural amino acid containing
      tetrazine functional group, and/or triazine functional group.

<400> SEQUENCE: 20

Ser Ala Val Lys Ala Ala Arg Tyr Gly Lys Asp Asn Val Arg Val Tyr
1               5               10              15

Lys Val His Lys Asp Glu Lys Thr Gly Val Gln Thr Val Tyr Glu Met
              20              25              30

Thr Val Cys Val Leu Leu Glu Gly Glu Ile Glu Thr Ser Tyr Thr Lys
          35              40              45

Ala Asp Asn Ser Val Ile Val Ala Thr Asp Ser Ile Lys Asn Thr Ile
      50              55              60

Tyr Ile Thr Ala Lys Gln Asn Pro Val Thr Pro Glu Leu Phe Gly
65              70              75              80

Ser Ile Leu Gly Thr His Phe Ile Glu Lys Tyr Asn His Ile His Ala
              85              90              95

Ala His Val Asn Ile Val Cys His Arg Trp Thr Arg Met Asp Ile Asp
              100             105             110

Gly Lys Pro His Pro His Ser Phe Ile Arg Asp Ser Glu Glu Lys Arg
          115             120             125

Asn Val Gln Val Asp Val Val Glu Gly Xaa Gly Ile Asp Ile Lys Ser
      130             135             140

Ser Leu Ser Gly Leu Thr Val Leu Lys Ser Thr Asn Ser Gln Phe Trp
145             150             155             160

Gly Phe Leu Arg Asp Glu Tyr Thr Thr Leu Lys Glu Thr Trp Asp Arg
              165             170             175

Ile Leu Ser Thr Asp Val Asp Ala Thr Trp Gln Trp Lys Asn Phe Ser
              180             185             190

Gly Leu Gln Glu Val Arg Ser His Val Pro Lys Phe Asp Ala Thr Trp
          195             200             205

Ala Thr Ala Arg Glu Val Thr Leu Lys Thr Phe Ala Glu Asp Asn Ser
      210             215             220

Ala Ser Val Gln Ala Thr Met Tyr Lys Met Ala Glu Gln Ile Leu Ala
225             230             235             240

Arg Gln Gln Leu Ile Glu Thr Val Glu Tyr Ser Leu Pro Asn Lys His
              245             250             255

Tyr Phe Glu Ile Asp Leu Ser Trp His Lys Gly Leu Gln Asn Thr Gly
              260             265             270
```

```
Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
        290                 295                 300

<210> SEQ ID NO 21
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 21

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
        20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Xaa His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
        290                 295                 300
```

<210> SEQ ID NO 22
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (199)..(199)
<223> OTHER INFORMATION: Xaa is unnatural amino acid containing
      tetrazine functional group, and/or triazine functional group.

<400> SEQUENCE: 22

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Xaa His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300

<210> SEQ ID NO 23
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (272)..(272)
<223> OTHER INFORMATION: Xaa is unnatural amino acid containing
      tetrazine functional group, and/or triazine functional group.

<400> SEQUENCE: 23

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Xaa
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300
```

<210> SEQ ID NO 24
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 24

Ser Ala Val Xaa Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300

<210> SEQ ID NO 25
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (112)..(112)
<223> OTHER INFORMATION: Xaa is unnatural amino acid containing
      tetrazine functional group, and/or triazine functional group.

<400> SEQUENCE: 25

Ser Ala Val Lys Ala Ala Arg Tyr Gly Lys Asp Asn Val Arg Val Tyr
1               5                   10                  15

-continued

```
Lys Val His Lys Asp Glu Lys Thr Gly Val Gln Thr Val Tyr Glu Met
        20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Xaa
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300
```

<210> SEQ ID NO 26
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (267)..(267)
<223> OTHER INFORMATION: Xaa is unnatural amino acid containing
      tetrazine functional group, and/or triazine functional group.

<400> SEQUENCE: 26

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45
```

```
Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
                100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Xaa Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300
```

```
<210> SEQ ID NO 27
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 27
```

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
                20                  25                  30

Thr Val Cys Val Leu Leu Glu Gly Glu Ile Glu Thr Ser Tyr Thr Lys
                35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80
```

-continued

```
Ser Ile Leu Gly Thr His Phe Ile Glu Lys Tyr Asn His Ile His Ala
                85              90              95

Ala His Val Asn Ile Val Cys His Arg Trp Thr Arg Met Asp Ile Asp
            100             105             110

Gly Xaa Pro His Pro His Ser Phe Ile Arg Asp Ser Glu Glu Lys Arg
        115             120             125

Asn Val Gln Val Asp Val Val Glu Gly Lys Gly Ile Asp Ile Lys Ser
    130             135             140

Ser Leu Ser Gly Leu Thr Val Leu Lys Ser Thr Asn Ser Gln Phe Trp
145             150             155             160

Gly Phe Leu Arg Asp Glu Tyr Thr Thr Leu Lys Glu Thr Trp Asp Arg
            165             170             175

Ile Leu Ser Thr Asp Val Asp Ala Thr Trp Gln Trp Lys Asn Phe Ser
            180             185             190

Gly Leu Gln Glu Val Arg Ser His Val Pro Lys Phe Asp Ala Thr Trp
        195             200             205

Ala Thr Ala Arg Glu Val Thr Leu Lys Thr Phe Ala Glu Asp Asn Ser
    210             215             220

Ala Ser Val Gln Ala Thr Met Tyr Lys Met Ala Glu Gln Ile Leu Ala
225             230             235             240

Arg Gln Gln Leu Ile Glu Thr Val Glu Tyr Ser Leu Pro Asn Lys His
            245             250             255

Tyr Phe Glu Ile Asp Leu Ser Trp His Lys Gly Leu Gln Asn Thr Gly
            260             265             270

Lys Asn Ala Glu Val Phe Ala Pro Gln Ser Asp Pro Asn Gly Leu Ile
        275             280             285

Lys Cys Thr Val Gly Arg Ser Ser Leu Lys Ser Lys Leu
    290             295             300

<210> SEQ ID NO 28
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (70)..(70)
<223> OTHER INFORMATION: Xaa is unnatural amino acid containing
      tetrazine functional group, and/or triazine functional group.

<400> SEQUENCE: 28

Ser Ala Val Lys Ala Ala Arg Tyr Gly Lys Asp Asn Val Arg Val Tyr
1               5               10              15

Lys Val His Lys Asp Glu Lys Thr Gly Val Gln Thr Val Tyr Glu Met
            20              25              30

Thr Val Cys Val Leu Leu Glu Gly Glu Ile Glu Thr Ser Tyr Thr Lys
            35              40              45

Ala Asp Asn Ser Val Ile Val Ala Thr Asp Ser Ile Lys Asn Thr Ile
    50              55              60

Tyr Ile Thr Ala Lys Xaa Asn Pro Val Thr Pro Pro Glu Leu Phe Gly
65              70              75              80

Ser Ile Leu Gly Thr His Phe Ile Glu Lys Tyr Asn His Ile His Ala
                85              90              95

Ala His Val Asn Ile Val Cys His Arg Trp Thr Arg Met Asp Ile Asp
            100             105             110
```

```
Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
        130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
        210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
        290                 295                 300

<210> SEQ ID NO 29
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (174)..(174)
<223> OTHER INFORMATION: Xaa is unnatural amino acid containing
      tetrazine functional group, and/or triazine functional group.

<400> SEQUENCE: 29

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
                20                  25                  30

Thr Val Cys Val Leu Leu Glu Gly Glu Ile Glu Thr Ser Tyr Thr Lys
                35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
                100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
        130                 135                 140
```

-continued

```
Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Xaa Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300
```

<210> SEQ ID NO 30
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 30

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175
```

-continued

```
Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Xaa Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300

<210> SEQ ID NO 31
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (41)..(41)
<223> OTHER INFORMATION: Xaa is unnatural amino acid containing
      tetrazine functional group, and/or triazine functional group.

<400> SEQUENCE: 31

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Xaa Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205
```

-continued

```
Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300

<210> SEQ ID NO 32
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (261)..(261)
<223> OTHER INFORMATION: Xaa is unnatural amino acid containing
      tetrazine functional group, and/or triazine functional group.

<400> SEQUENCE: 32

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240
```

-continued

```
Arg Gln Gln Leu Ile Glu Thr Val Glu Tyr Ser Leu Pro Asn Lys His
              245                 250                 255

Tyr Phe Glu Ile Xaa Leu Ser Trp His Lys Gly Leu Gln Asn Thr Gly
              260                 265                 270

Lys Asn Ala Glu Val Phe Ala Pro Gln Ser Asp Pro Asn Gly Leu Ile
          275                 280                 285

Lys Cys Thr Val Gly Arg Ser Ser Leu Lys Ser Lys Leu
      290                 295                 300
```

<210> SEQ ID NO 33
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 33

```
Ser Ala Val Lys Ala Ala Arg Tyr Gly Lys Asp Asn Val Arg Val Tyr
1               5                 10                  15

Lys Val His Lys Asp Glu Lys Thr Xaa Val Gln Thr Val Tyr Glu Met
              20                  25                  30

Thr Val Cys Val Leu Leu Glu Gly Glu Ile Glu Thr Ser Tyr Thr Lys
          35                  40                  45

Ala Asp Asn Ser Val Ile Val Ala Thr Asp Ser Ile Lys Asn Thr Ile
      50                  55                  60

Tyr Ile Thr Ala Lys Gln Asn Pro Val Thr Pro Glu Leu Phe Gly
65                  70                  75                  80

Ser Ile Leu Gly Thr His Phe Ile Glu Lys Tyr Asn His Ile His Ala
              85                  90                  95

Ala His Val Asn Ile Val Cys His Arg Trp Thr Arg Met Asp Ile Asp
              100                 105                 110

Gly Lys Pro His Pro His Ser Phe Ile Arg Asp Ser Glu Glu Lys Arg
          115                 120                 125

Asn Val Gln Val Asp Val Val Glu Gly Lys Gly Ile Asp Ile Lys Ser
      130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
              165                 170                 175

Ile Leu Ser Thr Asp Val Asp Ala Thr Trp Gln Trp Lys Asn Phe Ser
              180                 185                 190

Gly Leu Gln Glu Val Arg Ser His Val Pro Lys Phe Asp Ala Thr Trp
          195                 200                 205

Ala Thr Ala Arg Glu Val Thr Leu Lys Thr Phe Ala Glu Asp Asn Ser
      210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
              245                 250                 255

Tyr Phe Glu Ile Asp Leu Ser Trp His Lys Gly Leu Gln Asn Thr Gly
              260                 265                 270
```

-continued

```
Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
        290                 295                 300

<210> SEQ ID NO 34
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (52)..(52)
<223> OTHER INFORMATION: Xaa is unnatural amino acid containing
      tetrazine functional group, and/or triazine functional group.

<400> SEQUENCE: 34

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
        20                  25                  30

Thr Val Cys Val Leu Leu Glu Gly Glu Ile Glu Thr Ser Tyr Thr Lys
        35                  40                  45

Ala Asp Asn Xaa Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
        290                 295                 300
```

-continued

```
<210> SEQ ID NO 35
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (241)..(241)
<223> OTHER INFORMATION: Xaa is unnatural amino acid containing
      tetrazine functional group, and/or triazine functional group.

<400> SEQUENCE: 35

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Xaa Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300

<210> SEQ ID NO 36
<211> LENGTH: 301
<212> TYPE: PRT
<213> ORGANISM: Artificial Sequence
<220> FEATURE:
<223> OTHER INFORMATION: Asp.Uox Variant Subunit
```

<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 36

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
        130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Xaa Val Thr Leu Lys Thr Phe Ala Glu Asp Asn Ser
        210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
        290                 295                 300
```

<210> SEQ ID NO 37
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (274)..(274)
<223> OTHER INFORMATION: Xaa is unnatural amino acid containing
      tetrazine functional group, and/or triazine functional group.

-continued

<400> SEQUENCE: 37

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
                195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Xaa Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300
```

<210> SEQ ID NO 38
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (221)..(221)
<223> OTHER INFORMATION: Xaa is unnatural amino acid containing
      tetrazine functional group, and/or triazine functional group.

<400> SEQUENCE: 38

```
Ser Ala Val Lys Ala Ala Arg Tyr Gly Lys Asp Asn Val Arg Val Tyr
1               5                   10                  15
```

-continued

```
Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Xaa Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300
```

```
<210> SEQ ID NO 39
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 39
```

```
Ser Ala Val Lys Ala Ala Arg Tyr Gly Lys Asp Asn Val Arg Val Tyr
1                   5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45
```

```
Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
                100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Xaa Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300

<210> SEQ ID NO 40
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (236)..(236)
<223> OTHER INFORMATION: Xaa is unnatural amino acid containing
      tetrazine functional group, and/or triazine functional group.

<400> SEQUENCE: 40

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
                20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80
```

-continued

```
Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
               100                 105                 110

Gly Lys Pro His Pro His Ser Phe Ile Arg Asp Ser Glu Glu Lys Arg
               115                 120                 125

Asn Val Gln Val Asp Val Val Glu Gly Lys Gly Ile Asp Ile Lys Ser
           130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
               165                 170                 175

Ile Leu Ser Thr Asp Val Asp Ala Thr Trp Gln Trp Lys Asn Phe Ser
               180                 185                 190

Gly Leu Gln Glu Val Arg Ser His Val Pro Lys Phe Asp Ala Thr Trp
               195                 200                 205

Ala Thr Ala Arg Glu Val Thr Leu Lys Thr Phe Ala Glu Asp Asn Ser
           210                 215                 220

Ala Ser Val Gln Ala Thr Met Tyr Lys Met Ala Xaa Gln Ile Leu Ala
225                 230                 235                 240

Arg Gln Gln Leu Ile Glu Thr Val Glu Tyr Ser Leu Pro Asn Lys His
               245                 250                 255

Tyr Phe Glu Ile Asp Leu Ser Trp His Lys Gly Leu Gln Asn Thr Gly
               260                 265                 270

Lys Asn Ala Glu Val Phe Ala Pro Gln Ser Asp Pro Asn Gly Leu Ile
               275                 280                 285

Lys Cys Thr Val Gly Arg Ser Ser Leu Lys Ser Lys Leu
           290                 295                 300

<210> SEQ ID NO 41
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (164)..(164)
<223> OTHER INFORMATION: Xaa is unnatural amino acid containing
      tetrazine functional group, and/or triazine functional group.

<400> SEQUENCE: 41

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
               20                  25                  30

Thr Val Cys Val Leu Leu Glu Gly Glu Ile Glu Thr Ser Tyr Thr Lys
           35                  40                  45

Ala Asp Asn Ser Val Ile Val Ala Thr Asp Ser Ile Lys Asn Thr Ile
           50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
               100                 105                 110
```

-continued

```
Gly Lys Pro His Pro His Ser Phe Ile Arg Asp Ser Glu Glu Lys Arg
        115             120             125

Asn Val Gln Val Asp Val Val Glu Gly Lys Gly Ile Asp Ile Lys Ser
    130             135             140

Ser Leu Ser Gly Leu Thr Val Leu Lys Ser Thr Asn Ser Gln Phe Trp
145             150             155             160

Gly Phe Leu Xaa Asp Glu Tyr Thr Thr Leu Lys Glu Thr Trp Asp Arg
            165             170             175

Ile Leu Ser Thr Asp Val Asp Ala Thr Trp Gln Trp Lys Asn Phe Ser
            180             185             190

Gly Leu Gln Glu Val Arg Ser His Val Pro Lys Phe Asp Ala Thr Trp
        195             200             205

Ala Thr Ala Arg Glu Val Thr Leu Lys Thr Phe Ala Glu Asp Asn Ser
    210             215             220

Ala Ser Val Gln Ala Thr Met Tyr Lys Met Ala Glu Gln Ile Leu Ala
225             230             235             240

Arg Gln Gln Leu Ile Glu Thr Val Glu Tyr Ser Leu Pro Asn Lys His
            245             250             255

Tyr Phe Glu Ile Asp Leu Ser Trp His Lys Gly Leu Gln Asn Thr Gly
            260             265             270

Lys Asn Ala Glu Val Phe Ala Pro Gln Ser Asp Pro Asn Gly Leu Ile
        275             280             285

Lys Cys Thr Val Gly Arg Ser Ser Leu Lys Ser Lys Leu
        290             295             300

<210> SEQ ID NO 42
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 42

Ser Ala Val Lys Ala Ala Arg Tyr Gly Lys Asp Asn Val Arg Val Tyr
1               5               10              15

Lys Val His Lys Asp Glu Lys Thr Gly Val Gln Thr Val Tyr Glu Met
            20              25              30

Thr Val Cys Val Leu Leu Glu Gly Glu Ile Glu Thr Ser Tyr Thr Lys
            35              40              45

Ala Asp Asn Ser Val Ile Val Ala Thr Asp Ser Ile Lys Asn Thr Ile
    50              55              60

Tyr Ile Thr Ala Lys Gln Asn Pro Val Thr Pro Pro Glu Leu Phe Gly
65              70              75              80

Ser Ile Leu Gly Thr His Phe Ile Glu Lys Tyr Asn His Ile His Ala
            85              90              95

Ala His Val Asn Ile Val Cys His Arg Trp Thr Arg Met Asp Ile Asp
            100             105             110

Gly Lys Pro His Pro His Ser Phe Ile Arg Asp Ser Glu Glu Lys Arg
        115             120             125

Asn Val Gln Val Asp Val Val Glu Gly Lys Gly Ile Asp Ile Lys Ser
    130             135             140
```

```
Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Xaa Asn Thr Gly
                260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300
```

```
<210> SEQ ID NO 43
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (136)..(136)
<223> OTHER INFORMATION: Xaa is unnatural amino acid containing
      tetrazine functional group, and/or triazine functional group.

<400> SEQUENCE: 43

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Xaa Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175
```

-continued

```
Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300
```

<210> SEQ ID NO 44
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (259)..(259)
<223> OTHER INFORMATION: Xaa is unnatural amino acid containing
      tetrazine functional group, and/or triazine functional group.

<400> SEQUENCE: 44

```
Ser Ala Val Lys Ala Ala Arg Tyr Gly Lys Asp Asn Val Arg Val Tyr
1                   5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205
```

```
Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Xaa Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300
```

<210> SEQ ID NO 45
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
      tetrazine functional group, and/or triazine functional group.

<400> SEQUENCE: 45

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240
```

```
Arg Gln Gln Leu Ile Xaa Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
        275                 280                 285

Lys Cys Thr Val Gly Arg Ser Ser Leu Lys Ser Lys Leu
    290                 295                 300

<210> SEQ ID NO 46
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (49)..(49)
<223> OTHER INFORMATION: Xaa is unnatural amino acid containing
      tetrazine functional group, and/or triazine functional group.

<400> SEQUENCE: 46

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Xaa Asp Asn Ser Val Ile Val Ala Thr Asp Ser Ile Lys Asn Thr Ile
    50                  55                  60

Tyr Ile Thr Ala Lys Gln Asn Pro Val Thr Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
        115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
        195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270
```

-continued

```
Lys Asn Ala Glu Val Phe Ala Pro Gln Ser Asp Pro Asn Gly Leu Ile
    275                 280                 285

Lys Cys Thr Val Gly Arg Ser Ser Leu Lys Ser Lys Leu
    290                 295                 300

<210> SEQ ID NO 47
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (148)..(148)
<223> OTHER INFORMATION: Xaa is unnatural amino acid containing
      tetrazine functional group, and/or triazine functional group.

<400> SEQUENCE: 47

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
                20                  25                  30

Thr Val Cys Val Leu Leu Glu Gly Glu Ile Glu Thr Ser Tyr Thr Lys
                35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
                100                 105                 110

Gly Lys Pro His Pro His Ser Phe Ile Arg Asp Ser Glu Glu Lys Arg
                115                 120                 125

Asn Val Gln Val Asp Val Val Glu Gly Lys Gly Ile Asp Ile Lys Ser
    130                 135                 140

Ser Leu Ser Xaa Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
                195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
    275                 280                 285

Lys Cys Thr Val Gly Arg Ser Ser Leu Lys Ser Lys Leu
    290                 295                 300
```

-continued

<210> SEQ ID NO 48
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: MISC_FEATURE
<222> LOCATION: (1)..(301)
<223> OTHER INFORMATION: Xaa is unnatural amino acid containing
        tetrazine functional group, and/or triazine functional group.

<400> SEQUENCE: 48

Ser Ala Val Lys Ala Ala Arg Tyr Gly Lys Asp Asn Val Arg Val Tyr
1               5                   10                  15

Lys Val Xaa Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
        35                  40                  45

Ala Asp Asn Ser Val Ile Val Ala Thr Asp Ser Ile Lys Asn Thr Ile
    50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
            85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
    130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
            165                 170                 175

Ile Leu Ser Thr Asp Val Asp Ala Thr Trp Gln Trp Lys Asn Phe Ser
            180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
    210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
            245                 250                 255

Tyr Phe Glu Ile Asp Leu Ser Trp His Lys Gly Leu Gln Asn Thr Gly
            260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
    290                 295                 300

<210> SEQ ID NO 49
<211> LENGTH: 301
<212> TYPE: PRT
<213> ORGANISM: Artificial Sequence
<220> FEATURE:
<223> OTHER INFORMATION: Asp.Uox Variant Subunit

```
<220> FEATURE:
<221> NAME/KEY: misc_feature
<222> LOCATION: (296)..(296)
<223> OTHER INFORMATION: Xaa is unnatural amino acid containing
      tetrazine functional group, and/or triazine functional group.

<400> SEQUENCE: 49

Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
            20                  25                  30

Thr Val Cys Val Leu Leu Glu Gly Glu Ile Glu Thr Ser Tyr Thr Lys
            35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
            100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
        130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
        210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Xaa Leu Lys Ser Lys Leu
    290                 295                 300

<210> SEQ ID NO 50
<211> LENGTH: 301
<212> TYPE: PRT
<213> ORGANISM: Artificial Sequence
<220> FEATURE:
<223> OTHER INFORMATION: Asp.Uox Variant Subunit
<220> FEATURE:
<221> NAME/KEY: misc_feature
<222> LOCATION: (47)..(47)
<223> OTHER INFORMATION: Xaa is unnatural amino acid containing
      tetrazine functional group, and/or triazine functional group.
```

<400> SEQUENCE: 50

```
Ser Ala Val Lys Ala Ala Arg Tyr Gly Lys Asp Asn Val Arg Val Tyr
1               5                   10                  15

Lys Val His Lys Asp Glu Lys Thr Gly Val Gln Thr Val Tyr Glu Met
                20                  25                  30

Thr Val Cys Val Leu Leu Glu Gly Glu Ile Glu Thr Ser Tyr Xaa Lys
            35                  40                  45

Ala Asp Asn Ser Val Ile Val Ala Thr Asp Ser Ile Lys Asn Thr Ile
        50                  55                  60

Tyr Ile Thr Ala Lys Gln Asn Pro Val Thr Pro Pro Glu Leu Phe Gly
65                  70                  75                  80

Ser Ile Leu Gly Thr His Phe Ile Glu Lys Tyr Asn His Ile His Ala
                85                  90                  95

Ala His Val Asn Ile Val Cys His Arg Trp Thr Arg Met Asp Ile Asp
                100                 105                 110

Gly Lys Pro His Pro His Ser Phe Ile Arg Asp Ser Glu Glu Lys Arg
            115                 120                 125

Asn Val Gln Val Asp Val Val Glu Gly Lys Gly Ile Asp Ile Lys Ser
        130                 135                 140

Ser Leu Ser Gly Leu Thr Val Leu Lys Ser Thr Asn Ser Gln Phe Trp
145                 150                 155                 160

Gly Phe Leu Arg Asp Glu Tyr Thr Thr Leu Lys Glu Thr Trp Asp Arg
                165                 170                 175

Ile Leu Ser Thr Asp Val Asp Ala Thr Trp Gln Trp Lys Asn Phe Ser
                180                 185                 190

Gly Leu Gln Glu Val Arg Ser His Val Pro Lys Phe Asp Ala Thr Trp
            195                 200                 205

Ala Thr Ala Arg Glu Val Thr Leu Lys Thr Phe Ala Glu Asp Asn Ser
        210                 215                 220

Ala Ser Val Gln Ala Thr Met Tyr Lys Met Ala Glu Gln Ile Leu Ala
225                 230                 235                 240

Arg Gln Gln Leu Ile Glu Thr Val Glu Tyr Ser Leu Pro Asn Lys His
                245                 250                 255

Tyr Phe Glu Ile Asp Leu Ser Trp His Lys Gly Leu Gln Asn Thr Gly
                260                 265                 270

Lys Asn Ala Glu Val Phe Ala Pro Gln Ser Asp Pro Asn Gly Leu Ile
            275                 280                 285

Lys Cys Thr Val Gly Arg Ser Ser Leu Lys Ser Lys Leu
        290                 295                 300
```

<210> SEQ ID NO 51
<211> LENGTH: 303
<212> TYPE: PRT
<213> ORGANISM: Candida Utilis

<400> SEQUENCE: 51

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60
```

-continued

```
Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300
```

```
<210> SEQ ID NO 52
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 52
```

```
Met Ser Thr Thr Leu Ser Ser Ser Thr Tyr Gly Lys Asp Asn Val Lys
1                   5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
                35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95
```

```
Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
            130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
            210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Xaa Lys Leu
            290                 295                 300
```

```
<210> SEQ ID NO 53
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: misc_feature
<222> LOCATION: (26)..(26)
<223> OTHER INFORMATION: Xaa is unnatural amino acid containing
      tetrazine functional group, and/or triazine functional group.

<400> SEQUENCE: 53
```

```
Met Ser Thr Thr Leu Ser Ser Ser Thr Tyr Gly Lys Asp Asn Val Lys
1                   5                   10                  15

Phe Leu Lys Val Lys Lys Asp Pro Gln Xaa Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
            50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125
```

```
Glu Lys Arg Ile Thr Asp Leu Tyr Tyr Lys Arg Ser Gly Asp Tyr Lys
    130             135             140

Leu Ser Ser Ala Ile Lys Asp Leu Thr Val Leu Lys Ser Thr Gly Ser
145             150             155             160

Met Phe Tyr Gly Tyr Asn Lys Cys Asp Phe Thr Thr Leu Gln Pro Thr
            165             170             175

Thr Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Lys
            195             200             205

Gly Ile Phe Asp Asn Val Tyr Asn Gln Ala Arg Glu Ile Thr Leu Thr
    210             215             220

Thr Phe Ala Leu Glu Asn Ser Pro Ser Val Gln Ala Thr Met Phe Asn
225             230             235             240

Met Ala Thr Gln Ile Leu Glu Lys Ala Cys Ser Val Tyr Ser Val Ser
            245             250             255

Tyr Ala Leu Pro Asn Lys His Tyr Phe Leu Ile Asp Leu Lys Trp Lys
            260             265             270

Gly Leu Glu Asn Asp Asn Glu Leu Phe Tyr Pro Ser Pro His Pro Asn
    275             280             285

Gly Leu Ile Lys Cys Thr Val Val Arg Lys Glu Lys Thr Lys Leu
    290             295             300
```

<210> SEQ ID NO 54
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: misc_feature
<222> LOCATION: (303)..(303)
<223> OTHER INFORMATION: Xaa is unnatural amino acid containing
      tetrazine functional group, and/or triazine functional group.

<400> SEQUENCE: 54

```
Met Ser Thr Thr Leu Ser Ser Ser Thr Tyr Gly Lys Asp Asn Val Lys
1               5               10              15

Phe Leu Lys Val Lys Lys Asp Pro Gln Asn Pro Lys Lys Gln Glu Val
            20              25              30

Met Glu Ala Thr Val Thr Cys Leu Leu Glu Gly Gly Phe Asp Thr Ser
        35              40              45

Tyr Thr Glu Ala Asp Asn Ser Ser Ile Val Pro Thr Asp Thr Val Lys
    50              55              60

Asn Thr Ile Leu Val Leu Ala Lys Thr Thr Glu Ile Trp Pro Ile Glu
65              70              75              80

Arg Phe Ala Ala Lys Leu Ala Thr His Phe Val Glu Lys Tyr Ser His
            85              90              95

Val Ser Gly Val Ser Val Lys Ile Val Gln Asp Arg Trp Val Lys Tyr
            100             105             110

Ala Val Asp Gly Lys Pro His Asp His Ser Phe Ile His Glu Gly Gly
        115             120             125

Glu Lys Arg Ile Thr Asp Leu Tyr Tyr Lys Arg Ser Gly Asp Tyr Lys
    130             135             140

Leu Ser Ser Ala Ile Lys Asp Leu Thr Val Leu Lys Ser Thr Gly Ser
145             150             155             160
```

-continued

```
Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Xaa
    290                 295                 300
```

```
<210> SEQ ID NO 55
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 55
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
            130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190
```

-continued

```
Asn Xaa Lys Ile Gly Ser Val Tyr Asp Ile Ala Lys Ala Ala Asp Lys
    195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
                275                 280                 285

Gly Leu Ile Lys Cys Thr Val Val Arg Lys Glu Lys Thr Lys Leu
                290                 295                 300
```

```
<210> SEQ ID NO 56
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: misc_feature
<222> LOCATION: (95)..(95)
<223> OTHER INFORMATION: Xaa is unnatural amino acid containing
      tetrazine functional group, and/or triazine functional group.

<400> SEQUENCE: 56
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
                35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Xaa His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Gly Asp Tyr Lys
                130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
    210                 215                 220
```

-continued

```
Thr Phe Ala Leu Glu Asn Ser Pro Ser Val Gln Ala Thr Met Phe Asn
225                 230             235             240

Met Ala Thr Gln Ile Leu Glu Lys Ala Cys Ser Val Tyr Ser Val Ser
            245             250             255

Tyr Ala Leu Pro Asn Lys His Tyr Phe Leu Ile Asp Leu Lys Trp Lys
        260             265             270

Gly Leu Glu Asn Asp Asn Glu Leu Phe Tyr Pro Ser Pro His Pro Asn
        275             280             285

Gly Leu Ile Lys Cys Thr Val Val Arg Lys Glu Lys Thr Lys Leu
        290             295             300
```

```
<210> SEQ ID NO 57
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 57
```

```
Met Ser Thr Thr Leu Ser Ser Ser Thr Tyr Gly Lys Asp Asn Val Lys
1               5               10              15

Phe Leu Lys Val Lys Lys Asp Pro Gln Asn Pro Lys Lys Gln Glu Val
            20              25              30

Met Glu Ala Thr Val Thr Cys Leu Leu Glu Gly Gly Phe Asp Thr Ser
        35              40              45

Tyr Thr Glu Ala Asp Asn Ser Ser Ile Val Pro Thr Asp Thr Val Lys
        50              55              60

Asn Thr Ile Leu Val Leu Ala Lys Thr Thr Glu Ile Trp Pro Ile Glu
65              70              75              80

Arg Phe Ala Ala Lys Leu Ala Thr His Phe Val Glu Lys Tyr Ser His
            85              90              95

Val Ser Gly Val Ser Val Lys Ile Val Gln Asp Arg Trp Val Lys Tyr
            100             105             110

Ala Val Asp Gly Lys Pro His Asp His Ser Phe Ile His Glu Gly Gly
        115             120             125

Glu Lys Arg Ile Thr Asp Leu Tyr Tyr Lys Arg Xaa Gly Asp Tyr Lys
        130             135             140

Leu Ser Ser Ala Ile Lys Asp Leu Thr Val Leu Lys Ser Thr Gly Ser
145             150             155             160

Met Phe Tyr Gly Tyr Asn Lys Cys Asp Phe Thr Thr Leu Gln Pro Thr
            165             170             175

Thr Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Lys
        195             200             205

Gly Ile Phe Asp Asn Val Tyr Asn Gln Ala Arg Glu Ile Thr Leu Thr
        210             215             220

Thr Phe Ala Leu Glu Asn Ser Pro Ser Val Gln Ala Thr Met Phe Asn
225             230             235             240

Met Ala Thr Gln Ile Leu Glu Lys Ala Cys Ser Val Tyr Ser Val Ser
            245             250             255
```

```
Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
            290                 295                 300

<210> SEQ ID NO 58
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 58

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Xaa Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285
```

-continued

```
Gly Leu Ile Lys Cys Thr Val Val Arg Lys Glu Lys Thr Lys Leu
    290                 295                 300
```

<210> SEQ ID NO 59
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 59

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Xaa Leu
    290                 295                 300
```

<210> SEQ ID NO 60
<211> LENGTH: 303
<212> TYPE: PRT

<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 60

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Xaa Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
    290                 295                 300
```

<210> SEQ ID NO 61
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
     tetrazine functional group, and/or triazine functional group.

<400> SEQUENCE: 61

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Xaa Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
    290                 295                 300

<210> SEQ ID NO 62
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
     tetrazine functional group, and/or triazine functional group.

-continued

<400> SEQUENCE: 62

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Xaa Lys Thr Lys Leu
    290                 295                 300

<210> SEQ ID NO 63
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
       tetrazine functional group, and/or triazine functional group.

<400> SEQUENCE: 63

Met Ser Thr Thr Leu Ser Ser Ser Thr Tyr Gly Lys Asp Asn Val Lys
1               5                   10                  15

-continued

```
Phe Leu Lys Val Lys Lys Asp Xaa Gln Asn Pro Lys Lys Gln Glu Val
         20                  25                  30

Met Glu Ala Thr Val Thr Cys Leu Leu Glu Gly Gly Phe Asp Thr Ser
         35                  40                  45

Tyr Thr Glu Ala Asp Asn Ser Ser Ile Val Pro Thr Asp Thr Val Lys
         50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                 85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Gly Asp Tyr Lys
         130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                 165                 170                 175

Thr Asp Arg Ile Leu Ser Thr Asp Val Asp Ala Thr Trp Val Trp Asp
                 180                 185                 190

Asn Lys Lys Ile Gly Ser Val Tyr Asp Ile Ala Lys Ala Ala Asp Lys
                 195                 200                 205

Gly Ile Phe Asp Asn Val Tyr Asn Gln Ala Arg Glu Ile Thr Leu Thr
         210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                 245                 250                 255

Tyr Ala Leu Pro Asn Lys His Tyr Phe Leu Ile Asp Leu Lys Trp Lys
                 260                 265                 270

Gly Leu Glu Asn Asp Asn Glu Leu Phe Tyr Pro Ser Pro His Pro Asn
         275                 280                 285

Gly Leu Ile Lys Cys Thr Val Val Arg Lys Glu Lys Thr Lys Leu
         290                 295                 300
```

```
<210> SEQ ID NO 64
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 64
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
         20                  25                  30

Met Glu Ala Thr Val Thr Cys Leu Leu Glu Gly Gly Phe Asp Thr Ser
         35                  40                  45
```

-continued

```
Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Xaa Lys
                260                 265                 270

Gly Leu Glu Asn Asp Asn Glu Leu Phe Tyr Pro Ser Pro His Pro Asn
    275                 280                 285

Gly Leu Ile Lys Cys Thr Val Val Arg Lys Glu Lys Thr Lys Leu
    290                 295                 300
```

```
<210> SEQ ID NO 65
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 65
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80
```

```
Arg Phe Ala Ala Lys Leu Ala Thr His Phe Val Glu Lys Tyr Ser His
                 85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Xaa Asn Glu Leu Phe Tyr Pro Ser Pro His Pro Asn
                275                 280                 285

Gly Leu Ile Lys Cys Thr Val Val Arg Lys Glu Lys Thr Lys Leu
        290                 295                 300
```

```
<210> SEQ ID NO 66
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 66
```

```
Met Ser Thr Thr Leu Ser Ser Ser Thr Tyr Gly Lys Asp Asn Val Lys
1                 5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110
```

```
Ala Val Asp Gly Lys Pro His Asp His Ser Phe Ile His Glu Gly Gly
        115             120             125

Glu Lys Arg Ile Thr Asp Leu Tyr Tyr Lys Arg Ser Gly Asp Tyr Lys
    130             135             140

Leu Ser Ser Ala Ile Lys Asp Leu Thr Val Leu Lys Ser Thr Gly Ser
145             150             155             160

Met Phe Tyr Gly Tyr Asn Lys Cys Xaa Phe Thr Thr Leu Gln Pro Thr
            165             170             175

Thr Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Lys
            195             200             205

Gly Ile Phe Asp Asn Val Tyr Asn Gln Ala Arg Glu Ile Thr Leu Thr
    210             215             220

Thr Phe Ala Leu Glu Asn Ser Pro Ser Val Gln Ala Thr Met Phe Asn
225             230             235             240

Met Ala Thr Gln Ile Leu Glu Lys Ala Cys Ser Val Tyr Ser Val Ser
            245             250             255

Tyr Ala Leu Pro Asn Lys His Tyr Phe Leu Ile Asp Leu Lys Trp Lys
            260             265             270

Gly Leu Glu Asn Asp Asn Glu Leu Phe Tyr Pro Ser Pro His Pro Asn
    275             280             285

Gly Leu Ile Lys Cys Thr Val Val Arg Lys Glu Lys Thr Lys Leu
    290             295             300

<210> SEQ ID NO 67
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 67

Met Ser Thr Thr Leu Ser Ser Ser Thr Tyr Gly Lys Asp Asn Val Lys
1               5               10              15

Phe Leu Lys Val Lys Lys Asp Pro Gln Asn Pro Lys Lys Gln Glu Val
            20              25              30

Met Glu Ala Thr Val Thr Cys Leu Leu Glu Gly Gly Phe Asp Thr Ser
        35              40              45

Tyr Thr Glu Ala Asp Asn Ser Ser Ile Val Pro Thr Asp Thr Val Lys
    50              55              60

Asn Thr Ile Leu Val Leu Ala Lys Thr Thr Glu Ile Trp Pro Ile Glu
65              70              75              80

Arg Phe Ala Ala Lys Leu Ala Thr His Phe Val Glu Lys Tyr Ser His
            85              90              95

Val Ser Gly Val Ser Val Lys Ile Val Gln Asp Arg Trp Val Lys Tyr
            100             105             110

Ala Val Asp Gly Lys Xaa His Asp His Ser Phe Ile His Glu Gly Gly
        115             120             125

Glu Lys Arg Ile Thr Asp Leu Tyr Tyr Lys Arg Ser Gly Asp Tyr Lys
    130             135             140
```

-continued

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300

<210> SEQ ID NO 68
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
       tetrazine functional group, and/or triazine functional group.

<400> SEQUENCE: 68

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

```
Xaa Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Lys
            195             200             205

Gly Ile Phe Asp Asn Val Tyr Asn Gln Ala Arg Glu Ile Thr Leu Thr
            210             215             220

Thr Phe Ala Leu Glu Asn Ser Pro Ser Val Gln Ala Thr Met Phe Asn
225                     230             235             240

Met Ala Thr Gln Ile Leu Glu Lys Ala Cys Ser Val Tyr Ser Val Ser
                245             250             255

Tyr Ala Leu Pro Asn Lys His Tyr Phe Leu Ile Asp Leu Lys Trp Lys
            260             265             270

Gly Leu Glu Asn Asp Asn Glu Leu Phe Tyr Pro Ser Pro His Pro Asn
            275             280             285

Gly Leu Ile Lys Cys Thr Val Val Arg Lys Glu Lys Thr Lys Leu
            290             295             300
```

```
<210> SEQ ID NO 69
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 69
```

```
Met Ser Thr Thr Leu Ser Ser Ser Thr Tyr Gly Lys Asp Asn Val Lys
1               5               10              15

Phe Leu Lys Val Lys Lys Asp Pro Gln Asn Pro Lys Lys Gln Glu Val
            20              25              30

Met Glu Ala Thr Val Thr Cys Leu Leu Glu Gly Gly Phe Asp Thr Ser
            35              40              45

Tyr Thr Glu Ala Asp Asn Ser Ser Ile Val Pro Thr Asp Thr Val Lys
            50              55              60

Asn Thr Ile Leu Val Leu Ala Lys Thr Thr Glu Ile Trp Pro Ile Glu
65                      70              75              80

Arg Phe Ala Ala Lys Leu Ala Thr His Phe Val Glu Lys Tyr Ser His
                85              90              95

Val Ser Gly Val Ser Val Lys Ile Val Gln Asp Arg Trp Val Lys Tyr
            100             105             110

Ala Val Asp Gly Lys Pro His Asp His Ser Phe Ile His Glu Gly Gly
            115             120             125

Glu Lys Arg Ile Thr Asp Leu Tyr Tyr Lys Arg Ser Gly Asp Tyr Lys
            130             135             140

Leu Ser Ser Ala Ile Lys Asp Leu Thr Val Leu Lys Ser Thr Gly Ser
145                     150             155             160

Met Phe Tyr Gly Tyr Asn Lys Cys Asp Phe Thr Thr Leu Xaa Pro Thr
                165             170             175

Thr Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Lys
            195             200             205
```

Gly Ile Phe Asp Asn Val Tyr Asn Gln Ala Arg Glu Ile Thr Leu Thr
    210             215             220

Thr Phe Ala Leu Glu Asn Ser Pro Ser Val Gln Ala Thr Met Phe Asn
225             230             235             240

Met Ala Thr Gln Ile Leu Glu Lys Ala Cys Ser Val Tyr Ser Val Ser
            245             250             255

Tyr Ala Leu Pro Asn Lys His Tyr Phe Leu Ile Asp Leu Lys Trp Lys
            260             265             270

Gly Leu Glu Asn Asp Asn Glu Leu Phe Tyr Pro Ser Pro His Pro Asn
        275             280             285

Gly Leu Ile Lys Cys Thr Val Val Arg Lys Glu Lys Thr Lys Leu
    290             295             300

<210> SEQ ID NO 70
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 70

Met Ser Thr Thr Leu Ser Ser Ser Thr Tyr Gly Lys Asp Asn Val Lys
1               5               10              15

Phe Leu Lys Val Lys Lys Asp Pro Gln Asn Pro Lys Lys Gln Glu Val
            20              25              30

Met Glu Ala Thr Val Thr Cys Leu Leu Glu Gly Gly Phe Asp Thr Ser
            35              40              45

Tyr Thr Glu Ala Asp Asn Ser Ser Ile Val Pro Thr Asp Thr Val Lys
    50              55              60

Asn Thr Ile Leu Val Leu Ala Lys Thr Thr Glu Ile Trp Pro Ile Glu
65              70              75              80

Arg Phe Ala Ala Lys Leu Ala Thr His Phe Val Glu Lys Tyr Ser His
            85              90              95

Val Ser Gly Val Ser Val Lys Ile Val Gln Asp Arg Trp Val Lys Tyr
            100             105             110

Ala Val Asp Gly Lys Pro His Asp His Ser Phe Ile His Glu Gly Gly
        115             120             125

Glu Lys Arg Ile Thr Asp Leu Tyr Tyr Lys Arg Ser Gly Asp Tyr Lys
    130             135             140

Leu Ser Ser Ala Ile Lys Asp Leu Thr Val Leu Lys Ser Thr Gly Ser
145             150             155             160

Met Phe Tyr Gly Tyr Asn Lys Cys Asp Phe Thr Thr Leu Gln Pro Thr
            165             170             175

Thr Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Xaa
        195             200             205

Gly Ile Phe Asp Asn Val Tyr Asn Gln Ala Arg Glu Ile Thr Leu Thr
    210             215             220

Thr Phe Ala Leu Glu Asn Ser Pro Ser Val Gln Ala Thr Met Phe Asn
225             230             235             240

```
Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300
```

<210> SEQ ID NO 71
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 71

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270
```

-continued

```
Gly Leu Xaa Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300
```

<210> SEQ ID NO 72
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 72

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Xaa Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300
```

-continued

<210> SEQ ID NO 73
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 73

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Xaa Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300

<210> SEQ ID NO 74
<211> LENGTH: 303
<212> TYPE: PRT
<213> ORGANISM: Artificial Sequence
<220> FEATURE:
<223> OTHER INFORMATION: Candida.Uox Variant Subunit

```
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 74

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Xaa Asp Ile Ala Lys Ala Ala Asp Lys
                195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300

<210> SEQ ID NO 75
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.
```

-continued

<400> SEQUENCE: 75

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Xaa Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300
```

<210> SEQ ID NO 76
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
       tetrazine functional group, and/or triazine functional group.

<400> SEQUENCE: 76

```
Met Ser Thr Thr Leu Ser Ser Ser Thr Tyr Gly Lys Asp Asn Val Lys
1               5                   10                  15
```

-continued

```
Phe Leu Lys Val Lys Lys Asp Pro Gln Asn Pro Lys Lys Gln Glu Val
              20                  25                  30

Met Glu Ala Thr Val Thr Cys Leu Leu Glu Gly Gly Phe Asp Thr Ser
              35                  40                  45

Tyr Thr Glu Ala Asp Asn Ser Ser Ile Val Pro Thr Asp Thr Val Lys
              50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                    85                  90                  95

Val Ser Gly Val Ser Val Lys Ile Val Gln Asp Arg Trp Val Lys Tyr
                    100                 105                 110

Ala Val Asp Gly Lys Pro His Asp His Ser Phe Ile His Glu Gly Gly
              115                 120                 125

Glu Lys Arg Ile Thr Asp Leu Tyr Tyr Lys Arg Ser Gly Asp Tyr Lys
              130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                    165                 170                 175

Thr Asp Arg Ile Leu Ser Thr Asp Val Asp Ala Thr Trp Val Trp Asp
                    180                 185                 190

Asn Lys Lys Ile Gly Ser Val Tyr Asp Ile Ala Lys Ala Ala Asp Lys
              195                 200                 205

Gly Ile Phe Asp Asn Val Tyr Asn Gln Ala Arg Glu Ile Thr Leu Thr
              210                 215                 220

Thr Phe Ala Leu Glu Asn Ser Pro Ser Val Gln Ala Thr Met Phe Asn
225                 230                 235                 240

Met Ala Thr Gln Ile Leu Xaa Lys Ala Cys Ser Val Tyr Ser Val Ser
                    245                 250                 255

Tyr Ala Leu Pro Asn Lys His Tyr Phe Leu Ile Asp Leu Lys Trp Lys
              260                 265                 270

Gly Leu Glu Asn Asp Asn Glu Leu Phe Tyr Pro Ser Pro His Pro Asn
              275                 280                 285

Gly Leu Ile Lys Cys Thr Val Val Arg Lys Glu Lys Thr Lys Leu
     290                 295                 300
```

```
<210> SEQ ID NO 77
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 77
```

```
Met Ser Thr Thr Leu Ser Ser Ser Thr Tyr Gly Lys Asp Asn Val Lys
1                   5                   10                  15

Phe Leu Lys Val Lys Lys Asp Pro Gln Asn Pro Lys Lys Gln Glu Val
              20                  25                  30

Met Glu Ala Thr Val Thr Cys Leu Leu Glu Gly Gly Phe Asp Thr Ser
              35                  40                  45
```

```
Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
    210                 215                 220

Thr Phe Ala Xaa Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
                275                 280                 285

Gly Leu Ile Lys Cys Thr Val Val Arg Lys Glu Lys Thr Lys Leu
    290                 295                 300
```

```
<210> SEQ ID NO 78
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 78
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80
```

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Xaa Thr Lys Leu
    290                 295                 300

<210> SEQ ID NO 79
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 79

Met Ser Thr Thr Leu Ser Ser Ser Thr Tyr Gly Lys Asp Asn Val Lys
1                   5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

-continued

```
Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Xaa Ala Ala Asp Lys
                195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300
```

```
<210> SEQ ID NO 80
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 80
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
        35                  40                  45

Tyr Thr Xaa Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
        130                 135                 140
```

-continued

```
Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300
```

```
<210> SEQ ID NO 81
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 81
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175
```

-continued

```
Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Xaa Lys
            195                 200                 205

Gly Ile Phe Asp Asn Val Tyr Asn Gln Ala Arg Glu Ile Thr Leu Thr
            210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
            290                 295                 300
```

<210> SEQ ID NO 82
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 82

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
            50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Xaa Pro His Asp His Ser Phe Ile His Glu Gly Gly
            115                 120                 125

Glu Lys Arg Ile Thr Asp Leu Tyr Tyr Lys Arg Ser Gly Asp Tyr Lys
            130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205
```

```
Gly Ile Phe Asp Asn Val Tyr Asn Gln Ala Arg Glu Ile Thr Leu Thr
    210             215                 220

Thr Phe Ala Leu Glu Asn Ser Pro Ser Val Gln Ala Thr Met Phe Asn
225             230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
    290                 295                 300
```

<210> SEQ ID NO 83
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 83

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210             215                 220

Thr Phe Ala Leu Glu Asn Ser Pro Ser Val Gln Ala Thr Met Phe Asn
225             230                 235                 240
```

-continued

```
Met Ala Thr Gln Ile Leu Glu Lys Ala Xaa Ser Val Tyr Ser Val Ser
                245                 250             255

Tyr Ala Leu Pro Asn Lys His Tyr Phe Leu Ile Asp Leu Lys Trp Lys
                260                 265             270

Gly Leu Glu Asn Asp Asn Glu Leu Phe Tyr Pro Ser Pro His Pro Asn
            275                 280             285

Gly Leu Ile Lys Cys Thr Val Val Arg Lys Glu Lys Thr Lys Leu
        290                 295             300
```

```
<210> SEQ ID NO 84
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 84
```

```
Met Ser Thr Thr Leu Ser Ser Ser Thr Tyr Gly Lys Asp Asn Val Lys
1                 5                 10              15

Phe Leu Lys Val Lys Lys Asp Pro Gln Asn Pro Lys Lys Gln Glu Val
                20                25               30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Xaa Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250             255

Tyr Ala Leu Pro Asn Lys His Tyr Phe Leu Ile Asp Leu Lys Trp Lys
                260                 265             270
```

-continued

```
Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300

<210> SEQ ID NO 85
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
        tetrazine functional group, and/or triazine functional group.

<400> SEQUENCE: 85

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Xaa Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300
```

<210> SEQ ID NO 86
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 86

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Xaa Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300

<210> SEQ ID NO 87
<211> LENGTH: 303
<212> TYPE: PRT
<213> ORGANISM: Artificial Sequence
<220> FEATURE:
<223> OTHER INFORMATION: Candida.Uox Variant Subunit

```
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 87

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Xaa Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
    290                 295                 300

<210> SEQ ID NO 88
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.
```

<400> SEQUENCE: 88

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Xaa Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300
```

<210> SEQ ID NO 89
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 89

```
Met Ser Thr Thr Leu Ser Ser Ser Thr Tyr Gly Lys Asp Asn Val Lys
1               5                   10                  15
```

```
Phe Leu Lys Val Lys Lys Asp Pro Gln Asn Pro Lys Lys Gln Glu Val
        20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Xaa Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300
```

```
<210> SEQ ID NO 90
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 90
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
        20                  25                  30

Met Glu Ala Thr Val Thr Cys Leu Leu Glu Gly Gly Phe Asp Thr Ser
        35                  40                  45
```

-continued

```
Tyr Thr Glu Ala Asp Asn Ser Ser Ile Val Pro Thr Asp Thr Val Lys
    50                  55                  60

Asn Thr Ile Leu Val Leu Ala Lys Xaa Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
    290                 295                 300
```

```
<210> SEQ ID NO 91
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 91
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Xaa Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80
```

-continued

```
Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
                275                 280                 285

Gly Leu Ile Lys Cys Thr Val Val Arg Lys Glu Lys Thr Lys Leu
        290                 295                 300
```

```
<210> SEQ ID NO 92
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 92
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110
```

-continued

```
Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
        210                 215                 220

Thr Phe Ala Leu Glu Xaa Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300
```

```
<210> SEQ ID NO 93
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 93
```

```
Met Ser Thr Thr Leu Ser Ser Ser Thr Tyr Gly Lys Asp Asn Val Lys
1               5                   10                  15

Phe Leu Lys Val Lys Lys Asp Pro Xaa Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
        130                 135                 140
```

-continued

```
Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300
```

```
<210> SEQ ID NO 94
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 94
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175
```

-continued

```
Thr Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Lys
            195             200             205

Gly Ile Phe Asp Asn Val Tyr Xaa Gln Ala Arg Glu Ile Thr Leu Thr
            210             215             220

Thr Phe Ala Leu Glu Asn Ser Pro Ser Val Gln Ala Thr Met Phe Asn
225             230             235             240

Met Ala Thr Gln Ile Leu Glu Lys Ala Cys Ser Val Tyr Ser Val Ser
            245             250             255

Tyr Ala Leu Pro Asn Lys His Tyr Phe Leu Ile Asp Leu Lys Trp Lys
            260             265             270

Gly Leu Glu Asn Asp Asn Glu Leu Phe Tyr Pro Ser Pro His Pro Asn
            275             280             285

Gly Leu Ile Lys Cys Thr Val Val Arg Lys Glu Lys Thr Lys Leu
            290             295             300
```

<210> SEQ ID NO 95
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 95

```
Met Ser Thr Thr Leu Ser Ser Ser Thr Tyr Gly Lys Asp Asn Val Lys
1               5               10              15

Phe Leu Lys Val Lys Lys Asp Pro Gln Asn Pro Lys Lys Gln Glu Val
            20              25              30

Met Glu Ala Thr Val Thr Cys Leu Leu Glu Gly Gly Phe Asp Thr Ser
            35              40              45

Tyr Thr Glu Ala Asp Asn Xaa Ser Ile Val Pro Thr Asp Thr Val Lys
            50              55              60

Asn Thr Ile Leu Val Leu Ala Lys Thr Thr Glu Ile Trp Pro Ile Glu
65              70              75              80

Arg Phe Ala Ala Lys Leu Ala Thr His Phe Val Glu Lys Tyr Ser His
            85              90              95

Val Ser Gly Val Ser Val Lys Ile Val Gln Asp Arg Trp Val Lys Tyr
            100             105             110

Ala Val Asp Gly Lys Pro His Asp His Ser Phe Ile His Glu Gly Gly
            115             120             125

Glu Lys Arg Ile Thr Asp Leu Tyr Tyr Lys Arg Ser Gly Asp Tyr Lys
            130             135             140

Leu Ser Ser Ala Ile Lys Asp Leu Thr Val Leu Lys Ser Thr Gly Ser
145             150             155             160

Met Phe Tyr Gly Tyr Asn Lys Cys Asp Phe Thr Thr Leu Gln Pro Thr
            165             170             175

Thr Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Lys
            195             200             205
```

-continued

```
Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
    290                 295                 300
```

```
<210> SEQ ID NO 96
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 96

Met Ser Thr Thr Leu Ser Ser Ser Thr Tyr Gly Lys Asp Asn Val Lys
1                 5                   10                  15

Phe Leu Lys Val Lys Lys Asp Pro Gln Asn Pro Xaa Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240
```

-continued

```
Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300
```

```
<210> SEQ ID NO 97
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 97
```

```
Met Ser Thr Thr Leu Xaa Ser Ser Thr Tyr Gly Lys Asp Asn Val Lys
1               5                 10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270
```

-continued

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300

<210> SEQ ID NO 98
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 98

Met Ser Thr Thr Leu Ser Ser Ser Thr Tyr Gly Lys Asp Asn Val Lys
1               5                   10                  15

Phe Leu Lys Val Lys Lys Asp Pro Gln Asn Xaa Lys Lys Gln Glu Val
                20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300

<210> SEQ ID NO 99
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 99

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Xaa Glu Lys Thr Lys Leu
    290                 295                 300

<210> SEQ ID NO 100
<211> LENGTH: 303
<212> TYPE: PRT
<213> ORGANISM: Artificial Sequence
<220> FEATURE:
<223> OTHER INFORMATION: Candida.Uox Variant Subunit

```
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 100

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Xaa Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300

<210> SEQ ID NO 101
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.
```

<400> SEQUENCE: 101

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Xaa Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
                275                 280                 285

Gly Leu Ile Lys Cys Thr Val Val Arg Lys Glu Lys Thr Lys Leu
    290                 295                 300

<210> SEQ ID NO 102
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 102

Met Ser Thr Thr Leu Ser Ser Ser Thr Tyr Gly Lys Asp Asn Val Lys
1               5                   10                  15

-continued

```
Phe Leu Lys Val Lys Lys Asp Pro Gln Asn Pro Lys Lys Gln Glu Val
            20              25              30

Met Glu Ala Thr Val Thr Cys Leu Leu Glu Gly Gly Phe Asp Thr Ser
            35              40              45

Tyr Thr Glu Ala Asp Asn Ser Ser Ile Val Pro Thr Asp Thr Val Lys
        50              55              60

Asn Thr Ile Leu Val Leu Ala Lys Thr Thr Glu Ile Trp Pro Ile Glu
65              70              75              80

Arg Phe Ala Ala Lys Leu Ala Thr His Phe Val Glu Lys Tyr Ser His
                85              90              95

Val Ser Gly Val Ser Val Lys Ile Val Gln Asp Arg Trp Val Lys Tyr
            100             105             110

Ala Val Asp Gly Lys Pro His Asp His Ser Phe Ile His Glu Gly Gly
            115             120             125

Glu Lys Arg Ile Thr Asp Leu Tyr Tyr Lys Arg Ser Gly Asp Tyr Lys
        130             135             140

Leu Ser Ser Ala Ile Lys Asp Leu Thr Val Leu Lys Ser Thr Gly Ser
145             150             155             160

Met Phe Tyr Gly Tyr Asn Lys Cys Asp Phe Thr Thr Leu Gln Pro Thr
                165             170             175

Thr Asp Arg Ile Leu Ser Thr Asp Val Asp Ala Thr Trp Val Trp Asp
            180             185             190

Asn Lys Lys Ile Gly Ser Val Tyr Asp Ile Ala Lys Ala Ala Asp Lys
        195             200             205

Gly Ile Phe Asp Asn Val Tyr Asn Gln Ala Arg Xaa Ile Thr Leu Thr
    210             215             220

Thr Phe Ala Leu Glu Asn Ser Pro Ser Val Gln Ala Thr Met Phe Asn
225             230             235             240

Met Ala Thr Gln Ile Leu Glu Lys Ala Cys Ser Val Tyr Ser Val Ser
            245             250             255

Tyr Ala Leu Pro Asn Lys His Tyr Phe Leu Ile Asp Leu Lys Trp Lys
            260             265             270

Gly Leu Glu Asn Asp Asn Glu Leu Phe Tyr Pro Ser Pro His Pro Asn
            275             280             285

Gly Leu Ile Lys Cys Thr Val Val Arg Lys Glu Lys Thr Lys Leu
    290             295             300
```

```
<210> SEQ ID NO 103
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 103
```

```
Met Ser Thr Thr Leu Ser Ser Ser Thr Tyr Gly Lys Asp Asn Val Lys
1               5               10              15

Phe Leu Lys Val Lys Lys Asp Pro Gln Asn Pro Lys Lys Gln Glu Val
            20              25              30

Met Glu Ala Thr Val Thr Cys Leu Leu Glu Gly Gly Phe Asp Thr Ser
            35              40              45
```

```
Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Xaa Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
    275                 280                 285

Gly Leu Ile Lys Cys Thr Val Val Arg Lys Glu Lys Thr Lys Leu
    290                 295                 300
```

```
<210> SEQ ID NO 104
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 104
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80
```

```
Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Xaa Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300
```

```
<210> SEQ ID NO 105
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 105
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110
```

-continued

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Xaa Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
    275                 280                 285

Gly Leu Ile Lys Cys Thr Val Val Arg Lys Glu Lys Thr Lys Leu
    290                 295                 300

<210> SEQ ID NO 106
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 106

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

-continued

```
Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Xaa Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300
```

```
<210> SEQ ID NO 107
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 107
```

```
Met Ser Thr Thr Leu Ser Ser Ser Thr Tyr Gly Lys Asp Asn Val Lys
1                   5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Xaa Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175
```

-continued

```
Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
            210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
            290                 295                 300
```

```
<210> SEQ ID NO 108
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 108
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65              70                  75                  80

Arg Phe Ala Ala Lys Leu Ala Thr His Phe Val Glu Lys Tyr Ser His
                85                  90                  95

Val Ser Gly Val Ser Val Xaa Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205
```

```
Gly Ile Phe Asp Asn Val Tyr Asn Gln Ala Arg Glu Ile Thr Leu Thr
    210             215                 220

Thr Phe Ala Leu Glu Asn Ser Pro Ser Val Gln Ala Thr Met Phe Asn
225             230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
    290                 295                 300
```

```
<210> SEQ ID NO 109
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 109
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Xaa
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
    210             215                 220

Thr Phe Ala Leu Glu Asn Ser Pro Ser Val Gln Ala Thr Met Phe Asn
225             230                 235                 240
```

-continued

```
Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300
```

```
<210> SEQ ID NO 110
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 110
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Xaa Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270
```

-continued

```
Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300

<210> SEQ ID NO 111
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 111

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Xaa Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300
```

<210> SEQ ID NO 112
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 112

Met Ser Thr Thr Leu Ser Xaa Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300

<210> SEQ ID NO 113
<211> LENGTH: 303
<212> TYPE: PRT
<213> ORGANISM: Artificial Sequence
<220> FEATURE:
<223> OTHER INFORMATION: Candida.Uox Variant Subunit

US 12,622,951 B2

319                       320

-continued

```
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 113

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Xaa Leu Thr Val Leu Lys Ser Thr Gly Ser
145                 150                 155                 160

Met Phe Tyr Gly Tyr Asn Lys Cys Asp Phe Thr Thr Leu Gln Pro Thr
            165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
    290                 295                 300

<210> SEQ ID NO 114
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.
```

-continued

<400> SEQUENCE: 114

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Xaa Lys Glu Lys Thr Lys Leu
    290                 295                 300
```

```
<210> SEQ ID NO 115
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.
```

<400> SEQUENCE: 115

```
Met Ser Thr Thr Leu Ser Ser Ser Thr Tyr Gly Lys Asp Asn Val Lys
1               5                   10                  15
```

-continued

```
Phe Leu Lys Val Lys Lys Asp Pro Gln Asn Pro Lys Lys Gln Glu Val
         20                  25                  30

Met Glu Ala Thr Val Thr Cys Leu Leu Glu Gly Gly Phe Asp Thr Ser
         35                  40                  45

Tyr Thr Glu Ala Asp Asn Ser Ser Ile Val Pro Thr Asp Thr Val Lys
         50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                 85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
         115                 120                 125

Glu Lys Arg Ile Thr Asp Leu Tyr Tyr Lys Arg Ser Gly Asp Tyr Lys
         130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
         195                 200                 205

Gly Ile Phe Asp Asn Val Tyr Asn Gln Ala Arg Glu Ile Thr Leu Thr
         210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Xaa
                260                 265                 270

Gly Leu Glu Asn Asp Asn Glu Leu Phe Tyr Pro Ser Pro His Pro Asn
         275                 280                 285

Gly Leu Ile Lys Cys Thr Val Val Arg Lys Glu Lys Thr Lys Leu
         290                 295                 300
```

```
<210> SEQ ID NO 116
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
      tetrazine functional group, and/or triazine functional group.

<400> SEQUENCE: 116
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
         20                  25                  30

Met Glu Ala Thr Val Thr Cys Leu Leu Glu Gly Gly Phe Asp Thr Ser
         35                  40                  45
```

```
Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
                115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
                180                 185                 190

Asn Lys Lys Ile Gly Ser Val Tyr Asp Ile Ala Lys Ala Ala Asp Lys
                195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Xaa Glu Leu Phe Tyr Pro Ser Pro His Pro Asn
    275                 280                 285

Gly Leu Ile Lys Cys Thr Val Val Arg Lys Glu Lys Thr Lys Leu
    290                 295                 300
```

```
<210> SEQ ID NO 117
<211> LENGTH: 303
<212> TYPE: PRT
<213> ORGANISM: Artificial Sequence
<220> FEATURE:
<223> OTHER INFORMATION: Candida.Uox Variant Subunit
<220> FEATURE:
<221> NAME/KEY: MISC_FEATURE
<222> LOCATION: (1)..(303)
<223> OTHER INFORMATION: Xaa is unnatural amino acid containing
     tetrazine functional group, and/or triazine functional group.

<400> SEQUENCE: 117
```

```
Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80
```

```
Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Xaa Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300
```

```
<210> SEQ ID NO 118
<211> LENGTH: 302
<212> TYPE: PRT
<213> ORGANISM: Arthrobacter Globiformis

<400> SEQUENCE: 118

Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
        50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
            115                 120                 125

Lys Ser Glu Val Arg Thr Ala Val Leu Glu Ile Ser Gly Ser Glu Gln
        130                 135                 140
```

```
Ala Ile Val Ala Gly Ile Glu Gly Leu Thr Val Leu Lys Ser Thr Gly
145             150             155             160

Ser Glu Phe His Gly Phe Pro Arg Asp Lys Tyr Thr Thr Leu Gln Glu
            165             170             175

Thr Thr Asp Arg Ile Leu Ala Thr Asp Val Ser Ala Arg Trp Arg Tyr
            180             185             190

Asn Thr Val Glu Val Asp Phe Asp Ala Val Tyr Ala Ser Val Arg Gly
            195             200             205

Leu Leu Leu Lys Ala Phe Ala Glu Thr His Ser Leu Ala Leu Gln Gln
    210             215             220

Thr Met Tyr Glu Met Gly Arg Ala Val Ile Glu Thr His Pro Glu Ile
225             230             235             240

Asp Glu Ile Lys Met Ser Leu Pro Asn Lys His His Phe Leu Val Asp
            245             250             255

Leu Gln Pro Phe Gly Gln Asp Asn Pro Asn Glu Val Phe Tyr Ala Ala
            260             265             270

Asp Arg Pro Tyr Gly Leu Ile Glu Ala Thr Ile Gln Arg Glu Gly Ser
            275             280             285

Arg Ala Asp His Pro Ile Trp Ser Asn Ile Ala Gly Phe Cys
    290             295             300
```

<210> SEQ ID NO 119
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 119

```
Met Thr Ala Thr Ala Glu Thr Ser Thr Gly Thr Lys Val Val Leu Gly
1               5               10              15

Gln Asn Gln Tyr Gly Lys Ala Glu Val Arg Leu Val Lys Val Thr Arg
            20              25              30

Asn Thr Ala Arg His Glu Ile Gln Asp Leu Asn Val Thr Ser Gln Leu
    35              40              45

Arg Gly Asp Phe Glu Ala Ala His Thr Ala Gly Asp Asn Ala His Val
    50              55              60

Val Ala Thr Asp Thr Gln Lys Asn Thr Val Tyr Ala Phe Ala Arg Xaa
65              70              75              80

Gly Phe Ala Thr Thr Glu Glu Phe Leu Leu Arg Leu Gly Lys His Phe
            85              90              95

Thr Glu Gly Phe Asp Trp Val Thr Gly Gly Arg Trp Ala Ala Gln Gln
            100             105             110

Phe Phe Trp Asp Arg Ile Asn Asp His Asp His Ala Phe Ser Arg Asn
            115             120             125

Lys Ser Glu Val Arg Thr Ala Val Leu Glu Ile Ser Gly Ser Glu Gln
    130             135             140

Ala Ile Val Ala Gly Ile Glu Gly Leu Thr Val Leu Lys Ser Thr Gly
145             150             155             160

Ser Glu Phe His Gly Phe Pro Arg Asp Lys Tyr Thr Thr Leu Gln Glu
            165             170             175
```

-continued

```
Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe Cys
    290                 295                 300
```

<210> SEQ ID NO 120
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 120

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Xaa Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
            115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
            195                 200                 205
```

-continued

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe Cys
    290                 295                 300

<210> SEQ ID NO 121
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 121

Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Xaa Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
    115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

```
Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe Cys
        290                 295                 300

<210> SEQ ID NO 122
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 122

Met Thr Ala Thr Ala Glu Thr Ser Thr Gly Thr Lys Val Val Leu Gly
1                5                  10                  15

Gln Asn Gln Tyr Gly Lys Ala Glu Val Arg Leu Val Lys Val Thr Arg
                20                  25                  30

Asn Thr Ala Arg His Glu Ile Gln Asp Leu Asn Val Thr Ser Gln Leu
            35                  40                  45

Arg Gly Asp Phe Glu Ala Ala His Thr Ala Gly Asp Asn Ala His Val
        50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Xaa Trp Val Thr Gly Gly Arg Trp Ala Ala Gln Gln
                100                 105                 110

Phe Phe Trp Asp Arg Ile Asn Asp His Asp His Ala Phe Ser Arg Asn
            115                 120                 125

Lys Ser Glu Val Arg Thr Ala Val Leu Glu Ile Ser Gly Ser Glu Gln
        130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
                180                 185                 190

Asn Thr Val Glu Val Asp Phe Asp Ala Val Tyr Ala Ser Val Arg Gly
                195                 200                 205

Leu Leu Leu Lys Ala Phe Ala Glu Thr His Ser Leu Ala Leu Gln Gln
        210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270
```

-continued

```
Asp Arg Pro Tyr Gly Leu Ile Glu Ala Thr Ile Gln Arg Glu Gly Ser
    275                 280                 285

Arg Ala Asp His Pro Ile Trp Ser Asn Ile Ala Gly Phe Cys
    290                 295                 300

<210> SEQ ID NO 123
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 123

Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
                20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Xaa Trp Asp Arg Ile Asn Asp His Asp His Ala Phe Ser Arg Asn
    115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
    275                 280                 285

Arg Ala Asp His Pro Ile Trp Ser Asn Ile Ala Gly Phe Cys
    290                 295                 300
```

<210> SEQ ID NO 124
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 124

Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
                20                  25                  30

Asn Thr Ala Arg His Glu Ile Gln Asp Leu Asn Val Thr Ser Gln Leu
            35                  40                  45

Arg Gly Asp Phe Glu Ala Ala His Thr Ala Gly Asp Asn Ala His Val
        50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
                100                 105                 110

Phe Phe Trp Asp Arg Ile Xaa Asp His Asp His Ala Phe Ser Arg Asn
            115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
                180                 185                 190

Asn Thr Val Glu Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe Cys
    290                 295                 300

<210> SEQ ID NO 125
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 125

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
                20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
        50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
                100                 105                 110

Phe Phe Trp Asp Arg Ile Asn Xaa His Asp His Ala Phe Ser Arg Asn
        115                 120                 125

Lys Ser Glu Val Arg Thr Ala Val Leu Glu Ile Ser Gly Ser Glu Gln
        130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
                180                 185                 190

Asn Thr Val Glu Val Asp Phe Asp Ala Val Tyr Ala Ser Val Arg Gly
                195                 200                 205

Leu Leu Leu Lys Ala Phe Ala Glu Thr His Ser Leu Ala Leu Gln Gln
        210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
        275                 280                 285

Arg Ala Asp His Pro Ile Trp Ser Asn Ile Ala Gly Phe Cys
        290                 295                 300
```

<210> SEQ ID NO 126
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

-continued

<400> SEQUENCE: 126

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
                20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
        50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
                100                 105                 110

Phe Phe Trp Asp Arg Ile Asn Asp His Asp His Ala Phe Ser Arg Asn
        115                 120                 125

Lys Ser Glu Val Arg Thr Ala Val Leu Glu Ile Ser Gly Xaa Glu Gln
        130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
                180                 185                 190

Asn Thr Val Glu Val Asp Phe Asp Ala Val Tyr Ala Ser Val Arg Gly
                195                 200                 205

Leu Leu Leu Lys Ala Phe Ala Glu Thr His Ser Leu Ala Leu Gln Gln
        210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
        275                 280                 285

Arg Ala Asp His Pro Ile Trp Ser Asn Ile Ala Gly Phe Cys
        290                 295                 300
```

```
<210> SEQ ID NO 127
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.
```

<400> SEQUENCE: 127

```
Met Thr Ala Thr Ala Glu Thr Ser Thr Gly Thr Lys Val Val Leu Gly
1               5                   10                  15
```

-continued

```
Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
            35                  40                  45

Arg Gly Asp Phe Glu Ala Ala His Thr Ala Gly Asp Asn Ala His Val
        50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
            115                 120                 125

Lys Ser Glu Val Arg Thr Ala Val Leu Glu Ile Ser Gly Ser Xaa Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe Cys
    290                 295                 300
```

```
<210> SEQ ID NO 128
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 128
```

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
            35                  40                  45
```

-continued

```
Arg Gly Asp Phe Glu Ala Ala His Thr Ala Gly Asp Asn Ala His Val
    50              55              60

Val Ala Thr Asp Thr Gln Lys Asn Thr Val Tyr Ala Phe Ala Arg Asp
65              70              75              80

Gly Phe Ala Thr Thr Glu Glu Phe Leu Leu Arg Leu Gly Lys His Phe
            85              90              95

Thr Glu Gly Phe Asp Trp Val Thr Gly Gly Arg Trp Ala Ala Gln Gln
            100             105             110

Phe Phe Trp Asp Arg Ile Asn Asp His Asp His Ala Phe Ser Arg Asn
            115             120             125

Lys Ser Glu Val Arg Thr Ala Val Leu Glu Ile Ser Gly Ser Glu Gln
    130             135             140

Ala Ile Val Ala Gly Ile Glu Gly Leu Thr Val Leu Lys Ser Thr Gly
145             150             155             160

Ser Glu Phe His Gly Phe Pro Arg Asp Lys Tyr Thr Thr Leu Xaa Glu
            165             170             175

Thr Thr Asp Arg Ile Leu Ala Thr Asp Val Ser Ala Arg Trp Arg Tyr
            180             185             190

Asn Thr Val Glu Val Asp Phe Asp Ala Val Tyr Ala Ser Val Arg Gly
            195             200             205

Leu Leu Leu Lys Ala Phe Ala Glu Thr His Ser Leu Ala Leu Gln Gln
    210             215             220

Thr Met Tyr Glu Met Gly Arg Ala Val Ile Glu Thr His Pro Glu Ile
225             230             235             240

Asp Glu Ile Lys Met Ser Leu Pro Asn Lys His His Phe Leu Val Asp
            245             250             255

Leu Gln Pro Phe Gly Gln Asp Asn Pro Asn Glu Val Phe Tyr Ala Ala
            260             265             270

Asp Arg Pro Tyr Gly Leu Ile Glu Ala Thr Ile Gln Arg Glu Gly Ser
            275             280             285

Arg Ala Asp His Pro Ile Trp Ser Asn Ile Ala Gly Phe Cys
    290             295             300
```

<210> SEQ ID NO 129
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
     tetrazine functional group, and/or triazine functional group.

<400> SEQUENCE: 129

```
Met Thr Ala Thr Ala Glu Thr Ser Thr Gly Thr Lys Val Val Leu Gly
1               5               10              15

Gln Asn Gln Tyr Gly Lys Ala Glu Val Arg Leu Val Lys Val Thr Arg
            20              25              30

Asn Thr Ala Arg His Glu Ile Gln Asp Leu Asn Val Thr Ser Gln Leu
        35              40              45

Arg Gly Asp Phe Glu Ala Ala His Thr Ala Gly Asp Asn Ala His Val
    50              55              60

Val Ala Thr Asp Thr Gln Lys Asn Thr Val Tyr Ala Phe Ala Arg Asp
65              70              75              80
```

-continued

```
Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
        115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Xaa Glu Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe Cys
    290                 295                 300
```

```
<210> SEQ ID NO 130
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 130
```

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
                20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110
```

-continued

```
Phe Phe Trp Asp Arg Ile Asn Asp His Asp His Ala Phe Ser Arg Asn
        115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Xaa Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe Cys
    290                 295                 300
```

```
<210> SEQ ID NO 131
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 131
```

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
                100                 105                 110

Phe Phe Trp Asp Arg Ile Asn Asp His Asp His Ala Phe Ser Arg Asn
        115                 120                 125

Lys Ser Glu Val Arg Thr Ala Val Leu Glu Ile Ser Gly Ser Glu Gln
    130                 135                 140
```

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
                180                 185                 190

Asn Thr Val Glu Val Asp Phe Asp Ala Val Tyr Ala Ser Val Arg Gly
                195                 200                 205

Leu Leu Leu Lys Ala Phe Ala Glu Thr Xaa Ser Leu Ala Leu Gln Gln
        210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
        275                 280                 285

Arg Ala Asp His Pro Ile Trp Ser Asn Ile Ala Gly Phe Cys
    290                 295                 300

<210> SEQ ID NO 132
<211> LENGTH: 302
<212> TYPE: PRT
<213> ORGANISM: Artificial Sequence
<220> FEATURE:
<223> OTHER INFORMATION: Arth.Uox Variant Subunit
<220> FEATURE:
<221> NAME/KEY: MISC_FEATURE
<222> LOCATION: (1)..(302)
<223> OTHER INFORMATION: Xaa is unnatural amino acid containing
      tetrazine functional group, and/or triazine functional group.

<400> SEQUENCE: 132

Met Thr Ala Thr Ala Glu Thr Ser Thr Gly Thr Lys Val Val Leu Gly
1               5               10              15

Gln Asn Gln Tyr Gly Lys Ala Glu Val Arg Leu Val Lys Val Thr Arg
            20              25              30

Asn Thr Ala Arg His Glu Ile Gln Asp Leu Asn Val Thr Ser Gln Leu
        35              40              45

Arg Gly Asp Phe Glu Ala Ala His Thr Ala Gly Asp Asn Ala His Val
    50              55              60

Val Ala Thr Asp Thr Gln Lys Asn Thr Val Tyr Ala Phe Ala Arg Asp
65              70              75              80

Gly Phe Ala Thr Thr Glu Glu Phe Leu Leu Arg Leu Gly Lys His Phe
            85              90              95

Thr Glu Gly Phe Asp Trp Val Thr Gly Gly Arg Trp Ala Ala Gln Gln
            100             105             110

Phe Phe Trp Asp Arg Ile Asn Asp His Asp His Ala Phe Ser Arg Asn
            115             120             125

Lys Ser Glu Val Arg Thr Ala Val Leu Glu Ile Ser Gly Ser Glu Gln
    130             135             140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

-continued

```
Thr Thr Asp Arg Ile Leu Ala Thr Asp Val Ser Ala Arg Trp Arg Tyr
        180                 185                 190

Asn Thr Val Glu Val Asp Phe Asp Ala Val Tyr Ala Ser Val Arg Gly
        195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Xaa Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
                260                 265                 270

Asp Arg Pro Tyr Gly Leu Ile Glu Ala Thr Ile Gln Arg Glu Gly Ser
        275                 280                 285

Arg Ala Asp His Pro Ile Trp Ser Asn Ile Ala Gly Phe Cys
        290                 295                 300

<210> SEQ ID NO 133
<211> LENGTH: 585
<212> TYPE: PRT
<213> ORGANISM: Homo sapiens

<400> SEQUENCE: 133

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

-continued

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

```
<210> SEQ ID NO 134
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 134

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30
```

-continued

```
Gln Cys Pro Phe Glu Asp His Val Lys Leu Val Asn Glu Val Thr Glu
    35              40              45

Phe Ala Lys Thr Cys Val Ala Asp Glu Ser Ala Glu Asn Cys Asp Lys
50              55              60

Ser Leu His Thr Leu Phe Gly Asp Lys Leu Cys Thr Val Ala Thr Leu
65              70              75              80

Arg Glu Thr Tyr Gly Glu Met Ala Asp Cys Cys Ala Lys Gln Glu Pro
                85              90              95

Glu Arg Asn Glu Cys Phe Leu Gln His Lys Asp Asp Asn Pro Asn Leu
            100             105             110

Pro Arg Leu Val Arg Pro Glu Val Asp Val Met Cys Thr Ala Phe His
            115             120             125

Asp Asn Glu Glu Thr Phe Leu Lys Lys Tyr Leu Tyr Glu Ile Ala Arg
    130             135             140

Arg His Pro Tyr Phe Tyr Ala Pro Glu Leu Leu Phe Phe Ala Lys Arg
145             150             155             160

Tyr Lys Ala Ala Phe Thr Glu Cys Cys Gln Ala Ala Asp Lys Ala Ala
                165             170             175

Cys Leu Leu Pro Lys Leu Asp Glu Leu Arg Asp Glu Gly Lys Ala Ser
            180             185             190

Ser Ala Lys Gln Arg Leu Lys Cys Ala Ser Leu Gln Lys Phe Gly Glu
            195             200             205

Arg Ala Phe Lys Ala Trp Ala Val Ala Arg Leu Ser Gln Arg Phe Pro
    210             215             220

Lys Ala Glu Phe Ala Glu Val Ser Lys Leu Val Thr Asp Leu Thr Lys
225             230             235             240

Val His Thr Glu Cys Cys His Gly Asp Leu Leu Glu Cys Ala Asp Asp
                245             250             255

Arg Ala Asp Leu Ala Lys Tyr Ile Cys Glu Asn Gln Asp Ser Ile Ser
            260             265             270

Ser Lys Leu Lys Glu Cys Cys Glu Lys Pro Leu Leu Glu Lys Ser His
            275             280             285

Cys Ile Ala Glu Val Glu Asn Asp Glu Met Pro Ala Asp Leu Pro Ser
    290             295             300

Leu Ala Ala Asp Phe Val Glu Ser Lys Asp Val Cys Lys Asn Tyr Ala
305             310             315             320

Glu Ala Lys Asp Val Phe Leu Gly Met Phe Leu Tyr Glu Tyr Ala Arg
                325             330             335

Arg His Pro Asp Tyr Ser Val Val Leu Leu Leu Arg Leu Ala Lys Thr
            340             345             350

Tyr Glu Thr Thr Leu Glu Lys Cys Cys Ala Ala Ala Asp Pro His Glu
            355             360             365

Cys Tyr Ala Lys Val Phe Asp Glu Phe Lys Pro Leu Val Glu Glu Pro
    370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
                405             410             415

Gln Met Ser Thr Pro Thr Leu Val Glu Val Ser Arg Asn Leu Gly Lys
            420             425             430

Val Gly Ser Lys Cys Cys Lys His Pro Glu Ala Lys Arg Met Pro Cys
            435             440             445
```

```
Ala Glu Asp Tyr Leu Ser Val Val Leu Asn Gln Leu Cys Val Leu His
    450             455                 460

Glu Lys Thr Pro Val Ser Asp Arg Val Thr Lys Cys Cys Thr Glu Ser
465             470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 135
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 135

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
    210                 215                 220
```

```
Lys Ala Glu Phe Ala Glu Val Ser Lys Leu Val Thr Asp Leu Thr Lys
225             230             235             240

Val His Thr Glu Cys Cys His Gly Asp Leu Leu Glu Cys Ala Asp Asp
            245             250             255

Arg Ala Asp Leu Ala Lys Tyr Ile Cys Glu Asn Gln Asp Ser Ile Ser
            260             265             270

Ser Lys Leu Lys Glu Cys Cys Glu Lys Pro Leu Leu Glu Lys Ser His
            275             280             285

Cys Ile Ala Glu Val Glu Asn Asp Glu Met Pro Ala Asp Leu Pro Ser
    290             295             300

Leu Ala Ala Asp Phe Val Glu Ser Lys Asp Val Cys Lys Asn Tyr Ala
305             310             315             320

Glu Ala Lys Asp Val Phe Leu Gly Met Phe Leu Tyr Glu Tyr Ala Arg
            325             330             335

Arg His Pro Asp Tyr Ser Val Val Leu Leu Leu Arg Leu Ala Lys Thr
            340             345             350

Tyr Glu Thr Thr Leu Glu Lys Cys Cys Ala Ala Ala Asp Pro His Glu
            355             360             365

Cys Tyr Ala Lys Val Phe Asp Glu Phe Lys Pro Leu Val Glu Glu Pro
    370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
            405             410             415

Gln Val Ser Ala Pro Thr Leu Val Glu Val Ser Arg Asn Leu Gly Lys
            420             425             430

Val Gly Ser Lys Cys Cys Lys His Pro Glu Ala Lys Arg Met Pro Cys
            435             440             445

Ala Glu Asp Tyr Leu Ser Val Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
            515             520             525

Leu Val Glu Leu Val Lys His Lys Pro Lys Ala Thr Lys Glu Gln Leu
            530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585
```

<210> SEQ ID NO 136
<211> LENGTH: 585
<212> TYPE: PRT
<213> ORGANISM: Artificial Sequence
<220> FEATURE:
<223> OTHER INFORMATION: Human Serum Albumin Variant -continued

<400> SEQUENCE: 136

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400
```

-continued

_____

```
Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Arg Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585
```

<210> SEQ ID NO 137
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 137

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
            50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
            130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175
```

-continued

```
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Gly Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 138
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 138

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365
```

-continued

```
Cys Tyr Ala Lys Val Phe Asp Glu Phe Lys Pro Leu Val Glu Glu Pro
    370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
            405             410             415

Gln Val Ser Thr Pro Thr Leu Val Glu Val Ser Arg Asn Leu Gly Lys
            420             425             430

Val Gly Ser Lys Cys Cys Lys His Pro Glu Ala Lys Arg Met Pro Cys
            435             440             445

Ala Glu Asp Tyr Leu Ser Val Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
            515             520             525

Leu Val Glu Leu Val Lys His Lys Pro Lys Ala Thr Lys Glu Gln Leu
    530             535             540

Lys Ala Ala Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585
```

```
<210> SEQ ID NO 139
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 139

Asp Ala His Lys Ser Glu Val Ala His Arg Phe Lys Asp Leu Gly Glu
1               5               10              15

Glu Asn Phe Lys Ala Leu Val Leu Ile Ala Phe Ala Gln Tyr Leu Gln
            20              25              30

Gln Cys Pro Phe Glu Asp His Val Lys Leu Val Asn Glu Val Thr Glu
            35              40              45

Phe Ala Lys Thr Cys Val Ala Asp Glu Ser Ala Glu Asn Cys Asp Lys
    50              55              60

Ser Leu His Thr Leu Phe Gly Asp Lys Leu Cys Thr Val Ala Thr Leu
65              70              75              80

Arg Glu Thr Tyr Gly Glu Met Ala Asp Cys Cys Ala Lys Gln Glu Pro
            85              90              95

Glu Arg Asn Glu Cys Phe Leu Gln His Lys Asp Asp Asn Pro Asn Leu
            100             105             110

Pro Arg Leu Val Arg Pro Glu Val Asp Val Met Cys Thr Ala Phe His
            115             120             125

Asp Asn Glu Glu Thr Phe Leu Lys Lys Tyr Leu Tyr Glu Ile Ala Arg
            130             135             140
```

-continued

```
Arg His Pro Tyr Phe Tyr Ala Pro Glu Leu Leu Phe Phe Ala Lys Arg
145             150             155             160

Tyr Lys Ala Ala Phe Thr Glu Cys Cys Gln Ala Ala Asp Lys Ala Ala
            165             170             175

Cys Leu Leu Pro Lys Leu Asp Glu Leu Arg Asp Glu Gly Lys Ala Ser
            180             185             190

Ser Ala Lys Gln Arg Leu Lys Cys Ala Ser Leu Gln Lys Phe Gly Glu
            195             200             205

Arg Ala Phe Lys Ala Trp Ala Val Ala Arg Leu Ser Gln Arg Phe Pro
    210             215             220

Lys Ala Glu Phe Ala Glu Val Ser Lys Leu Val Thr Asp Leu Thr Lys
225             230             235             240

Val His Thr Glu Cys Cys His Gly Asp Leu Leu Glu Cys Ala Asp Asp
            245             250             255

Arg Ala Asp Leu Ala Lys Tyr Ile Cys Glu Asn Gln Asp Ser Ile Ser
            260             265             270

Ser Lys Leu Lys Glu Cys Cys Glu Lys Pro Leu Leu Glu Lys Ser His
            275             280             285

Cys Ile Ala Glu Val Glu Asn Asp Glu Met Pro Ala Asp Leu Pro Ser
    290             295             300

Leu Ala Ala Asp Phe Val Glu Ser Lys Asp Val Cys Lys Asn Tyr Ala
305             310             315             320

Glu Ala Lys Asp Val Phe Leu Gly Met Phe Leu Tyr Glu Tyr Ala Arg
            325             330             335

Arg His Pro Asp Tyr Ser Val Val Leu Leu Leu Arg Leu Ala Lys Thr
            340             345             350

Tyr Glu Thr Thr Leu Glu Lys Cys Cys Ala Ala Ala Asp Pro His Glu
            355             360             365

Cys Tyr Ala Lys Val Phe Asp Glu Phe Lys Pro Leu Val Glu Glu Pro
    370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
            405             410             415

Gln Val Ser Thr Pro Thr Leu Val Glu Val Ser Arg Asn Leu Gly Lys
            420             425             430

Val Gly Ser Lys Cys Cys Lys His Pro Glu Ala Lys Arg Met Pro Cys
            435             440             445

Ala Glu Asp Tyr Leu Ser Val Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
            515             520             525

Leu Val Glu Leu Val Lys His Lys Pro Lys Ala Thr Lys Glu Gln Leu
            530             535             540

Lys Ala Val Met Asp Asp Phe Ala Ala Phe Val Glu Lys Cys Cys Lys
545             550             555             560
```

-continued

---

```
Ala Asp Asp Lys Glu Thr Cys Phe Ala Glu Glu Gly Tyr Lys Leu Val
                565                 570                 575

Ala Ala Ser Gln Ala Ala Leu Gly Leu
                580                 585

<210> SEQ ID NO 140
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 140

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
            130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335
```

-continued

Arg His Pro Asp Tyr Ser Val Val Leu Leu Leu Arg Leu Ala Lys Thr
                340                         345                         350

Tyr Glu Thr Thr Leu Glu Lys Cys Cys Ala Ala Ala Asp Pro His Glu
                355                         360                         365

Cys Tyr Ala Lys Val Phe Asp Glu Phe Lys Pro Leu Val Glu Glu Pro
                370                         375                         380

Gln Asn Leu Ile Lys Gln Asn Cys Glu Leu Phe Glu Gln Leu Gly Glu
385                         390                         395                         400

Tyr Lys Phe Gln Asn Ala Leu Leu Val Arg Tyr Thr Lys Lys Val Pro
                405                         410                         415

Gln Val Ser Thr Pro Thr Leu Ile Glu Val Ser Arg Asn Leu Gly Lys
                420                         425                         430

Val Gly Ser Lys Cys Cys Lys His Pro Glu Ala Lys Arg Met Pro Cys
                435                         440                         445

Ala Glu Asp Tyr Leu Ser Val Val Leu Asn Gln Leu Cys Val Leu His
                450                         455                         460

Glu Lys Thr Pro Val Ser Asp Arg Val Thr Lys Cys Cys Thr Glu Ser
465                         470                         475                         480

Leu Val Asn Arg Arg Pro Cys Phe Ser Ala Leu Glu Val Asp Glu Thr
                485                         490                         495

Tyr Val Pro Lys Glu Phe Asn Ala Glu Thr Phe Thr Phe His Ala Asp
                500                         505                         510

Ile Cys Thr Leu Ser Glu Lys Glu Arg Gln Ile Lys Lys Gln Thr Ala
                515                         520                         525

Leu Val Glu Leu Val Lys His Lys Pro Lys Ala Thr Lys Glu Gln Leu
                530                         535                         540

Lys Ala Val Met Asp Asp Phe Ala Ala Phe Val Glu Lys Cys Cys Lys
545                         550                         555                         560

Ala Asp Asp Lys Glu Thr Cys Phe Ala Glu Glu Gly Lys Lys Leu Val
                565                         570                         575

Ala Ala Ser Gln Ala Ala Leu Gly Leu
                580                         585

<210> SEQ ID NO 141
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 141

Asp Ala His Lys Ser Glu Val Ala His Arg Phe Lys Asp Leu Gly Glu
1                           5                           10                          15

Glu Asn Phe Lys Ala Leu Val Leu Ile Ala Phe Ala Gln Tyr Leu Gln
                20                          25                          30

Gln Cys Pro Phe Glu Asp His Val Lys Leu Val Asn Glu Val Thr Glu
                35                          40                          45

Phe Ala Lys Thr Cys Val Ala Asp Glu Ser Ala Glu Asn Cys Asp Lys
                50                          55                          60

Ser Leu His Thr Leu Phe Gly Asp Lys Leu Cys Thr Val Ala Thr Leu
65                          70                          75                          80

Arg Glu Thr Tyr Gly Glu Met Ala Asp Cys Cys Ala Lys Gln Glu Pro
                85                          90                          95

Glu Arg Asn Glu Cys Phe Leu Gln His Lys Asp Asp Asn Pro Asn Leu
                100                         105                         110

-continued

```
Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asp Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525
```

-continued

```
Leu Val Glu Leu Val Lys His Lys Pro Lys Ala Thr Lys Glu Gln Leu
    530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585

<210> SEQ ID NO 142
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 142

Asp Ala His Lys Ser Glu Val Ala His Arg Phe Lys Asp Leu Gly Glu
1               5               10              15

Glu Asn Phe Lys Ala Leu Val Leu Ile Ala Phe Ala Gln Tyr Leu Gln
            20              25              30

Gln Cys Pro Phe Glu Asp His Val Lys Leu Val Asn Glu Val Thr Glu
        35              40              45

Phe Ala Lys Thr Cys Val Ala Asp Glu Ser Ala Glu Asn Cys Asp Lys
    50              55              60

Ser Leu His Thr Leu Phe Gly Asp Lys Leu Cys Thr Val Ala Thr Leu
65              70              75              80

Arg Glu Thr Tyr Gly Glu Met Ala Asp Cys Cys Ala Lys Gln Glu Pro
                85              90              95

Glu Arg Asn Glu Cys Phe Leu Gln His Lys Asp Asp Asn Pro Asn Leu
            100             105             110

Pro Arg Leu Val Arg Pro Glu Val Asp Val Met Cys Thr Ala Phe His
        115             120             125

Asp Asn Glu Glu Thr Phe Leu Lys Lys Tyr Leu Tyr Glu Ile Ala Arg
        130             135             140

Arg His Pro Tyr Phe Tyr Ala Pro Glu Leu Leu Phe Phe Ala Lys Arg
145             150             155             160

Tyr Lys Ala Ala Phe Thr Glu Cys Cys Gln Ala Ala Asp Lys Ala Ala
            165             170             175

Cys Leu Leu Pro Lys Leu Asp Glu Leu Arg Asp Glu Gly Lys Ala Ser
            180             185             190

Ser Ala Lys Gln Arg Leu Lys Cys Ala Ser Leu Gln Lys Phe Gly Glu
        195             200             205

Arg Ala Phe Lys Ala Trp Ala Val Ala Arg Leu Ser Gln Arg Phe Pro
    210             215             220

Lys Ala Glu Phe Ala Glu Val Ser Lys Leu Val Thr Asp Leu Thr Lys
225             230             235             240

Val His Thr Glu Cys Cys His Gly Asp Leu Leu Glu Cys Ala Asp Asp
                245             250             255

Arg Ala Asp Leu Ala Lys Tyr Ile Cys Glu Asn Gln Asp Ser Ile Ser
            260             265             270

Ser Lys Leu Lys Glu Cys Cys Glu Lys Pro Leu Leu Glu Lys Ser His
        275             280             285

Cys Ile Ala Glu Val Glu Asn Asp Glu Met Pro Ala Asp Leu Pro Ser
    290             295             300
```

```
Leu Ala Ala Asp Phe Val Glu Ser Lys Asp Val Cys Lys Asn Tyr Ala
305               310               315               320

Glu Ala Lys Asp Val Phe Leu Gly Met Phe Leu Tyr Glu Tyr Ala Arg
              325               330               335

Arg His Pro Asp Tyr Ser Val Val Leu Leu Leu Arg Leu Ala Lys Thr
              340               345               350

Tyr Glu Thr Thr Leu Glu Lys Cys Cys Ala Ala Ala Asp Pro His Glu
              355               360               365

Cys Tyr Ala Lys Val Phe Asp Glu Phe Lys Pro Leu Val Glu Glu Pro
    370               375               380

Gln Asn Leu Ile Lys Gln Asn Cys Glu Leu Phe Glu Gln Leu Gly Glu
385               390               395               400

Tyr Lys Phe Gln Asn Ala Leu Leu Val Arg Tyr Thr Lys Lys Val Pro
              405               410               415

Gln Val Ser Thr Pro Thr Leu Val Glu Val Ser Arg Asn Leu Gly Lys
              420               425               430

Val Gly Ser Lys Cys Cys Lys His Pro Glu Ala Lys Arg Met Pro Cys
              435               440               445

Val Glu Asp Tyr Leu Ser Val Val Leu Asn Gln Leu Cys Val Leu His
    450               455               460

Glu Lys Thr Pro Val Ser Asp Arg Val Thr Lys Cys Cys Thr Glu Ser
465               470               475               480

Leu Val Asn Arg Arg Pro Cys Phe Ser Ala Leu Glu Val Asp Glu Thr
              485               490               495

Tyr Val Pro Lys Glu Phe Asn Ala Glu Thr Phe Thr Phe His Ala Asp
              500               505               510

Ile Cys Thr Leu Ser Glu Lys Glu Arg Gln Ile Lys Lys Gln Thr Ala
              515               520               525

Leu Val Glu Leu Val Lys His Lys Pro Lys Ala Thr Lys Glu Gln Leu
    530               535               540

Lys Ala Val Met Asp Asp Phe Ala Ala Phe Val Glu Lys Cys Cys Lys
545               550               555               560

Ala Asp Asp Lys Glu Thr Cys Phe Ala Glu Glu Gly Lys Lys Leu Val
              565               570               575

Ala Ala Ser Gln Ala Ala Leu Gly Leu
              580               585
```

<210> SEQ ID NO 143
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 143

```
Asp Ala His Lys Ser Glu Val Ala His Arg Phe Lys Asp Leu Gly Glu
1               5                 10                15

Glu Asn Phe Lys Ala Leu Val Leu Ile Ala Phe Ala Gln Tyr Leu Gln
              20                25                30

Gln Cys Pro Phe Glu Asp His Val Lys Leu Val Asn Glu Val Thr Glu
    35                40                45

Phe Ala Lys Thr Cys Val Ala Asp Glu Ser Ala Glu Asn Cys Asp Lys
    50                55                60

Ser Leu His Thr Leu Phe Gly Asp Lys Leu Cys Thr Val Ala Thr Leu
65                70                75                80
```

-continued

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Met Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

-continued

```
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
    545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 144
<211> LENGTH: 585
<212> TYPE: PRT
<213> ORGANISM: Artificial Sequence
<220> FEATURE:
<223> OTHER INFORMATION: Human Serum Albumin Variant

<400> SEQUENCE: 144

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

-continued

```
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Thr Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
        580                 585
```

<210> SEQ ID NO 145
<211> LENGTH: 20
<212> TYPE: DNA
<213> ORGANISM: Artificial Sequence
<220> FEATURE:
<223> OTHER INFORMATION: pTAC linearize-F

<400> SEQUENCE: 145
caagcttggc tgttttggcg                                              20

<210> SEQ ID NO 146
<211> LENGTH: 25
<212> TYPE: DNA
<213> ORGANISM: Artificial Sequence
<220> FEATURE:

<223> OTHER INFORMATION: pTAC linearize-R

<400> SEQUENCE: 146
ctatatctcc ttcttaaagt taaac                                    25

<210> SEQ ID NO 147
<211> LENGTH: 34
<212> TYPE: DNA
<213> ORGANISM: Artificial Sequence
<220> FEATURE:
<223> OTHER INFORMATION: tacP-RBS-MCS-rrnBt1t2-F

<400> SEQUENCE: 147
aagaaggaga tatagatgtc tgctgtgaag gccg                          34

<210> SEQ ID NO 148
<211> LENGTH: 36
<212> TYPE: DNA
<213> ORGANISM: Artificial Sequence
<220> FEATURE:
<223> OTHER INFORMATION: tacP-RBS-MCS-rrnBt1t2-R

<400> SEQUENCE: 148
aaacagccaa gcttgttaca gcttgctctt cagaga                        36

<210> SEQ ID NO 149
<211> LENGTH: 20
<212> TYPE: DNA
<213> ORGANISM: Artificial Sequence
<220> FEATURE:
<223> OTHER INFORMATION: pTAC-sequencing-F

<400> SEQUENCE: 149
gcctagagca agacgtttcc                                          20

<210> SEQ ID NO 150
<211> LENGTH: 19
<212> TYPE: DNA
<213> ORGANISM: Artificial Sequence
<220> FEATURE:
<223> OTHER INFORMATION: pTAC-sequencing-R

<400> SEQUENCE: 150
ttaatgcagc tggcacgac                                           19

<210> SEQ ID NO 151
<211> LENGTH: 23
<212> TYPE: DNA
<213> ORGANISM: Artificial Sequence
<220> FEATURE:
<223> OTHER INFORMATION: Ribosome binding site sequence

<400> SEQUENCE: 151
tttgtttaac tttaagaagg aga                                      23

<210> SEQ ID NO 152
<211> LENGTH: 909
<212> TYPE: DNA
<213> ORGANISM: Artificial Sequence
<220> FEATURE:
<223> OTHER INFORMATION: Asp.Uox Variant Coding DNA

<400> SEQUENCE: 152
atgtctgctg tgaaggccgc aagatatggc aaggataatg tgagggtgta caaggtgcat    60
aaggacgaaa agactggcgt gcagacagtg tacgagatga ccgtgtgcgt cctgctggag   120

-continued

```
ggcgaaatcg agacttctta taccaaagcc gacaactccg tgattgtggc cacagattct      180
atcaagaaca ctatctatat caccgccaaa cagaacccag tgacaccacc tgaactgttc      240
ggcagcattc tcggcacaca ctttattgag aagtacaacc acatccatgc tgcacacgtg      300
aatatcgtgt gtcatcgctg gacccgcatg gacatctagg gaaagccaca cccccactct      360
tttatcagag actctgaaga aaagagaaac gtgcaggtcg acgtggtgga gggaaaaggt      420
atcgacatca agagctcact ctccggcctg accgtgctga agagtaccaa ttcacagttt      480
tgggggtttc tgagagacga atacactaca ctgaaggaga cttgggatag aatcctgagt      540
accgacgtgg atgcaacctg gcagtggaag aatttttccg ggctgcagga agtgcggtcc      600
cacgtgccca agtttgatgc aacctgggca accgcaaggg aggtgacact gaaaaccttt      660
gccgaggaca actccgctag cgtgcaggcc acaatgtaca agatggccga acagatcctg      720
gccagacagc agctgattga gactgtggag tactctctgc ctaacaagca ctatttcgaa      780
atcgacctgt cctggcacaa gggactgcag aatactggta aaaacgcaga ggtgttcgcc      840
cctcagagtg atcccaatgg tctgatcaaa tgcacagtgg ggagatcctc tctgaagagc      900
aagctgtaa                                                             909
```

<210> SEQ ID NO 153
<211> LENGTH: 909
<212> TYPE: DNA
<213> ORGANISM: Artificial Sequence
<220> FEATURE:
<223> OTHER INFORMATION: Asp.Uox Variant Coding DNA

<400> SEQUENCE: 153

```
atgtctgctg tgaaggccgc aagatatggc aaggataatg tgagggtgta caaggtgcat       60
aaggacgaaa agactggcgt gcagacagtg tacgagatga ccgtgtgcgt cctgctggag      120
ggcgaaatcg agacttctta taccaaagcc gacaactccg tgattgtggc cacagattct      180
atcaagaaca ctatctatat caccgccaaa cagaacccag tgacaccacc tgaactgttc      240
ggcagcattc tcggcacaca ctttattgag aagtacaacc acatccatgc tgcacacgtg      300
aatatcgtgt gtcatcgctg gacccgcatg gacatcgacg gaaagccaca cccccactct      360
tttatcagag actctgaaga aaagagaaac gtgcaggtcg acgtggtgga gggaaaaggt      420
atcgacatca agagctcact ctccggcctg accgtgctga agagtaccaa ttcacagttt      480
tagggttttc tgagagacga atacactaca ctgaaggaga cttgggatag aatcctgagt      540
accgacgtgg atgcaacctg gcagtggaag aatttttccg ggctgcagga agtgcggtcc      600
cacgtgccca agtttgatgc aacctgggca accgcaaggg aggtgacact gaaaaccttt      660
gccgaggaca actccgctag cgtgcaggcc acaatgtaca agatggccga acagatcctg      720
gccagacagc agctgattga gactgtggag tactctctgc ctaacaagca ctatttcgaa      780
atcgacctgt cctggcacaa gggactgcag aatactggta aaaacgcaga ggtgttcgcc      840
cctcagagtg atcccaatgg tctgatcaaa tgcacagtgg ggagatcctc tctgaagagc      900
aagctgtaa                                                             909
```

<210> SEQ ID NO 154
<211> LENGTH: 909
<212> TYPE: DNA
<213> ORGANISM: Artificial Sequence
<220> FEATURE:
<223> OTHER INFORMATION: Asp.Uox Variant Coding DNA

<400> SEQUENCE: 154
atgtctgctg tgaaggccgc aagatatggc aaggataatg tgagggtgta caaggtgcat    60
aaggacgaaa agactggcgt gcagacagtg tacgagatga ccgtgtgcgt cctgctggag    120
ggcgaaatcg agacttctta taccaaagcc gacaactccg tgattgtggc cacagattct    180
atcaagaaca ctatctatat caccgccaaa cagaacccag tgacaccacc tgaactgttc    240
ggcagcattc tcggcacaca ctttattgag aagtacaacc acatccatgc tgcacacgtg    300
aatatcgtgt gtcatcgctg gacccgcatg gacatcgacg gaaagccaca cccccactct    360
tttatcagag actctgaaga aaagagaaac gtgcaggtcg acgtggtgga gggaaaaggt    420
atcgacatca gagctcact ctccggcctg accgtgctga agagtaccaa ttcacagttt    480 tggggggtttc tgagagacga atacactaca ctgaaggaga cttaggatag aatcctgagt    540
accgacgtgg atgcaacctg gcagtggaag aattttttccg ggctgcagga agtgcggtcc    600
cacgtgccca gtttgatgc aacctgggca accgcaaggg aggtgacact gaaaaccttt    660
gccgaggaca actccgctag cgtgcaggcc acaatgtaca agatggccga acagatcctg    720
gccagacagc agctgattga gactgtggag tactctctgc ctaacaagca ctatttcgaa    780
atcgacctgt cctggcacaa gggactgcag aatactggta aaaacgcaga ggtgttcgcc    840
cctcagagtg atcccaatgg tctgatcaaa tgcacagtgg ggagatcctc tctgaagagc    900
aagctgtaa                                                           909

<210> SEQ ID NO 155
<211> LENGTH: 912
<212> TYPE: DNA
<213> ORGANISM: Artificial Sequence
<220> FEATURE:
<223> OTHER INFORMATION: Candida.Uox Variant Coding DNA

<400> SEQUENCE: 155
atgagcacca cactgagcag cagcacctat ggtaaagata atgtgaaatt cctgaaagtg    60
aaaaaagatc cgcagaaccc gaaaaaacaa gaagttatgg aagcaaccgt tacctgtctg    120
ctggaaggtg gttttgatac cagctatacc gaagcagata atagcagcat tgttccgacc    180
gataccgtga aaataccat tctggttctg gcaaaaacca ccgaaatttg gccgattgaa    240
cgttttgcag ccaaactggc aacccatttt gttgagaaat attctcatgt tagcggtgtg    300
agcgttaaaa ttgttcagga tcgttgggtt aaatatgccg ttgatggtaa accgcatgat    360
cacagcttta ttcatgaagg tggtgaaaaa cgtatcaccg acctgtatta caaacgtagc    420
ggtgattata aactgtccag cgcaattaaa gatctgaccg ttctgaaaag caccggcagc    480 atgtttttagg gttataacaa atgcgatttc acaaccctgc agccgaccac cgatcgtatt    540
ctgagcaccg atgttgatgc aacctgggtt tgggataata agaaaattgg tagcgtgtac    600
gatattgcca aagcagcaga taaaggcatc ttcgataatg tgtataatca ggcacgtgaa    660
attaccctga ccacctttgc actggaaaat agcccgagcg ttcaggcaac catgtttaat    720
atggcgaccc agattctgga aaaagcgtgt agcgtttata gcgttagcta tgcactgccg    780
aacaaacact attttctgat tgacctgaaa tggaagggcc ttgaaaatga taacgaactg    840
ttttatccga gtccgcatcc gaatggtctg attaaatgta ccgttgtgcg taaagagaaa    900
accaaactgt aa                                                        912

<210> SEQ ID NO 156

<211> LENGTH: 912
<212> TYPE: DNA
<213> ORGANISM: Artificial Sequence
<220> FEATURE:
<223> OTHER INFORMATION: Candida.Uox Variant Coding DNA

<400> SEQUENCE: 156
atgagcacca cactgagcag cagcaccat ggtaaagata atgtgaaatt cctgaaagtg      60
aaaaaagatc cgcagaaccc gaaaaaacaa gaagttatgg aagcaaccgt tacctgtctg     120
ctggaaggtg gttttgatac cagctatacc gaagcagata atagcagcat tgttccgacc     180
gataccgtga aaaataccat tctggttctg gcaaaaacca ccgaaatttg gccgattgaa     240
cgttttgcag ccaaactggc aacccatttt gttgagaaat attctcatgt tagcggtgtg     300
agcgttaaaa ttgttcagga tcgttgggtt aaatatgccg ttgatggtaa accgcatgat     360
cacagcttta ttcatgaagg tggtgaaaaa cgtatcaccg acctgtatta caaacgtagc     420
ggtgattata aactgtccag cgcaattaaa gatctgaccg ttctgaaaag caccggcagc     480 atgtttatg gttataacaa atgcgatttc acaaccctgc agccgaccac cgatcgtatt     540
ctgagcaccg atgttgatgc aacctgggtt tgggataata agaaaattgg tagcgtgtag     600
gatattgcca aagcagcaga taaaggcatc ttcgataatg tgtataatca ggcacgtgaa     660
attaccctga ccacctttgc actggaaaat agcccgagcg ttcaggcaac catgtttaat     720
atggcgaccc agattctgga aaaagcgtgt agcgtttata gcgttagcta tgcactgccg     780
aacaaacact attttctgat tgacctgaaa tggaagggcc ttgaaaatga taacgaactg     840
ttttatccga gtccgcatcc gaatggtctg attaaatgta ccgttgtgcg taaagagaaa     900
accaaactgt aa                                                        912

<210> SEQ ID NO 157
<211> LENGTH: 912
<212> TYPE: DNA
<213> ORGANISM: Artificial Sequence
<220> FEATURE:
<223> OTHER INFORMATION: Candida.Uox Variant Coding DNA

<400> SEQUENCE: 157
atgagcacca cactgagcag cagcaccat ggtaaagata atgtgaaatt cctgaaagtg      60
aaaaaagatc cgcagaaccc gaaaaaacaa gaagttatgg aagcaaccgt tacctgtctg     120
ctggaaggtg gttttgatac cagctatacc gaagcagata atagcagcat tgttccgacc     180
gataccgtga aaaataccat tctggttctg gcaaaaacca ccgaaatttg gccgattgaa     240
cgttttgcag ccaaactggc aacccatttt gttgagaaat attctcatgt tagcggtgtg     300
agcgttaaaa ttgttcagga tcgttgggtt aaatatgccg ttgatggtaa accgcatgat     360
cacagcttta ttcatgaagg tggtgaaaaa cgtatcaccg acctgtatta caaacgtagc     420
ggtgattata aactgtccag cgcaattaaa gatctgaccg ttctgaaaag caccggcagc     480 atgtttatg gttataacaa atgcgatttc acaaccctgc agccgaccac cgatcgtatt     540
ctgagcaccg atgttgatgc aacctgggtt tgggataata agaaaattgg tagcgtgtac     600
gatattgcca aagcagcaga taaaggcatc ttcgataatg tgtataatca ggcacgtgaa     660
attaccctga ccacctttgc actggaaaat agcccgagcg ttcaggcaac catgtttaat     720
atggcgaccc agattctgga aaaagcgtgt agcgtttata gcgttagcta tgcactgccg     780

-continued

```
aacaaacact attttctgat tgacctgaaa tagaagggcc ttgaaaatga taacgaactg      840
ttttatccga gtccgcatcc gaatggtctg attaaatgta ccgttgtgcg taaagagaaa      900
accaaactgt aa                                                          912
```

```
<210> SEQ ID NO 158
<211> LENGTH: 909
<212> TYPE: DNA
<213> ORGANISM: Artificial Sequence
<220> FEATURE:
<223> OTHER INFORMATION: Arth.Uox Variant Coding DNA

<400> SEQUENCE: 158
atgaccgcaa ccgcagaaac cagcaccggc accaaagttg ttctgggtca gaatcagtat       60
ggtaaagcag aagttcgtct ggttaaagtt acccgtaata ccgcacgtca tgaaattcag      120
gatctgaatg ttaccagcca gctgcgtggt gattttgaag cagcacatac cgcaggcgat      180
aatgcacatg ttgttgcaac cgatacacag aaaaacaccg tttatgcatt tgcccgtgat      240
ggttttgcaa ccaccgaaga atttctgctg cgtctgggta acatttcac cgaaggtttt      300 gattgggtta ccggtggtcg ttgggcagca cagcagtttt tctgggatcg tatttaggat      360
cacgatcatg cctttagccg caataaaagc gaagtgcgta ccgcagttct ggaaattagc      420
ggtagcgaac aggcaattgt tgcaggtatt gaaggtctga ccgttctgaa aagcaccggt      480
agcgagtttc atggttttcc gcgtgataaa tacaccacac tgcaagaaac caccgatcgt      540
attctggcaa ccgatgttag cgcacgttgg cgttataata ccgttgaagt tgattttgat      600
gcggtttatg caagcgttcg tggtctgctg ctgaaagcat ttgcagaaac ccatagcctg      660
gcactgcagc agacaatgta tgaaatgggt cgtgcagtta ttgaaaccca tccggaaatt      720
gatgagatca aaatgagcct gccgaacaaa catcatttc tggttgatct gcagccgttt      780
ggtcaggata tccgaatga agtgttttat gcagcagatc gtccgtatgg tctgattgaa      840
gcaaccattc agcgtgaagg tagccgtgca gatcatccga tttggagtaa tattgcaggt      900
ttttgctaa                                                            909
```

```
<210> SEQ ID NO 159
<211> LENGTH: 909
<212> TYPE: DNA
<213> ORGANISM: Artificial Sequence
<220> FEATURE:
<223> OTHER INFORMATION: Arth.Uox Variant Coding DNA

<400> SEQUENCE: 159
atgaccgcaa ccgcagaaac cagcaccggc accaaagttg ttctgggtca gaatcagtat       60
ggtaaagcag aagttcgtct ggttaaagtt acccgtaata ccgcacgtca tgaaattcag      120
gatctgaatg ttaccagcca gctgcgtggt gattttgaag cagcacatac cgcaggcgat      180
aatgcacatg ttgttgcaac cgatacacag aaaaacaccg tttatgcatt tgcccgtgat      240
ggttttgcaa ccaccgaaga atttctgctg cgtctgggta acatttcac cgaaggtttt      300 gattgggtta ccggtggtcg ttgggcagca cagcagtttt tctgggatcg tattaatgat      360
cacgatcatg cctttagccg caataaaagc gaagtgcgta ccgcagttct ggaaattagc      420
ggttaggaac aggcaattgt tgcaggtatt gaaggtctga ccgttctgaa aagcaccggt      480
```

```
agcgagtttc atggtttttcc gcgtgataaa tacaccacac tgcaagaaac caccgatcgt      540
attctggcaa ccgatgttag cgcacgttgg cgttataata ccgttgaagt tgattttgat      600
gcggtttatg caagcgttcg tggtctgctg ctgaaagcat ttgcagaaac ccatagcctg      660
gcactgcagc agacaatgta tgaaatgggt cgtgcagtta ttgaaaccca tccggaaatt      720
gatgagatca aaatgagcct gccgaacaaa catcattttc tggttgatct gcagccgttt      780
ggtcaggata atccgaatga agtgtttat gcagcagatc gtccgtatgg tctgattgaa      840
gcaaccattc agcgtgaagg tagccgtgca gatcatccga tttggagtaa tattgcaggt      900
ttttgctaa                                                             909
```

```
<210> SEQ ID NO 160
<211> LENGTH: 909
<212> TYPE: DNA
<213> ORGANISM: Artificial Sequence
<220> FEATURE:
<223> OTHER INFORMATION: Arth.Uox Variant Coding DNA

<400> SEQUENCE: 160
atgaccgcaa ccgcagaaac cagcaccggc accaaagttg ttctgggtca gaatcagtat       60
ggtaaagcag aagttcgtct ggttaaagtt acccgtaata ccgcacgtca tgaaattcag      120
gatctgaatg ttaccagcca gctgcgtggt gattttgaag cagcacatac cgcaggcgat      180
aatgcacatg ttgttgcaac cgatacacag aaaaacaccg tttatgcatt tgcccgtgat      240
ggttttgcaa ccaccgaaga atttctgctg cgtctgggta aacatttcac cgaaggtttt      300
gattgggtta ccggtggtcg ttgggcagca cagcagtttt tctgggatcg tattaatgat      360
cacgatcatg cctttagccg caataaaagc gaagtgcgta ccgcagttct ggaaattagc      420
ggtagcgaac aggcaattgt tgcaggtatt gaaggtctga ccgttctgaa aagcaccggt      480
agcgagtttc atggtttttcc gcgtgataaa tacaccacac tgcaagaaac caccgatcgt      540
attctggcaa ccgatgttag cgcacgttgg cgttataata ccgtttaggt tgattttgat      600
gcggtttatg caagcgttcg tggtctgctg ctgaaagcat ttgcagaaac ccatagcctg      660
gcactgcagc agacaatgta tgaaatgggt cgtgcagtta ttgaaaccca tccggaaatt      720
gatgagatca aaatgagcct gccgaacaaa catcattttc tggttgatct gcagccgttt      780
ggtcaggata atccgaatga agtgtttat gcagcagatc gtccgtatgg tctgattgaa      840
gcaaccattc agcgtgaagg tagccgtgca gatcatccga tttggagtaa tattgcaggt      900
ttttgctaa                                                             909
```

```
<210> SEQ ID NO 161
<211> LENGTH: 25
<212> TYPE: DNA
<213> ORGANISM: Artificial Sequence
<220> FEATURE:
<223> OTHER INFORMATION: pBAD-AgUox_F

<400> SEQUENCE: 161
gccgccatgg tgtctgctgt gaagg                                             25
```

```
<210> SEQ ID NO 162
<211> LENGTH: 25
<212> TYPE: DNA
<213> ORGANISM: Artificial Sequence
<220> FEATURE:
<223> OTHER INFORMATION: pBAD-AgUox_R
```

-continued

```
<400> SEQUENCE: 162
gccgagatct ttaatggtga tggtg                                              25

<210> SEQ ID NO 163
<211> LENGTH: 37
<212> TYPE: DNA
<213> ORGANISM: Artificial Sequence
<220> FEATURE:
<223> OTHER INFORMATION: AgUox-196Amb_F

<400> SEQUENCE: 163
gtcgaagtcc acctatacgg tgttgtaacg ccaacgg                                 37

<210> SEQ ID NO 164
<211> LENGTH: 37
<212> TYPE: DNA
<213> ORGANISM: Artificial Sequence
<220> FEATURE:
<223> OTHER INFORMATION: AgUox-196Amb_R

<400> SEQUENCE: 164
ccgttggcgt tacaacaccg tataggtgga cttcgac                                 37

<210> SEQ ID NO 165
<211> LENGTH: 16
<212> TYPE: PRT
<213> ORGANISM: Artificial Sequence
<220> FEATURE:
<223> OTHER INFORMATION: AgUox-WT fregment

<400> SEQUENCE: 165

Tyr Asn Thr Val Glu Val Asp Phe Asp Ala Val Tyr Ala Ser Val Arg
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: AgUox-frTet fregment
<220> FEATURE:
<221> NAME/KEY: misc_feature
<222> LOCATION: (5)..(5)
<223> OTHER INFORMATION: Xaa is unnatural amino acid containing
      tetrazine functional group, and/or triazine functional group.

<400> SEQUENCE: 166

Tyr Asn Thr Val Xaa Val Asp Phe Asp Ala Val Tyr Ala Ser Val Arg
1               5                   10                  15

<210> SEQ ID NO 167
<211> LENGTH: 19
<212> TYPE: PRT
<213> ORGANISM: Artificial Sequence
<220> FEATURE:
<223> OTHER INFORMATION: fregment control

<400> SEQUENCE: 167

Ala Val Ile Glu Thr His Pro Glu Ile Asp Glu Ile Lys Met Ser Leu
1               5                   10                  15

Pro Asn Lys
```

URATE OXIDASE-ALBUMIN CONJUGATE, PREPARATION METHOD THEREOF, AND USE THEREOF

CROSS-REFERENCE TO RELATED APPLICATIONS

This application is a National Stage Application of International Application No. PCT/KR2021/013037, filed Sep. 24, 2021, which claims the benefit of Korean Application Nos. 10-2020-0125215, filed Sep. 25, 2020, and 10-2021-0013537, filed Jan. 29, 2021, the entire contents of which are incorporated herein by reference.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Aug. 22, 2022, is named "PYH-01101_Sequence Listing" and is 453,880 bytes in size.

TECHNICAL FIELD

The present description discloses a urate oxidase variant into which a nonnatural amino acid is introduced site-specifically a preparation method thereof, a conjugate in which the urate oxidase variant and albumin are conjugated by a linker, and a preparation method thereof. In addition, the present description discloses the use of the urate oxidase-albumin conjugate.

BACKGROUND ART

Urate oxidase (Uricase) is a type of enzyme that cannot be synthesized in primates including humans, and it functions to break down uric acid into allantoin. Urate oxidase has a direct therapeutic mechanism of decomposing uric acid, which is the main cause of gout, into an excretable form, and thus has the advantage of a strong uric acid lowering effect. However, urate oxidase has limited use for treatment of gout because 1) it can only be used as an injection due to a short half-life in the body, and 2) an immune response occurs when administered to the body because it is an externally derived protein, resulting in side effects.

On the other hand, therapeutic protein has been reported to be effective in the treatment of various diseases, and it is one of the important growth motives in the pharmaceutical industry. However, there is a problem in that therapeutic protein is continuously removed by glomerular filtration, pinocytosis, and immune response in a patient's body. Therefore, when developing a therapeutic protein, it is very important to extend the duration of the drug effect by lowering the rate at which it is removed from the patient's body due to such a phenomenon. A technique for improving the half-life to solve the problem by physically or chemically binding albumin to a therapeutic protein is called albumination.

In the present description, in order to solve the above-described problems that may occur when urate oxidase is used as a therapeutic agent, a urate oxidase-albumin conjugate produced through albumination of urate oxidase is disclosed.

DISCLOSURE

Technical Problem

The present description is intended to provide a urate oxidase-albumin conjugate.

The present description is intended to provide a method of preparing the urate oxidase-albumin conjugate.

The present description is intended to provide a urate oxidase variant included in the urate oxidase-albumin conjugate.

The present description is intended to provide a method of preparing the urate oxidase variant.

The present description is intended to provide a pharmaceutical composition including the urate oxidase-albumin conjugate.

The present description is intended to provide a use of the urate oxidase-albumin conjugate.

Technical Solution

In the present description, a urate oxidase-albumin conjugate, which is represented by Formula 1: [Formula 1] Uox-$[J_1$-A-$J_2$-HSA$]_n$ in which Uox is a urate oxidase variant, $J_1$ is a urate oxidase-linker junction, A is an anchor, $J_2$ is an albumin-linker junction, HSA is human serum albumin, the urate oxidase variant includes three or more nonnatural amino acids having a diene functional group, the urate oxidase-linker junction is formed by Inverse Electron Demand Diels-Alder (IEDDA) reaction of a diene functional group of the nonnatural amino acid and a dienophile functional group connected to the anchor, and n is 3 or 4.

Provided herein is a urate oxidase-albumin conjugate including: 3 or 4 albumin-subunit conjugates represented by Formula 2: [Formula 2]p'-$J_1$-A-$J_2$-HSA, where p' is a urate oxidase variant subunit, $J_1$ is a urate oxidase-linker junction, A is an anchor, $J_2$ is an albumin-linker junction, and HSA is human serum albumin. The urate oxidase variant subunit is formed by substituting at least one amino acid in the sequence of a wild-type urate oxidase subunit with a nonnatural amino acid containing a tetrazine functional group or a triazine functional group. The urate oxidase-linker junction is formed by an inverse electron demand Diels-Alder (IEDDA) reaction between a tetrazine or triazine functional group of the nonnatural amino acid and a trans-cyclooctene functional group connected to the anchor; and Optionally, one urate oxidase variant subunit, when the urate oxidase-albumin conjugate includes three albumin-subunit complexes, and the urate oxidase-albumin conjugate includes one urate oxidase variant subunit, the urate oxidase variant subunit of each of the albumin-subunit complexes and one urate oxidase variant subunit oligomerize to form a tetramer. When the urate oxidase-albumin conjugate includes four albumin-subunit complexes, the urate oxidase-albumin conjugate includes no urate oxidase variant subunits, and the urate oxidase variant subunits of the respective albumin-subunit complexes oligomerize to form a tetramer.

The present description discloses a pharmaceutical composition for preventing or treating uric acid-related diseases, the pharmaceutical composition including: a therapeutically effective amount of the urate oxidase-albumin conjugate and a pharmaceutically acceptable carrier.

In one embodiment, the uric acid-related disease is any one of hyperuricemia, acute gouty arthritis, intermittent gout, chronic nodular gout, chronic kidney disease, and tumor lysis syndrome (TLS).

In one embodiment, the pharmaceutically acceptable carrier includes one or more selected from the followings: binders such as lactose, saccharose, sorbitol, mannitol, starch, amylopectin, cellulose or gelatin; excipients such as dicalcium phosphate and the like; disintegrants such as corn starch or sweet potato starch; lubricants such as magnesium stearate, calcium stearate, sodium stearyl fumarate or polyethylene glycol wax; sweetener; air freshener; syrup; liquid carriers such as fatty oils; sterile aqueous solution; propylene glycol; polyethylene glycol; injectable esters such as ethyl oleate; suspending agent; emulsion; freeze-dried preparations; external preparations; stabilizer; buffer; animal oil; vegetable oil; wax; paraffin; starch; tragacanth; cellulose derivatives; polyethylene glycol; silicon; bentonite; silica; talc; and zinc oxide.

The present description discloses a use of the urate oxidase-albumin conjugate as an application in preparation of a treatment agent for uric acid-related diseases.

The present description discloses a method of preparing a urate oxidase-albumin conjugate, the method including: reacting albumin and a linker, in which the linker includes a dienophile functional group, an anchor, and a thiol reactive moiety, in which the thiol reactive moiety of the linker is bound with the thiol moiety of albumin through reaction to form an albumin-linker conjugate; and reacting the albumin-linker conjugate and a urate oxidase variant, in which the urate oxidase variant is formed by substituting three or more amino acids in a sequence of a wild urate oxidase with nonnatural amino acids including a dien functional group, in which the dien functional group of the urate oxidase variant and the dienophile functional group of the albumin-linker conjugate combine through an inverse electron demand Diels-Alder (IEDDA) reaction to form a urate oxidase-albumin conjugate, in which the urate oxidase variant is characterized in that three or more albumins are bound via linkers.

The present description discloses a urate oxidase-albumin conjugate including: three or more nonnatural amino acids in a sequence thereof, in which each of the nonnatural amino acids includes a tetrazine functional group or a triazine functional group.

In one embodiment, the urate oxidase variant is a tetramer formed by oligomerization of one wild-type urate oxidase subunit and three urate oxidase variant subunits, in which each of the urate oxidase variant subunit is formed by substituting one or more amino acids in the sequence of the wild-type urate oxidase subunit with nonnatural amino acids including a tetrazine functional group or a triazine functional group.

In one embodiment, the urate oxidase variant is a tetramer formed by oligomerization of four urate oxidase variant subunits, in which each of the urate oxidase variant subunit is formed by substituting one or more amino acids in the sequence of the wild-type urate oxidase subunit with nonnatural amino acids including a tetrazine functional group or a triazine functional group.

The present description discloses a vector capable of expressing the urate oxidase variant.

The present description discloses a method of preparing a urate oxidase variant, the method including: preparing a cell line including a vector capable of expressing an orthogonal tRNA/synthetase pair and a urate oxidase variant expression vector, in which the vector capable of expressing an orthogonal tRNA/synthetase pair is a vector capable of an exogenous suppressor tRNA and an exogenous tRNA synthetase, the exogenous suppressor tRNA can recognize a specific stop codon, the exogenous tRNA synthetase can recognize a nonnatural amino acid including a tetrazine functional group and/or a triazine functional group and connect the recognized functional group to the exogenous suppressor tRNA, and the urate oxidase variant expression vector is a vector capable of expressing the urate oxidase variant, in which the location of a sequence corresponding to the nonnatural amino acid of the urate oxidase variant is a sequence part encoded by the specific stop codon; and culturing the cell line in a medium containing one or more types of nonnatural amino acid including a tetrazine functional group and/or a triazine functional group.

Advantageous Effects

According to the technical problem and the solution thereof disclosed herein, a urate oxidase-albumin conjugate is provided. The urate oxidase-albumin conjugate has improved half-life and reduced immunogenicity compared to wild-type urate oxidase, so the urate oxidase-albumin conjugate can be used as an effective therapeutic agent for uric acid-related diseases.

DESCRIPTION OF DRAWINGS

FIG. 2 is a schematic diagram illustrating a urate oxidase-albumin conjugate in which four albumin proteins are conjugated, and FIG. 3 is a schematic diagram illustrating a urate oxidase-albumin conjugate in which three albumin proteins are conjugated;

FIG. 5 shows the result of observing the cloning sequence of pTAC-Uox-W174amb (SEQ ID NO: 154);

FIG. 15 shows the SEC-HPLC analysis result of Uox-HSA;

FIG. 16 shows the PK profile results for each route of administration of Fasturtec and Uox-HSA, in which 1) Fasturtec_IV represents a profile for a case of intravenous administration (IV) of a wild-type urate oxidase, 2) Uox-HSA_IV represents a profile for a case of intravenous administration (IV) of a urate oxidase-albumin conjugate, 3) Uox-HSA_IP represents a profile for a case of intraperitoneal administration (IP) of the urate oxidase-albumin conjugate, and 4) Uox-HSA_IM represents a profile for a case of intramuscular administration (IM) of the urate oxidase-albumin conjugate.

FIG. 17 shows data of the PK profile results for each route of administration of Fasturtec and Uox-HSA, in which Fasturtec_IV, Uox-HSA_IV, Uox-HSA_IP, and Uox-HSA_IM are the same as described in FIG. 16, AVG represents the average value of each ICR mouse data (n=5), SD represents the standard deviation, AUC represents an area under curve of the PK profile result, T1/2 represents the half-life expressed in units of time, Tmax is the time when the blood concentration of the drug is the highest, and Cmax is the concentration of the drug at the time when the blood concentration of the drug is the highest;

FIG. 19 shows data of the results of a pharmacodynamic evaluation test for observation of reduction in uric acid in blood according to administration of Uox-HSA in a repeated hyperuricemia animal model, in which the negative control, Uox-HSA 1 mg/kg, Uox-HSA 4 mg/kg, Uox-HSA 10 mg/kg, Fasturtec 1.33 mg/kg, and Febuxostat 10 mg/kg are the same as described in FIG. 18, and AVG is each animal model data mean value, and SD represents the standard deviation;

FIG. 23 to FIG. 27 illustrate examples of nonnatural amino acids that can be introduced into urate oxidase variants;

FIG. 28 illustrates an example of a urate oxidase-linker junction structure and an example of a nonnatural amino acid related thereto, in which moiety (1) is linked to the remaining residue moiety of the nonnatural amino acid, and moiety (2) is linked to an anchor;

FIG. 29 illustrates an example of an anchor structure;

FIG. 30 illustrates an example of an albumin-linker junction structure, in which $J_1$ represents a urate oxidase-linker junction and $J_2$ represents an albumin-linker junction;

FIG. 31 illustrates an example of a linker structure;

BEST MODE

Figure 1:
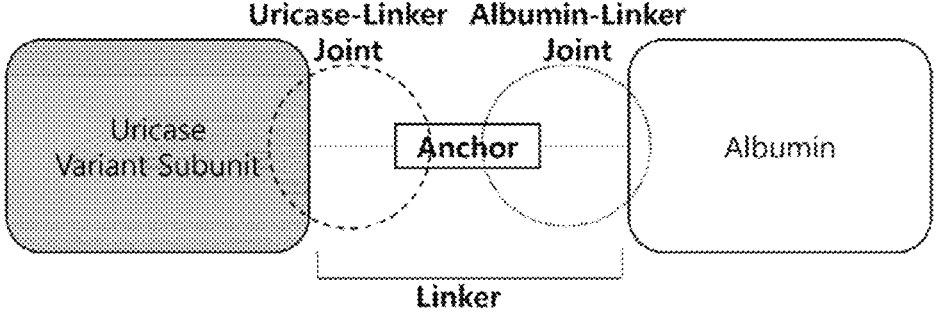
FIG. 1 schematically illustrates an albumin-subunit conjugate.
Figure 2:
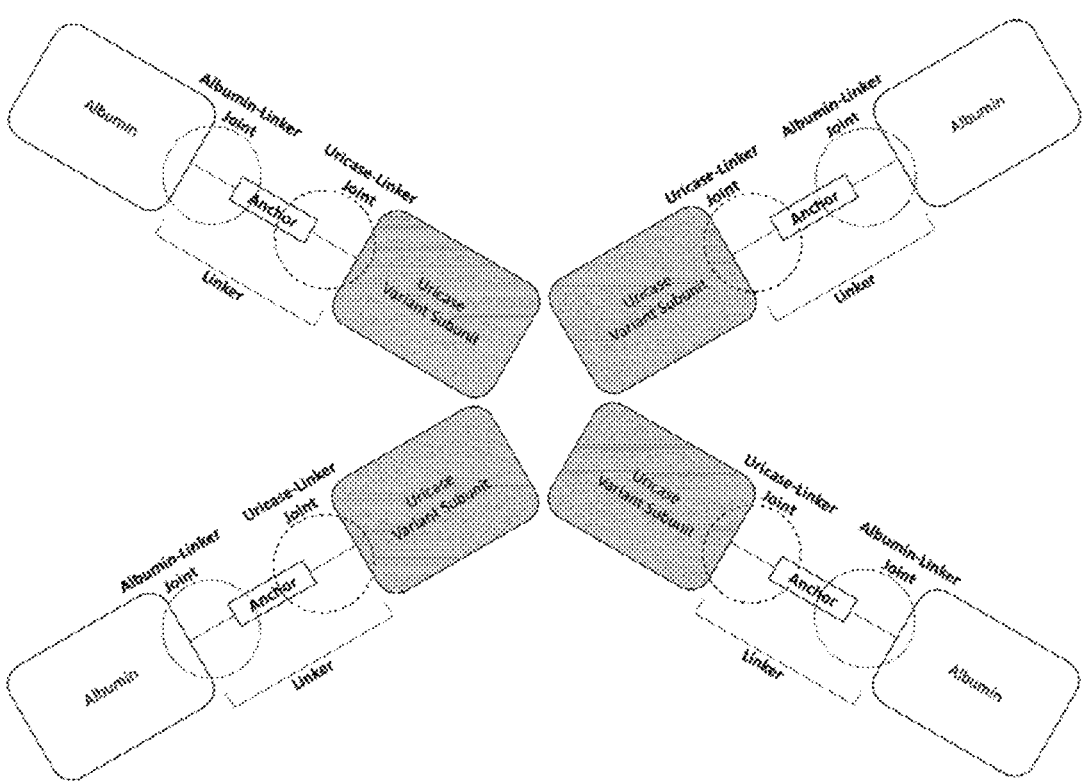
FIGS. 2 to 3 schematically illustrates an example of a urate oxidase-albumin conjugate.
Figure 3:
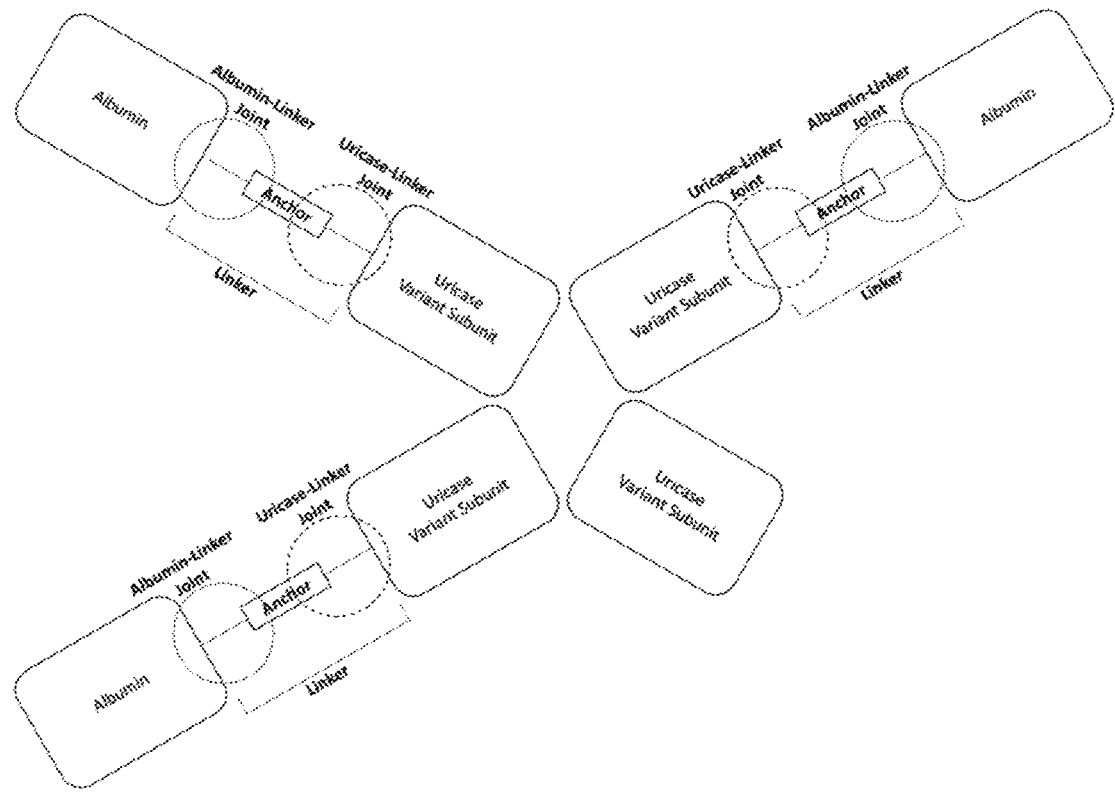

Hereinafter, with reference to the accompanying drawings, the invention will be described in more detail through specific embodiments and examples. It should be noted that the accompanying drawings include some, but not all, embodiments of the invention. The details of the invention disclosed by the present specification may be embodied in various forms and are not limited to the specific embodiments described herein. These embodiments are considered to be provided in order to satisfy the statutory requirements applicable herein. Those skilled in the art to which the invention disclosed herein pertains will come up with many modifications and other embodiments of the subject matter disclosed herein. Accordingly, it is to be understood that the subject matter disclosed herein is not limited to the specific embodiments described herein, and that modifications and other embodiments thereof also fall within the scope of the claims.

Definition of Terms

About
As used herein, the term "about" refers to a degree close to a certain quantity, and it refers to an amount, level, value, number, frequency, percent, dimension, size, amount, weight, or length that varies by to the extent of 30%, 25%, 20%, 25%, 10%, 9%, 8%, 7%, 6%, 5%, 4%, 3%, 2%, or 1% with respect to a reference amount, level, value, number, frequency, percentage, dimension, size, amount, weight, or length.

Click Chemistry
Herein, "Click Chemistry" is a term that was introduced by K. B. Sharpless in Scripps Research Institute to describe complementary chemical functional groups and chemical reactions designed such that two molecules can form a covalent bond fast and stably. The click chemistry does not mean a specific reaction but is a term for a fast and stable reaction. Click chemistry creates only byproducts that are not significant and is modular, wide in scope, high-yielding, stereospecific, biologically stable, large in thermodynamic dynamic (for example, 84 kJ/mol or more), and high in atomic economy. Example of the click chemistry include 1)

Huisgen 1,3-dipolar cycloaddition (see Tomoe et al. Journal of Organic Chemistry (2002) 67: 3075-3064, etc.), 2) Diels-Alder reaction, 3) Nucleophilic addition to small strained rings such as epoxide and aziridine, 4) a nucleophilic addition reaction to an activated carbonyl group, and 5) an addition reaction to a carbon-carbon double bond or triple bond. The meaning of the click chemistry should be appropriately interpreted according to the context, and the click chemistry includes all other meanings that can be recognized by those skilled in the art.

Bioorthogonal Reaction

Herein, the term "bioorthogonal reaction" refers to any chemical reaction in which externally introduced residues react with each other without interfering with native biochemical processes. When a certain reaction is "bioorthogonal", the reaction has a characteristic that it is very stable in the body because in vivo intrinsic molecules are not involved in the reaction or reaction product.

Standard Amino Acid

As used herein, the term "standard amino acid" refers to 20 amino acids synthesized through the transcription and translation processes of genes in the body of an organism. Specifically, the standard amino acid includes alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys K), methionine (Met, M), phenylalanine (Phe, F), proline (Pro, P), serine (Ser, S), threonine (Thr, T), tryptophan (Trp, W), tyrosine (Tyr, Y), and valine (Val, V). The standard amino acid has a corresponding DNA codon and can be represented by a general one-letter or three-letter notation of an amino acid. The subjects being referred to by the term standard amino acid should be appropriately interpreted according to the context, and they include all other meanings that can be recognized by those skilled in the art.

Nonnatural Amino Acid

As used herein, the term "nonnatural amino acid" refers to an amino acid that is not synthesized in the body but synthesized artificially. The nonnatural amino acid includes, for example, 4-(1,2,3,4-tetrazin-3-yl) phenylalanine, and 4-(6-methyl-s-tetrazin-3-yl)phenylalanine. Since the nonnatural amino acid does not have a corresponding DNA codon, it cannot be represented by a general one-letter or three-letter notation of an amino acid, and it is written using other characters and explained via additional explanation. The subjects being referred to by the term nonnatural amino acids should be appropriately interpreted according to the context, and they include all other meanings that can be recognized by those skilled in the art.

Description of Peptide Sequence

Unless otherwise stated, when describing the sequence of a peptide in the present specification, single letter notation or three letter notation of an amino acid is used, and it is written in the direction from the N-terminus to the C-terminus. For example, when expressed as RNVP, it refers to a peptide in which arginine, asparagine, valine, and proline are sequentially linked in the direction from the N-terminus to the C-terminus. For another example, when expressed as Thr-Leu-Lys, it refers to a peptide in which threonine, leucine, and lysine are sequentially linked in the direction from the N-terminus to the C-terminus. In the case of amino acids that cannot be represented by the one-letter or three-letter notation, other letters are used to describe these amino acids, and will be explained via additional explanation.

Inmunogenicity

As used herein, the term "immunogenicity" collectively refers to "the property of acting as an antigen capable of inducing an immune response" in the dictionary. There are various methods for measuring the immunogenicity of a specific antigen, and the methods may be appropriately adopted or designed according to the purpose. For example, the methods may include 1) a method for confirming whether IgG, IgA, and/or IgE type antibodies are generated in the body of a subject when the antigen is administered into the body of the subject, 2) a method for confirming the time when the IgG, IgA, and/or IgE type antibodies are generated depending on the administration cycle, 3) a method for confirming the titer of the induced antibodies to the antigen, and 4) when the mechanism of action of the induced antibodies is found, a method for measuring the effect according to the mechanism of action, but the methods are not limited thereto. The subjects being referred to by the term immunogenicity should be appropriately interpreted according to the context, and they include all other meanings that can be recognized by those skilled in the art.

Mechanism of Treatment of Gout by Urate Oxidase

Causes of Gout

Gout arthritis is caused by an inflammatory reaction to monosodium urate monohydrate crystals (MSU) secondary to hyperuricemia, which is a symptom in which blood uric acid concentration is higher than the normal range. Gout is caused by accumulation of uric acid in the body due to overproduction of uric acid in the liver and small intestine and/or decreased excretion of uric acid. Gout usually starts with hyperuricemia, goes through acute gouty arthritis, then goes through intermittent gout, and progresses to chronic nodular gout.

Mechanism of Treatment of Gout by Urate Oxidase

Urate oxidase (Uricase) is a type of enzyme that cannot be synthesized in primates including humans, and it functions to break down uric acid into allantoin. The allantoin has a solubility 5 to 10 times higher than that of uric acid, so it is easy to be excreted by the kidneys. Therefore, when urate oxidase is used as a therapeutic agent, it is possible to treat gout by preventing the accumulation of uric acid, which is the main cause of gout, and by excreting uric acid from the body.

Limitations of Urate Oxidase as a Therapeutic Agent for Gout

The urate oxidase has a direct therapeutic mechanism for decomposing uric acid, which is the main cause of gout, into an excretable form, and thus has the advantage of having a strong uric acid lowering effect. However, since the urate oxidase is a protein drug, 1) it can be used only as an injection due to its short half-life in the body. In addition, 2) since it is an externally-derived protein, an immune response occurs when administered into the body, resulting in side effects. Therefore, there are restrictions on its use as a therapeutic agent for gout.

Limitations of Conventional Art

Limitations of Commercially Available Urate Oxidase-Based Drugs

In a urate oxidase-based drug (KRYSTEXXA; pegloticase) currently available on the market, polyethylene glycol (PEG) is randomly bound to a urate oxidase to improve the short half-life which is a restriction factor of the urate oxidase. However, it has limitations in that 1) the urate oxidase is randomly pegylated, blocking the active site of the enzyme, resulting in reduction in efficacy, and 2) the PEG has a side effect of causing an allergic reaction in the body.

Limitations of Conventional Urate Oxidase-Albumin Conjugate Technology

The inventors have disclosed a urate oxidase-albumin conjugate in the literature "KR 1637010 B1". The urate oxidase-albumin conjugate disclosed in the literature replaces one or more amino acids of a urate oxidase with a nonnatural amino acid and conjugates the urate oxidase with albumin using a linker having a dibenzocyclooctyne (DBCO) reactive group. However, the urate oxidase-albumin conjugate disclosed in the literature has a problem that the yield is very low due to the slow speed of the strain-promoted cycloaddition (SPAAC), which is the binding reaction of AzF and DBCO at the junction. Therefore, in the urate oxidase-albumin conjugate disclosed in the literature, despite the fact that there are at least four sites for albumin conjugation in a urate oxidase, there is a limitation in that only urate oxidase-albumin conjugates in which one or two albumins are conjugated per one urate oxidase can be obtained due to the inefficiency of the SPAAC reaction. Due to the limitations described above, the urate oxidase-albumin conjugate disclosed in the literature has problems in that 1) the effect of albumin conjugation, including an increase in the half-life or reduction in immunogenicity, is limited, 2) unexpected reactions may be occurred in the body due to exposure of the residue of AzF to which albumin is not conjugated.

Urate Oxidase-Albumin Conjugate

Overview of Urate Oxidase-Albumin Conjugate

Disclosed herein is a urate oxidase-albumin conjugate. The urate oxidase-albumin conjugate is a structure in which a urate oxidase variant and albumin are linked through a linker. The urate oxidase-albumin conjugate is characterized in that three or more albumins are conjugated to the urate oxidase variant through the linker. The urate oxidase variant is obtained by substituting at least one amino acid in the sequence of a wild-type urate oxidase with a nonnatural amino acid, and the linker and the albumin are bound through the residue of the nonnatural amino acid. Specifically, the urate oxidase-albumin conjugate includes: a urate oxidase variant; a urate oxidase-linker junction formed by conjugation of a urate oxidase variant and a linker; an anchor contained within the linker; an albumin-linker junction formed by conjugation of albumin and a linker; and albumin. Hereinafter, each component (urate oxidase variant, albumin, and linker) and the structure of the urate oxidase-albumin conjugate resulting from conjugation of the components will be described in more detail.

Component 1 of Urate Oxidase-Albumin Conjugate—Urate Oxidase Variant

Urate oxidase is an enzyme that has the function of decomposing uric acid into allantoin in the body, and can be used to treat various diseases or disorders caused by the accumulation of uric acid. The urate oxidase is a tetramer formed by oligomerization of four urate oxidase subunits. The urate oxidase-albumin conjugate disclosed herein includes a urate oxidase variant, which is one or more amino acids are substituted with an nonnatural amino acid, from a wild-type urate oxidase sequence. Specifically, the urate oxidase variant is a tetrameric protein which means that three or four subunits among the four subunits are urate oxidase variant subunits. In this case, the sequence of the urate oxidase variant subunit is what one or more amino acids are substituted with nonnatural amino acids, compared to the sequence of wild-type urate oxidase subunit. The purpose of creating a urate oxidase variant by inserting a nonnatural amino acid into a wild urate oxidase is to bind a moiety of the nonnatural amino acid to a linker through a reverse electron-demand Diels-Alder reaction (IEDDA reaction).

Component 2 of Urate Oxidase-Albumin Conjugate—Albumin

The albumin refers to human serum albumin and/or a variant of human serum albumin, and serves as a drug carrier for the urate oxidase variant. The albumin allows the urate oxidase-albumin conjugate to exhibit improved in vivo half-life and low immunogenicity compared to the case where the urate oxidase variant is present alone.

Component 3 of Urate Oxidase-Albumin Conjugate—Linker

The linker binds the urate oxidase variant to the albumin, and includes an IEDDA reactive group capable of binding to the urate oxidase variant, a thiol reactive group capable of binding to albumin, and an anchor. In the urate oxidase-albumin conjugate, the IEDDA reactive group and the thiol reactive group are bound to the urate oxidase variant and the albumin, respectively. Therefore, the IEDDA reactive group and the thiol reactive group do not exist in original forms but exist in modified forms such as a urate oxidase-linker junction and an albumin-linker junction.

Urate Oxidase-Albumin Conjugate 1—Subunit-Albumin Conjugate

The urate oxidase variant of the urate oxidase-albumin conjugate disclosed herein is a tetramer formed by oligomerization of four subunits, in which three or more of the subunits are conjugated to albumin through linkers. Among the subunits constituting the urate oxidase variant, the subunit conjugated to albumin through a linker is referred to as a subunit-albumin conjugate. The urate oxidase variant of the urate oxidase-albumin conjugate includes three or more urate oxidase variant subunits. In this case, some or all of the urate oxidase variant subunits are each a subunit-albumin conjugate in which the subunit is conjugated with albumin.

Urate Oxidase-Albumin Conjugate 2—Urate oxidase-Linker Junction

The urate oxidase-albumin conjugate disclosed herein is one in which a urate oxidase variant and albumin are conjugated through a linker. In this case, the portion where the urate oxidase variant and the linker are joined is called a urate oxidase-linker junction. The urate oxidase variant and the linker are characterized in that they are conjugated through an IEDDA reaction.

Urate Oxidase-Albumin Conjugate 3—Albumin-Linker Junction

The urate oxidase-albumin conjugate disclosed herein is one in which a urate oxidase variant and albumin are conjugated through a linker. In this case, the portion where the albumin and the linker are joined is called an albumin-linker junction.

Urate Oxidase-Albumin Conjugate 4—Anker

The linker includes an IEDDA reactive group capable of being conjugated to the urate oxidase variant, and a thiol reactive group capable of being conjugated to albumin, and an anchor that links the reactive groups to each other. Since the anchor is a part not involved in the reaction for linking the urate oxidase and the albumin, it is characterized in that the structure of the anchor remains unchanged in the urate oxidase-albumin conjugate.

Urate Oxidase-Albumin Conjugate Example 1—from Perspective of Urate Oxidase-Linker In one embodiment, the urate oxidase-albumin conjugate is represented by Formula 1 below:

$$Uox\text{-}[J_1\text{-}A\text{-}J_2\text{-}HSA]_n \qquad \text{[Formula 1]}$$

in which Uox is a urate oxidase variant,
$J_1$ is a urate oxidase-linker junction,
A is an anchor,
$J_2$ is an albumin-linker junction,
HSA is Human Serum Albumin, and
n is 3 or 4.

Urate Oxidase-Albumin Conjugate Example 2—from Perspective of Urate Oxidase-Linker In one embodiment, the subunit-albumin conjugate is represented by Formula 2 below:

$$p'\text{-}J1\text{-}A\text{-}J2\text{-}HSA \qquad \text{[Formula 2]}$$

In Formula 2, p' is a urate oxidase variant subunit, and the other parts are the same as defined above.

In one embodiment, the urate oxidase-albumin conjugate includes one wild urate oxidase subunit and three subunit-albumin conjugates. Specifically, in the urate oxidase-albumin conjugate, one wild urate oxidase subunit and three urate oxidase variant subunits included in each of the subunit-albumin conjugates oligomerize to form a tetramer.

In one embodiment, the urate oxidase-albumin conjugate includes one urate oxidase variant subunit and three subunit-albumin conjugates. Specifically, in the urate oxidase-albumin conjugate, one urate oxidase variant subunit and three urate oxidase variant subunits included in the respective subunit-albumin conjugates oligomerize to form a tetramer.

In one embodiment, the urate oxidase-albumin conjugate includes four subunit-albumin conjugates. Specifically, in the urate oxidase-albumin conjugate, the four urate oxidase urate oxidase variant subunits included in the respective subunit-albumin conjugates oligomerize to form a tetramer.

Characteristic of Urate Oxidase-Albumin Conjugate 1—Effect of Increase in Half-Life Through Albumin Conjugation As described above, when albumin is bound to a drug molecule, there is an effect of increasing the half-life of the drug in the body. The urate oxidase-albumin conjugate disclosed herein is characterized in that the half-life of a urate oxidase, which is a therapeutic protein, in the body is increased by conjugating albumin to the urate oxidase. The improved half-life in the body can be confirmed through a pharmacokinetics profile experiment after the urate oxidase-albumin conjugate is administered to the body, and can be confirmed in Experimental Example 4.

Characteristic of Urate Oxidase-Albumin Conjugate 2—not Inhibiting Activity of Urate Oxidase One of the limitations of the conventional art is that a drug carrier, for example, albumin, or polyethylene glycol (PEG), etc. is bound to a urate oxidase to increase efficacy, but the three-dimensional structure of the drug carrier inhibits the activity by blocking the active site of the urate oxidase, thereby reducing the drug efficacy. The urate oxidase-albumin conjugate disclosed in the present description is characterized in that albumin is site-specifically bound to a moiety that does not inhibit the activity of the urate oxidase, thereby not reducing drug efficacy.

Characteristic of Urate Oxidase-Albumin Conjugate 3—Immunogenicity Reduction Effect It is known that humans do not produce urate oxidase, and thus urate oxidase mainly used for treatment is an enzyme derived from microorganisms. Since such urate oxidase is a foreign protein derived from microorganisms, when administered solely in the body, the urate oxidase causes an immune response, resulting in side effects. Therefore, it is an important task to reduce the immunogenicity of the urate oxidase. The urate oxidase-albumin conjugate disclosed in the present description is characterized in that the immunogenicity of urate oxidase is reduced by conjugating the urate oxidase with albumin, which is a human plasma protein. The albumin is a protein constituting most of the plasma, is very stable in the human body, and hardly exhibits immunogenicity. Therefore, the urate oxidase-albumin conjugate exhibits significantly low immunogenicity compared to a case where urate oxidase is solely administered into the body.

Characteristic of Urate Oxidase-Albumin Conjugate 4—Three or Four Albumins in Urate Oxidase The conventional urate oxidase-albumin conjugate technology linked a urate oxidase variant and an albumin through a strain-promoted Alkyne-Azide Cycloaddition reaction (SPAAC reaction). The SPAAC reaction has a limitation in that it can produce a urate oxidase-albumin conjugate in which only one or two albumins are bound to a urate oxidase variant due to a relatively slow reaction rate and low yield. The urate oxidase-albumin conjugate provided herein is characterized in that three or more albumins are conjugated to one urate oxidase variant because the conjugation occurs through an IEDDA reaction which enables fast reaction between urate oxidase variants and albumins, resulting in high yield. Due to the characteristics described above, 1) the half-life improvement effect and the immunogenicity reduction effect of the urate oxidase-albumin conjugate can be maximized, and 2) the exposure of residues of nonnatural amino acids is minimized, resulting in side effects being minimized.

Urate Oxidase Variant

Overview of Urate Oxidase Variant
The urate oxidase variant included in the urate oxidase-albumin conjugate disclosed herein is characterized in that a portion of the sequence of amino acid of a wild urate oxidase derived from a microorganism is modified. The urate oxidase variant contains three or more nonnatural amino acids, and can be site-specifically conjugated to albumins through the moiety of each of the nonnatural amino acids. Specifically, the urate oxidase variant is a tetramer formed by oligomerization of four urate oxidase variant subunits, and each urate oxidase variant subunit is characterized in that at least one amino acid in the sequence thereof is substituted with at least one nonnatural amino acid when compared with a wild urate oxidase subunit.

Microorganisms from which Wild Urate Oxidase is Derived
The wild urate oxidase, which is the prototype of the urate oxidase variant provided herein, is derived from a microorganism. In one embodiment, the wild urate oxidase may be a urate oxidase derived from a microorganism selected from *Aspergillus Flavus, Arthrobacter globiformis*, and *Candidas Utilis*.

Exemplary Sequence of Wild Urate Oxidase

The wild urate oxidase is a tetramer protein in which four wild urate oxidase subunits that are the same are oligomerized.

In one embodiment, when the wild urate oxidase is a urate oxidase derived from *Aspergillus Flavus*, the peptide sequence of the subunit may be

```
                                      (SEQ ID NO: 1)
SAVKAARYGKDNVRVYKVHKDEKTGVQTVYEMTVCVLLEGEIETSYTKAD

NSVIVATDSIKNTIYITAKQNPVTPPELFGSILGTHFIEKYNHIHAAHVN

IVCHRWTRMDIDGKPHPHSFIRDSEEKRNVQVDVVEGKGIDIKSSLSGLT

VLKSTNSQFWGFLRDEYTTLKETWDRILSTDVDATWQWKNFSGLQEVRSH

VPKFDATWATAREVTLKTFAEDNSASVQATMYKMAEQILARQQLIETVEY

SLPNKHYFEIDLSWHKGLQNTGKNAEVFAPQSDPNGLIKCTVGRSSLKSK

L
``` from the N-terminus to the C-terminus.

In another embodiment, when the wild urate oxidase is a urate oxidase derived from *Candida Utilis*, the peptide sequence of the subunit may be

```
                                      (SEQ ID NO: 51)
MSTTLSSSTYGKDNVKFLKVKKDPQNPKKQEVMEATVTCLLEGGFDTSYTEADNSSIVPTDTV

KNTILVLAKTTEIWPIERFAAKLATHFVEKYSHVSGVSVKIVQDRWVKYAVDGKPHDHSFIHE

GGEKRITDLYYKRSGDYKLSSAIKDLTVLKSTGSMFYGYNKCDFTTLQPTTDRILSTDVDATW

VWDNKKIGSVYDIAKAADKGIFDNVYNQAREITLTTFALENSPSVQATMFNMATQILEKACSV

YSVSYALPNKHYFLIDLKWKGLENDNELFYPSPHPNGLIKCTVVRKEKTKL
``` from the N-terminus to the C-terminus.

In a further embodiment, when the wild urate oxidase is a urate oxidase derived from *Arthrobacter globiformis*, the peptide sequence of the subunit may be

```
                                      (SEQ ID NO: 118)
MTATAETSTGTKVVLGQNQYGKAEVRLVKVTRNTARHEIQDLNVTSQLRGDFEAAHTAGDN

AHVVATDTQKNTVYAFARDGFATTEEFLLRLGKHFTEGFDWVTGGRWAAQQFFWDRINDHD

HAFSRNKSEVRTAVLEISGSEQAIVAGIEGLTVLKSTGSEFHGFPRDKYTTLQETTDRILATDVS

ARWRYNTVEVDFDAVYASVRGLLLKAFAETHSLALQQTMYEMGRAVIETHPEIDEIKMSLPN

KHHFLVDLQPFGQDNPNEVFYAADRPYGLIEATIQREGSRADHPIWSNIAGFC
``` from the N-terminus to the C-terminus.

Urate Oxidase Variant Subunit

Like the wild urate oxidase, the urate oxidase variant is also a tetrameric protein including four subunits. The urate oxidase variant includes 3 or 4 urate oxidase variant subunits, and the urate oxidase variant subunit is a subunit formed by substituting one or more original amino acids with nonnatural amino acids, in a wild-type urate oxidase subunit. In one embodiment, the urate oxidase variant may include three urate oxidase variant subunits and one wild urate oxidase subunit. In another embodiment, the urate oxidase variant may include four urate oxidase variant subunits. A more specific description will be provided in the section titled "Urate Oxidase Variant Subunit".

Urate Oxidase Variant Preparation Method

The present description discloses a method of preparing the urate oxidase variant. The urate oxidase variant includes one or more unnatural amino acids. However, in nature, nucleic acid codons corresponding to unnatural amino acids do not exist. In order to biosynthesize a protein containing such a nonnatural amino acid in a cell, it is necessary to solve the problem that there is no nucleic acid codon corresponding to a nonnatural amino acid. Literature "Korean Patent No. 1637010 B1" discloses a method for effectively solving this problem by using the fact that three types of stop codons used in nature does not encode an amino acid. The urate oxidase variant preparation method refers to the method disclosed in the literature "KR 1637010 B1". In the method, 1) an orthogonal tRNA/synthetase pair having a function of recognizing a stop codon and introducing a nonnatural amino acid into the sequence is used, and 2) a nucleic acid encoding a nonnatural amino acid site in the sequence of a urate oxidase variant with a stop codon is used. A more specific description will be provided in the section titled "Urate Oxidase Variant Preparation Method".

Vector Encoding Urate Oxidase Variant

The present description discloses a vector encoding a urate oxidase variant used in the urate oxidase variant preparation method. The vector encoding the urate oxidase variant is characterized in that in a nucleic acid sequence encoding a wild-type urate oxidase, a nucleic acid codon at a position at which the nucleic acid is to be substituted with a nonnatural amino acid is changed to a stop codon. A more specific description will be provided in the section titled "Vector Encoding Urate Oxidase Variant".

Urate Oxidase Variant Subunit

Urate Oxidase Variant Subunit 1—Substitution with Nonnatural Amino Acid

The urate oxidase variant subunit includes at least one nonnatural amino acid, and the nonnatural amino acid has a functional group capable of being bound to a linker through an IEDDA reaction. In one embodiment, the nonnatural amino acid may be an amino acid including a dien functional group capable of causing an IEDDA reaction. Specifically, the dien functional group may be a tetrazine functional group or a derivative thereof and/or a triazine functional group or a derivative thereof. More specifically, the non-natural amino acid may be selected from the group consisting of 4-(1,2,3,4-tetrazin-3-yl) phenylalanine (frTet), 4-(6-methyl-s-tetrazin-3-yl)phenylalanine (Tet-v2.0), 3-(4-(1,2,4-triazin-6-yl)phenyl)-2-aminopropanoic acid, 2-amino-3-(4-(2-(6-methyl-1,2,4,5-tetrazin-3-yl)ethyl)phenyl) propanoic acid, 2-amino-3-(4-(6-phenyl-1,2,4,5-tetrazin-3-yl)phenyl)propanoic acid, 3-(4-((1,2,4,5-tetrazin-3-yl)amino)phenyl)-2-aminopropanoic acid, 3-(4-(2-(1,2,4,5-tetrazin-3-yl)ethyl)phenyl)-2-aminopropanoic acid, 3-(4-((1,2,4,5-tetrazin-3-yl)thio)phenyl)-2-aminopropanoic acid, 2-amino-3-(4-((6-methyl-1,2,4,5-tetrazin-3-yl)thio)phenyl) propanoic acid, 3-(4-((1,2,4,5-tetrazin-3-yl)oxy)phenyl)-2-aminopropanoic acid, 2-amino-3-(4-((6-methyl-1,2,4,5-tetrazin-3-yl)oxy)phenyl)propanoic acid, 3-(4'-(1,2,4,5-tetrazin-3-yl)-[1,1'-biphenyl]-4-yl)-2-aminopropanoic acid, 2-amino-3-(4'-(6-methyl-1,2,4,5-tetrazin-3-yl)-[1,1'-biphenyl]-4-yl)propanoic acid, 2-amino-3-(6-(6-(pyridin-2-yl)-1,2,4,5-tetrazin-3-yl)pyridin-3-yl)propanoic acid, 3-(4-(1,2,4,5-tetrazin-3-yl)phenyl)-2-aminopropanoic acid, and 2-amino-3-(4-(6-methyl-1,2,4,5-tetrazin-3-yl)phenyl)propanoic acid.

Urate Oxidase Variant Subunit 2—Example of Nonnatural Amino Acid

In one embodiment, the nonnatural amino acid may be selected from the following:

[UAA01]

[UAA02]

[UAA03]

16

-continued

[UAA04]

[UAA05]

[UAA06]

[UAA07]

[UAA08][UAA09]

R = H or CH₃

-continued

[UAA10][UAA11]

R = H or CH₃

[UAA12][UAA13]

R = H or CH₃

, and

[UAA14]

.

Urate Oxidase Variant Subunit 3—Substitution Site

When a urate oxidase variant is formed by inserting a nonnatural amino acid into a wild urate oxidase, the structure and function of the original urate oxidase should not be affected as much as possible. Therefore, an amino acid that plays an important role in the activity and structure of a urate oxidase cannot be substituted with a nonnatural amino acid. In addition, since the nonnatural amino acid needs to bind to the linker during the preparation of the urate oxidase-albumin conjugate, it is advantageous to substitute the amino acid at a position with relatively high accessibility to a solvent, in the three-dimensional structure of the urate oxidase. Various methods can be used to select sites with high solvent accessibility while minimally affecting the structure and function of the wild urate oxidase. For example, molecular modeling calculations can select candidate sites that are similar in intrinsic atomic energy to the wild urate oxidase and which are high in solvent accessibility.

In one embodiment, the site for substitution with a nonnatural amino acid in the sequence of the wild urate oxidase to make a urate oxidase variant may be determined by referring to molecular modeling simulation results. Specifically, the molecular modeling simulation result may be a scoring result of the Rosetta molecular modeling package.

Urate Oxidase Variant Subunit 4—Example of Substitution Site

In one embodiment, the urate oxidase variant subunit may be one in which one or more amino acids selected from the following are substituted with one or more nonnatural amino acids: glycine at position 137, glutamic acid at position 22, asparagine at position 92, lysine at position 23, serine at position 295, glycine at position 113, lysine at position 273, lysine at position 171, alanine at position 240, glutamic acid at position 89, lysine at position 266, threonine at position 24, lysine at position 48, serine at position 192, proline at position 202, aspartic acid at position 110, glutamine at position 243, glutamine at position 195, lysine at position 138, proline at position 115, serine at position 199, glycine at position 272, lysine4, aspartic acid at position 112, glycine at position 267, lysine at position 114, glutamine at position 70, tryptophan at position 174, asparagine at position 223, glutamic acid at position 41, aspartic acid at position 261, glycine at position 25, serine at position 52, arginine at position 241, glutamic acid at position 213, asparagine at position 274, glutamic acid at position 221, alanine at position 206, glutamic acid at position 236, arginine at position 164, glutamine at position 269, glutamic acid at position 136, glutamic acid at position 259, glutamic acid at position 246, alanine at position 49, glycine at position 148, histidine at position 19, serine at position 296, and threonine at position 47 of the peptide sequence of SEQ ID NO: 1.

In one embodiment, the urate oxidase variant subunit may be one in which one or more amino acids selected from the following are substituted with one or more nonnatural amino acids: threonine at position 301, asparagine at position 26, leucine at position 303, lysine at position 194, serine at position 95, serine at position 140, glycine at position 116, lysine at position 302, lysine at position 167, aspartic acid at position 115, glutamic acid, proline at position 24, tryptophan at position 271, aspartic acid at position 277, aspartic acid at position 169, proline at position 118, threonine at position 177, glutamine at position 174, lysine at position 208, glutamic acid at position 275, leucine at position 266, glycine at position 273, tyrosine at 200, glutamic acid at position 92, glutamic acid at position 247, leucine at position 228, lysine at position 300, lysine at position 204, glutamic acid at position 51, aspartic acid at position 207, lysine at position 117, cysteine at position 250, proline at position 175, lysine at position 270, aspartic acid at position 268, glycine at position 44, asparagine at position 193, glycine at position 164, threonine at position 73, lysine at 29, asparagine at position 230, glutamine at position 25, asparagine at position 216, Serine at position 55, lysine at position 28, serine at position 6, proline at position 27, lysine at position 298, alanine at position 113, asparagine at position 213, glutamic acid at position 220, glycine at position 141, tyrosine at position 163, tyrosine at position 253, aspartic acid at position 178, lysine at position 93, lysine at position 103, lysine at position 144, arginine at position 139, lysine at position 138, serine7, aspartic acid at position 151, arginine at position 297, lysine at position 272, asparagine at position 278, and phenylalanine at position 265 of the peptide sequence of SEQ ID NO: 51.

In one embodiment, the urate oxidase variant subunit may be one in which one or more amino acids selected from the following are substituted with one or more nonnatural amino acids: aspartic acid at position 80, phenylalanine at position 82, phenylalanine at position 100, aspartic acid at position 101, phenylalanine at position 114, asparagine at position 119, aspartic acid at position 120, serine at position 142, glutamic acid at position 143, glycine at position 175, valine at position 195, glutamic acid at position 196, histidine at position 218, and proline at position 238 of the peptide sequence of SEQ ID NO: 118.

Urate Oxidase Variant Subunit 5—Exemplary Sequence

In one embodiment, when the urate oxidase variant is obtained by partially modifying the sequence of a urate oxidase derived from *Aspergillus Flavus*, the urate oxidase variant subunit may be represented by SEQ ID NOs: 2 to 50. In this case, X in the sequence may be selected from the group consisting of 4-(1,2,4,5-tetrazin-3-yl) phenylalanine (frTet), 4-(6-methyl-s-tetrazin-3-yl)phenylalanine (Tet-v2.0), 3-(4-(1,2,4-triazin-6-yl)phenyl)-2-aminopropanoic acid, 2-amino-3-(4-(2-(6-methyl-1,2,4,5-tetrazin-3-yl)ethyl) phenyl)propanoic acid, 2-amino-3-(4-(6-phenyl-1,2,4,5-tetrazin-3-yl)phenyl)propanoic acid, 3-(4-((1,2,4,5-tetrazin-3-yl)amino)phenyl)-2-aminopropanoic acid, 3-(4-(2-(1,2,4,5-tetrazin-3-yl)ethyl)phenyl)-2-aminopropanoic acid, 3-(4-((1,2,4,5-tetrazin-3-yl)thio)phenyl)-2-aminopropanoic acid, 2-amino-3-(4-((6-methyl-1,2,4,5-tetrazin-3-yl)thio)phenyl) propanoic acid, 3-(4-((1,2,4,5-tetrazin-3-yl)oxy)phenyl)-2-aminopropanoic acid, 2-amino-3-(4-((6-methyl-1,2,4,5-tetrazin-3-yl)oxy)phenyl)propanoic acid, 3-(4'-(1,2,4,5-tetrazin-3-yl)-[1,1'-biphenyl]-4-yl)-2-aminopropanoic acid, 2-amino-3-(4'-(6-methyl-1,2,4,5-tetrazin-3-yl)-[1,1'-biphenyl]-4-yl)propanoic acid, 2-amino-3-(6-(6-(pyridin-2-yl)-1, 2,4,5-tetrazin-3-yl)pyridin-3-yl)propanoic acid, 3-(4-(1,2,4, 5-tetrazin-3-yl)phenyl)-2-aminopropanoic acid, 및 2-amino-3-(4-(6-methyl-1,2,4,5-tetrazin-3-yl)phenyl)propanoic acid.

In one embodiment, when the urate oxidase variant is a variant obtained by partially modifying the sequence of a urate oxidase derived from *Candida Utilis*, the urate oxidase variant subunit may be represented by SEQ ID NOs: 52 to 117. In this case, X in the sequence may be selected from the group consisting of 4-(1,2,4,5-tetrazin-3-yl) phenylalanine (frTet), 4-(6-methyl-s-tetrazin-3-yl)phenylalanine (Tet-v2.0), 3-(4-(1,2,4-triazin-6-yl)phenyl)-2-aminopropanoic acid, 2-amino-3-(4-(2-(6-methyl-1,2,4,5-tetrazin-3-yl)ethyl) phenyl)propanoic acid, 2-amino-3-(4-(6-phenyl-1,2,4,5-tetrazin-3-yl)phenyl)propanoic acid, 3-(4-((1,2,4,5-tetrazin-3-yl)amino)phenyl)-2-aminopropanoic acid, 3-(4-(2-(1,2,4,5-tetrazin-3-yl)ethyl)phenyl)-2-aminopropanoic acid, 3-(4-((1,2,4,5-tetrazin-3-yl)thio)phenyl)-2-aminopropanoic acid, 2-amino-3-(4-((6-methyl-1,2,4,5-tetrazin-3-yl)thio)phenyl) propanoic acid, 3-(4-((1,2,4,5-tetrazin-3-yl)oxy)phenyl)-2-aminopropanoic acid, 2-amino-3-(4-((6-methyl-1,2,4,5-tetrazin-3-yl)oxy)phenyl)propanoic acid, 3-(4'-(1,2,4,5-tetrazin-3-yl)-[1,1'-biphenyl]-4-yl)-2-aminopropanoic acid, 2-amino-3-(4'-(6-methyl-1,2,4,5-tetrazin-3-yl)-[1,1'-biphenyl]-4-yl)propanoic acid, 2-amino-3-(6-(6-(pyridin-2-yl)-1, 2,4,5-tetrazin-3-yl)pyridin-3-yl)propanoic acid, 3-(4-(1,2,4, 5-tetrazin-3-yl)phenyl)-2-aminopropanoic acid, 및 2-amino-3-(4-(6-methyl-1,2,4,5-tetrazin-3-yl)phenyl)propanoic acid.

In one embodiment, when the urate oxidase variant is obtained by partially modifying the sequence of a urate oxidase derived from *Arthrobacter globiformis*, the urate oxidase variant subunit may be represented by SEQ ID NOs: 119 to 132. In this case, X in the sequence may be selected from the group consisting of 4-(1,2,4,5-tetrazin-3-yl) phenylalanine (frTet), 4-(6-methyl-s-tetrazin-3-yl)phenylalanine (Tet-v2.0), 3-(4-(1,2,4-triazin-6-yl)phenyl)-2-aminopropanoic acid, 2-amino-3-(4-(2-(6-methyl-1,2,4,5-tetrazin-3-yl)ethyl)phenyl)propanoic acid, 2-amino-3-(4-(6-phenyl-1,2,4,5-tetrazin-3-yl)phenyl)propanoic acid, 3-(4-((1,2,4,5-tetrazin-3-yl)amino)phenyl)-2-aminopropanoic acid, 3-(4-(2-(1,2,4,5-tetrazin-3-yl)ethyl)phenyl)-2-aminopropanoic acid, 3-(4-((1,2,4,5-tetrazin-3-yl)thio)phenyl)-2-aminopropanoic acid, 2-amino-3-(4-((6-methyl-1,2,4,5-tetrazin-3-yl) thio)phenyl)propanoic acid, 3-(4-((1,2,4,5-tetrazin-3-yl)

oxy)phenyl)-2-aminopropanoic acid, 2-amino-3-(4-((6-methyl-1,2,4,5-tetrazin-3-yl)oxy)phenyl)propanoic acid, 3-(4'-(1,2,4,5-tetrazin-3-yl)-[1,1'-biphenyl]-4-yl)-2-aminopropanoic acid, 2-amino-3-(4'-(6-methyl-1,2,4,5-tetrazin-3-yl)-[1,1'-biphenyl]-4-yl)propanoic acid, 2-amino-3-(6-(6-(pyridin-2-yl)-1,2,4,5-tetrazin-3-yl)pyridin-3-yl)propanoic acid, 3-(4-(1,2,4,5-tetrazin-3-yl)phenyl)-2-aminopropanoic acid, and 2-amino-3-(4-(6-methyl-1,2,4,5-tetrazin-3-yl)phenyl)propanoic acid.

Urate Oxidase Variant Subunit 6—Including A Sequence Similar to The Exemplary Sequence In one embodiment, the urate oxidase variant subunit may have a sequence that is 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from SEQ ID NOs: 1 to 132. In one embodiment, the urate oxidase variant subunit may have a sequence similar or identical to a sequence selected from SEQ ID NOs: 1 to 132 by a degree corresponding to one of the percentages described above. In one embodiment, the urate oxidase variant subunit may have a sequence similar or identical to a sequence selected from SEQ ID NOs: 1 to 132 by a degree in the range of 80% to 100%. In one embodiment, the urate oxidase variant subunit may have a sequence similar or identical to a sequence selected from SEQ ID NOs: 1 to 132 by a degree in the range of 95% or more.

Urate Oxidase Variant Preparation Method

Overview of Urate Oxidase Variant Preparation Method

The present description discloses a method of preparing a urate oxidase variant. The following matters are involved in the urate oxidase preparation method: a cell line to express a urate oxidase variant; an exogenous suppressor tRNA to recognize a specific stop codon; a foreign tRNA synthetase; and a vector encoding a urate oxidase variant in which a nonnatural amino acid is encoded with the stop codon. Here, the exogenous suppressor tRNA and the exogenous tRNA synthetase are not the suppressor tRNA and tRNA synthetase specific to the expression cell line but a suppressor tRNA and tRNA synthetase derived from cells different from the expression cell line. Therefore, the exogenous suppressor tRNA is characterized in that it does not react with the tRNA synthetase unique to the expression cell line. The exogenous tRNA synthetase i) reacts only with the exogenous suppressor tRNA and ii) shows activity only in the nonnatural amino acid to be included in the urate oxidase variant. As a result, when the exogenous tRNA synthetase is used, the nonnatural amino acid is specifically linked to the exogenous suppressor tRNA so that the nonnatural amino acid can be introduced into the peptide sequence.

The urate oxidase variant preparation method is a method in which 1) in the cell line, 2) the exogenous suppressor tRNA and the exogenous tRNA synthetase are involved in 4) expressing the urate oxidase variant, 3) based on a vector encoding the urate oxidase variant. In the urate oxidase variant preparation method, the order of each process is not particularly limited if the urate oxidase variant can be expressed in the cell line, and additional processes may be included if necessary.

21

Cell Line Expressing Urate Oxidase Variant

The urate oxidase variant preparation method is characterized in that it is obtained by expressing a urate oxidase variant in a cell line. The urate oxidase variant expression cell line is not particularly limited if it can produce a urate oxidase variant. However, when a release factor recognizing the stop codon in the cell line normally functions, the release factor competes with the exogenous tRNA, thereby reducing the yield. Therefore, it is preferable to use a cell line in which the release factor that recognizes the stop codon is inactivated.

In one embodiment, the cell line expressing the urate oxidase variant may be selected from the following:

Escherichia genus; Erwinia genus; Serratia genus; Providencia genus; Corynebacterium genus; Pseudomonas genus; Leptospira genus; Salmonella genus; Brevibacterium genus; Hypomonas genus; chromobacterium genus; norcardia genus; fungi; and yeast.

In one embodiment, the cell line may be a cell line in which a release factor that recognizes a stop codon and terminates translation is inactivated. Specifically, the stop codon is any one selected from among an amber codon (5'-UAG-3'), an ocher codon (5'-UAA-3'), and an opal codon (5'-UGA-3').

In one embodiment, the cell line expressing the urate oxidase variant may be the cell line used in the method disclosed in the literature "KR 1637010 B1". Specifically, the cell line may be E. Coli C321.ΔA.exp (Addgene, ID: 49018).

Exogenous Suppressor tRNA

The exogenous suppressor tRNA is a tRNA that recognizes a specific stop codon, and does not react with a tRNA synthetase unique to the expression cell line. The exogenous suppressor tRNA specifically reacts with the exogenous tRNA synthetase, and the exogenous tRNA synthetase functions to link a nonnatural amino acid to the exogenous suppressor tRNA. As a result, the exogenous suppressor tRNA can recognize the specific stop codon and introduce the nonnatural amino acid at the corresponding position.

Specifically, the suppressor tRNA may recognizes anyone selected from among an amber codon (5'-UAG-3'), an ocher codon (5'-UAA-3'), and an opal codon (5'-UGA-3'). Preferably, the suppressor tRNA may recognize an amber codon. For example, the suppressor tRNA may be a suppressor tRNA (MjtRNA$^{Tyr}_{CUA}$) derived from Methanococcus jannaschii (Yang et. al, Temporal Control of Efficient In Vivo Bioconjugation Using a Genetically Encoded Tetrazine-Mediated Inverse-Electron-Demand Diels-Alder Reaction, Bioconjugate Chemistry, 2020, 2456-2464).

Exogenous tRNA Synthetase

The exogenous tRNA synthetase selectively reacts with a specific nonnatural amino acid, and functions to link the specific nonnatural amino acid to the exogenous suppressor tRNA. The exogenous tRNA synthetase does not react with the a suppressor tRNA unique to the expression cell line and specifically reacts with only the exogenous suppressor tRNA. In one embodiment, the tRNA synthetase may have a function of linking a nonnatural amino acid including a tetrazine derivative and/or a triazine derivative to the exogenous suppressor tRNA. In one embodiment, the tRNA synthetase may be a tyrosyl-tRNA synthetase (MjTyrRS) derived from Methanococcus jannaschii (Yang et. al, Temporal Control of Efficient In Vivo Bioconjugation Using a Genetically Encoded Tetrazine-Mediated Inverse-Electron-Demand Diels-Alder Reaction, Bioconjugate Chemistry, 2020, 2456-2464). Preferably, the tRNA synthetase may be a C11 variant of the MjTyrRS.

22

Orthogonal tRNA/Synthetase Pair

In the present description, 1) an exogenous suppressor tRNA that specifically reacts with only the exogenous tRNA synthetase, and 2) the exogenous tRNA synthetase are collectively called an orthogonal tRNA/synthetase pair. In the urate oxidase variant preparation method disclosed herein, it is important to express the orthogonal tRNA/synthetase pair in the expression cell line. The method is not particularly limited if this objective can be achieved. In one embodiment, the urate oxidase variant preparation method includes transforming the cell line with a vector capable of expressing the orthogonal tRNA/synthetase pair. Specifically, the vector capable of expressing the orthogonal tRNA/synthetase pair may be pDUle_C11 reported by Yang et. al. (Temporal Control of Efficient In Vivo Bioconjugation Using a Genetically Encoded Tetrazine-Mediated Inverse-Electron-Demand Diels-Alder Reaction, Bioconjugate Chemistry, 2020, 2456-2464).

Vector Encoding Urate Oxidase Variant

The urate oxidase variant preparation method includes a process of introducing or transfecting a vector encoding a urate oxidase variant into an expression cell line. A more specific description will be provided in the section titled "Vector Encoding Urate Oxidase Variant".

Example of Urate Oxidase Variant Preparation Method

In one embodiment, a urate oxidase variant preparation method includes the following:

preparing a cell line including a vector capable of expressing an orthogonal tRNA/synthetase pair, and a vector encoding a urate oxidase variant, in which the orthogonal tRNA/synthetase pair includes an exogenous suppressor tRNA and an exogenous tRNA synthetase, the urate oxidase variant is a variant in which three or more amino acids in a wild-type urate oxidase sequence are substituted with nonnatural amino acids each including a tetrazine derivative or a triazine derivative, and in the vector encoding the urate oxidase variant, the codon corresponding to the nonnatural amino acid is an amber codon (5'-UAG-3'); and culturing the cell line in a medium which contains a nonnatural amino acid including a tetrazine functional group and/or a triazine functional group, in which the exogenous suppressor tRNA can recognize the amber codon (5'-UAG-3'), the exogenous tRNA synthetase may link the nonnatural amino acid to the exogenous tRNA, and accordingly, when the cell line expresses the vector encoding the urate oxidase variant, the cell line expresses a peptide in which the nonnatural amino acid is linked to a position corresponding to the amber codon.

Vector Encoding Urate Oxidase Variant

Overview of Vector Encoding Urate Oxidase Variant

The present description discloses a vector encoding a urate oxidase variant. The vector encoding a urate oxidase variant is characterized in that the nonnatural amino acid in the sequence of the urate oxidase variant is encoded with a stop codon. In one embodiment, in the vector encoding a urate oxidase variant, a standard amino acid in the sequence of the urate oxidase variant is encoded with a codon corresponding to a standard amino acid found in nature, and a nonnatural amino acid may be encoded with a stop codon. For example, the stop codon is any one selected from among an amber codon (5'-UAG-3'), an ocher codon (5'-UAA-3'), and an opal codon (5'-UGA-3'). Alternatively, the stop codon may be selected from among 5'-TAG-3', 5'-TAA-3', and 5'-TGA-3'. In one embodiment, the vector encoding a urate oxidase variant may be codon-optimized for the expression cell line. For example, the vector encoding a urate oxidase variant may be an *E. coli* codon-optimized one.

Example of Vector Sequence Encoding Urate Oxidase Variant

In one embodiment, when the urate oxidase variant is obtained by partially modifying the sequence of a urate oxidase derived from *Aspergillus Flavus*, the vector encoding the urate oxidase variant may include a sequence selected from SEQ ID NOs: 152 to 154.

In one embodiment, when the urate oxidase variant is obtained by partially modifying the sequence of a urate oxidase derived from *Candida Utilis*, the urate oxidase variant may include a sequence selected from SEQ ID NOs: 155 to 157.

In one embodiment, when the urate oxidase variant is obtained by partially modifying the sequence of a urate oxidase derived from *Arthrobacter Globiformis*, the urate oxidase variant may include a sequence selected from SEQ ID NOs: 158 to 160.

Including A Sequence Similar to An Exemplary Sequence of The Vector Encoding A Urate Oxidase Variant In one embodiment, the vector encoding a urate oxidase variant may include a sequence that is 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from SEQ ID NOs: 145 to 160. In one embodiment, the vector encoding a urate oxidase variant may include a sequence similar or identical to a sequence selected from SEQ ID NOs: 145 to 160 by a degree corresponding to one of the percentages described above. In one embodiment, the vector encoding a urate oxidase variant subunit may include a sequence similar or identical to a sequence selected from SEQ ID NOs: 145 to 160 by a degree in the range of 80% to 100%. In one embodiment, the vector encoding a urate oxidase variant subunit may include a sequence similar or identical to a sequence selected from SEQ ID NOs: 145 to 160 by a degree in the range of 95% or more.

Albumin

Overview of Albumin

Albumin included in the urate oxidase-albumin conjugate disclosed herein refers to a conventional albumin protein. The albumin serves to increase the half-life of a urate oxidase by conjugating with a urate oxidase and/or to decrease immunogenicity. The albumin is not limited if it can have the above-described functions, and may be a wild-type albumin found in nature or a genetically engineered albumin (albumin variant) from a wild-type albumin.

Example of Albumin

In one embodiment, the albumin may be mammalian albumin. Specifically, the albumin may be human serum albumin. In one embodiment, the albumin may be wild-type human serum albumin. In one embodiment, the albumin may be recombinant albumin genetically engineered from wild-type human serum albumin.

Example of Sequence of Albumin

In one embodiment, the albumin may be represented by a sequence selected from SEQ ID NOs: 133 to 144.

Including Sequence Similar to Exemplary Albumin Sequence

In one embodiment, the albumin may include a sequence that is 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from SEQ ID NOs: 133 to 144. In one embodiment, the albumin may include a sequence similar or identical to a sequence selected from SEQ ID NOs: 133 to 144 by a degree corresponding to one of the percentages described above. For example, the albumin may include a sequence similar or identical to a sequence selected from SEQ ID NOs: 133 to 144 by a degree in the range of 80% to 100%. Alternatively, the albumin may include a sequence similar or identical to a sequence selected from SEQ ID NOs: 133 to 144 by a degree in the range of 95% or more.

Linker

Overview of Linker

The urate oxidase-albumin conjugate disclosed herein is one in which a urate oxidase variant and albumin are conjugated through a linker. In this case, the linker refers to a material used to link a urate oxidase variant and an albumin when preparing the urate oxidase-albumin conjugate.

Specifically, the linker includes: an IEDDA reactive group; an anchor; and a thiol reactive group capable of binding to the albumin. In the process of preparing a urate oxidase-albumin conjugate, the urate oxidase variant and the linker bind to each other via an IEDDA reactive group, and the albumin and the linker bind to each other via the thiol reactive group. Specific bonding processes can be understood by referring to the relevant paragraph. Therefore, the linker of the urate oxidase-albumin conjugate does not exist in its original form, but exists in a form of 1) a urate oxidase-linker junction, 2) an anchor, and 3) an albumin-linker junction.

Linker Structure 1—IEDDA Reactive Group

The linker includes an IEDDA reactive group capable of causing an inverse electron-demand Diels-Alder reaction (IEDDA reaction). The IEDDA reactive group is configured to be linked to the urate oxidase variant, and reacts with residues of nonnatural amino acids of the urate oxidase variant to form a urate oxidase-linker junction. In one embodiment, the IEDDA reactive group may include a dienophile functional group. Specifically, the IEDDA reactive group may be trans-cyclooctene or a derivative thereof.

In one embodiment, the IEDDA reactive group may be selected from the following:

Linker Structure 2—Thiol Reactive Group

The linker includes a thiol reactive group capable of reacting with thiol. The thiol group is configured to be linked to the albumin, and reacts with the thiol group included in the albumin to form an albumin-linker junction. In one embodiment, the thiol reactive group may be maleimide (MAL) or a derivative thereof, and/or 3-arylpropiolonitriles (APN) or a derivative thereof.

Specifically, the thiol reactive group may be selected from the following:

-continued

Linker Structure 3—Anchor

The linker includes an anchor that links the IEDDA reactive group and the thiol reactive group. The anchor binds the IEDDA reactive group and the thiol reactive group into one molecule, and the structure of the anchor is not particularly limited as long as it does not affect the activity of the urate oxidase and/or albumin. In one embodiment, the anchor may have a linear structure. In another embodiment, the anchor may have a branched structure. In one embodiment, the anchor may include polyethylene glycol (PEG).

Example of Linker

In one embodiment, the linker may be any one selected from the following:

Urate Oxidase-Linker Junction

Overview of Urate Oxidase-Linker Junction

The urate oxidase-albumin conjugate disclosed herein include a urate oxidase-linker junction. The urate oxidase-linker junction is generated by combining a urate oxidase variant and a linker through an IEDDA reaction. Specifically, the IEDDA reaction refers to a reaction between the residue of the nonnatural amino acid of the urate oxidase variant and the IEDDA reactive group of the linker, and, after the reaction, the structure of the urate oxidase-linker junction is determined depending on the residue of the nonnatural amino acid and the type of the IEDDA reactive group. Since the urate oxidase-albumin conjugate includes three or more albumin conjugates, the urate oxidase-albumin conjugate includes three or more urate oxidase-linker junctions. As described above, the urate oxidase-albumin conjugate includes three or more subunit-albumin conjugates. The subunit-albumin conjugate is a structure in which a urate oxidase variant subunit and an albumin are bound through a linker. Accordingly, each of the subunit-albumin conjugates includes at least one urate oxidase-linker junction.

Position of Urate Oxidase-Linker Junction

The urate oxidase-linker junction is present at a position at which a nonnatural amino acid of a urate oxidase variant and the anchor of a linker are linked. As described above, since the urate oxidase-albumin conjugate is formed through the reaction of the residue of the nonnatural amino acid and the IEDDA reactive group, the urate oxidase-albumin conjugate is positioned to correspond to the residue of the nonnatural amino acid of the urate oxidase variant. In other words, the urate oxidase-linker junction is present at a position corresponding to the IEDDA reactive group of the linker.

Reaction for Forming Urate Oxidase-Linker Junction

The reaction for forming the urate oxidase-linker junction is a kind of an inverse electron-demand Diels-Alder reaction (IEDDA reaction). A specific reaction mode may vary depending on the type of the functional group of the nonnatural amino acid of the urate oxidase variant and the IEDDA reactive group of the linker. In one embodiment, the urate oxidase-linker junction formation reaction may be any one of the following:

-continued
and

Here, A2 is a linker portion excluding the IEDDA reactive group, Rx may vary depending on the type of the nonnatural amino acid (refer to the above-described examples of nonnatural amino acids), and A1 is a urate oxidase variant portion excluding a tetrazine functional group of a nonnatural amino acid.

Structure of Urate Oxidase-Linker Junction

In one embodiment, structure of the urate oxidase-linker junction may be any one of the following:

here, R is selected from H, CH₃,

, and , the (1) part is linked to the urate oxidase variant, and the (2) part is linked to the anchor of the linker; and here, the (1) part is linked to the urate oxidase variant, and the (2) part is linked to the anchor of the linker.

Albumin-Linker Junction

Overview of Albumin-Linker Junction

The urate oxidase-albumin conjugate disclosed herein include a urate oxidase-linker junction. The albumin-linker junction is generated by combining a thiol group included in albumin with a thiol group included in the linker. In this case, the thiol group of the albumin mediating the binding is characterized in that it is positioned to be spaced apart from the FcRn-binding domain of the albumin in order not to inhibit the half-life enhancing function of the albumin. Since the urate oxidase-albumin conjugate includes three or more albumin conjugates, the urate oxidase-albumin conjugate includes three or more albumin-linker junctions. As described above, the urate oxidase-albumin conjugate includes three or more subunit-albumin conjugates. The subunit-albumin conjugate is a structure in which a urate oxidase variant and an albumin are bound through a linker. Accordingly, each of the subunit-albumin conjugates includes at least one urate oxidase-linker junction.

Position of Albumin-Linker Junction

The albumin-linker junction is present at a position at which the thiol moiety of the albumin and the anchor of the linker are linked. Since the urate oxidase-albumin conjugate disclosed herein has the purpose of increasing the half-life in the body by conjugating albumin to uric acid oxidase, the position where the albumin and the linker are connected must be a position spaced apart from the FcRn binding domain of albumin. As described above, since the urate oxidase-albumin conjugate is formed by reacting the thiol group of the albumin and the thiol reactive group of the linker, the albumin-linker junction is present at a position corresponding to the thiol group of the albumin. In other words, the albumin-linker junction is present at a position corresponding to the thiol reactive group of the linker. The position of the albumin-linker junction is selected from among the thiol groups included in albumin, which do not affect the structure, function, and/or activity of albumin.

Exemplary Position of Albumin-Linker Junction

In one embodiment, the albumin-linker junction may be located in a thiol group included in the residue of the 34th cysteine of albumin represented by SEQ ID NOs: 133 to S016.

Albumin-Linker Junction Formation Reaction

The reaction for forming the albumin-linker junction is a kind of thiol reaction. A specific reaction mode may vary depending on the type of thiol group of the linker.

In one embodiment, the urate albumin-linker junction formation reaction may be any one of the following:

-continued
and

Here, R1 is an albumin moiety excluding the thiol group, and R2 is a linker moiety excluding the thiol group.

Exemplary Structure of Albumin-Linker Junction

In one embodiment, the structure of the albumin-linker junction may be any one of the following:

here, the (1) part is linked to albumin, and the (2) part is linked to the anchor of the linker.

Anchor

Overview of Anchor

The anchor disclosed herein refers to a structure connected between the urate oxidase-linker junction and the albumin-linker junction. The anchor binds the urate oxidase variant, the urate oxidase-linker junction, the albumin-linker junction, and the albumin into one structure. The anchor functions to regulate the distance between the urate oxidase variant and the albumin in the urate oxidase-albumin conjugate according to the structure thereof.

Example of Structure of Anchor

In one embodiment, the anchor may be any one selected from the following:

(A01)

-continued (A02)

(A03)

(A04)

, and (A05)

Herein $J_1$ is a urate oxidase-linker junction, and $J_2$ is an albumin-linker junction.

Urate Oxidase-Albumin Conjugate Preparation Method

Overview of Preparation Method for Urate Oxidase-Albumin Conjugate

The present description discloses a method of preparing a urate oxidase-albumin conjugate. The following elements are involved in preparing a urate oxidase-albumin conjugate: a urate oxidase variant; a linker; and an albumin. Herein, the details of the elements are the same as described above.

The urate oxidase-albumin conjugate preparation method is to prepare the above-described urate oxidase-albumin conjugate by appropriately reacting each of the elements. Specifically, the urate oxidase-albumin conjugate preparation method includes: reacting a nonnatural amino acid residue included in a urate oxidase variant with an IEDDA reactive group of a linker to make a urate oxidase-linker junction (urate oxidase-linker conjugation reaction); and reacting a thiol group of an albumin with a thiol reactive group of a linker to form an albumin-linker junction (albumin-linker conjugation reaction). In this case, the order in which the uric acid oxidase-linker conjugation reaction and the albumin-linker conjugation reaction occur is irrelevant, and both reactions may occur simultaneously. In addition, depending on the sequence of each reaction, intermediate products of the reaction may be produced. The urate oxidase-albumin conjugate preparation method will be described below in more detail.

Urate Oxidase-Albumin Conjugate Preparation Method 1—Method of Binding Albumin and Linker First In one embodiment, the urate oxidase-albumin conjugate preparation method includes the following:
  reacting an albumin and a linker,
  in which a thiol moiety of the albumin and a thiol reactive moiety of the linker come into contact with each other to create an albumin-linker conjugate; and reacting the albumin-linker conjugate and the urate oxidase variant,
  here, the IEDDA reactive group of the albumin-linker conjugate and the dien functional group of the nonnatural amino acid of the urate oxidase variant come into contact to produce a urate oxidase-albumin conjugate.
The urate oxidase variant, the linker, and the albumin, and elements included therein areas described above.

Urate Oxidase-Albumin Conjugate Preparation Method 2—Method of Binding Urate Oxidase and Linker First In one embodiment, the urate oxidase-albumin conjugate preparation method includes the following:
  reacting a urate oxidase variant and a linker,
  here, the IEDDA reactive group of the linker and the dien functional group of the nonnatural amino acid of the urate oxidase variant come into contact to produce a urate oxidase-linker conjugate; and
  reacting the urate oxidase-linker conjugate and the albumin,
  here, the thiol moiety of the albumin and the thiol moiety of the urate oxidase-linker conjugate come into contact to produce a urate oxidase-albumin conjugate.
The urate oxidase variant, the linker, and the albumin, and elements included therein areas described above.

Urate Oxidase-Albumin Conjugate Preparation Method 3—Method of Binding Urate Oxidase, Linker, and Albumin Simultaneously In one embodiment, the urate oxidase-albumin conjugate preparation method can be performed by adding all reactants and reacting them simultaneously.

In this case, the urate oxidase-albumin conjugate preparation method includes the following:
  reacting a urate oxidase variant, a linker, and an albumin,
  in which a thiol moiety of the albumin and a thiol moiety of the linker react to bind with each other,
  the dien functional group contained in the nonnatural amino acid of the urate oxidase variant and the IEDDA reactive group of the linker are conjugated through a reaction, and
  as a result of the reaction, the urate oxidase-albumin conjugate is produced.
The urate oxidase variant, the linker, and the albumin, and elements included therein are as described above.

Characteristic of Urate Oxidase-Albumin Conjugate Preparation Method 1—High Stability in Body Due to Bioorthogonal Reaction In the method for preparing the urate oxidase-albumin conjugate, the urate oxidase variant and the albumin are conjugated through an IEDDA reaction, which is a kind of bioorthogonal reaction. Since a chemical functional group involved in the conjugation reaction does not exist in a molecule in the body, the urate oxidase-albumin conjugate prepared by the preparation method has an advantage that the stability of the bond is very high even when introduced into the body.

Characteristic of Urate Oxidase-Albumin Conjugate Preparation Method 2—High Yield Due to IEDDA Reaction In the urate oxidase-albumin conjugate preparation method, an inverse electron demand Diels-Alder reaction (IEDDA reaction) is used for conjugation of the urate oxidase variant and the linker. Since the IEDDA reaction occurs at a very fast reaction rate and the reaction environment can be easily constructed, the yield is very high when preparing the conjugate compared to the case of using the Strain-Promoted Azide-Alkyne Cycloaddition (SPAAC) reaction.

Characteristic of Urate Oxidase-Albumin Conjugate 3—Inclusion of Three or Four Albumins Per Conjugate According to the urate oxidase-albumin conjugate preparation method disclosed herein, since an IEDDA reaction with a very high yield is used, a urate oxidase-albumin conjugate in which 3 or 4 albumins are conjugated per unit of urate oxidase can be obtained. This is clearly an improved characteristic compared to the limitation of the urate oxidase-albumin conjugate preparation method disclosed in the literature "KR 1637010 B1" by which only a urate oxidase-albumin conjugate in which one or two albumins are conjugated per unit of urate oxidase is obtained.

Urate Oxidase-Linker Conjugation Method

The urate oxidase-albumin conjugate preparation method disclosed herein includes conjugating a urate oxidase variant and a linker. Specifically, the urate oxidase-linker conjugation method includes bringing the residue of the nonnatural amino acid of the urate oxidase variant into contact with the IEDDA reactive group of the linker. The urate oxidase-linker conjugation method is not affected by the site at which the albumin and the linker are conjugated or by whether the albumin and the linker are conjugated or not. Therefore, the urate oxidase-linker conjugation method disclosed below is applicable to both the binding of the "linker" to the "urate oxidase variant" and the binding of the "albumin-linker conjugate" to the "urate oxidase variant". The urate oxidase-linker conjugation method may be performed independently of the albumin-linker conjugation method.

The urate oxidase-linker conjugation method is not limited as long as it is a method capable of causing the reaction described in the section "Urate Oxidase-Linker Junction Formation Reaction", and a person skilled in the art may use a known method capable of causing the reaction.

Here, when the IEDDA reaction between the tetrazine functional group and the trans-cyclooctene functional group is caused by the urate oxidase-linker conjugation method, the tetrazine functional group is reduced in a basic pH environment to increase the likelihood that the IEDDA reaction does not occur. Therefore, it is preferable that the IEDDA reaction proceeds in a neutral pH environment. In one embodiment, the urate oxidase-linker conjugation method may be performed in a neutral pH environment. In one embodiment, the urate oxidase-linker conjugation method may be performed in an environment of pH 8.0 or less, pH 9.0 or less, pH 10.0 or less, pH 11.0 or less, pH 11.0 or less, pH 13.0 or less, pH 14.0 or less.

Albumin-Linker Conjugation Method

The urate oxidase-albumin conjugate preparation method disclosed herein includes conjugating an albumin with a linker. Specifically, the albumin-linker conjugation method includes bringing the thiol moiety of the albumin into contact with the thiol moiety of the liner. The albumin-linker conjugation method is not affected by the site at which the urate oxidase and the linker are conjugated or by whether the urate oxidase and the linker are conjugated or not. Therefore, the albumin-linker conjugation method disclosed below is applicable to both the binding of the "linker" to the "albumin" and the binding of the "urate oxidase-linker conjugate" to the "albumin". The albumin-linker conjugation method may be performed independently of the urate oxidase-linker conjugation method.

Use of Urate Oxidase-Albumin Conjugate

Overview of Use of Urate Oxidase-Albumin Conjugate

The present description discloses a use of a urate oxidase-albumin conjugate. The urate oxidase-albumin conjugate has a long half-life in the body thereby being stable in the body, and has a low immunogenicity. Thus, the urate oxidase-albumin conjugate has an excellent uric acid lowering effect due to the above characteristics. Accordingly, the urate oxidase-albumin conjugate can be used to prevent or treat various diseases, disorders and/or indications caused by uric acid.

Preventive and/or Therapeutic Use of Urate Oxidase-Albumin Conjugate 1—Indication In one embodiment, the uric acid oxidase-albumin conjugate may be used to prevent or treat hyperuricemia, acute gouty arthritis, intermittent gout, and chronic nodular gout, chronic kidney disease and/or tumor lysis syndrome (TLS).

Preventive and/or Therapeutic Use of Urate Oxidase-Albumin Conjugate 2—Administration Method In one embodiment, the urate oxidase-albumin conjugate may be administered to patients through appropriate formulation to prevent or treat various diseases, disorders, and/or indications caused by uric acid. For example, the administration method may be one selected from oral administration, parenteral administration, intravenous administration, intraperitoneal administration, intramuscular administration, transdermal administration, and subcutaneous administration. Alternatively, the administration may be intravenous infusion.

Preventive and/or Therapeutic Use of Urate Oxidase 3—Albumin Conjugate—Dosage In one embodiment, an appropriate dose of the urate oxidase-albumin conjugate may be administered to patients through appropriate formulation to prevent or treat various diseases, disorders, and/or indications caused by uric acid. For example, the dosage may be 0.01 mg/kg to 1000 mg/kg based on the urate oxidase-albumin conjugate.

Preventive and/or Therapeutic Use of Urate Oxidase-Albumin Conjugate 4—Administration Interval In one embodiment, the urate oxidase-albumin conjugate may be administered to patients through appropriate formulation to prevent or treat various diseases, disorders, and/or indications caused by uric acid at appropriate intervals. For example, the administration interval may be once a day. That is, an interval at which the appropriate dose of the urate oxidase-albumin conjugate may be administered once a day. Alternatively, the urate oxidase-albumin conjugate may be administered two times a day. In this case, the dosage per administration is half the appropriate dose per day. Further alternatively, the administration interval may be 1 hour, 2 hours, 6 hours, 12 hours, 24 hours, 2 days, 3 days, one week, two weeks, one month, or three months for the appropriate dosage of the urate oxidase-albumin conjugate.

Pharmaceutical Composition Including Urate Oxidase-Albumin Conjugate

Overview of Pharmaceutical Composition Including Urate Oxidase-Albumin Conjugate To use the urate oxidase-albumin conjugate for diseases, disorders, and/or indications caused by uric acid, the urate oxidase-albumin conjugate must undergo appropriate formulation. Disclosed herein is a pharmaceutical composition suitably formulated to use a urate oxidase-albumin conjugate as a therapeutic agent, and a pharmaceutically acceptable carrier required for formulation is disclosed. For example, the urate oxidase-albumin conjugate may be formulated for oral use, parenteral use, injection, aerosol, and/or transdermal use, and may include a pharmaceutically acceptable carrier for this purpose.

Composition for Formulation 1—Oral Preparations

In one embodiment, the urate oxidase-albumin conjugate may be formulated as troches, lozenges, tablets, aqueous suspensions, oily suspensions, prepared powders, granules, emulsions, hard capsules, soft capsules, syrups, or elixirs.

In one embodiment, to formulating the urate oxidase-albumin conjugate as oral preparations, the following may be used: binders such as lactose, saccharose, sorbitol, mannitol, starch, amylopectin, cellulose or gelatin; excipients such as dicalcium phosphate and the like; disintegrants such as corn starch or sweet potato starch; and lubricants such as magnesium stearate, calcium stearate, sodium stearyl fumarate or polyethylene glycol wax. In addition, sweeteners, air fresheners, and syrups may be used. Furthermore, in the case of capsules, in addition to the above-mentioned substances, a liquid carrier such as fatty oil may be additionally used.

Composition 2 for Formulation—Parenteral Preparations

In one embodiment, the urate oxidase-albumin conjugate may be formulated as an injection solution, suppository, powder for respiratory inhalation, aerosol for spray, ointment, powder for application, oil, or cream.

In one embodiment, in order to formulate the urate oxidase-albumin conjugate for parenteral administration, a sterile aqueous solution, a non-aqueous solvent, a suspension, an emulsion, a freeze-dried preparation, an external preparation, etc. may be used. As the non-aqueous solvent and the suspension, propylene glycol, polyethylene glycol, vegetable oils such as olive oil, and injectable esters such as ethyl oleate may be used.

Composition 3 for Formulation—Injection Preparations

In one embodiment, in order to formulate the uric acid oxidase-albumin conjugate as an injection solution, the binder for the urate oxidase-albumin conjugate is mixed with a stabilizer or buffer in water to prepare a solution or suspension, and the solution or suspension may be formulated to be administered in units of an ampoule or vial.

Composition 4 for Formulation—Aerosol Preparations

In one embodiment, the binder for the uric acid oxidase-albumin conjugate may be mixed with a propellant along with additives to prepare an aqueous dispersion concentrate or wet powder which may be subsequently formulated as aerosol preparations.

Composition 5 for Formulation—Transdermal Preparations

In one embodiment, when the uric acid oxidase-albumin conjugate is formulated for transdermal use, animal oil, vegetable oil, wax, paraffin, starch, tragacanth, cellulose derivative, polyethylene glycol, silicone, bentonite, silica, talc, zinc oxide, etc. may be added as a carrier to the binder for the urate oxidase-albumin conjugate to prepare ointment, cream, powder for application, oil, external preparation for skin, etc.

Composition 6 for Formulation—Adjuvants and Other Components

In one embodiment, the pharmaceutical composition including the urate oxidase-aluminum conjugate may include: water, saline, dextrose, ethanol, glycerol, sodium chloride, dextrose, mannitol, sorbitol, lactose, gelatin, albumin, aluminum hydroxide, Freund's incomplete adjuvant and complete adjuvant (Pifco Laboratories, Detroit, Mich.), Merck Adjuvant 65 (Merck and Company, Inc., Rahway, NJ.), Alhydrogel (Al(OH)$_3$), aluminum hydroxide gel (alum), or aluminum salt such as aluminum phosphate, AS04 series, MF, squalene, MF59, QS21, calcium, iron or zinc salt, insoluble suspension of acylated tyrosine, acylated fructose, cationically or anionically derived polysaccharides, polyphosphazenes, biodegradable microspheres, and Quil A, toll-like receptor (TLR) agonists, PHAD [Avanti polar lipid, Monophosphoryl Lipid A (synthetic)], monophosphoryl lipid A (MPL), synthetic lipid A, lipid A mimics or analogues, aluminum salts, cytokines, saponins, prolactin, growth hormone deoxycholic acid, betaglucan, polyribonucleotides, muramyl dipeptide (MDP) derivatives, CpG oligo, lipopolysaccharide (LPS) of Gram-negative bacteria, polyphosphazene, emulsion, virosome, cochleate, poly(lactide-co-glycolide)(PLG) microparticles, poloxamer particles, microparticles, liposomes, or suitable combinations thereof.

Possible Example of Invention

Urate Oxidase-Albumin Conjugate 1

Example 1, Urate Oxidase-Albumin Conjugate

A urate oxidase-albumin conjugate represented by [formula 1]:

$$\text{Uox-}[J_1\text{-A-}J_2\text{-HSA}]_n \qquad \text{[formula 1]}$$

wherein Uox is a urate oxidase variant, J1 is a urate oxidase-linker junction, A is an anchor, J2 is an albumin-linker junction, and HSA is Human Serum Albumin,

the urate oxidase variant includes three or more nonnatural amino acids having a diene functional group,
the urate oxidase-linker junction is a structure in which a diene functional group of the nonnatural amino acid and a dienophile functional group connected to the anchor are bound through an IEDDA reaction, and
n is 3 or 4.

Example 2, Limitation of Microorganism for Deriving Urate Oxidase

In Example 1, the urate oxidase variant is a substance resulting from substitution of three or more amino acids in a wild-type uric acid oxidase sequence derived from a microorganism with nonnatural amino acids, and the microorganism is selected from the following: *Aspergillus Flavus, Arthrobacter Globiformis,* and *Candida Utilis.*

Example 3, Four Variant Subunits

The urate oxidase-albumin conjugate of any one of Examples 1 to 2, in which the urate oxidase variant is a tetramer formed by oligomerization of four urate oxidase variant subunits, and the urate oxidase variant subunit is a subunit obtained by substituting one or more amino acids in the sequence of a wild-type urate oxidase subunit with nonnatural amino acids.

Example 4, Three Variant Subunits, One Wild Subunit

The urate oxidase-albumin conjugate of any one of Examples 1 to 2, in which the urate oxidase variant is a tetramer formed by oligomerization of three urate oxidase variant subunits and one wild-type urate oxidase subunit, and the urate oxidase variant subunit is a subunit obtained by substituting one or more amino acids in the sequence of a wild urate oxidase subunit with nonnatural amino acids.

Example 5, Nonnatural Amino Acid, Limitation of Tetrazine Functional Group

The urate oxidase-albumin conjugate of any one of Examples 1 to 4, in which the dien functional group is a triazine functional group or a derivative, or a tetrazine functional group or a derivative thereof.

Example 6, Example of Nonnatural Amino Acid (Name)

The urate oxidase-albumin of Example 5, in which the nonnatural amino acid is any one selected from the following:
4-(1,2,3,4-tetrazin-3-yl) phenylalanine (frTet), 4-(6-methyl-s-tetrazin-3-yl)phenylalanine (Tet-v2.0), 3-(4-(1,2,4-triazin-6-yl)phenyl)-2-aminopropanoic acid, 2-amino-3-(4-(2-(6-methyl-1,2,4,5-tetrazin-3-yl)ethyl)phenyl) propanoic acid, 2-amino-3-(4-(6-phenyl-1,2,4,5-tetrazin-3-yl)phenyl)propanoic acid, 3-(4-((1,2,4,5-tetrazin-3-yl) amino)phenyl)-2-aminopropanoic acid, 3-(4-(2-(1,2,4,5-tetrazin-3-yl)ethyl)phenyl)-2-aminopropanoic acid, 3-(4-((1,2,4,5-tetrazin-3-yl)thio)phenyl)-2-aminopropanoic acid, 2-amino-3-(4-((6-methyl-1,2,4,5-tetrazin-3-yl)thio)phenyl) propanoic acid, 3-(4-((1,2,4,5-tetrazin-3-yl)oxy)phenyl)-2-aminopropanoic acid, 2-amino-3-(4-((6-methyl-1,2,4,5-tetrazin-3-yl)oxy)phenyl)propanoic acid, 3-(4'-(1,2,4,5-tetrazin-3-yl)-[1,1'-biphenyl]-4-yl)-2-aminopropanoic acid, 2-amino-3-(4'-(6-methyl-1,2,4,5-tetrazin-3-yl)-[1,1'-biphenyl]-4-yl)propanoic acid, 2-amino-3-(6-(6-(pyridin-2-yl)-1,2,4,5-tetrazin-3-yl)pyridin-3-yl)propanoic acid, 3-(4-(1,2,4,5-tetrazin-3-yl)phenyl)-2-aminopropanoic acid, and 2-amino-3-(4-(6-methyl-1,2,4,5-tetrazin-3-yl)phenyl)propanoic acid.

Example 7, Example of Nonnatural Amino Acid (Chemical Formula)

The urate oxidase-albumin conjugate of Example 5, in which the nonnatural amino acids are each independently selected from the tables of FIGS. 23 to 27.

Example 8, Subunit Sequence Example 1, Asp.Uox

The urate oxidase-albumin conjugate of any one of Examples 2 to 7, in which the urate oxidase variant subunit is represented by a sequence selected from the following:

(SEQ ID NO: 2)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEXKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 3)
SAVKAARYGKDNVRVYKVHKDXKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 4)
SAVKAARYGKDNVRVYKVHKDEKTGVQTVYEMTVCVLLEGEIETSYTKADNSVIVA

TDSIKNTIYITAKQNPVTPPELFGSILGTHFIEKYXHIHAAHVNIVCHRWTRMDIDGKPHPHSFIR

-continued

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 5)
SAVKAARYGKDNVRVYKVHKDEXTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 6)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRXSLKSKL;

(SEQ ID NO: 7)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDXKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 8)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGXNAEVFAPQSDPNGLIKCTVGRSSLKSKL;

(SEQ ID NO: 9)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLXETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 10)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILXRQQLIE

TVEYSLPNKHYFEIDLSWHKGLQNTGKNAEVFAPQSDPNGLIKCTVGRSSLKSKL;

(SEQ ID NO: 11)
SAVKAARYGKDNVRVYKVHKDEKTGVQTVYEMTVCVLLEGEIETSYTKADNSVIVA

TDSIKNTIYITAKQNPVTPPELFGSILGTHFIXKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

-continued

TVEYSLPNKHYFEIDLSWHKGLQNTGKNAEVFAPQSDPNGLIKCTVGRSSLKSKL;

(SEQ ID NO: 12)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHXGLQNTGKNAEVFAPQSDPNGLIKCTVGRSSLKSKL;

(SEQ ID NO: 13)

SAVKAARYGKDNVRVYKVHKDEKXGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 14)

SAVKAARYGKDNVRVYKVHKDEKTGVQTVYEMTVCVLLEGEIETSYTXADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 15)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFXGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 16)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVXKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 17)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMXIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 18)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQXLIE

TVEYSLPNKHYFEIDLSWHKGLQNTGKNAEVFAPQSDPNGLIKCTVGRSSLKSKL;

-continued (SEQ ID NO: 19)
```
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLXEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;
```

(SEQ ID NO: 20)
```
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGXGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;
```

(SEQ ID NO: 21)
```
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKXHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;
```

(SEQ ID NO: 22)
```
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRXHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;
```

(SEQ ID NO: 23)
```
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTXKNAEVFAPQSDPNGLIKCTVGRSSLKSKL;
```

(SEQ ID NO: 24)
```
SAVXAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;
```

(SEQ ID NO: 25)
```
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIXGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;
```

-continued (SEQ ID NO: 26)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKXLQNTGKNAEVFAPQSDPNGLIKCTVGRSSLKSKL;

(SEQ ID NO: 27)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGXPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 28)

SAVKAARYGKDNVRVYKVHKDEKTGVQTVYEMTVCVLLEGEIETSYTKADNSVIVA

TDSIKNTIYITAKXNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 29)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETXDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 30)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDXSASVQATMYKMAEQILARQQLIE

TVEYSLPNKHYFEIDLSWHKGLQNTGKNAEVFAPQSDPNGLIKCTVGRSSLKSKL;

(SEQ ID NO: 31)

SAVKAARYGKDNVRVYKVHKDEKTGVQTVYEMTVCVLLEGXIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 32)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIXLSWHKGLQNTGKNAEVFAPQSDPNGLIKCTVGRSSLKSKL;

-continued (SEQ ID NO: 33)
SAVKAARYGKDNVRVYKVHKDEKTXVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 34)
SAVKAARYGKDNVRVYKVHKDEKTGVQTVYEMTVCVLLEGEIETSYTKADNXVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 35)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILAXQQLIE

TVEYSLPNKHYFEIDLSWHKGLQNTGKNAEVFAPQSDPNGLIKCTVGRSSLKSKL;

(SEQ ID NO: 36)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATARXVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 37)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKXAEVFAPQSDPNGLIKCTVGRSSLKSKL;

(SEQ ID NO: 38)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAXDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 39)
SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDXTWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

-continued (SEQ ID NO: 40)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAXQILARQQLIE

TVEYSLPNKHYFEIDLSWHKGLQNTGKNAEVFAPQSDPNGLIKCTVGRSSLKSKL;

(SEQ ID NO: 41)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLXDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 42)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLXNTGKNAEVFAPQSDPNGLIKCTVGRSSLKSKL;

(SEQ ID NO: 43)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVXGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 44)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFXIDLSWHKGLQNTGKNAEVFAPQSDPNGLIKCTVGRSSLKSKL;

(SEQ ID NO: 45)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIX

TVEYSLPNKHYFEIDLSWHKGLQNTGKNAEVFAPQSDPNGLIKCTVGRSSLKSKL;

(SEQ ID NO: 46)

SAVKAARYGKDNVRVYKVHKDEKTGVQTVYEMTVCVLLEGEIETSYTKXDNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

-continued (SEQ ID NO: 47)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSXLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 48)

SAVKAARYGKDNVRVYKVXKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL;

(SEQ ID NO: 49)

SAVKAARYGKDNVRVYKVHKDEKTGVQTVYEMTVCVLLEGEIETSYTKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSXLKSKL;
and (SEQ ID NO: 50)

SAVKAARYGKDNVRVYKVHKDEKTGVQTVYEMTVCVLLEGEIETSYXKADNSVIVA

TDSIKNTIYITAKQNPVTPPELFGSILGTHFIEKYNHIHAAHVNIVCHRWTRMDIDGKPHPHSFIR

DSEEKRNVQVDVVEGKGIDIKSSLSGLTVLKSTNSQFWGFLRDEYTTLKETWDRILSTDVDAT

WQWKNFSGLQEVRSHVPKFDATWATAREVTLKTFAEDNSASVQATMYKMAEQILARQQLIE

TVEYSLPNKHYFEIDLSWHKGLQNTGKNAEVFAPQSDPNGLIKCTVGRSSLKSKL, where X is selected from the nonnatural amino acids disclosed in the
tables of FIGS. 23 to 27.

Example 9, Subunit Sequence Example 2, *Candida. Uox*

The urate oxidase-albumin conjugate of any one of Examples 2 to 7,
in which the urate oxidase variant subunit is represented by a sequence
selected from the following:

(SEQ ID NO: 52)

MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKXKL;

(SEQ ID NO: 53)

MSTTLSSSTYGKDNVKFLKVKKDPQXPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

-continued (SEQ ID NO: 54)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKX;

(SEQ ID NO: 55)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNXKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 56)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYXHVSGVSVKIVQDRWVKYAVDGKPHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;

(SEQ ID NO: 57)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRXGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 58)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDXKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 59)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTXL;

(SEQ ID NO: 60)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNXCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

-continued (SEQ ID NO: 61)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVXGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 62)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKXKTKL;

(SEQ ID NO: 63)
MSTTLSSSTYGKDNVKFLKVKKDXQNPKKQEVMEATVTCLLEGGFDTSYTEADNSSI

VPTDTVKNTILVLAKTTEIWPIERFAAKLATHFVEKYSHVSGVSVKIVQDRWVKYAVDGKPHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;

(SEQ ID NO: 64)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKXKGLENDNELFYPSPHPNGLIKCTVVRKEKTKL;

(SEQ ID NO: 65)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENXNELFYPSPHPNGLIKCTVVRKEKTKL;

(SEQ ID NO: 66)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCXFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 67)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKXHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;

-continued (SEQ ID NO: 68)
```
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTXDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;
```

(SEQ ID NO: 69)
```
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLXPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;
```

(SEQ ID NO: 70)
```
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADXGIFDNVYNQAREITLTTFALENSPSVQATMFNMATQILE

KACSVYSVSYALPNKHYFLIDLKWKGLENDNELFYPSPHPNGLIKCTVVRKEKTKL;
```

(SEQ ID NO: 71)
```
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLXNDNELFYPSPHPNGLIKCTVVRKEKTKL;
```

(SEQ ID NO: 72)
```
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFXIDLKWKGLENDNELFYPSPHPNGLIKCTVVRKEKTKL;
```

(SEQ ID NO: 73)
```
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKXLENDNELFYPSPHPNGLIKCTVVRKEKTKL;
```

(SEQ ID NO: 74)
```
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVXDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;
```

-continued (SEQ ID NO: 75)
MSTTLSSSTYGKDNVKFLKVKKDPQNPKKQEVMEATVTCLLEGGFDTSYTEADNSSIV

PTDTVKNTILVLAKTTEIWPIERFAAKLATHFVXKYSHVSGVSVKIVQDRWVKYAVDGKPHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;

(SEQ ID NO: 76)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILX

KACSVYSVSYALPNKHYFLIDLKWKGLENDNELFYPSPHPNGLIKCTVVRKEKTKL;

(SEQ ID NO: 77)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFAXENSPSVQATMFNMATQILE

KACSVYSVSYALPNKHYFLIDLKWKGLENDNELFYPSPHPNGLIKCTVVRKEKTKL;

(SEQ ID NO: 78)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEXTKL;

(SEQ ID NO: 79)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAXAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 80)
MSTTLSSSTYGKDNVKFLKVKKDPQNPKKQEVMEATVTCLLEGGFDTSYTXADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 81)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAAXKGIFDNVYNQAREITLTTFALENSPSVQATMFNMATQILE

KACSVYSVSYALPNKHYFLIDLKWKGLENDNELFYPSPHPNGLIKCTVVRKEKTKL;

-continued (SEQ ID NO: 82)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGXPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 83)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KAXSVYSVSYALPNKHYFLIDLKWKGLENDNELFYPSPHPNGLIKCTVVRKEKTKL;

(SEQ ID NO: 84)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQXTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 85)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLXWKGLENDNELFYPSPHPNGLIKCTVVRKEKTKL;

(SEQ ID NO: 86)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIXLKWKGLENDNELFYPSPHPNGLIKCTVVRKEKTKL;

(SEQ ID NO: 87)
MSTTLSSSTYGKDNVKFLKVKKDPQNPKKQEVMEATVTCLLEGXFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 88)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDXKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

-continued (SEQ ID NO: 89)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYXYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 90)
MSTTLSSSTYGKDNVKFLKVKKDPQNPKKQEVMEATVTCLLEGGFDTSYTEADNSSIV

PTDTVKNTILVLAKXTEIWPIERFAAKLATHFVEKYSHVSGVSVKIVQDRWVKYAVDGKPHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;

(SEQ ID NO: 91)
MSTTLSSSTYGKDNVKFLKVKKDPQNPKXQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 92)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALEXSPSVQATMFNMATQILE

KACSVYSVSYALPNKHYFLIDLKWKGLENDNELFYPSPHPNGLIKCTVVRKEKTKL;

(SEQ ID NO: 93)
MSTTLSSSTYGKDNVKFLKVKKDPXNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 94)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYXQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 95)
MSTTLSSSTYGKDNVKFLKVKKDPQNPKKQEVMEATVTCLLEGGFDTSYTEADNXSI

VPTDTVKNTILVLAKTTEIWPIERFAAKLATHFVEKYSHVSGVSVKIVQDRWVKYAVDGKPHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;

-continued

```
                                              (SEQ ID NO: 96)
MSTTLSSSTYGKDNVKFLKVKKDPQNPXKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;
```

```
                                              (SEQ ID NO: 97)
MSTTLXSSTYGKDNVKFLKVKKDPQNPKKQEVMEATVTCLLEGGFDTSYTEADNSSI

VPTDTVKNTILVLAKTTEIWPIERFAAKLATHFVEKYSHVSGVSVKIVQDRWVKYAVDGKPHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;
```

```
                                              (SEQ ID NO: 98)
MSTTLSSSTYGKDNVKFLKVKKDPQNXKKQEVMEATVTCLLEGGFDTSYTEADNSSI

VPTDTVKNTILVLAKTTEIWPIERFAAKLATHFVEKYSHVSGVSVKIVQDRWVKYAVDGKPHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;
```

```
                                              (SEQ ID NO: 99)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRXEKTKL;
```

```
                                              (SEQ ID NO: 100)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYXVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;
```

```
                                              (SEQ ID NO: 101)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDXVYNQAREITLTTFALENSPSVQATMFNMATQILE

KACSVYSVSYALPNKHYFLIDLKWKGLENDNELFYPSPHPNGLIKCTVVRKEKTKL;
```

```
                                              (SEQ ID NO: 102)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQARXITLTTFALENSPSVQATMFNMATQILE

KACSVYSVSYALPNKHYFLIDLKWKGLENDNELFYPSPHPNGLIKCTVVRKEKTKL;
```

-continued (SEQ ID NO: 103)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSXDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 104)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFXGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 105)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVXSVSYALPNKHYFLIDLKWKGLENDNELFYPSPHPNGLIKCTVVRKEKTKL;

(SEQ ID NO: 106)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTXRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 107)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEXYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 108)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVXIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 109);
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYXLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL

-continued (SEQ ID NO: 110)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKXSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 111)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYXRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 112)
MSTTLSXSTYGKDNVKFLKVKKDPQNPKKQEVMEATVTCLLEGGFDTSYTEADNSSI

VPTDTVKNTILVLAKTTEIWPIERFAAKLATHFVEKYSHVSGVSVKIVQDRWVKYAVDGKPHD

HSFIHEGGEKRITDLYYKRSGDYKLSSAIKDLTVLKSTGSMFYGYNKCDFTTLQPTTDRILSTD

VDATWVWDNKKIGSVYDIAKAADKGIFDNVYNQAREITLTTFALENSPSVQATMFNMATQIL

EKACSVYSVSYALPNKHYFLIDLKWKGLENDNELFYPSPHPNGLIKCTVVRKEKTKL;

(SEQ ID NO: 113)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKXLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVRKEKTKL;

(SEQ ID NO: 114)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDNELFYPSPHPNGLIKCTVVXKEKTKL;

(SEQ ID NO: 115)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWXGLENDNELFYPSPHPNGLIKCTVVRKEKTKL;

(SEQ ID NO: 116)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYFLIDLKWKGLENDXELFYPSPHPNGLIKCTVVRKEKTKL;

-continued and

```
                                                    (SEQ ID NO: 117)
MSTTLSSSTYGKDNVKFLKVKKDPQNPKKQEVMEATVTCLLEGGFDTSYTEADNSSIV

PTDTVKNTILVLAKTTEIWPIERFAAKLATHFVEKYSHVSGVSVKIVQDRWVKYAVDGKPHDH

SFIHEGGEKRITDLYYKRSGDYKLSSAIKDLTVLKSTGSMFYGYNKCDFTTLQPTTDRILSTDV

DATWVWDNKKIGSVYDIAKAADKGIFDNVYNQAREITLTTFALENSPSVQATMFNMATQILE

KACSVYSVSYALPNKHYXLIDLKWKGLENDNELFYPSPHPNGLIKCTVVRKEKTKL,
``` where X is selected from the nonnatural amino acids disclosed in the
tables of FIGS. 23 to 27.

Example 10, Subunit Sequence Example 3, Arth. Vox

The urate oxidase-albumin conjugate of any one of Examples 2 to 7,
wherein the urate oxidase variant subunit is represented by a sequence
selected from the following:

```
                                                    (SEQ ID NO: 119)
MTATAETSTGTKVVLGQNQYGKAEVRLVKVTRNTARHEIQDLNVTSQLRGDFEAAHT

AGDNAHVVATDTQKNTVYAFARXGFATTEEFLLRLGKHFTEGFDWVTGGRWAAQQFFWDRI

NDHDHAFSRNKSEVRTAVLEISGSEQAIVAGIEGLTVLKSTGSEFHGFPRDKYTTLQETTDRILA

TDVSARWRYNTVEVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;
```

```
                                                    (SEQ ID NO: 120)
MTATAETSTGTKVVLGQNQYGKAEVRLVKVTRNTARHEIQDLNVTSQLRGDFEAAHT

AGDNAHVVATDTQKNTVYAFARDGXATTEEFLLRLGKHFTEGFDWVTGGRWAAQQFFWDR

INDHDHAFSRNKSEVRTAVLEISGSEQAIVAGIEGLTVLKSTGSEFHGFPRDKYTTLQETTDRIL

ATDVSARWRYNTVEVDFDAVYASVRGLLLKAFAETHSLALQQTMYEMGRAVIETHPEIDEIK

MSLPNKHHFLVDLQPFGQDNPNEVFYAADRPYGLIEATIQREGSRADHPIWSNIAGFC;
```

```
                                                    (SEQ ID NO: 121)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGXDWVTGGRWAAQQFFWDR

INDHDHAFSRNKSEVRTAVLEISGSEQAIVAGIEGLTVLKSTGSEFHGFPRDKYTTLQETTDRIL

ATDVSARWRYNTVEVDFDAVYASVRGLLLKAFAETHSLALQQTMYEMGRAVIETHPEIDEIK

MSLPNKHHFLVDLQPFGQDNPNEVFYAADRPYGLIEATIQREGSRADHPIWSNIAGFC;
```

```
                                                    (SEQ ID NO: 122)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFXWVTGGRWAAQQFFWDRI

NDHDHAFSRNKSEVRTAVLEISGSEQAIVAGIEGLTVLKSTGSEFHGFPRDKYTTLQETTDRILA

TDVSARWRYNTVEVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;
```

```
                                                    (SEQ ID NO: 123)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFXWDR

INDHDHAFSRNKSEVRTAVLEISGSEQAIVAGIEGLTVLKSTGSEFHGFPRDKYTTLQETTDRIL

ATDVSARWRYNTVEVDFDAVYASVRGLLLKAFAETHSLALQQTMYEMGRAVIETHPEIDEIK

MSLPNKHHFLVDLQPFGQDNPNEVFYAADRPYGLIEATIQREGSRADHPIWSNIAGFC;
```

```
                                                    (SEQ ID NO: 124)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI
```

-continued

XDHDHAFSRNKSEVRTAVLEISGSEQAIVAGIEGLTVLKSTGSEFHGFPRDKYTTLQETTDRILA

TDVSARWRYNTVEVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;

(SEQ ID NO: 125)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI

NXHDHAFSRNKSEVRTAVLEISGSEQAIVAGIEGLTVLKSTGSEFHGFPRDKYTTLQETTDRILA

TDVSARWRYNTVEVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;

(SEQ ID NO: 126)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI

NDHDHAFSRNKSEVRTAVLEISGXEQAIVAGIEGLTVLKSTGSEFHGFPRDKYTTLQETTDRILA

TDVSARWRYNTVEVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;

(SEQ ID NO: 127)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI

NDHDHAFSRNKSEVRTAVLEISGSXQAIVAGIEGLTVLKSTGSEFHGFPRDKYTTLQETTDRILA

TDVSARWRYNTVEVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;

(SEQ ID NO: 128)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI

NDHDHAFSRNKSEVRTAVLEISGSEQAIVAGIEGLTVLKSTGSEFHGFPRDKYTTLXETTDRILA

TDVSARWRYNTVEVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;

(SEQ ID NO: 129)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI

NDHDHAFSRNKSEVRTAVLEISGSEQAIVAGIEGLTVLKSTGSEFHGFPRDKYTTLQETTDRILA

TDVSARWRYNTXEVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;

(SEQ ID NO: 130)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI

NDHDHAFSRNKSEVRTAVLEISGSEQAIVAGIEGLTVLKSTGSEFHGFPRDKYTTLQETTDRILA

TDVSARWRYNTVXVDFDAVYASVRGLLLKAFAETHSLALQQTMYEMGRAVIETHPEIDEIKM

SLPNKHHFLVDLQPFGQDNPNEVFYAADRPYGLIEATIQREGSRADHPIWSNIAGFC;

(SEQ ID NO: 131)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI

NDHDHAFSRNKSEVRTAVLEISGSEQAIVAGIEGLTVLKSTGSEFHGFPRDKYTTLQETTDRILA

-continued

TDVSARWRYNTVEVDFDAVYASVRGLLLKAFAETXSLALQQTMYEMGRAVIETHPEIDEIKM

SLPNKHHFLVDLQPFGQDNPNEVFYAADRPYGLIEATIQREGSRADHPIWSNIAGFC;
and (SEQ ID NO: 132)
MTATAETSTGTKVVLGQNQYGKAEVRLVKVTRNTARHEIQDLNVTSQLRGDFEAAHT

AGDNAHVVATDTQKNTVYAFARDGFATTEEFLLRLGKHFTEGFDWVTGGRWAAQQFFWDRI

NDHDHAFSRNKSEVRTAVLEISGSEQAIVAGIEGLTVLKSTGSEFHGFPRDKYTTLQETTDRILA

TDVSARWRYNTVEVDFDAVYASVRGLLLKAFAETHSLALQQTMYEMGRAVIETHXEIDEIKM

SLPNKHHFLVDLQPFGQDNPNEVFYAADRPYGLIEATIQREGSRADHPIWSNIAGFC, where X is selected from the nonnatural amino acids disclosed in the tables of FIGS. 23 to 27.

Example 11, Example of Urate Oxidase-Linker Junction

The urate oxidase-albumin conjugate of any one of Examples 1 to 10, wherein the urate oxidase-linker junction is any one selected from the following:

here, R is any one selected from H, $CH_3$, here, the (1) part is linked to the urate oxidase variant, and the (2) part is linked to the anchor of the linker.

Example 12, Limitation of Albumin Sequence

The urate oxidase-albumin conjugate of any one of Examples 1 to 11, wherein the albumin is represented by a sequence selected from the following:

(SEQ ID NO: 133)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESLVNRRPCFSALEV

DETYVPKEFNAETFTFHADICTLSEKERQIKKQTALVELVKHKPKATKEQLKAVMDDFAAFVE

KCCKADDKETCFAEEGKKLVAASQAALGL;

(SEQ ID NO: 134)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

-continued

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQMSTPTLVEVSRNLG

KVGSKCCKHPEAKRMPCAEDYLSVVLNQLCVLHEKTPVSDRVTKCCTESLVNRRPCFSALEV

DETYVPKEFNAETFTFHADICTLSEKERQIKKQTALVELVKHKPKATKEQLKAVMDDFAAFVE

KCCKADDKETCFAEEGKKLVAASQAALGL;

(SEQ ID NO: 135)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSAPTLVEVSRNLG

KVGSKCCKHPEAKRMPCAEDYLSVVLNQLCVLHEKTPVSDRVTKCCTESLVNRRPCFSALEV

DETYVPKEFNAETFTFHADICTLSEKERQIKKQTALVELVKHKPKATKEQLKAVMDDFAAFVE

KCCKADDKETCFAEEGKKLVAASQAALGL;

(SEQ ID NO: 136)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESLVNRRPCFSALEV

DETYVPKEFNARTFTFHADICTLSEKERQIKKQTALVELVKHKPKATKEQLKAVMDDFAAFVE

KCCKADDKETCFAEEGKKLVAASQAALGL;

(SEQ ID NO: 137)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESLVNRRPCFSALEV

DETYVPKEFNAGTFTFHADICTLSEKERQIKKQTALVELVKHKPKATKEQLKAVMDDFAAFVE

KCCKADDKETCFAEEGKKLVAASQAALGL;

(SEQ ID NO: 138)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

-continued

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESLVNRRPCFSALEV

DETYVPKEFNAETFTFHADICTLSEKERQIKKQTALVELVKHKPKATKEQLKAAMDDFAAFVE

KCCKADDKETCFAEEGKKLVAASQAALGL;

(SEQ ID NO: 139)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESLVNRRPCFSALEV

DETYVPKEFNAETFTFHADICTLSEKERQIKKQTALVELVKHKPKATKEQLKAVMDDFAAFVE

KCCKADDKETCFAEEGYKLVAASQAALGL;

(SEQ ID NO: 140)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLIEVSRNLGK

VGSKCCKHPEAKRMPCAEDYLSVVLNQLCVLHEKTPVSDRVTKCCTESLVNRRPCFSALEVD

ETYVPKEFNAETFTFHADICTLSEKERQIKKQTALVELVKHKPKATKEQLKAVMDDFAAFVEK

CCKADDKETCFAEEGKKLVAASQAALGL;

(SEQ ID NO: 141)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRDLG

KVGSKCCKHPEAKRMPCAEDYLSVVLNQLCVLHEKTPVSDRVTKCCTESLVNRRPCFSALEV

DETYVPKEFNAETFTFHADICTLSEKERQIKKQTALVELVKHKPKATKEQLKAVMDDFAAFVE

KCCKADDKETCFAEEGKKLVAASQAALGL;

-continued (SEQ ID NO: 142)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRNLG

KVGSKCCKHPEAKRMPCVEDYLSVVLNQLCVLHEKTPVSDRVTKCCTESLVNRRPCFSALEV

DETYVPKEFNAETFTFHADICTLSEKERQIKKQTALVELVKHKPKATKEQLKAVMDDFAAFVE

KCCKADDKETCFAEEGKKLVAASQAALGL;

(SEQ ID NO: 143)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRNLG

KVGSKCCKHPEAKRMPCAEDYLSVVLNQLCVLHEKMPVSDRVTKCCTESLVNRRPCFSALEV

DETYVPKEFNAETFTFHADICTLSEKERQIKKQTALVELVKHKPKATKEQLKAVMDDFAAFVE

KCCKADDKETCFAEEGKKLVAASQAALGL;
and (SEQ ID NO: 144)
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVHT

ECCHGDLLECADDRADLAKYICENQDSISSKLKECCEKPLLEKSHCIAEVENDEMPADLPSLAA

DFVESKDVCKNYAEAKDVFLGMFLYEYARRHPDYSVVLLLRLAKTYETTLEKCCAAADPHE

CYAKVFDEFKPLVEEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESLVNRRPCFSALEV

DETYVPKEFNAETFTFHADICTLSEKERQIKKQTALVELVKHKPKATKEQLKAVMDDFTAFVE

KCCKADDKETCFAEEGKKLVAASQAALGL.

Example 13, Limitation of Albumin-Linker Junction

The urate oxidase-albumin conjugate of any one of Examples 1 to 12, wherein the albumin-linker junction formed by reaction of the thiol moiety of the albumin and the thiol moiety connected to the anchor.

Example 14, Limitation of Position of Albumin Bonding

The urate oxidase-albumin conjugate of Example 13, wherein the albumin sequence is selected from SEQ ID NO: 133 to 144, and the albumin-linker junction is formed by reaction the thiol moiety of the residue of cysteine at position 34 of the albumin sequence and the thiol reactive group connected to the anchor.

Example 15, Limitation of Albumin-Linker Junction

Figure 30:
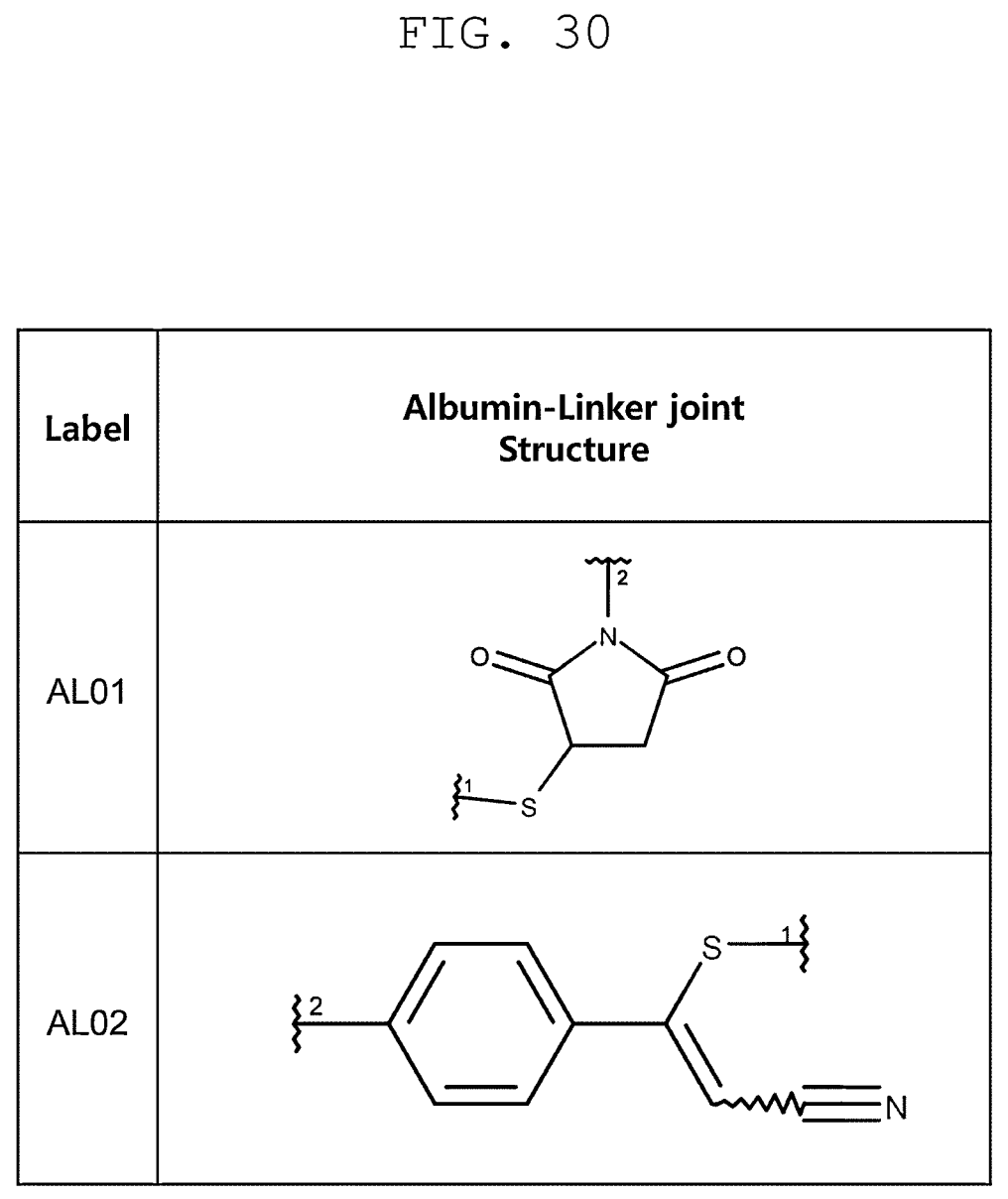

The urate oxidase-albumin conjugate of any one of Examples 13 to 14, wherein the urate oxidase-linker junction is any one selected from the examples in a table of FIG. 30.

US 12,622,951 B2

83

Example 16, Limitation of Anchor

The urate oxidase-albumin conjugate of any one of
Examples 1 to 15, wherein the anchor is selected from the
examples in a table of FIG. 40.

Urate Oxidase-Albumin Conjugate 2

Example 17, Urate Oxidase-Albumin Conjugate,
Perspective from Subunit

A urate oxidase-albumin conjugate including the follow-
ing:
  3 or 4 albumin-subunit conjugates, in which each of the
    albumin-subunit conjugates is represented by Formula
    2 below:

p'-J$_1$-A-J$_2$-HSA,                                    [Formula 2]

in which p' is a urate oxidase variant subunit, J$_1$ is a urate
    oxidase-linker junction, A is an anchor, J$_2$ is an albu-
    min-linker junction, and HSA is human serum albumin,
    and
  in which in the urate oxidase variant subunit, at least one
    amino acid in the sequence of a wild-type urate oxidase
    subunit is substituted with a nonnatural amino acid
    including a tetrazin functional group or a triazine
    functional group,
  in which in the urate oxidase-linker junction, the junction
    is formed by undergoing an inverse electron demand
    Diels-Alder (IEDDA) reaction between he tetrazine or
    triazine functional group of the nonnatural amino acid
    and the trans-cyclooctene functional group connected
    to the anchor; and
  optionally one urate oxidase variant subunit,
  in which, when the urate oxidase-albumin conjugate
    includes three albumin-subunit complexes, the urate
    oxidase-albumin conjugate includes one urate oxidase
    variant subunit, and the urate oxidase variant subunits
    included in the respective albumin-subunit complexes
    and one urate oxidase variant subunit oligomerize to
    form a tetramer,
  in which, when the urate oxidase-albumin conjugate
    includes four albumin-subunit conjugate the urate oxi-
    dase-albumin conjugate includes no urate oxidase vari-
    ant subunits, and the urate oxidase variant subunits
    included in the respective albumin-subunit complexes
    oligomerize to form a tetramer.

Example 18, Conjugation of Four Albumins

The urate oxidase-albumin conjugate of Example 17,
including the following:
  a first albumin-subunit conjugate,
  in which the first albumin-subunit conjugate includes a
    first urate oxidase variant subunit, a first urate oxidase-
    linker junction, a first anchor, a first albumin-linker
    junction, and a first albumin;
  a second albumin-subunit conjugate,
  in which the second albumin-subunit conjugate includes a
    second urate oxidase variant subunit, a second urate
    oxidase-linker junction, a second anchor, a second
    albumin-linker junction, and a second albumin;
  a third albumin-subunit conjugate,
  in which the third albumin-subunit conjugate includes a
    third urate oxidase variant subunit, a third urate oxi-
    dase-linker junction, a third anchor, a third albumin-
    linker junction, and a third albumin;

a fourth albumin-subunit conjugate,
  in which the fourth albumin-subunit conjugate includes a
    fourth urate oxidase variant subunit, a fourth urate
    oxidase-linker junction, a fourth anchor, a fourth albu-
    min-linker junction, and a fourth albumin; and
  in which the first urate oxidase variant subunit, the second
    urate oxidase variant subunit, the third urate oxidase
    variant subunit, and the fourth urate oxidase variant
    subunit oligomerize to form a tetramer.

Example 19, Conjugation of Four Albumins,
Constitutional Elements, Markush Claim The urate oxidase-albumin conjugate of Example 18,
having the following characteristics:
  in which the first urate oxidase variant subunit is repre-
    sented by a sequence selected from SEQ ID NOs: 1 to
    132 or a sequence that is at least 80% identical to the
    selected sequence, in which X included in the selected
    sequence is a nonnatural amino acid selected from
    tables of FIGS. 23 to 27,
  the first urate oxidase-linker junction is one disclosed in
    the table of FIG. 28 according to a nonnatural amino
    acid selected from the tables of FIGS. 23 to 27,
  in which the second urate oxidase variant subunit is
    represented by a sequence selected from SEQ ID NOs:
    1 to 132 or a sequence that is at least 80% identical to
    the selected sequence, in which X included in the
    selected sequence is a nonnatural amino acid selected
    from the tables of FIGS. 23 to 27,
  the second urate oxidase-linker junction is one disclosed
    in the table of FIG. 28 according to a nonnatural amino
    acid selected from the tables of FIGS. 23 to 27,
  in which the third urate oxidase variant subunit is repre-
    sented by a sequence selected from SEQ ID NOs: 1 to
    132 or a sequence that is at least 80% identical to the
    selected sequence, in which X included in the selected
    sequence is a nonnatural amino acid selected from
    tables of FIGS. 23 to 27,
  the third urate oxidase-linker junction is one disclosed in
    the table of FIG. 28 according to a nonnatural amino
    acid selected from the tables of FIGS. 23 to 27,
  in which the fourth urate oxidase variant subunit is
    represented by a sequence selected from SEQ ID NOs:
    1 to 132 or a sequence that is at least 80% identical to
    the selected sequence, in which X included in the
    selected sequence is a nonnatural amino acid selected
    from the tables of FIGS. 23 to 27,
  the fourth urate oxidase-linker junction is one disclosed in
    the table of FIG. 28 according to a nonnatural amino
    acid selected from the tables of FIGS. 23 to 27,
  the first anchor, the second anchor, the third anchor, and
    the fourth anchor are each independently selected from
    the table of FIG. 29,
  the first albumin-linker junction, the second albumin-
    linker junction, the third albumin-linker junction, and
    the fourth albumin linker junction are each indepen-
    dently selected from the table of FIG. 30,
  the first albumin, the second albumin, the third albumin,
    and the fourth albumin are each independently repre-
    sented by a sequence selected from SEQ ID NOs: 133
    to SEQ ID NO: 145, or a sequence that is 80% or more
    identical to the selected sequence,
  the first albumin-linker junction is formed by reaction of
    a thiol reactive moiety connected to the first anchor and
    a thiol moiety of cysteine at position 34 in the first
    albumin sequence, the second albumin-linker junction is formed by reaction of a thiol reactive moiety connected to the second anchor and a thiol moiety of cysteine at position 34 in the second albumin sequence, the third albumin-linker junction is formed by reaction of a thiol reactive moiety connected to the third anchor and a thiol moiety of cysteine at position 34 in the third albumin sequence, the fourth albumin-linker junction is formed by reaction of a thiol reactive moiety connected to the fourth anchor and a thiol moiety of cysteine at position 34 in the fourth albumin.

Example 20, Conjugation of Four Albumins, Limitation of Derivation of Urate Oxidase The urate oxidase-albumin conjugate of Example 19, in which the first urate oxidase variant subunit, the second urate oxidase variant subunit, the third urate oxidase variant subunit, and the fourth urate oxidase variant subunit are all derived from any one microorganism selected from *Aspergillus Flavus, Candida Utilis*, and *Arthrobacter Globiformis*.

Example 21, Conjugation of Three Albumins

The urate oxidase-albumin conjugate of Example 17, including the following:

a first albumin-subunit conjugate, in which the first albumin-subunit conjugate includes a first urate oxidase variant subunit, a first urate oxidase-linker junction, a first anchor, a first albumin-linker junction, and a first albumin;

a second albumin-subunit conjugate, in which the second albumin-subunit conjugate includes a second urate oxidase variant subunit, a second urate oxidase-linker junction, a second anchor, a second albumin-linker junction, and a second albumin;

a third albumin-subunit conjugate, in which the third albumin-subunit conjugate includes a third urate oxidase variant subunit, a third urate oxidase-linker junction, a third anchor, a third albumin-linker junction, and a third albumin;

a fourth urate oxidase variant subunit, in which the first urate oxidase mutant subunit, the second urate oxidase mutant subunit, the third urate oxidase mutant subunit, and the fourth urate oxidase mutant subunit oligomerize to form a tetramer.

Example 22, Conjugation of Three Albumins, Constitutional Elements, Markush Claim The urate oxidase-albumin conjugate of Example 21, having the following characteristics:

in which the first urate oxidase variant subunit is represented by a sequence selected from SEQ ID NOs: 1 to 132 or a sequence that is at least 80% identical to the selected sequence, in which X included in the selected sequence is a nonnatural amino acid selected from tables of FIGS. 23 to 27, the first urate oxidase-linker junction is one disclosed in the table of FIG. 28 according to a nonnatural amino acid selected from the tables of FIGS. 23 to 27, in which the second urate oxidase variant subunit is represented by a sequence selected from SEQ ID NOs: 1 to 132 or a sequence that is at least 80% identical to the selected sequence, in which X included in the selected sequence is a nonnatural amino acid selected from the tables of FIGS. 23 to 27, the second urate oxidase-linker junction is one disclosed in the table of FIG. 28 according to a nonnatural amino acid selected from the tables of FIGS. 23 to 27, in which the first urate oxidase variant subunit is represented by a sequence selected from SEQ ID NOs: 3 to 132 or a sequence that is at least 80% identical to the selected sequence, in which X included in the selected sequence is a nonnatural amino acid selected from tables of FIGS. 23 to 27, the third urate oxidase-linker junction is one disclosed in the table of FIG. 28 according to a nonnatural amino acid selected from the tables of FIGS. 23 to 27, in which the first urate oxidase variant subunit is represented by a sequence selected from SEQ ID NOs: 1 to 132 or a sequence that is at least 80% identical to the selected sequence, in which X included in the selected sequence is a nonnatural amino acid selected from tables of FIGS. 23 to 27, the first anchor, the second anchor, and the third anchor are each independently selected from the table of FIG. 29, the first albumin-linker junction, the second albumin-linker junction, and the third albumin-linker junction are each independently selected from the table of FIG. 30, the first albumin, the second albumin, the third albumin, and the fourth albumin are each independently represented by a sequence selected from SEQ ID NOs: 133 to SEQ ID NO: 145, or a sequence that is 80% or more identical to the selected sequence, the first albumin-linker junction is formed by reaction of a thiol reactive moiety connected to the first anchor and a thiol moiety of cysteine at position 34 in the first albumin sequence, the second albumin-linker junction is formed by reaction of a thiol reactive moiety connected to the second anchor and a thiol moiety of cysteine at position 34 in the second albumin sequence, the third albumin-linker junction is formed by reaction of a thiol reactive moiety connected to the third anchor and a thiol moiety of cysteine at position 34 in the third albumin.

Example 23, Conjugation of Four Albumins, Limitation of Derivation of Urate Oxidase The urate oxidase-albumin conjugate of Example 22, in which the first urate oxidase variant subunit, the second urate oxidase variant subunit, the third urate oxidase variant subunit, and the fourth urate oxidase variant subunit are all derived from any one microorganism selected from *Aspergillus Flavus, Candida Utilis*, and *Arthrobacter Globiformis*.

Pharmaceutical Composition Including Urate Oxidase-Albumin Conjugate

Example 24. Claim of Pharmaceutical Composition

A pharmaceutical composition for preventing or treating uric acid-related diseases, the pharmaceutical composition including:

a therapeutically effective amount of the urate oxidase-albumin conjugate of any one of Examples 1 to 23; and a pharmaceutically acceptable carrier.

Example 25, Limitation of Indications

The pharmaceutical composition of Example 24, in which the uric acid-related disease is any one of hyperuricemia, acute gouty arthritis, intermittent gout, chronic nodular gout, chronic kidney disease, and Tumor Lysis Syndrome (TLS).

Example 26, Example of Carrier

The pharmaceutical composition according to any one of Examples 24 to 25, in which the pharmaceutically acceptable carrier includes one or more of the following:

binders such as lactose, saccharose, sorbitol, mannitol, starch, amylopectin, cellulose or gelatin; excipients such as dicalcium phosphate and the like; disintegrants such as corn starch or sweet potato starch; lubricants such as magnesium stearate, calcium stearate, sodium stearyl fumarate or polyethylene glycol wax; sweetener; air freshener; syrup; liquid carriers such as fatty oils; sterile aqueous solution; propylene glycol; polyethylene glycol; injectable esters such as ethyl oleate; suspending agent; emulsion; freeze-dried preparations; external preparations; stabilizer; buffer; animal oil; vegetable oil; wax; paraffin; starch; tragacanth; cellulose derivatives; polyethylene glycol; silicon; bentonite; silica; talc; and zinc oxide.

A Treatment Method Using Urate Oxidase-Albumin Conjugate

Example 27, Treatment Method Using Pharmaceutical Composition

A method for preventing or treating uric acid-related disease, the method comprising:

Administering the pharmaceutical composition of any one of Examples 24-26 into the body of a patient Example 28, Limitation of Indications The pharmaceutical composition of Example 27, in which the uric acid-related disease is any one of hyperuricemia, acute gouty arthritis, intermittent gout, chronic nodular gout, chronic kidney disease, and Tumor Lysis Syndrome (TLS).

Example 29, Limitation of Administration Method

The method of any one of Examples 27 to 28, in which the administration method is selected from oral administration, parenteral administration, intravenous administration, intravenous infusion, intraperitoneal administration, intramuscular administration, transdermal administration, and subcutaneous administration.

Example 30, Limitation of Dosage

The method according to any one of Examples 27 to 29, in which the pharmaceutical composition is administered into the body of the patient at a dose of 0.01 mg/kg to 1000 mg/kg.

Example 31, Limitation of Administration Interval
1

The method of any one of Examples 27 to 30, in which the pharmaceutical composition is administered once a day.

Example 32, Limitation of Administration Interval
2

The method according to any one of Examples 27 to 30, in which the pharmaceutical composition is administered twice a day.

Use of Urate Oxidase-Albumin Conjugate

Example 33, Use as Preparation of Therapeutic Agent

A use of the urate oxidase-albumin conjugate of any one of Examples 1 to 23 for preparation of a therapeutic agent for Uric Acid-related Diseases Example 34, Limitation of Indications The use of Example 33, in which the uric acid-related disease is any one of hyperuricemia, acute gouty arthritis, intermittent gout, chronic nodular gout, chronic kidney disease, and Tumor Lysis Syndrome (TLS).

Urate Oxidase-Albumin Conjugate Preparation Method

Example 35, Albumin-Linker Conjugation First

A method for preparing a urate oxidase-albumin conjugate, the method comprising:

reacting an albumin and a linker,
wherein the linker comprises a dienophile functional group, an anchor, and a thiol reactive moiety,
wherein the thiol reactive moiety of the linker is bound with thiol moiety of albumin through reaction to form an albumin-linker conjugate; and
reacting the albumin-linker conjugate and the urate oxidase variant,
in which, the urate oxidase variant is one in which three or more amino acids in the sequence of a wild-type urate oxidase are substituted with non-natural amino acids containing a diene functional group,
a diene functional group of the urate oxidase variant and a dienophile functional group of the linker of the albumin-linker conjugate bind to each other through an Inverse Electron Demand Diels-Alder (IEDDA) reaction to form a urate oxidase-albumin conjugate, and
the urate oxidase-albumin conjugate is characterized in that three or more albumins are conjugated to the urate oxidase variant through the linkers.

Example 36, Urate Oxidase-Albumin Conjugation First

A method for preparing a urate oxidase-albumin conjugate, the method comprising:

reacting a urate oxidase variant and a linker,
in which, the urate oxidase variant is one in which three or more amino acids in the sequence of a wild-type urate oxidase are substituted with non-natural amino acids containing a diene functional group, the linker includes a dienophile functional group, an anchor, and a thiol reactive moiety, the diene functional group of the urate oxidase variant and the dienophile functional group of the linker bind to each other through an Inverse Electron Demand Diels-Alder (IEDDA) reaction to produce a urate oxidase-linker conjugated, and the urate oxidase-linker conjugate is characterized in that three or more linkers are conjugated to the urate oxidase variants; and reacting the urate oxidase-linker conjugate with albumin, in which the thiol-reactive group of the linker of the urate oxidase-linker conjugate and the thiol group of the albumin are combined through a reaction to generate a urate oxidase-albumin conjugate, and the urate oxidase-albumin conjugate is characterized in that three or more albumins are conjugated to the urate oxidase-linker conjugates.

Example 37, Urate Oxidase, Linker, and Albumin Simultaneously

A method for preparing a urate oxidase-albumin conjugate, the method comprising:

reacting a urate oxidase variant, a linker, and an albumin, in which, the urate oxidase variant is one in which three or more amino acids in the sequence of a wild-type urate oxidase are substituted with non-natural amino acids containing a diene functional group, the linker includes a dienophile functional group, an anchor, and a thiol reactive moiety, in which a thiol moiety of the albumin and a thiol moiety of the linker react to bind to each other, the dien functional group contained in the nonnatural amino acid of the urate oxidase variant and the IEDDA reactive group of the linker are conjugated through a reaction, and as a result of the reaction, the urate oxidase-albumin conjugate is produced.

Example 38, Limitation of Urate Oxidase Variant

The urate oxidase-albumin conjugate preparation method of any one of Examples 36 to 37, in which the urate oxidase variant is a tetramer obtained by oligomerization of four urate oxidase variant subunits, and the urate oxidase variant subunit is a subunit obtained by substituting one or more amino acids in the sequence of a wild urate oxidase subunit with one or more nonnatural amino acids.

Example 39, Limitation of Dien Functional Group of Nonnatural Amino Acid

The urate oxidase-albumin conjugate preparation method of anyone of Examples 35 to 37, in which the dien function group of the nonnatural amino acid is a tetrazine function group or a triazine functional group.

Example 40, Limitation of Dienophile Functional Group

The urate oxidase-albumin conjugate preparation method of any one of Examples 35 to 37, in which the dienophile function group of the linker is selected from trans-cyclooctene and derivatives thereof.

Example 41, Limitation of Thiol Reactive Group

The urate oxidase-albumin conjugate preparation method of any one of Examples 35 to 37, in which the thiol reactive group is selected from maleimide or derivatives thereof; and 3-arylpropiolonitriles or derivatives thereof.

Example 42, Limitation of Reaction Condition of Urate Oxidase-Linker

The urate oxidase-albumin conjugate preparation method of any one of Examples 35 to 37, in which the reacting of the urate oxidase variant and the liner is performed in a neutral pH environment.

Example 43: Markush Claim of Pharmaceutical Composition

Figure 31:
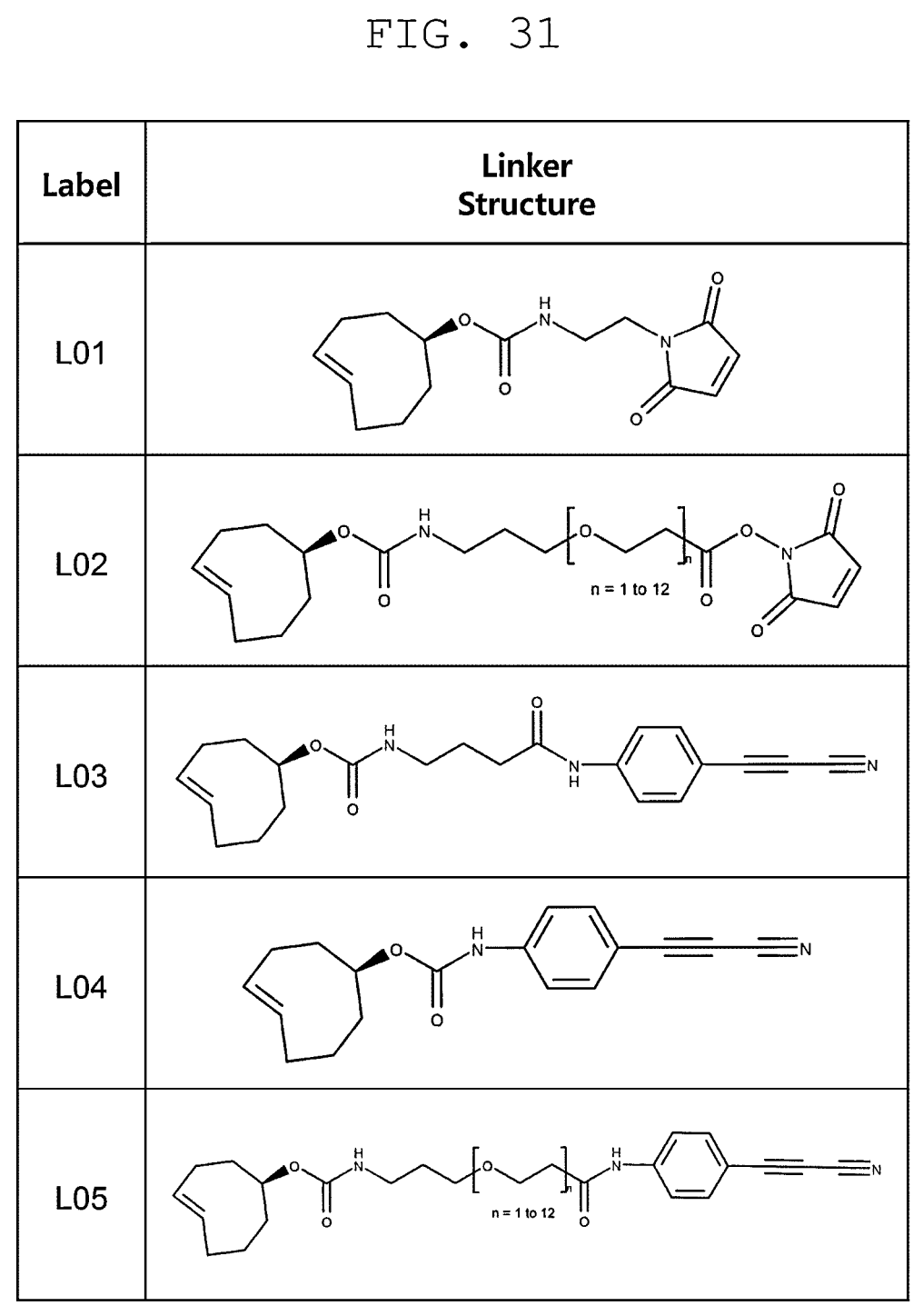

The method of any one of Examples 35 to 37, in which the urate oxidase variant is a tetramer formed by oligomerization of four urate oxidase variant subunits represented by a sequence, wherein the sequence of each subunit is independently selected from SEQ ID NOs: 1 to 132 or a sequence 80% or more identical to the selected sequence, in which X in the selected sequence is a nonnatural amino acid selected from the tables of FIGS. 23 to 27, the linker is selected from the table of FIG. 31, the albumin is represented by a sequence selected from SEQ ID NOs: 133 to 144 or a sequence 80% or more identical to the selected sequence, and the thiol moiety of the albumin is a thiol moiety of cysteine at position 34 in a sequence selected from SEQ ID NOs:133 to 144 or in a sequence that is 80% or more identical to the selected sequence.

Urate Oxidase Variant

Example 44, Urate Oxidase Variant

A urate oxidase variant including three or more unnatural amino acids in the sequence thereof, in which each of the nonnatural amino acids includes a tetrazine functional group or a triazine functional group.

Example 45, Inclusion of Three Urate Oxidase Variant Subunit

The urate oxidase variant of Example 44, in which the urate oxidase variant is a tetramer formed by oligomerization of one wild-type urate oxidase subunit and three urate oxidase variant subunits, in which the urate oxidase variant subunit is a subunit obtained by substituting at least one amino acid in the sequence of a wild-type urate oxidase subunit with a nonnatural amino acid including a tetrazin functional group or a triazine functional group.

Example 46, Inclusion of Four Urate Oxidase Variant Subunits

The urate oxidase variant of Example 44, in which the urate oxidase variant is a tetramer formed by oligomerization of four urate oxidase variant subunits, and in which the urate oxidase variant subunit is a subunit obtained by substituting at least one amino acid in the sequence of a wild-type urate oxidase subunit with a nonnatural amino acid including a tetrazin functional group or a triazine functional group.

Example 47, Exemplifying Origins of Urate Oxidase

The urate oxidase variant of Example 46, in which each of the urate oxidase variant subunits is obtained by modifying the sequence of a wild-type urate oxidase subunit derived from a microorganism selected from *Aspergillus Flavus, Candida Utilis*, and *Arthrobacter Globiformis.*

Example 48, Limitation of Position of Substitution of Urate Oxidase Variant

The urate oxidase variant of Example 46, in which each of the urate oxidase variant subunits is obtained by substituting one or more amino acids at appropriate positions for substitution in the sequence of a wild-type urate oxidase subunit with the nonnatural amino acid, and
the appropriate positions for substitution are determined as positions that do not affect the function and structure of urate oxidase subunits and at which accessibility to a solvent is high.

Example 49, Limitation of Substitution Position Determination Method for Urate Oxidase Variant The urate oxidase variant of Example 48, in which the appropriate position for substitution is determined preferably by referring to a scoring result of a Rosetta molecule modeling package as a result of a molecule modeling simulation result.

Example 50, *Aspergillus Flavus* Uox, Sequence Selection

The urate oxidase variant of Example 47, in which the urate oxidase variant includes a first urate oxidase variant subunit, a second urate oxidase variant subunit, a third urate oxidase variant subunit, and a fourth urate oxidase variant subunit,
the first urate oxidase variant subunit, the second urate oxidase variant subunit, the third urate oxidase variant subunit, and the fourth urate oxidase variant subunit are each independently represented by a sequence selected from SEQ ID NOs: 2 to SEQ ID NO: 50, or a sequence that is 80% or more identical to the selected sequence, and
X in each sequence is a nonnatural amino acid including a tetrazine functional group or a triazine functional group.

Example 51, *Aspergillus Flavus* Uox, Selection of Nonnatural Amino Acid

The urate oxidase variant of Example 50, in which in each of the urate oxidase variant subunits, X is a nonnatural amino acid selected independently from the tables of FIGS. 23 to 27.

Example 52, *Aspergillus Flavus* Uox, Sequence Unfication

The urate oxidase variant of Example 51, in which the first urate oxidase variant, the second urate oxidase variant, the third urate oxidase variant, and the fourth urate oxidase variant have the identical sequence.

Example 53, *Candida Utilis* Uox, Sequence Selection

The urate oxidase variant of Example 47, in which the urate oxidase variant includes a first urate oxidase variant subunit, a second urate oxidase variant subunit, a third urate oxidase variant subunit, and a fourth urate oxidase variant subunit,
the first urate oxidase variant subunit, the second urate oxidase variant subunit, the third urate oxidase variant subunit, and the fourth urate oxidase variant subunit are each independently represented by a sequence selected from SEQ ID NOs: 52 to 117, or a sequence that is 80% or more identical to the selected sequence, and
X in each sequence is a nonnatural amino acid including a tetrazine functional group or a triazine functional group.

Example 54, *Candida Utilis* Uox, Selection of Nonnatural Amino Acid

The urate oxidase variant of Example 53, in which in each of the urate oxidase variant subunits, X is a nonnatural amino acid selected independently from the tables of FIGS. 23 to 27.

Example 55, *Candida Utilis* Uox, Sequence Unification

The urate oxidase variant of Example 54, in which the first urate oxidase variant, the second urate oxidase variant, the third urate oxidase variant, and the fourth urate oxidase variant have the identical sequence.

Example 56, *Arthrobacter Globiformis* Uox, Sequence Selection

The urate oxidase variant of Example 47, in which the urate oxidase variant includes a first urate oxidase variant subunit, a second urate oxidase variant subunit, a third urate oxidase variant subunit, and a fourth urate oxidase variant subunit,
the first urate oxidase variant subunit, the second urate oxidase variant subunit, the third urate oxidase variant subunit, and the fourth urate oxidase variant subunit are each independently represented by a sequence selected from SEQ ID NOs: 119 to 132, or a sequence that is 80% or more identical to the selected sequence, and
X in each sequence is a nonnatural amino acid including a tetrazine functional group or a triazine functional group.

Example 57, *Arthrobacter Globiformis* Uox, Selection of Nonnatural Amino Acid

The urate oxidase variant of Example 56, in which in each of the urate oxidase variant subunits, X is a nonnatural amino acid selected independently from the tables of FIGS. 23 to 27.

Example 58, *Arthrobacter Globiformis* Uox, Sequence Unification

The urate oxidase variant of Example 57, in which the first urate oxidase variant, the second urate oxidase variant, the third urate oxidase variant, and the fourth urate oxidase variant have the identical sequence.

Vector Expressing Urate Oxidase Variant

Example 59, Vector Expressing Urate Oxidase Variant

A vector capable of expressing the urate oxidase variant of anyone of Examples 44 to 58, in which a part corresponding to a nonnatural amino acid in the urate oxidase variant is encoded with any one selected from an ambber codon (5'-UAG-3'), an ocher codon (5'-UAA-3'), and an opal codon (5'-UGA-3').

Example 60, Limitation of Vector Expressing Urate Oxidase Variant

The vector of Example 59, in which the vector includes one or more sequences selected from the following or includes sequences that are 80% or more identical to the selected sequences:

(SEQ ID NO: 152)
```
5'-ATGTCTGCTGTGAAGGCCGCAAGATATGGCAAGGATAATGTGAGGGTGTACAAGGTGCAT

AAGGACGAAAAGACTGGCGTGCAGACAGTGTACGAGATGACCGTGTGCGTCCTGCTGGA

GGGCGAAATCGAGACTTCTTATACCAAAGCCGACAACTCCGTGATTGTGGCCACAGATTC

TATCAAGAACACTATCTATATCACCGCCAAACAGAACCCAGTGACACCACCTGAACTGTT

CGGCAGCATTCTCGGCACACACTTTATTGAGAAGTACAACCACATCCATGCTGCACACGT

GAATATCGTGTGTCATCGCTGGACCCGCATGGACATCTAGGGAAAGCCACACCCCCACTC

TTTTATCAGAGACTCTGAAGAAAAGAGAAACGTGCAGGTCGACGTGGTGGAGGGAAAAG

GTATCGACATCAAGAGCTCACTCTCCGGCCTGACCGTGCTGAAGAGTACCAATTCACAGTT

TTGGGGGTTTCTGAGAGACGAATACACTACACTGAAGGAGACTTGGGATAGAATCCTGAG

TACCGACGTGGATGCAACCTGGCAGTGGAAGAATTTTTCCGGGCTGCAGGAAGTGCGGTC

CCACGTGCCCAAGTTTGATGCAACCTGGGCAACCGCAAGGGAGGTGACACTGAAAACCTT

TGCCGAGGACAACTCCGCTAGCGTGCAGGCCACAATGTACAAGATGGCCGAACAGATCCT

GGCCAGACAGCAGCTGATTGAGACTGTGGAGTACTCTCTGCCTAACAAGCACTATTTCGA

AATCGACCTGTCCTGGCACAAGGGACTGCAGAATACTGGTAAAAACGCAGAGGTGTTCGC

CCCTCAGAGTGATCCCAATGGTCTGATCAAATGCACAGTGGGGAGATCCTCTCTGAAGAG

CAAGCTGTAA-3';
```

(SEQ ID NO: 153)
```
5'-ATGTCTGCTGTGAAGGCCGCAAGATATGGCAAGGATAATGTGAGGGTGTACAAGGTGCAT

AAGGACGAAAAGACTGGCGTGCAGACAGTGTACGAGATGACCGTGTGCGTCCTGCTGGA

GGGCGAAATCGAGACTTCTTATACCAAAGCCGACAACTCCGTGATTGTGGCCACAGATTC

TATCAAGAACACTATCTATATCACCGCCAAACAGAACCCAGTGACACCACCTGAACTGTT

CGGCAGCATTCTCGGCACACACTTTATTGAGAAGTACAACCACATCCATGCTGCACACGT

GAATATCGTGTGTCATCGCTGGACCCGCATGGACATCGACGGAAAGCCACACCCCCACTC

TTTTATCAGAGACTCTGAAGAAAAGAGAAACGTGCAGGTCGACGTGGTGGAGGGAAAAG

GTATCGACATCAAGAGCTCACTCTCCGGCCTGACCGTGCTGAAGAGTACCAATTCACAGTT

TTAGGGGTTTCTGAGAGACGAATACACTACACTGAAGGAGACTTGGGATAGAATCCTGAG

TACCGACGTGGATGCAACCTGGCAGTGGAAGAATTTTTCCGGGCTGCAGGAAGTGCGGTC

CCACGTGCCCAAGTTTGATGCAACCTGGGCAACCGCAAGGGAGGTGACACTGAAAACCTT

TGCCGAGGACAACTCCGCTAGCGTGCAGGCCACAATGTACAAGATGGCCGAACAGATCCT

GGCCAGACAGCAGCTGATTGAGACTGTGGAGTACTCTCTGCCTAACAAGCACTATTTCGA

AATCGACCTGTCCTGGCACAAGGGACTGCAGAATACTGGTAAAAACGCAGAGGTGTTCGC

CCCTCAGAGTGATCCCAATGGTCTGATCAAATGCACAGTGGGGAGATCCTCTCTGAAGAG

CAAGCTGTAA-3';
```

-continued (SEQ ID NO: 154)

5'-ATGTCTGCTGTGAAGGCCGCAAGATATGGCAAGGATAATGTGAGGGTGTACAAGGTGCAT

AAGGACGAAAAGACTGGCGTGCAGACAGTGTACGAGATGACCGTGTGCGTCCTGCTGGA

GGGCGAAATCGAGACTTCTTATACCAAAGCCGACAACTCCGTGATTGTGGCCACAGATTC

TATCAAGAACACTATCTATATCACCGCCAAACAGAACCCAGTGACACCACCTGAACTGTT

CGGCAGCATTCTCGGCACACACTTTATTGAGAAGTACAACCACATCCATGCTGCACACGT

GAATATCGTGTGTCATCGCTGGACCCGCATGGACATCGACGGAAAGCCACACCCCCACTC

TTTTATCAGAGACTCTGAAGAAAGAGAAACGTGCAGGTCGACGTGGTGGAGGGAAAAG

GTATCGACATCAAGAGCTCACTCTCCGGCCTGACCGTGCTGAAGAGTACCAATTCACAGTT

TTGGGGGTTTCTGAGAGACGAATACACTACACTGAAGGAGACTTAGGATAGAATCCTGAG

TACCGACGTGGATGCAACCTGGCAGTGGAAGAATTTTTCCGGGCTGCAGGAAGTGCGGTC

CCACGTGCCCAAGTTTGATGCAACCTGGGCAACCGCAAGGGAGGTGACACTGAAAACCTT

TGCCGAGGACAACTCCGCTAGCGTGCAGGCCACAATGTACAAGATGGCCGAACAGATCCT

GGCCAGACAGCAGCTGATTGAGACTGTGGAGTACTCTCTGCCTAACAAGCACTATTTCGA

AATCGACCTGTCCTGGCACAAGGGACTGCAGAATACTGGTAAAAACGCAGAGGTGTTCGC

CCCTCAGAGTGATCCCAATGGTCTGATCAAATGCACAGTGGGGAGATCCTCTCTGAAGAG

CAAGCTGTAA-3';

(SEQ ID NO: 155)

5'-ATGAGCACCACACTGAGCAGCAGCACCTATGGTAAAGATAATGTGAAATTCCTGAAAGTG

AAAAAAGATCCGCAGAACCCGAAAAAACAAGAAGTTATGGAAGCAACCGTTACCTGTCT

GCTGGAAGGTGGTTTTGATACCAGCTATACCGAAGCAGATAATAGCAGCATTGTTCCGAC

CGATACCGTGAAAAATACCATTCTGGTTCTGGCAAAAACCACCGAAATTTGGCCGATTGA

ACGTTTTGCAGCCAAACTGGCAACCCATTTTGTTGAGAAATATTCTCATGTTAGCGGTGTG

AGCGTTAAAATTGTTCAGGATCGTTGGGTTAAATATGCCGTTGATGGTAAACCGCATGATC

ACAGCTTTATTCATGAAGGTGGTGAAAAACGTATCACCGACCTGTATTACAAACGTAGCG

GTGATTATAAACTGTCCAGCGCAATTAAAGATCTGACCGTTCTGAAAAGCACCGGCAGCA

TGTTTTAGGGTTATAACAAATGCGATTTCACAACCCTGCAGCCGACCACCGATCGTATTCT

GAGCACCGATGTTGATGCAACCTGGGTTTGGGATAATAAGAAAATTGGTAGCGTGTACGA

TATTGCCAAAGCAGCAGATAAAGGCATCTTCGATAATGTGTATAATCAGGCACGTGAAAT

TACCCTGACCACCTTTGCACTGGAAAATAGCCCGAGCGTTCAGGCAACCATGTTTAATATG

GCGACCCAGATTCTGGAAAAAGCGTGTAGCGTTTATAGCGTTAGCTATGCACTGCCGAAC

AAACACTATTTTCTGATTGACCTGAAATGGAAGGGCCTTGAAAATGATAACGAACTGTTTT

ATCCGAGTCCGCATCCGAATGGTCTGATTAAATGTACCGTTGTGCGTAAAGAGAAAACCA

AACTGTAA-3';

(SEQ ID NO: 156)

5'-ATGAGCACCACACTGAGCAGCAGCACCTATGGTAAAGATAATGTGAAATTCCTGAAAGTG

AAAAAAGATCCGCAGAACCCGAAAAAACAAGAAGTTATGGAAGCAACCGTTACCTGTCT

GCTGGAAGGTGGTTTTGATACCAGCTATACCGAAGCAGATAATAGCAGCATTGTTCCGAC

CGATACCGTGAAAAATACCATTCTGGTTCTGGCAAAAACCACCGAAATTTGGCCGATTGA

ACGTTTTGCAGCCAAACTGGCAACCCATTTTGTTGAGAAATATTCTCATGTTAGCGGTGTG

AGCGTTAAAATTGTTCAGGATCGTTGGGTTAAATATGCCGTTGATGGTAAACCGCATGATC

ACAGCTTTATTCATGAAGGTGGTGAAAAACGTATCACCGACCTGTATTACAAACGTAGCG

-continued

GTGATTATAAACTGTCCAGCGCAATTAAAGATCTGACCGTTCTGAAAAGCACCGGCAGCA

TGTTTTATGGTTATAACAAATGCGATTTCACAACCCTGCAGCCGACCACCGATCGTATTCT

GAGCACCGATGTTGATGCAACCTGGGTTTGGGATAATAAGAAAATTGGTAGCGTGTAGGA

TATTGCCAAAGCAGCAGATAAAGGCATCTTCGATAATGTGTATAATCAGGCACGTGAAAT

TACCCTGACCACCTTTGCACTGGAAAATAGCCCGAGCGTTCAGGCAACCATGTTTAATATG

GCGACCCAGATTCTGGAAAAAGCGTGTAGCGTTTATAGCGTTAGCTATGCACTGCCGAAC

AAACACTATTTTCTGATTGACCTGAAATGGAAGGGCCTTGAAAATGATAACGAACTGTTTT

ATCCGAGTCCGCATCCGAATGGTCTGATTAAATGTACCGTTGTGCGTAAAGAGAAAACCA

AACTGTAA-3';

(SEQ ID NO: 157)
5'-ATGAGCACCACACTGAGCAGCAGCACCTATGGTAAAGATAATGTGAAATTCCTGAAAGTG

AAAAAAGATCCGCAGAACCCGAAAAAACAAGAAGTTATGGAAGCAACCGTTACCTGTCT

GCTGGAAGGTGGTTTTGATACCAGCTATACCGAAGCAGATAATAGCAGCATTGTTCCGAC

CGATACCGTGAAAAATACCATTCTGGTTCTGGCAAAAACCACCGAAATTTGGCCGATTGA

ACGTTTTGCAGCCAAACTGGCAACCCATTTTGTTGAGAAATATTCTCATGTTAGCGGTGTG

AGCGTTAAAATTGTTCAGGATCGTTGGGTTAAATATGCCGTTGATGGTAAACCGCATGATC

ACAGCTTTATTCATGAAGGTGGTGAAAAACGTATCACCGACCTGTATTACAAACGTAGCG

GTGATTATAAACTGTCCAGCGCAATTAAAGATCTGACCGTTCTGAAAAGCACCGGCAGCA

TGTTTTATGGTTATAACAAATGCGATTTCACAACCCTGCAGCCGACCACCGATCGTATTCT

GAGCACCGATGTTGATGCAACCTGGGTTTGGGATAATAAGAAAATTGGTAGCGTGTACGA

TATTGCCAAAGCAGCAGATAAAGGCATCTTCGATAATGTGTATAATCAGGCACGTGAAAT

TACCCTGACCACCTTTGCACTGGAAAATAGCCCGAGCGTTCAGGCAACCATGTTTAATATG

GCGACCCAGATTCTGGAAAAAGCGTGTAGCGTTTATAGCGTTAGCTATGCACTGCCGAAC

AAACACTATTTTCTGATTGACCTGAAATAGAAGGGCCTTGAAAATGATAACGAACTGTTTT

ATCCGAGTCCGCATCCGAATGGTCTGATTAAATGTACCGTTGTGCGTAAAGAGAAAACCA

AACTGTAA-3';

(SEQ ID NO: 158)
5'-ATGACCGCAACCGCAGAAACCAGCACCGGCACCAAAGTTGTTCTGGGTCAGAATCAGTAT

GGTAAAGCAGAAGTTCGTCTGGTTAAAGTTACCCGTAATACCGCACGTCATGAAATTCAG

GATCTGAATGTTACCAGCCAGCTGCGTGGTGATTTTGAAGCAGCACATACCGCAGGCGAT

AATGCACATGTTGTTGCAACCGATACACAGAAAAACACCGTTTATGCATTTGCCCGTGATG

GTTTTGCAACCACCGAAGAATTTCTGCTGCGTCTGGGTAAACATTTCACCGAAGGTTTTGA

TTGGGTTACCGGTGGTCGTTGGGCAGCACAGCAGTTTTTCTGGGATCGTATTTAGGATCAC

GATCATGCCTTTAGCCGCAATAAAAGCGAAGTGCGTACCGCAGTTCTGGAAATTAGCGGT

AGCGAACAGGCAATTGTTGCAGGTATTGAAGGTCTGACCGTTCTGAAAAGCACCGGTAGC

GAGTTTCATGGTTTTCCGCGTGATAAATACACCACACTGCAAGAAACCACCGATCGTATTC

TGGCAACCGATGTTAGCGCACGTTGGCGTTATAATACCGTTGAAGTTGATTTTGATGCGGT

TTATGCAAGCGTTCGTGGTCTGCTGCTGAAAGCATTTGCAGAAACCCATAGCCTGGCACTG

CAGCAGACAATGTATGAAATGGGTCGTGCAGTTATTGAAACCCATCCGGAAATTGATGAG

ATCAAAATGAGCCTGCCGAACAAACATCATTTTCTGGTTGATCTGCAGCCGTTTGGTCAGG

ATAATCCGAATGAAGTGTTTTATGCAGCAGATCGTCCGTATGGTCTGATTGAAGCAACCAT

TCAGCGTGAAGGTAGCCGTGCAGATCATCCGATTTGGAGTAATATTGCAGGTTTTTGCTAA-3';

-continued (SEQ ID NO: 159)

```
5'-ATGACCGCAACCGCAGAAACCAGCACCGGCACCAAAGTTGTTCTGGGTCAGAATCAGTAT

GGTAAAGCAGAAGTTCGTCTGGTTAAAGTTACCCGTAATACCGCACGTCATGAAATTCAG

GATCTGAATGTTACCAGCCAGCTGCGTGGTGATTTTGAAGCAGCACATACCGCAGGCGAT

AATGCACATGTTGTTGCAACCGATACACAGAAAAACACCGTTTATGCATTTGCCCGTGATG

GTTTTGCAACCACCGAAGAATTTCTGCTGCGTCTGGGTAAACATTTCACCGAAGGTTTTGA

TTGGGTTACCGGTGGTCGTTGGGCAGCACAGCAGTTTTTCTGGGATCGTATTAATGATCAC

GATCATGCCTTTAGCCGCAATAAAAGCGAAGTGCGTACCGCAGTTCTGGAAATTAGCGGT

TAGGAACAGGCAATTGTTGCAGGTATTGAAGGTCTGACCGTTCTGAAAAGCACCGGTAGC

GAGTTTCATGGTTTTCCGCGTGATAAATACACCACACTGCAAGAAACCACCGATCGTATTC

TGGCAACCGATGTTAGCGCACGTTGGCGTTATAATACCGTTGAAGTTGATTTTGATGCGGT

TTATGCAAGCGTTCGTGGTCTGCTGCTGAAAGCATTTGCAGAAACCCATAGCCTGGCACTG

CAGCAGACAATGTATGAAATGGGTCGTGCAGTTATTGAAACCCATCCGGAAATTGATGAG

ATCAAAATGAGCCTGCCGAACAAACATCATTTTCTGGTTGATCTGCAGCCGTTTGGTCAGG

ATAATCCGAATGAAGTGTTTTATGCAGCAGATCGTCCGTATGGTCTGATTGAAGCAACCAT

TCAGCGTGAAGGTAGCCGTGCAGATCATCCGATTTGGAGTAATATTGCAGGTTTTTGCTAA-3';
and
```

(SEQ ID NO: 160)

```
5'-ATGACCGCAACCGCAGAAACCAGCACCGGCACCAAAGTTGTTCTGGGTCAGAATCAGTAT

GGTAAAGCAGAAGTTCGTCTGGTTAAAGTTACCCGTAATACCGCACGTCATGAAATTCAG

GATCTGAATGTTACCAGCCAGCTGCGTGGTGATTTTGAAGCAGCACATACCGCAGGCGAT

AATGCACATGTTGTTGCAACCGATACACAGAAAAACACCGTTTATGCATTTGCCCGTGATG

GTTTTGCAACCACCGAAGAATTTCTGCTGCGTCTGGGTAAACATTTCACCGAAGGTTTTGA

TTGGGTTACCGGTGGTCGTTGGGCAGCACAGCAGTTTTTCTGGGATCGTATTAATGATCAC

GATCATGCCTTTAGCCGCAATAAAAGCGAAGTGCGTACCGCAGTTCTGGAAATTAGCGGT

AGCGAACAGGCAATTGTTGCAGGTATTGAAGGTCTGACCGTTCTGAAAAGCACCGGTAGC

GAGTTTCATGGTTTTCCGCGTGATAAATACACCACACTGCAAGAAACCACCGATCGTATTC

TGGCAACCGATGTTAGCGCACGTTGGCGTTATAATACCGTTTAGGTTGATTTTGATGCGGT

TTATGCAAGCGTTCGTGGTCTGCTGCTGAAAGCATTTGCAGAAACCCATAGCCTGGCACTG

CAGCAGACAATGTATGAAATGGGTCGTGCAGTTATTGAAACCCATCCGGAAATTGATGAG

ATCAAAATGAGCCTGCCGAACAAACATCATTTTCTGGTTGATCTGCAGCCGTTTGGTCAGG

ATAATCCGAATGAAGTGTTTTATGCAGCAGATCGTCCGTATGGTCTGATTGAAGCAACCAT

TCAGCGTGAAGGTAGCCGTGCAGATCATCCGATTTGGAGTAATATTGCAGGTTTTTGCTAA-3'.
```

Urate Oxidase Variant Preparation Method

Example 61, Urate Oxidase Variant Preparation Method

A method for preparing a urate oxidase variant, the method comprising:
   preparing a cell line comprising a vector capable of expressing an orthogonal tRNA/synthetase pair, and a urate oxidase variant expression vector,
   wherein the vector capable of expressing orthogonal tRNA/synthetase is capable of expressing an exogenous suppressor tRNA and an exogenous tRNA synthetase, wherein the exogenous suppressor tRNA is capable of recognizing a specific stop codon,
the exogenous tRNA synthetase is capable of recognizing a nonnatural amino acid containing a tetrazine functional group and/or a triazine functional group and of linking the recognized amino acid to the exogenous suppressor tRNA,
wherein the urate oxidase variant expression vector is capable of expressing the urate oxidase variant of one of Examples 44 to 58 and is formed such that a position corresponding to the nonnatural amino acid in the urate oxidase variant is encoded with the specific stop codon; and culturing the cell line in a medium containing at least one kind of a nonnatural amino acid comprising a tetrazine functional group and/or a triazine functional group.

Example 62, Limitation of Stop Codon

The method of Example 61, in which the specific stop codon is any one selected from among an amber codon (5'-UAG-3'), an ocher codon (5'-UAA-3'), and an opal codon (5'-UGA-3').

Example 63, Cell Line Mutation

The method of Example 62, in which the cell line is a cell line in which a release factor recognizing the specific stop codon is inactivated.

Example 64, Limitation of Cell Line

The method of Example 63, in which the cell line is *E. Coli* C321.ΔA.exp(Addgene, ID:49018).

Example 65, Limitation of Orthogonal tRNA/Synthetase Pair

The method of Example 61, in which the orthogonal tRNA/synthetase pair is *Methanococcus jannaschii*-derived suppressor tRNA (MjtRNA$^{Tyr}_{CUA}$) and *Methanococcus jannaschii*-derived tyrosyl-tRNA synthetase (MjTyrRS).

Example 66, Limitation of Vector Expressing tRNA/Synthetase Pair

The method of Example 65, in which the vector capable of expressing the orthogonal tRNA/synthetase pair may be pDule_C11 reported by Yang et. al. (Temporal Control of Efficient In Vivo Bioconjugation Using a Genetically Encoded Tetrazine-Mediated Inverse-Electron-Demand Diels-Alder Reaction, Bioconjugate Chemistry, 2020, 2456-2464).

Example 67, Limitation of Urate Oxidase Variant

The method of Example 61, in which the vector expressing the urate oxidase variant is capable of expressing the urate oxidase variant of one of Example 51, Example 54, and Example 57, the nonnatural amino acid in the sequence of the urate oxidase variant is encoded with the specific stop codon.

MODE FOR INVENTION

Hereinafter, the invention provided by the present description will be described in more detail through experimental examples and examples. These examples are only for illustrative purposes, and it will be apparent to those skilled in the art that the scope of the disclosure of the present description is not limited by these examples.

Experimental Example 1: Obtainment of Urate Oxidase Variant

Experimental Example 1.1: Preparation of Vector for Expression of Urate Oxidase Variant A pTAC_Uox plasmid was constructed using the gene encoding Uox derived from *Aspergillus flavus* as a template. In order to apply a TAC promoter, the sequence information of the pTAC-MAT-TAG-1 expression vector (Sigma, E5530) was referred to, and the 5'-TITGTITAACTI-TAAGAAGGAGA-3' (Sequence ID NO: 151), which is a Ribosome binding site (RBS) sequence extended compared to the existing pQE80 vector, was applied. For recombinant protein expression of a pTAC vector, transcription control, rmBt1 terminator sequence, and rmBt2 terminator sequence were applied.

The DNA synthesis of the sequence of the rmbT1-rmbT2 terminator from the TAC promoter was performed by Macrogen at the request of the inventors, and cloning was performed on the pQE80L vector to prepare a pTAC-empty vector. Cloning of pTAC-empty was carried out through infusion cloning, and cloning was completed using an Infusion® HD cloning kit (Takara Korea Biomedical). The prepared pTAC-empty vector underwent sequencing analysis for verification.

Each sequence used for vector construction is shown in Table 1 below.

TABLE 1

| Label | Sequence(5' to 3') | SEQ ID NO | bp | GC (%) | TM (° C.) |
|---|---|---|---|---|---|
| pTAC linearize-F | CAA GCT TGG CTG TTT TGG CG | 145 | 20 | 55 | 64 |
| pTAC linearize-R | CTA TAT CTC CTT CTT AAA GTT AAA C | 146 | 25 | 28 | 53 |
| tacP-RBS-MCS-rrnBt1t2-F | AAG AAG GAG ATA TAG ATG TCT GCT GTG AAG GCC G | 147 | 34 | 47 | 62 |
| tacP-RBS-MCS-rrnBt1t2-R | AAA CAG CCA AGC TTG TTA CAG CTT GCT CTT CAG AGA | 148 | 36 | 44 | 59 |
| pTAC-sequencing-F | GCC TAG AGC AAG ACG TTT CC | 149 | 20 | 55 | 57 |
| pTAC-sequencing-R | TTA ATG CAG CTG GCA CGA C | 150 | 19 | 53 | 58 |

Figure 4:
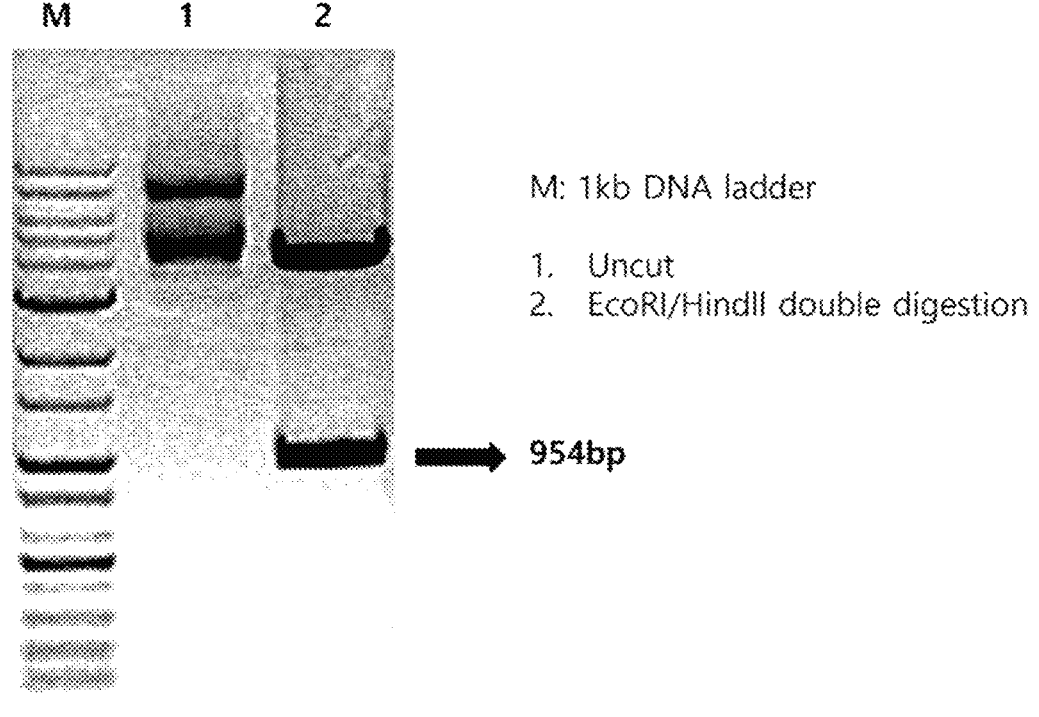
FIG. 4 shows the result of enzyme digestion electrophoresis of pTAC-Uox-W174amb.

In order to amplify the gene encoding Uox derived from *Aspergillus flavus* as a template, infusion cloning was performed on the pTAC-empty vector prepared by performing PCR-amplification on the previously cloned pQE80-Uox-W174amb vector. The infusion reaction was reflected by insert (Uox_W174amb) of 22 ng into 50 ng of vector, and was transformed into *E. Coli* DH5a after the reaction at 50° C. for 15 minutes. Subsequently, a single colony was picked up and inoculated in a 4-mL LB broth medium to perform mini-prep. EcoRI/HindIII restriction enzyme digestion was performed to investigate the band (953 bp) of Uox-W174amb, which is a cloning insert gene sequence (FIG. 4). The cloned pTAC-Uox-W174amb was requested for sequencing, and the cloning result was investigated using the NCBI's BLAST program (FIG. 5) (SEQ ID NO: 154).

Experimental Example 1.2: Expression and Purification of Urate Oxidase Variant Since position 174 in Uox was previously reported to have no structural/functional role (Lim, 2015), little or no perturbation to maintain enzymatic activity was expected even upon HSA conjugation. Therefore, for the conjugation of HSA and Uox, one reactive site was selected per monomer in Uox composed of a tetramer, so that a total of 4 reactive sites were secured. Specifically, Uox is a tetrameric protein in which four monomers are oligomerized. When one site is inserted per monomer, the oligomerized tetramer has four reactive sites.

Specifically, in order to express Uox-frTet, C321delAexp *Escherichia coli* host cells were co-transformed using the pDule_C11 and pTAC_Uox-174Amb plasmids prepared in Experimental Example 1.1 (C321delA.exp [pDule_C11] [pTAC_Uox-174Amb]), and the cells were cultured in a 2× YT medium. Expression of Uox-frTet was performed using a protocol in which 1-3 mM frTet, tetracycline (10 μg/mL), and kanamycin (35 μg/mL) were added. Next, IPTG was added to promote the expression of Uox-frTet, and the presence or absence of Uox-frTet expression was checked for each expression induction time.

Figure 6:
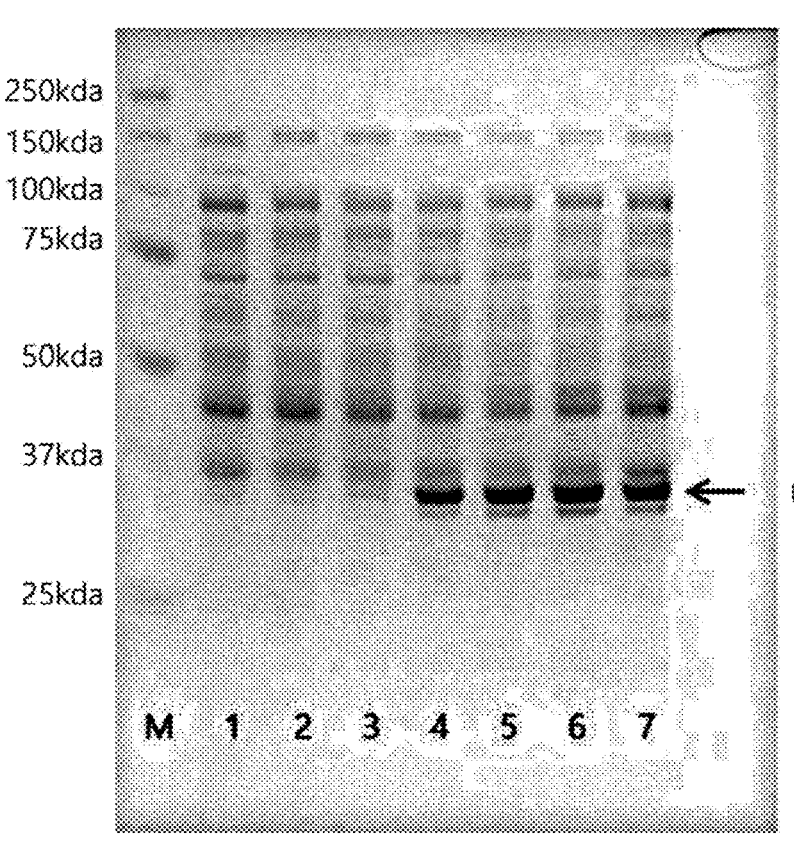
FIG. 6 shows the results of SDS-PAGE analysis to determine Uox-frTet expression.

As a result of SDS-PAGE analysis, it was found that a protein band with a molecular weight of about 34 kDa exists, it was confirmed that the tendency of the protein band to become stronger with each induction time. The findings are consistent with the expected molecular weight (34 kDa) of the monomer Uox. Expression of Uox-frTet was confirmed through the above results (See FIG. 6).

For separation and purification of Uox-frTet, the obtained cells were mixed with a buffer (20 mM Tris-HCl pH 9.0) at a ratio of 1:5 (w/w %), and cell disruption was performed using a sonicator. After cell disruption, centrifugation was performed at 9,500 rpm for 40 minutes to remove microbial debris, and the supernatant was collected.

Figure 7:
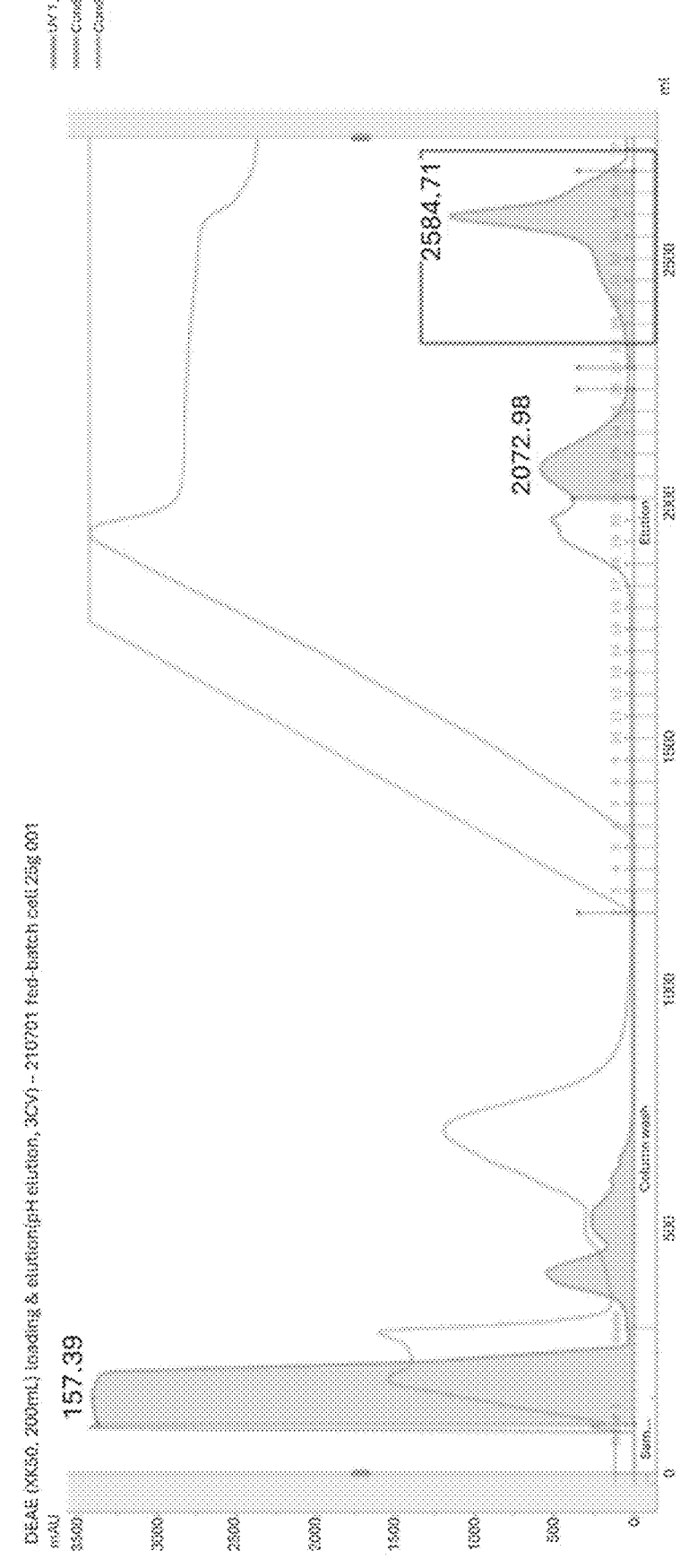
FIGS. 7 and 8 show the results of primary separation purification and SDS-PAGE analysis of Uox-frTet through a DEAE column.
Figure 8:
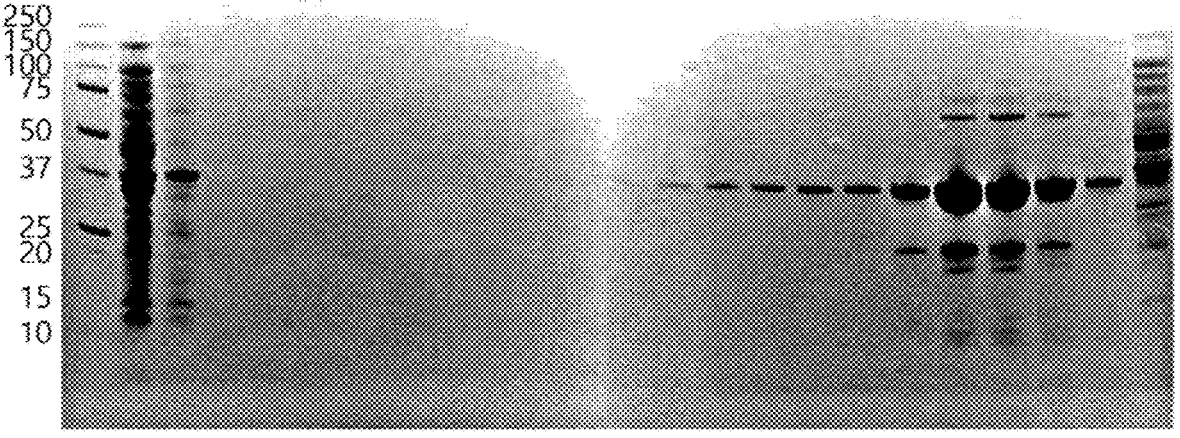

After filtering the collected supernatant through a 0.45-μm filter, primary separation and purification was performed with a DEAE Sepharose Fast Flow column (Cytiva, MA, USA)(refer to FIGS. 7 and 8), using an equilibration buffer (20 mM Tris-HCl pH 9.0) and an elution buffer (20 mM sodium phosphate pH 6.0).

Figure 9:
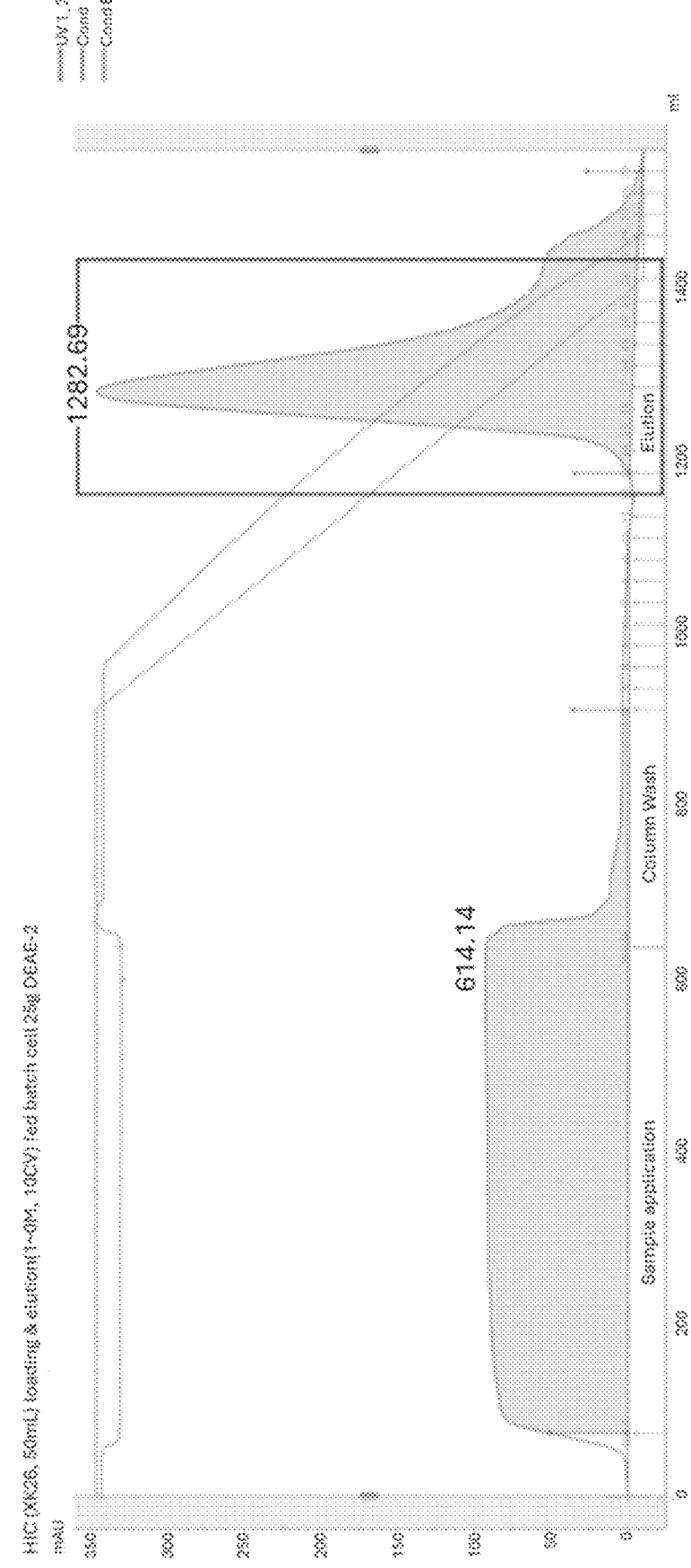
FIGS. 9 and 10 show the results of secondary separation purification and SDS-PAGE analysis of Uox-frTet through a phenyl fast flow column.
Figure 10:
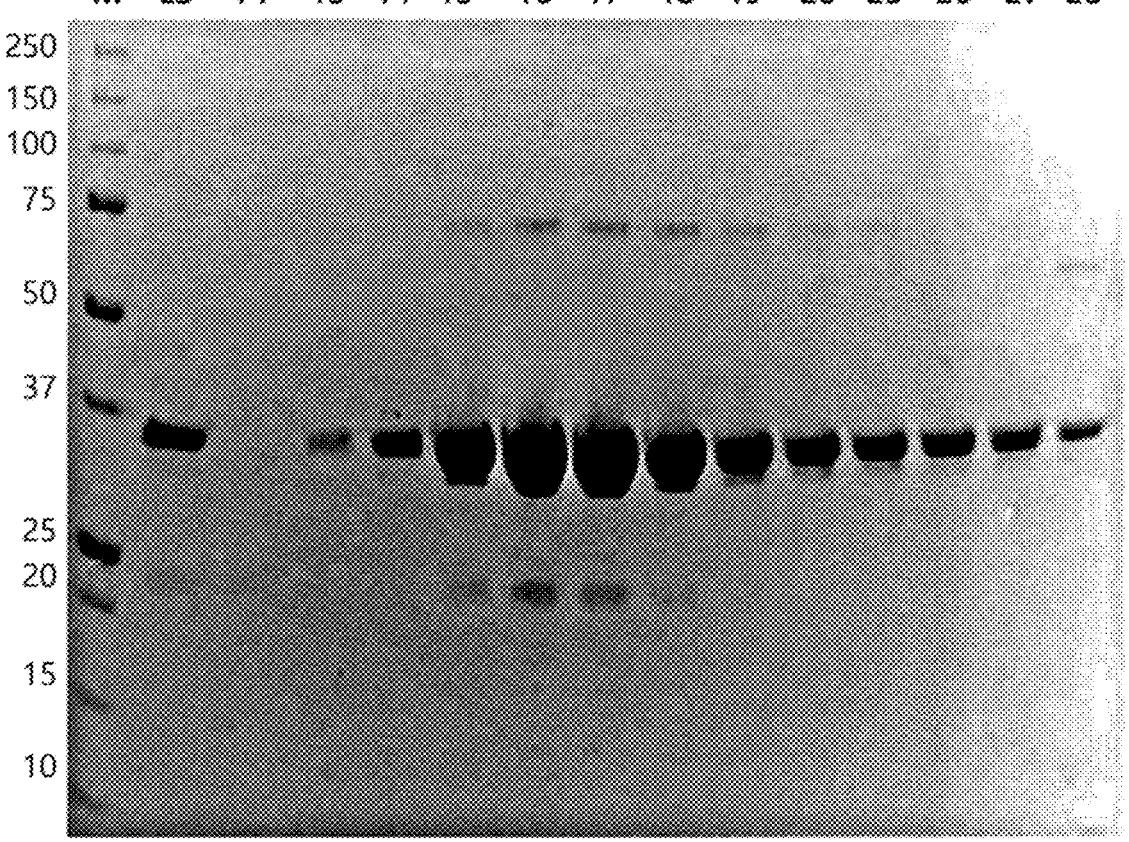

Fractions resulting from the primary purification were collected and secondary separation and purification was performed with a phenyl Fast Flow column (Cytiva, MA, USA), using an equilibration buffer (20 mM Tris-HCl pH 9.0+1M Ammonium sulfate) and an elution buffer (20 mM Tris-HCl pH 9.0) (See FIG. 9 and FIG. 10).

Figure 11:
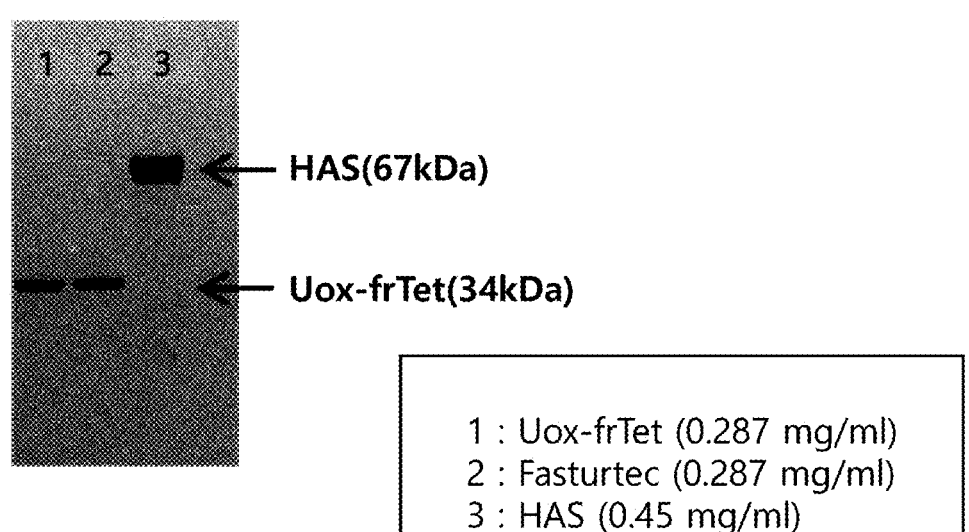
FIG. 11 shows the SDS-PAGE analysis result of Uox-frTet and Fasturtec.

The fractions resulting from the secondary purification were collected, and it was confirmed that highly pure Uox-frTest was obtained through analysis. After purification on Coomassie blue-stained protein gel, a single band with a molecular weight of about 34 kDa was present in the elution lane after the purification. In addition, the SDS-PAGE analysis result (FIG. 11) revealed that there was a molecular weight band matching with "FASTURTEC (Rasburicase, sanofi-aventis)", which is a commercially available urate oxidase.

Experimental Example 1.3: Verification of Purity of Urate Oxidase Variant

To verify the purity of Uox-frTet, the Uox-frTet was analyzed using a high performance liquid chromatography (HPLC). The analysis column was TSKgel G3000SWXL (TOSOH). The analysis was performed with a mobile phase of 20 mM sodium phosphate pH 7.0+0.3M NaCl at a rate of 0.6 mL/min at UV 220 nm.

Figure 12:
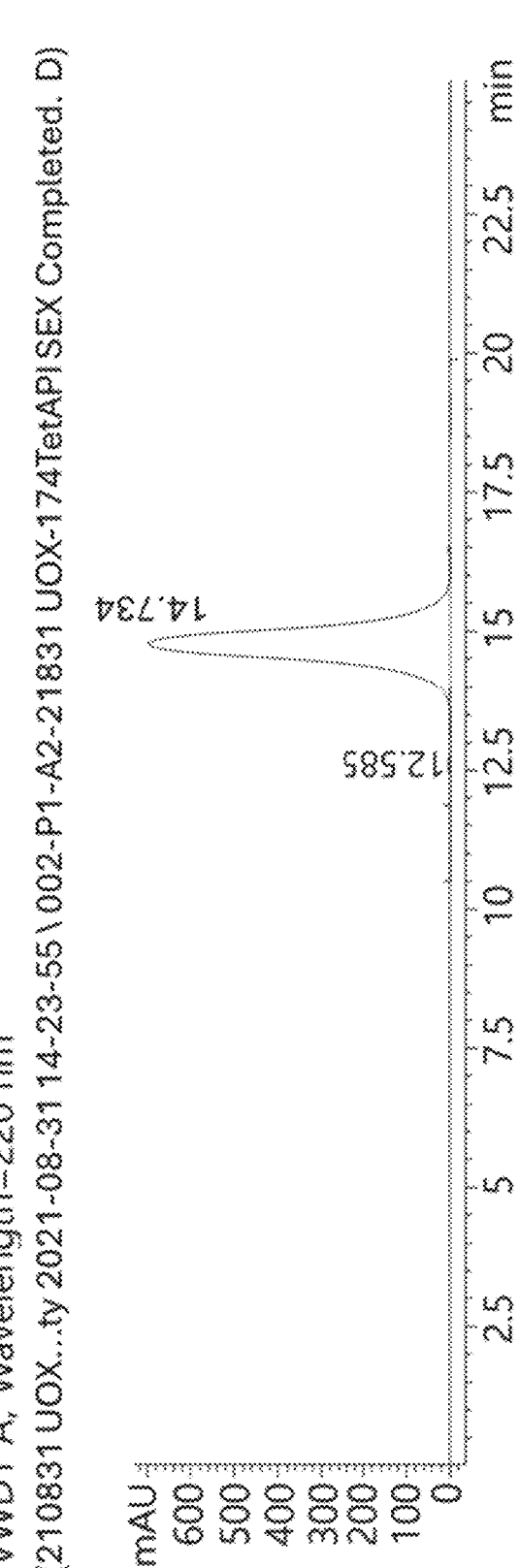
FIG. 12 shows the results of SEC-HPLC analysis of secondary purified Uox-frTet.

As a result, the secondary purified Uox-frTet was detected as a main peak at 14.7 minutes, and the purity was observed to be greater than 99%. It was confirmed that Uox-frTet was purified to a high purity (FIG. 12).

Experimental Example 1.4 Verification of Introduction of frTet into Urate Oxidase Variant Fluorescently labeled dye conjugation was used to investigate whether the genetically encoded frTet exhibits IEDDA reactivity. Specifically, for fluorescence labeling analysis, purified Uox-WT and Uox-frTet were mixed and reacted with Trans-Cyclooct-2-ene (TCO)-Cy3 dye in a molar ratio of 1:2 in PBS (pH 7.4) for 2 hours at room temperature. The reaction mixture was analyzed by SDS-PAGE. The fluorescence intensity of the gel was detected using a ChemiDoc XRS+ system (302 nm, filter 510/610 nm illumination; Bio-Rad Laboratories, Hercules, CA, USA) and then analyzed using Image Lab software (Bio-Rad Laboratories). Uox-WT samples with or without TCO-Cy3 were used as controls to verify IEDDA reactivity.

After fluorescence labeling analysis, Coomassie blue staining was performed for protein visualization. Protein gels were stained using Coomassie Brilliant Blue R-250 dye, and bands were detected using ChemiDoc XRS+ system (white illumination).

Figure 13:
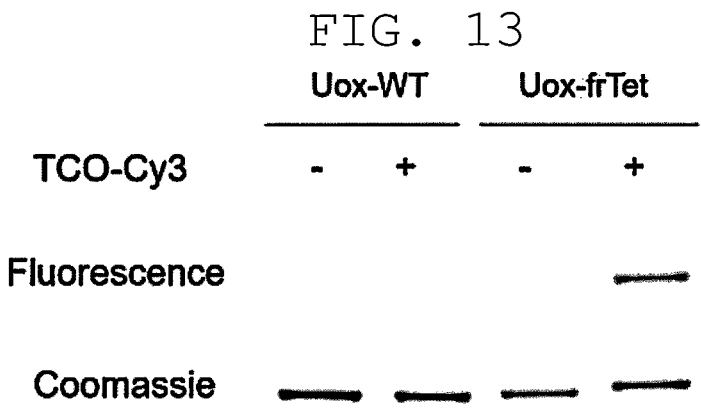
FIG. 13 shows the results of determining whether frTet is introduced into Uox through a fluorescent labeling dye (TCO-Cy3)

As a result, bands were identified in Uox-frTet incubated along with TCO-Cy3. Single protein bands were identified in all Uox variants after Coomassie blue staining regardless of incubation with TCO-Cy3. These results show that frTet introduced into Uox exhibits IEDDA reactivity (FIG. 13).

Experimental Example 2: Obtainment of Urate Oxidase-Albumin Conjugate

Figure 14:
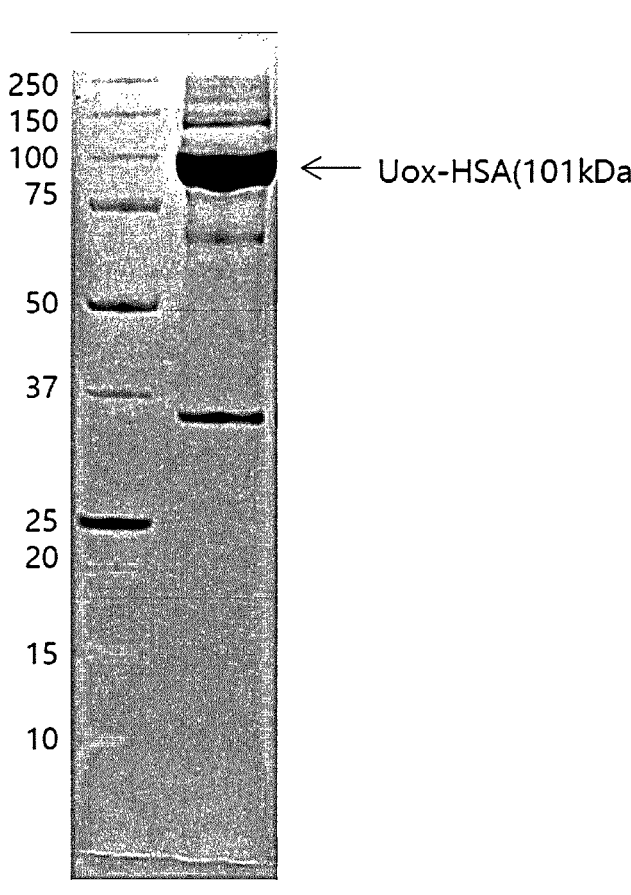
FIG. 14 shows the results of SDS-PAGE analysis of secondary purified Uox-HAS.

For the preparation of Uox-HSA, HSA and a TCO-Maleimide linker were combined at a ratio of 1:4 (molar ratio) at room temperature for 4 hours. To remove the unreacted remaining TCO-MAL linker, the reaction mixture was removed and desalted with a PBS buffer (pH 7.4) using a HiPrep 26/10 Desalting column. Thereafter, HSA-TCO and Uox-frTet were reacted at room temperature for 15 hours at a ratio of 5:1 (molar ratio). After filtering the sample through a 0.45-um filter, buffer exchange was performed with 20 mM sodium phosphate (pH 6.0), the sample was injected into an SP Sepharose column (Cytiva, MA. USA), and primary separation and purification was performed with an elution buffer (20 mM sodium phosphate, pH 6.0+1 M NaCl). The fractions resulting from the primary purification were collected, buffer exchange was performed with 20 mM Bis-Tris (pH 6.5), the collected sample was injected into a Q sepharose column, and secondary separation and purification was performed using an elution buffer (20 mM Bis-Tris pH 6.5+1 M NaCl). As a result of analysis of the secondary purified sample on Coomassie blue stained protein gel, a main band with a molecular weight of about 101 kDa was found to exist. This was consistent with the expected molecular weight (101 kDa) of the monomer Uox-HSA (FIG. 14). The secondary purified fractions were collected, and tertiary separation and purification was performed using a Superdex 200 Increase 10/300 GL column (Cytiva, MA, USA). As a result of analysis of the collected tertiary purified fractions, it was confirmed that high purity Uox-HSA was obtained. In addition, when analyzed with SEC-HPLC, a single peak showing a purity of 100% was determined (FIG. 15). Through this, a high-purity uric acid oxidase-albumin conjugate (Uox-HSA) was obtained.

Experimental Example 3: In Vitro Enzymatic Activity Analysis of Urate Oxidase-Albumin Conjugate To evaluate the in vitro enzymatic activity of Uox-frTet and Uox-HSA, the sample was diluted to a concentration of 10 nM, mixed with 111.1 uM of uric acid in a ratio of 1:9 (v/v %), and placed in a microplate. Then, absorbance 293 nm was measured at 15 second intervals for 10 minutes. As a result of measuring the in vitro enzymatic activity of Uox-frTet and Uox-HSA, uric acid showed a tendency to decrease, the slope was measured, and the activity was evaluated using the formula below.

$$U/mL = \frac{(\text{initial rate} \times \text{total volume (mL)})}{(\text{uric acid } 물흡광계수 \times \text{path length (cm)} \times 시료 \text{ volume (mL)})}$$

$$U/mg = \frac{1\ mL당\ 활성\ 값(U/mL)}{\text{final enzyme concentration}}$$

As a result, the activity per unit dose of Uox-frTet was 0.072 U/mL, and the activity per unit dose of Uox-HSA was 0.067 U/mL. It was confined that even though 4 albumins were bound to Uox-frTet, it did not significantly affect the decrease in enzymatic activity. In addition, the Uox-frTet exhibited a specific activity of 53 U/mg, and the Uox-HAS exhibited a specific activity of 16.6 U/mg.

Experimental Example 4: Pharmacokinetics (PK) Evaluation Of Urate Oxidase-Albumin Conjugates To evaluate the half-life of Uox-HSA, PK analysis was performed using ICR mice (n=5). The half-life of Uox-HSA was observed according to administration methods including intravenous (IV) administration, intraperitoneal (IP) administration, and intramuscular (IM) administration. As a control group, Fasturtec, which is a wild-type urate oxidase, was used for comparison. The dosage of Uox-HSA was 6.0 mg/kg (14.6 nmol/kg) (when administered by IV, IP, and IM), and the dosage of Fasturtec was 2.0 mg/kg (14.6 nmol/kg)(when administered by IV).

Figure 16:
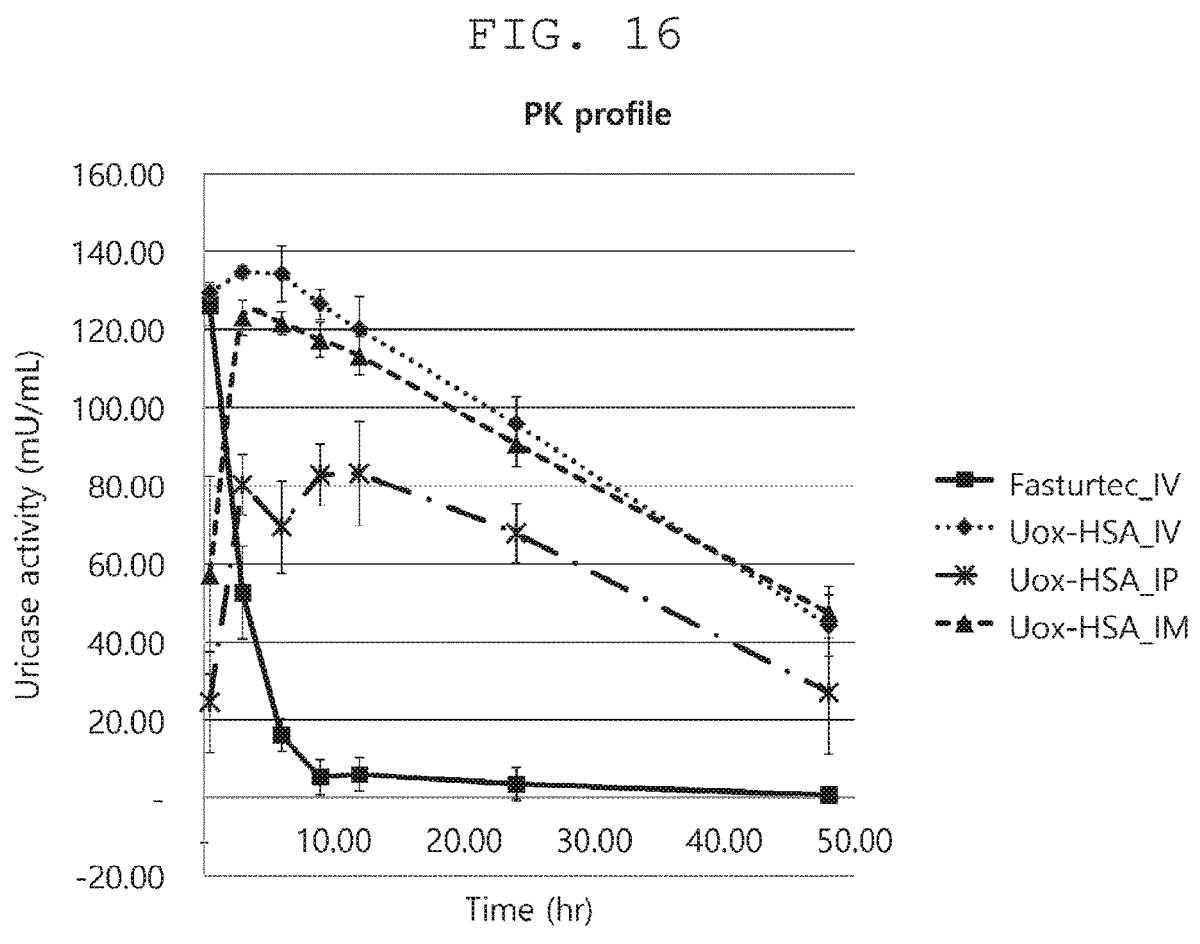

As a result, the area under curves (AUC) for the respective administration routes were higher in order of IV (4,471 mU/mL ×h), IP (4,180 mU/mL ×h), and IM (2,879 mU/mL ×h). That is, the AUC was highest when administered by IV. The AUC of Uox-WT was significantly lower than 476 mU/mL×h. In addition, the half-life of Uox-HSA was found to be 26.22 hours in the case of IV administration, 28.2 hours in the case of IP administration, and 21.61 hours in the case of IM administration, and the half-life of Fasturtec was 1.86 hours in the case of IV administration. That is, in the case of IV administration, it was confirmed that the half-life of Uox-HSA was improved by about 14 times compared to that of Fasturtec (FIGS. 16 to 17).

Experimental Example 5. Blood Uric Acid Reduction Effect of Urate Oxidase-Albumin Conjugate in Animal Model of Hyperuricemia A hyperuricemia animal model (Winster-SD rat) was prepared using hypoxanthine, a precursor of uric acid (Hypoxanthine, 500 mg/kg), which is a uric acid precursor and potassium oxonate (250 mg/kg), which is a urate oxidase inhibitor. Then, a pharmacodynamic evaluation test was performed to check the blood uric acid level by treating the animal model with the prepared Uox-HSA drug.

Hyperuricemia was induced twice before administration of the test drug and re-induced twice in 24 hours and 48 hours, respectively, after the administration of the test drug. At each observation point, the blood uric acid reduction effect and persistence were checked. Each of the dosage was Uox-HSA 1.0 mg/kg (2.4 nmol/kg), Uox-HSA 4.0 mg/kg (9.8 nmol/kg), Uox-HSA 10 mg/kg (24.6 nmol/kg), and Fasturtec (Rasburicase) 1.33 mg/kg (9.8 nmol/kg). These were administered intravenously. Febuxostat was administered orally at a dose of 10 mg/kg (positive control). As a result, the initial blood uric acid level after induction of hyperuricemia was 12 mg/dL in the negative control group (Hyperuricemia, negative control). That is, it was confirmed that hyperuricemia was induced in rats. In thirty minutes after drug administration, it was confirmed that the uric acid level was lowered to be below the normal level (6 mg/dL) in all drug administration groups, and the level continued for up to 12 hours.

Secondary induction (in 24 hours after drug administration) was performed to check the drug's persistence. As a result, the blood uric acid level was maintained low in the Uox-HSA group, whereas the uric acid level increased in the group administered with Uox-WT and Febuxostat as a positive control.

Figure 18:
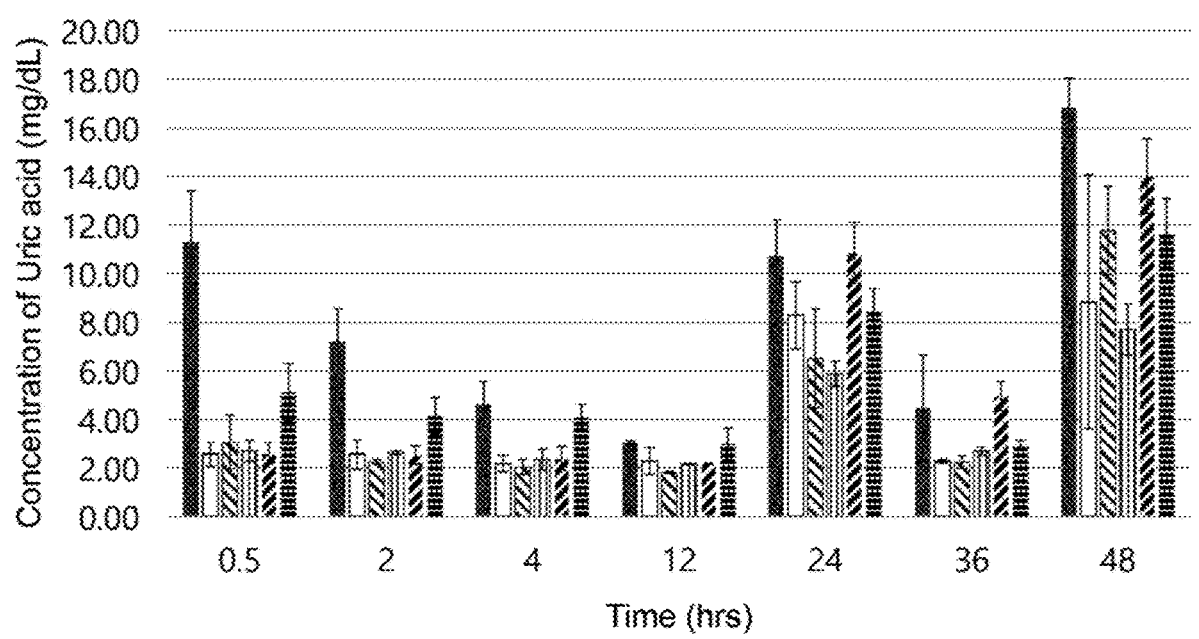
FIG. 18 shows the results of a pharmacodynamic evaluation test for observation of reduction in uric acid in blood according to administration of Uox-HSA in a repeated hyperuricemia animal model, in which 1) Negative control represents a negative control, 2) Uox-HSA 1 mg/kg represents a case where a urate oxidase-albumin conjugate is administered intravenously at a dose of 1 mg/kg, 3) Uox-HSA 4 mg/kg represents a case where a urate oxidase-albumin conjugate is administered intravenously at a dose of 4 mg/kg, 4) Uox-HSA 10 mg/kg represents a case where a urate oxidase-albumin conjugate is administered intravenously at a dose of 10 mg/kg, 5) Fasturtec 1.33 mg/kg represents a case where a wild-type urate oxidase (Fasturtec) is administered intravenously at a dose of 1.33 mg/kg, and 6) Febuxostat 10 mg/kg represents a case where Febuxostat is orally administered at a dose of 1 mg/kg.
Figure 20:
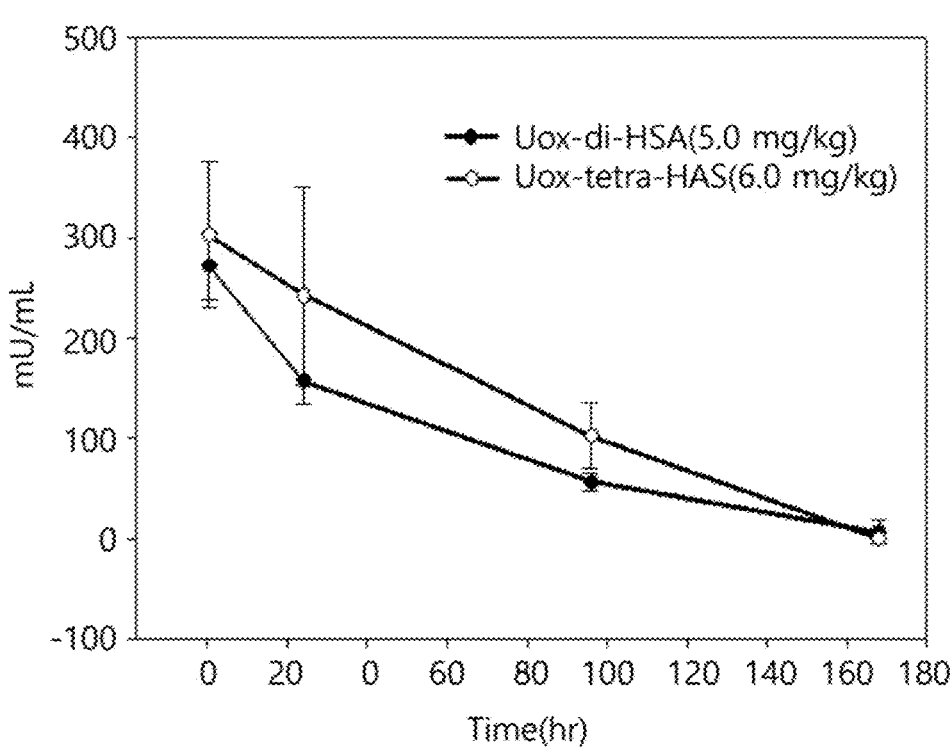
FIG. 20 shows a PK profile result for administration of TG Uox-HSA to a Human FcRn TG mouse, in which 1) Uox-HSA (Tetra) is a urate oxidase-albumin conjugate in which 4 albumins are conjugated per one urate oxidase, 2) Uox-HSA (tri/di) is a urate oxidase-albumin conjugate in which 2 to 3 albumins are conjugated per one urate oxidase, AUC is the Area Under Curve of the PK profile result, T1/2 is the half-life expressed in units of time, and Range is a pharmacokinetic evaluation time range.
Figures 21, 22:
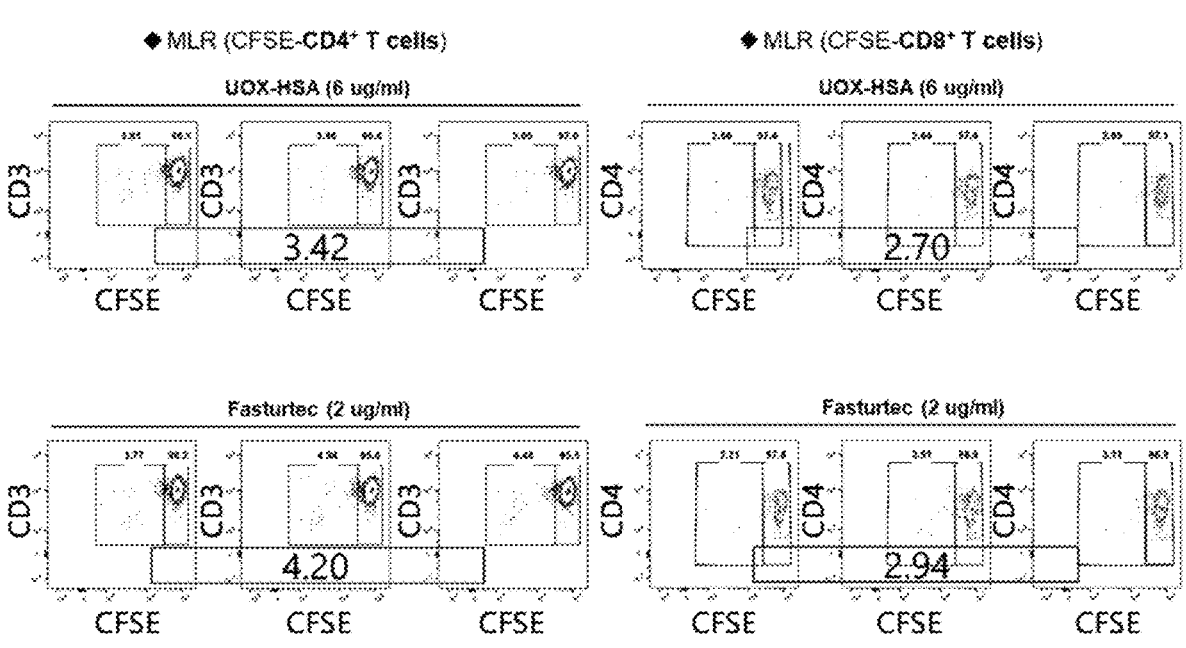
FIG. 21 shows an immunogenicity analysis result of Uox-HSA through PBMC.
FIG. 22 shows data of the immunogenicity analysis result of Uox-HSA through PBMC, in which 1) CD4 represents data for CFSE-CD4+ T cells, and 2) CD8 represents data for CFSE-CD8+ T cells, and in which in each table, data of #1 to #3 represent values for each subject, and Mean represents the average value of all subjects.

As a result of the third induction in 48 hours after drug administration, the Uox-HSA administration group showed an effect of reducing blood uric acid. It was confirmed that Uox-HSA continuously reduced blood uric acid in an animal model of hyperuricemia (FIGS. 18 to 19).

Experimental Example 6. Pharmacokinetic Evaluation (PK Profile) Using Human FcRn (+/+) TG Mice Uox-HSA is a drug to which human-derived albumin is bound, and its half-life improvement is not significant due to the poor binding ability to a mouse FcRn. Therefore, when using a mouse in which human FcRn is transgenic, the FcRn recycling effect can be expected due to the human-derived albumin. To evaluate this, the half-life of the prepared Uox-HSA was evaluated using Tg32 Alb–/– (human FcRn+/+) mice (n=4) (JAX #025201, The Jackson Laboratory). Uox-HSA (tetra-HSA) containing 4 albumins was administered by a single IV at a dose of 6.0 mg/kg, and Uox-HSA (tri/di-HSA) containing 2 to 3 albumins was administered by a single IV at a dose of 5.0 mg/kg. The activity of Uricase in the blood was checked by collecting blood in 0.5 hour, 1 day, 4 days, and 7 days after the single IV administration. As a result, in the case of Uox-HSA (tetra-HSA) in which 4 albumins were bound, the half-life was 60.3 hours. That is, the half-life increased by 2.3 times when confirmed in ICR mice, and the AUC increased by 4.2 times. In addition, in the case of Uox-HSA (tri/di-HSA) in which 2 to 3 albumins were bound, the half-life was 32.4 hours. It was confirmed that there was a large difference in the half-life according to the number of albumins. Specifically, when looking at the results of human FcRn TG mice, the half-life is expected to increase further when Uox-HSA (tetra-HSA) is administered to the human body.

Experimental Example 7. Human-derived PBMC-based In Vitro Immunogenicity Assay Although early prediction of the immunogenicity of biological products is an essential factor in determining the success or failure of the development of biological products, there is no laboratory animal model from which the immunogenicity of biological products can be reliably predicted before clinical trials due to differences in the immune systems between humans and laboratory animals. Therefore, immunogenicity analysis was performed using the immunogenicity analysis technique using human PBMC. Through this experiment, it is possible to obtain a reliable evaluation result for the immunogenicity of Uox-HSA before clinical trials.

After inducting differentiation from human mononuclear cells into dendritic cells which are known to be the most reliable so far, the reactivity (CD4+, CD8+ T cell activation) of immune cells induced by Uox-HSA was measured. As a result of CD4+ T cell activity analysis, it was obtained that Uox-HSA (6 ug/ml) and Fasturtec (2 ug/ml) both had SI values equal to or smaller than ($\leq$2), indicating that they would not show immunogenicity in the HLA types below. In a relative comparison, Fasturtec (2 ug/ml) showed slightly higher CD4+ T cell activity than Uox-HSA (6 ug/ml), but the result was not statistically significant. As a result of CD8+ T cell activity analysis, it was obtained that Uox-HSA (6 ug/ml) and Fasturtec (2 ug/ml) both had SI values equal to or smaller than ($\leq$2), indicating that they would not show immunogenicity in the HLA types below. As a result, it was analyzed that the immunogenicity would be lower than that of the original drug due to the binding of human albumins.

Experimental Example 8: Preparation of Urate Oxidase-Albumin Conjugate

Experimental Example 8.1: Preparation of Vector for Expression of Urate Oxidase Variant A vector for expression of a urate oxidase variant is prepared by the method disclosed in Experimental Example 1.1. Here, the sequence of the vector of the urate oxidase variant to be expressed includes one or more sequences selected from SEQ ID NOs: 152 to 160.

Experimental Example 8.2: Expression and Purification of Urate Oxidase Variant The urate oxidase variant is expressed and purified by the method disclosed in Experimental Example 1.2, using the vector for expression of the urate oxidase variant of Experimental Example 6.1.

Experimental Example 8.3: Obtainment and Verification of Urate Oxidase Variant By the method disclosed in Experimental Examples 1.3 to 1.4, the purity of the urate oxidase variant obtained in Experimental Example 8.2 is evaluated and whether the nonnatural amino acid is well introduced into the urate oxidase variant was determined.

Experimental Example 8.4: Preparation of Linker

The linker for conjugating the urate oxidase variant and the albumin is not limited if it has the structure disclosed above, and a person skilled in the art can use commercial linkers purchased or appropriately prepare linkers using a known method.

When using a linker containing tranc-cyclooctene (TCO) as an IEDDA reactive group that reacts with the urate oxidase variant and using 3-arylpropiolonitriles (APN) as a thiol reactive group that reacts with albumin, it is prepared according to the following method and is then used:

1) TCO-NHS ester (for example, purchased from CONJU-PROBE) and APN-amine (for example, purchased from CONJU-PROBE) are reacted in a 1:1 molar ratio in a dimethyl sulfoxide (DMSO) solvent at room temperature.

2) The reaction product is separated and purified by column chromatography using silica gel. In this case, the separation and purification degree is set to 95% or more.

Experimental Example 8.5: Obtainment of Urate Oxidase-Albumin Conjugate

Using the urate oxidase variant obtained in Experimental Example 8.2 and the linker obtained in Experimental Example 8.4, a urate oxidase-albumin conjugate is obtained through the method disclosed in Experimental Example 2.

Experimental Example 8.6: In Vitro Enzymatic Activity Analysis of Urate Oxidase-Albumin Conjugate Using the urate oxidase-albumin conjugate obtained in Experimental Example 8.5, the in vitro enzymatic activity of the urate oxidase-albumin conjugate is analyzed by the method disclosed in Experimental Example 3.

Experimental Example 8.7: Pharmacokinetic Evaluation of Urate Oxidase-Albumin Conjugate Using the urate oxidase-albumin conjugate obtained in Experimental Example 8.5, a pharmacokinetic evaluation experiment for the urate oxidase-albumin conjugate is performed through the method disclosed in Experimental Example 4.

Experimental Example 8.8: Blood Uric Acid Reduction Effect of Urate Oxidase-Albumin Conjugate in Animal Model of Hyperuricemia Using the urate oxidase-albumin conjugate obtained in Experimental Example 8.5, the blood uric acid reduction effect of the urate oxidase-albumin conjugate is analyzed by the method disclosed in Experimental Example 5.

Experimental Example 8.9: Pharmacokinetic Evaluation (PK Profile) Using Human FcRn (+/+) TG Mice Using the urate oxidase-albumin conjugate obtained in Experimental Example 8.5, the pharmacokinetic evaluation (PK profile) of the urate oxidase-albumin conjugate using Human FcRn (+/+) TG mice is performed by the method disclosed in Experimental Example 6.

Experimental Example 8.10: Human-derived PBMC-based In Vitro Immunogenicity Assay Using the urate oxidase-albumin conjugate obtained in Experimental Example 8.5, the pharmacokinetic evaluation (PK profile) of the urate oxidase-albumin conjugate using Human FcRn (+/+) TG mice is performed by the method disclosed in Experimental Example 6.

Experimental Example 9: Obtainment of *Arthrobacter Globiformis*-Derived Urate Oxidase-Albumin Conjugate and Verification of Effect Thereof

Experimental Example 9.1: Test Material 4-(1,2,3,4-tetrazin-3-yl)phenylalanine (frTet) was purchased from Aldlab Chemicals (Woburn, MA, USA). Trans-cylooctene (TCO)-Cy3 was purchased from AAT Bioquest (Sunnyvale, CA, USA). TCO-PEG4-maleimide (TCO-PEG4-MAL) and amine-axially substituted TCO (TCO-amine) were purchased from FutureChem (Seoul, Korea). Pentafluor-ophenyl ester (PFP)-PEG4-APN was purchased from CONJU-PROBE (San Diego, CA, USA). Disposable PD-10 desalting columns and Superdex 200 10/300 GL increase columns were purchased from Cytiva (Uppsala, Sweden). Vivaspin 6 centrifugal concentrators with molecular weight cut-off (MWCO) of 10 and 100 kDA were purchased from Sartorius (Göt-tingen, Germany). Human serum albumin (HSA) and all other chemical reagents were purchased from Sigma-Aldrich, unless otherwise noted herein.

Experimental Example 9.2: Vector Preparation for Obtaining Urate Oxidase Variant (AgUox-frTet) Derived from *Arthrobacter Globiformis*

The gene encoding *Arthrobacter globiformis*-derived urate oxidase (AgUox) and its variants was synthesized by Macrogen (Seoul, South Korea) at the request of the inventors. In order to express wild-type AgUox (AgUox-WT), or an AgUox variant (AgUox-frTet) having a sequence into which the nonnatural amino acid "frTet" is introduced, the synthesized gene was used as a template, and amplified through a polymerase chain reaction (PCR) using the primers "pBAD-AgUox_F (5'-GCCGCCATGGTGTCTGCTGT-GAAGG-3', SEQ ID NO: 161)" and "pBAD-AgUox_R (5'-GCCGAGATCTTTAATGGTGATGGTG-3', SEQ ID NO: 162)". The amplified gene was digested with two restriction enzymes (NcoI and BglIII), and the gene was inserted into the NcoI and BglII sites of the pBAD vector to synthesize pBAD_AgUox. To replace the glutamic acid codon at position 196 in the AgUox-WT sequence with an amber codon (UAG), the pBAD-AgUox was used as a template, and the primers "AgUox-196Amb_F (5'-GTCGAAGTCCACCTATACGGTGTTGTAACGC-CAACGG-3', SEQ ID NO: 163)" and "AgUox-196Amb_R (5'-CCGTIGGCGTTA-CAACACCGTATAGGTGGACTTCGAC-3', SEQ ID NO: 164)" was used to prepare pBAD-AgUox_196amb.

Experimental Example 9.3: Obtainment of AgUox-frTet

To express AgUox-frTet, the method disclosed in Bioconjugate Chemistry, 2020, 2456-2464 (by Yang et. al, titled "Temporal Control of Efficient In Vivo Bioconjugation Using a Genetically Encoded Tetrazine-Mediated Inverse-Electron-Demand Diels-Alder Reaction") was referred. Thus, AgUox-frTet was expressed in a manner described below, using C321ΔA.exp, pDule_C11, and pBAD_AgUox-196amb.

*E. coli* cells containing MjtRNATyr/MjTyrRS optimized for frTet were prepared. *E. coli* cells cultured in a Luria Broth (LB) medium containing ampicillin (100 g/mL) and tetracycline (10 μg/mL) were inoculated into a 2× YT medium under the same conditions under shaking overnight at 37° C. After 2.5 hours of shaking culture, when the medium containing the cells reached an optical density of 0.5 at 600 nm, frTet and L-(+)-arabinose were added to the medium such that the final concentrations thereof became 1 mM and 0.4% (w/v), respectively. After incubation for 5 hours, the cells were centrifuged at 5000 rpm at 4° C. for 10 minutes to obtain AgUox-frTet. The AgUox-frTet was purified through immobilized metal affinity chromatography at 4° C. according to the manufacturer's protocol (Qiagen). The purified AgUox-frTet was desalted with PBS (pH 7.4) using a PD-10 column. The expression and purification of AgUox-WT were performed in a similar manner to the expression and purification of the AgUox-frTet, except that tetracycline and frTet were not added to the culture medium during the expression step.

Experimental Example 9.3: Analysis and Verification of Prepared AgUox-frTet

To identify the prepared AgUox-frTet and AgUox-WT, AgUox-frTet and AgUox-WT were digested with trypsin according to the manufacturer's protocol. A total of 0.4 mg/mL of Uox variants (AgUox-WT and AgUox-frTet) were digested at 37° C. overnight and then desalted using ZipTip C18. The trypsinized mixture was mixed with a 2,5-dihydroxybenzoic acid (DHB) matrix solution (30:70 (v/v) acetonitrile: DHB 20 mg/mL in 0.1% trifluoroacetic acid), followed by analysis using Microflex MALDI-TOF/MS instrument (Bruker Corporation, Billerica, MA, USA).

Experimental Example 9.4: Site-specific Fluorescent Dye Labeling of AgUox-WT and AgUox-frTet Purified AgUox-WT and AgUox-frTet were reacted with TCO-Cy3 fluorescent dye in a molar ratio of 1:2 in PBS (pH 7.4) at room temperature. After 2 hours, the reaction mixture was subjected to sodium dodecyl sulfate polyacrylamide gel electrophoresis (SDS-PAGE). Fluorescence images of protein gels were obtained using a ChemiDoc XRS+ system (illumination at 302 nm, 510-610 nm filters, Bio-Rad Laboratories, Hercules, CA, USA). After fluorescence analysis, the protein gels were stained with Coomassie Brilliant Blue R-250 dye. Protein gel images were obtained using a ChemiDoc XRS+ system with white light illumination.

Figure 32:
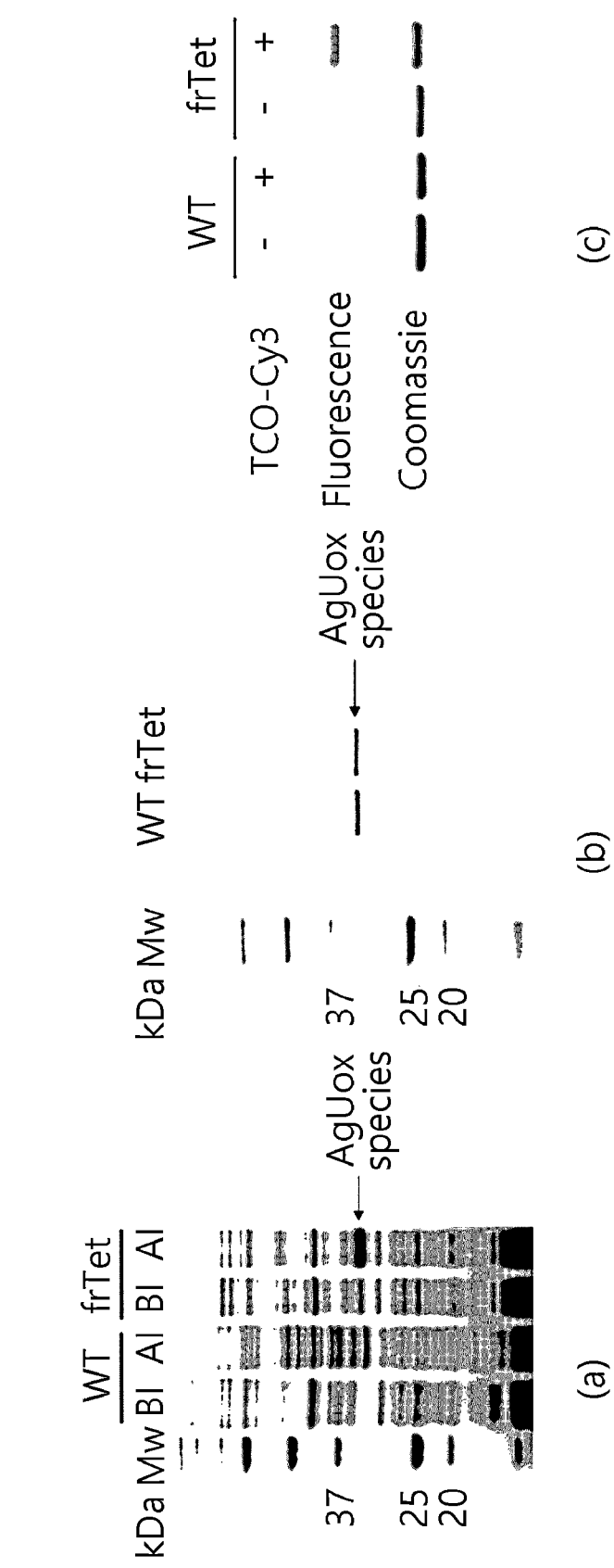
FIG. 32 shows the SDS-PAGE results of AgUox-WT and AgUox-frTet, in which (A) represents the results of Coomassie Brilliant Blue (CBB) staining of an AgUox variant, in which Mw is a molecular weight marker, BI is the result before induction, AI is the result after induction, (B) represents a CBB-stained protein gel of a purified AgUox variant, and (C) represents a phenotypic image and CBB-stained protein gel of AgUox variants cultured in the presence or absence of TCO-Cy3.
Figure 33:
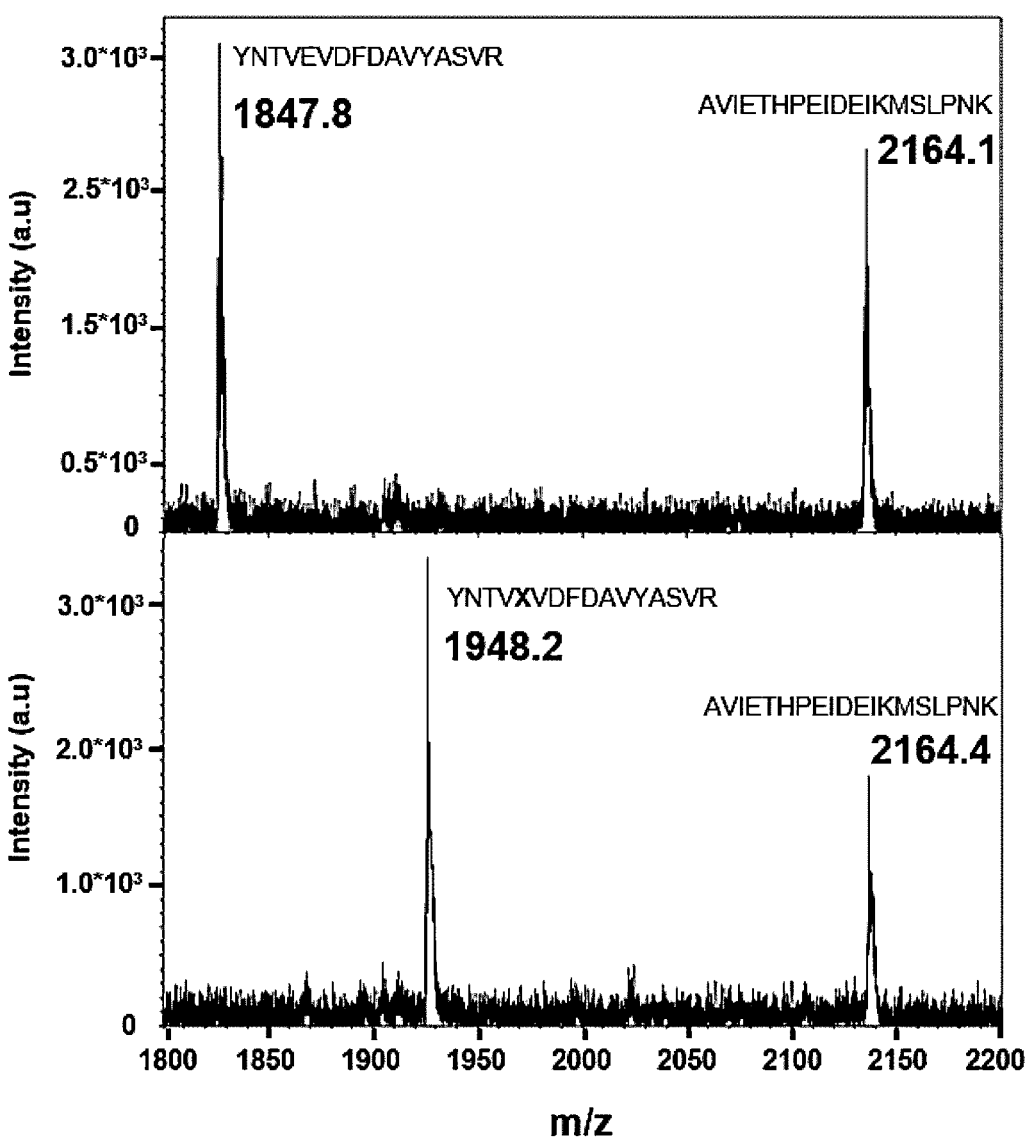
FIG. 33 shows flight mass spectra of trypsin-digested fragments of AgUox-WT (A) and AgUox-frTet (B), the mass of YNTVEVDFDAVYASVR (SEQ ID NO: 165), which is an AgUox-WT fragment, is compared with the mass of YNTVXVDFDAVYASVR (SEQ ID NO: 166, X represents frTet), which is an AgUox-frTet fragment, and AVIETHPEI-DEIKMSLPNK (SEQ ID NO: 167), which is the peak of the fragment, was used as a control.

The results of analysis of AgUox-WT and AgUox-frTet prepared in Experimental Examples 9.3 to 9.4 are shown in FIGS. 32 and 33.

Experimental Example 9.5: AgUox-HSA Conjugate Preparation (AgUox-MAL-HSA and AgUox-APN-HSA)

To perform site-specific albumination on AgUox, HSA was purified via anion exchange chromatography using a HiTrap Q HP anion exchange column. After desalting the purified HSA with PBS (pH 7.0), the HSA was reacted with TCO-MAL in a molar ratio of 1:4 in PBS (pH 7.0) at room temperature. After 2 hours, the reaction mixture was desalted with PBS (pH 7.4) using a PD-10 column, and unreacted TCO-PEG4-MAL linkers were removed to obtain a MAL-HSA conjugate. Purified Uox-frTet was reacted with MAL-HSA in a molar ratio of 1:4 in PBS (pH 7.4) at room temperature for 5 hours. After conjugation, the reaction mixture was applied to a size exclusion chromatography (SEC) using an NGC Quest 10 Plus chromatography system (Bio-Rad Laboratories Inc., Berkeley, CA, USA). The molecular weight and purity of the eluted fractions were analyzed using SDS-PAGE, and fractions corresponding to AgUox-frTet conjugated to four MAL-HSA molecules (AgUox-MAL-HSA) were selected and concentrated for further analysis.

To generate AgUox-HSA conjugates via a hetero-bifunctional cross-linker containing TCO and APN, TCO-amine was reacted with PFP-PEG4-APN. The reaction was performed in DMSO in a molar ratio of 1:1 at room temperature for 30 minutes. The purified HSA was buffer-exchanged with a 50 mM sodium borate buffer (pH 9.0). In a 50 mM sodium borate buffer (pH 9.0), purified HSA was reacted with TCO-PEG4-APN in a molar ratio of 1:4 at room temperature for 2 hours. To remove unreacted TCO-APN linker, the reaction mixture was desalted with PBS (pH 7.4) using a PD-10 column. Conjugation (AgUox-APN-HSA) and purification of AgUox-frTet conjugated to four HSA molecules via linkers containing APN were performed in a similar manner to AgUox-MAL-HSA.

Figure 34:
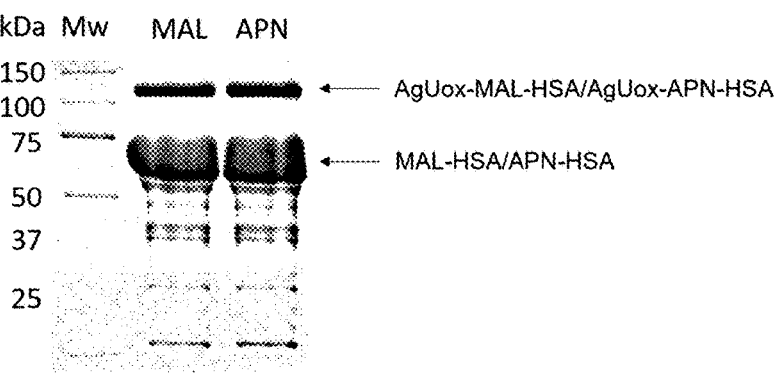
FIG. 34 represents protein gel of a reaction mixture of AgUox-frTet and MAL-HSA (denoted by MAL) or APN-HSA (denoted by APN), in which Mw represents a molecular weight standard.
Figure 35:
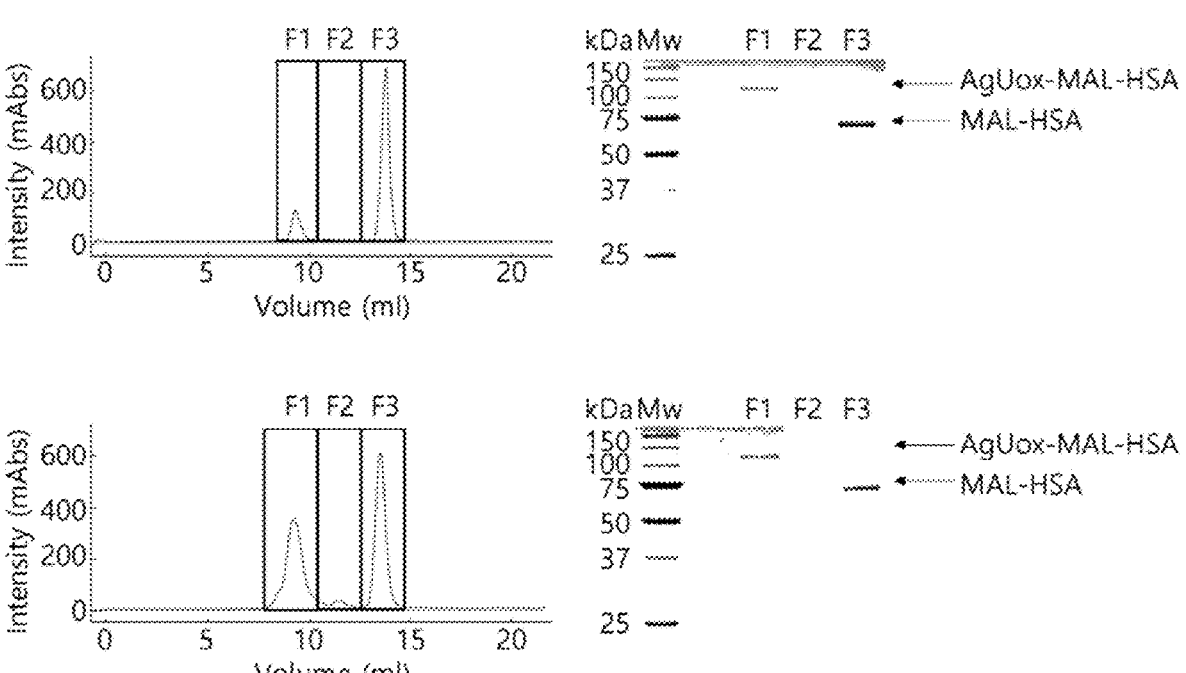
FIG. 35 represents size exclusion chromatograms and protein gels of fractions of a conjugate mixture of AgUox-frTet and MAL-HSA (A) or APN-HSA (B), in which the eluted fractions were loaded on a protein gel and stained with Coomassie Brilliant Blue.

The results of preparation of the AgUox-HSA conjugate according to Experimental Example 9.5 are shown in FIGS. 34 and 35.

Experimental Example 9.6: In Vivo Half-Life Evaluation (PK Profile) of AgUox-HSA Conjugate Stability analysis of AgUox-HSA conjugates in mice was performed according to the guidelines of the Animal Care and Use Committee of Gwangju Institute of Science and Technology (GIST-2020-037). Each of AgUox-WT, AgUox-MAL-HSA, and AgUox-APN-HSA was injected into the tail vein of young female BALB/c mice (n=4) in an amount corresponding to 5.0 nmol of AgUox in 200 μL PBS at pH 7.4. In the case of AgUox-WT, blood samples were taken through retro-orbital bleeding after 15 minutes, 3 hours, 6 hours, and 12 hours, and in the case of AgUox-HSA conjugates, blood samples were collected in the same manner at 15 minutes, 12 hours, 24 hours, 48 hours, 72 hours, 84 hours, 96 hours, 108 hours, and 120 hours. After separating the serum from the collected blood, the serum activity of each of AgUox-WT, AgUox-MAL-HSA, and AgUox-APN-HSA was measured. The serum activity was measured by adding 100 μL of enzyme activity assay buffer containing 100 μM uric acid to 100 μL enzyme activity buffer containing 5 μL of serum, and measuring the change in absorbance at 293 nm.

Figure 36:
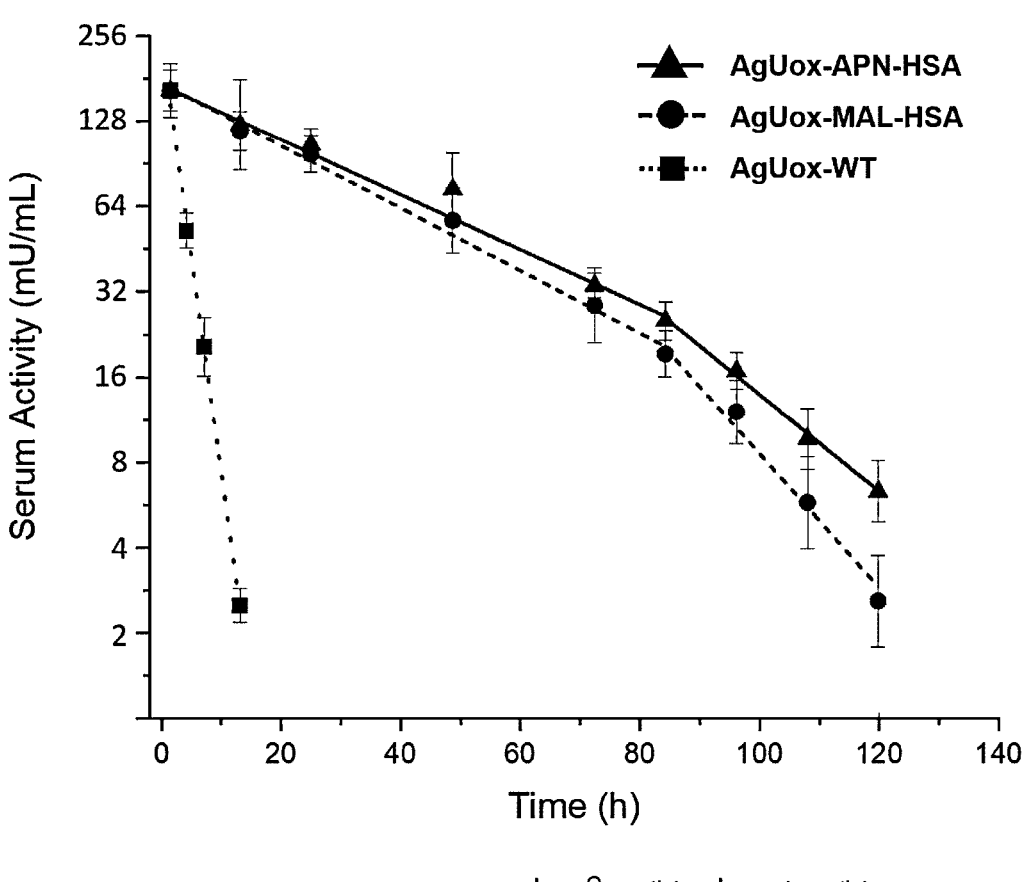
FIG. 36 shows the results of pharmacokinetic analysis (PK profile) of AgUox-WT and AgUox-HSA conjugates, in which serum activity of residual AgUox-WT and AgUox-HSA conjugates was measured at the early stage (0-84 h) and the late stage (84-120 h), and $t^e1/2$ and $t^l1/2$ represent early and late serum half-lives, respectively.

The in vivo half-life evaluation results are shown in FIG. 36.

As a result of the experiment, it was confirmed that AgUox-APN-HSA and AgUox-MAL-HSA exhibited a significant increase in half-life compared to AgUox-WT which is not conjugated with albumin.

INDUSTRIAL APPLICABILITY

The present description discloses a urate oxidase-albumin conjugate, a method of preparing the same, a urate oxidase variant included in the urate oxidase-albumin conjugate, and a method of preparing the same. The urate oxidase-albumin conjugate can be used to prevent or treat various diseases, disorders, or indications caused by uric acid.

---

The invention claimed is:

1. A urate oxidase-albumin conjugate represented by [Formula 1]:

Uox-[J1-A-J2-HSA]$_n$      [Formula 1]

wherein Uox is a urate oxidase variant, J1 is a urate oxidase-linker junction, A is an anchor, J2 is an albumin-linker junction, and HSA is Human Serum Albumin, n is 3 or 4, the urate oxidase variant is a tetramer formed by oligomerization of four urate oxidase variant subunits, each of the urate oxidase variant subunit is a peptide independently selected from SEQ ID NOs:2 to 50, or a peptide which is 90% or more identical to the peptide selected from SEQ ID NOs:2 to 50, the peptide selected from SEQ ID NOs:2 to 50 comprises a nonnatural amino acid X which is 4-(1,2,3,4-tetrazine-3-yl) phenylalanine (frTet), the urate oxidase-linker junction is a structure formed through Inverse Electron Demand Diels-Alder (IEDDA) reaction between a tetrazine moiety of the nonnatural amino acid of the urate oxidase variant and a trans-cyclooctene moiety linked to the anchor, the urate oxidase-linker junction is represented by following, wherein the (1) is linked to the residue of the nonnatural amino acid, and the (2) is linked to the anchor, wherein the anchor is selected from the following:

wherein J$_1$ is urate oxidase-linker junction, and J$_2$ is albumin-linker junction, wherein the albumin-linker junction is a structure formed through a reaction between a thiol moiety of the albumin and a thiol reactive moiety of the anchor, wherein the albumin-linker junction is selected from the following:

wherein (1) is linked to the albumin and (2) is linked to the anchor.

2. The urate oxidase-albumin conjugate of claim 1, wherein the urate oxidase variant comprises four urate oxidase variant subunit of SEQ ID NO: 49, wherein a nonnatural amino acid X of the SEQ ID NO: 49 is frTet.

3. The urate oxidase-albumin conjugate of claim 1, wherein the albumin is a sequence selected from SEQ ID NOs:133 to 144, or a sequence that is 90% or more identical to the sequence selected from SEQ ID NOs:133 to 144.

4. A method for manufacturing a urate oxidase-albumin conjugate, the method comprising:

reacting an albumin and a linker, wherein the linker comprises a dienophile functional group, an anchor, and a thiol reactive moiety, wherein the dienophile functional group is a trans-cyclooctene or a derivative of trans-cyclooctene, and the thiol reactive moiety is selected from a maleimide or a derivative of maleimide, and a 3-arylpropiolonitriles or a derivative of 3-aryl-propiolonitriles, wherein the thiol reactive moiety of the linker is bound with thiol moiety of albumin through reaction to form an albumin-linker conjugate; and reacting the albumin-linker conjugate and the urate oxidase variant, wherein the urate oxidase is a tetramer in which four urate oxidase subunits are oligomerized, wherein each of the urate oxidase subunit is represented by a sequence independently selected from SEQ ID NOs:2 to 50, or a sequence that is 90% or more identical to the sequence selected from SEQ ID NOs:2 to 50, wherein the X of a sequence of SEQ ID NOs:2 to 50 is nonnatural amino acid which is 4-(1,2,3,4-tetrazine-3-yl) phenylalanine (frTet), wherein the urate oxidase variant comprises four frTets, wherein a tetrazine functional group of a residue of the frTet is bound with the dienophile functional group of the linker through Inverse Electron Demand Diels-Alder (IEDDA) reaction to form a urate oxidase-albumin conjugate, and wherein the urate oxidase-albumin conjugate is characterized in that three or more albumins are conjugated to the urate oxidase variant through the linkers.

5. The method of claim 4, the linker is selected from the following:

n = 1 to 12;

n = 1 to 12;

N;

N; and n = 1 to 12.

6. The method of claim 4, wherein the urate oxidase variant is a tetramer that four urate oxidase variant subunits represented by SEQ ID NO: 29 are oligomerized, wherein the X of SEQ ID NO: 29 is frTet.

7. The method of claim 4, wherein the albumin is represented by a sequence selected from SEQ ID NOs: 133 to 144 or a sequence 90% or more identical with the sequence selected from SEQ ID NOs: 133 to 144, wherein the thiol reactive moiety of the linker is bound with thiol group of 34th cysteine of the sequence of the albumin through reaction.

8. The method of claim 4, wherein the reacting of the urate oxidase variant with the linker is performed at pH of 6 to 8.

9. A method for treating uric acid-related disease, the method comprising:
administering the urate oxidase-albumin conjugate of claim 1 into a subject.

10. The method of claim 9, wherein the uric acid-related disease is any one of hyperuricemia, acute gouty arthritis, intermittent gout, chronic nodular gout, Chronic Kidney Disease, and Tumor Lysis Syndrome (TLS).

11. The method of claim 9, wherein the administering the pharmaceutical composition into a subject is selected from oral administration, parenteral administration, intravenous administration, intravenous infusion, intraperitoneal administration, intramuscular administration, transdermal administration, and subcutaneous administration.

12. The method of claim 9, wherein the dosage of the pharmaceutical composition is 1 mg/kg to 10 mg/kg, based on the mass of the administered urate oxidase-albumin conjugate relative to the mass of the subject.

* * * * *